United States Patent
Ohkawa et al.

[11] Patent Number: 5,834,463
[45] Date of Patent: Nov. 10, 1998

[54] CONDENSED HETEROCYCLIC COMPOUNDS, THEIR PRODUCTION AND USE

[75] Inventors: Shigenori Ohkawa; Nobuhiro Fujii, both of Osaka; Koichi Kato, Tsukuba; Masaomi Miyamoto, Takarazuka, all of Japan

[73] Assignee: Takeda Chemical Industries, Ltd., Osaka, Japan

[21] Appl. No.: 464,885

[22] PCT Filed: Apr. 26, 1995

[86] PCT No.: PCT/JP95/00829
  § 371 Date: Jun. 26, 1995
  § 102(e) Date: Jun. 26, 1995

[87] PCT Pub. No.: WO95/29900
  PCT Pub. Date: Nov. 9, 1995

[30] Foreign Application Priority Data

| | | | |
|---|---|---|---|
| Apr. 29, 1994 | [JP] | Japan | 6-114000 |
| May 9, 1994 | [JP] | Japan | 6-095272 |
| Oct. 6, 1994 | [JP] | Japan | 6-242561 |
| Dec. 9, 1994 | [JP] | Japan | 6-305858 |

[51] Int. Cl.[6] .......................... A61K 31/55; C07D 243/12
[52] U.S. Cl. .......................... 514/220; 514/221; 540/517; 540/518; 540/495; 540/557; 540/567
[58] Field of Search .......................... 540/518, 517, 540/495, 557, 567; 514/220, 221

[56] References Cited

U.S. PATENT DOCUMENTS

| | | | |
|---|---|---|---|
| 3,312,689 | 4/1967 | Schmutz et al. | 540/557 |
| 3,347,849 | 10/1967 | Schmutz et al. | 540/537 |

FOREIGN PATENT DOCUMENTS

| | | |
|---|---|---|
| 0389189 | 9/1990 | European Pat. Off. . |
| 0487155 | 5/1992 | European Pat. Off. . |
| 54-135788 | 10/1979 | Japan . |
| WO 94/17075 | 8/1994 | WIPO . |

OTHER PUBLICATIONS

Puodziunate, Chem Abs 110, 192788x (1988).
Essassi, Heterocycles 23, 799(1985.
Bauer, Archiv. Pharm. 305(8), 557 (1972).
Vernin Chemica Scripta 16, 157–162 (1980).

Primary Examiner—Mark L. Berch
Attorney, Agent, or Firm—Fitzpatrick, Cella, Harper & Scinto

[57] ABSTRACT

Compounds represented by the formula:

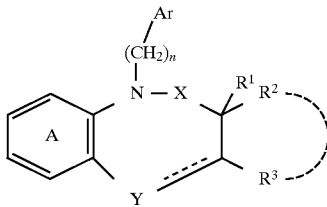

wherein ring A is benzene; Ar is aromatic group; $R^1$, $R^2$ and $R^3$ each stands for H, acyl, hydrocarbon or heterocyclic, or $R^2$ and $R^3$, taken together, may form non-aromatic cyclic hydrocarbon; X is methylene or carbonyl; ......... is single bond or double bond; when ......... is single bond, Y is —$NR^4$— ($R^4$ is H, acyl, hydrocarbon or heterocyclic), when ......... is double bond, Y is N; n is 1–3, provided that, X is carbonyl and, at the same time, $R^2$ and $R^3$, taken together, form non-aromatic cyclic hydrocarbon, ......... is double bond or $R^4$ is a heterocyclic or —$Z(CH_2)_m$—W (Z is methylene or carbonyl, W is optionally substituted amino, and m denotes 0–5), or salts thereof have an excellent GnRH receptor antagonistic action and/or an action of improving sleep disturbances.

26 Claims, No Drawings

CONDENSED HETEROCYCLIC COMPOUNDS, THEIR PRODUCTION AND USE

This application is a 371 of PCT/JP 95/00829, filed Apr. 26, 1995.

TECHNICAL FIELD

This invention relates to a novel condensed heterocyclic compound or a salt thereof having an excellent gonadotropin releasing hormone (GnRH) receptor antagonistic action and/or an excellent action to improve sleeping disturbances, a process for producing it, and a pharmaceutical composition containing it.

GnRH is a decapeptide consisting of 10 amino acids produced in hypothalamus, and controls secretion of, for example, luteinizing hormone or follicle stimulating hormone through a receptor considered to exist in an anterior lobe of pituitary gland, and, as a result, GnRH has been known as showing various physiological activities including induction of ovulation. Therefore, specific and selective antagonistic or agonistic agents for these receptors control an action of hormone produced from hypothalamus and suppress the secretion of anterior pipuitary hormone, thus these agents are expected to serve as prophylaxis or therapy of diseases dependent on anterior lobe of hypophysis.

Since 1971 when GnRH was discovered, a number of its analogues have been synthesized expecting their agonistic or antagonistic activities. For example, leuprorelin, which is a peptide, has a higher affinity to GnRH receptor than GnRH obtained from natural sources, and, is hardly susceptible to metabolism.

Leuprorelin acetate, which has 20 to 50 times as much activity as natural-type GnRH, by its repeated administration, reduced the release and production of gonadotropin, causing, for example, decreased reactivity to gonadotropin in testicle to reduce the productivity of testosterone to the level of castration. As a result, it has been known that leuprorelin acetate shows anti-tumor activity against such hormone-dependent cancers, for example, prostatic cancer. In practice, leuprorelin acetate has been widely used as a therapeutic agent of, for example, prostatic cancer and endometriosis in the clinical field.

However, these GnRH agonists are peptide and poor in oral absorbability, thus the administration forms are necessarily restricted, and, showing a transient agonistic activity, increasing the concentration of serum steroid hormone, and, in some cases, a transient aggravation such as osseus pain is observed.

On the other hand, in the modern society, those who have various mental disturbances and complain of sleeping disturbances, accompanied with social structure becoming more and more complicated and with increase of number of aged people, have increased. Sleeping disturbances include, for example, insomnia caused by stress, poriomania at night and depression of activity in day time due to abnormal circadian rhythm, jet lag caused by overseas travel and abnormal physical conditions caused by a three-shift system. Those who complain of these symptoms are, in general, administered with hypnotics such as 1,4-benzodiazepine type drugs, and all of these drugs have 1,4-benzodiazepine structure. This basic structure is thus considered to be essential for the action to induce sleeping.

While benzodiazepine-type drugs have been considered relatively safe, several problematic points are still found in them. More specifically, so-far known benzodiazepine-type hypnotics increase, among two fundamental sleeping conditions, i.e. REM sleep and non-REM sleep, increase REM-sleep latent period (time elapsing between the start of sleeping and the occurrence of the first episode), and decrease the REM-sleep period. Besides, suppression of REM sleep known as relating to fixation of memory is considered to possibly cause anterograde amnesia. Therefore, administration of such drugs as above to patients readily suffering from defects of memory such as senile dementia is not desirable. Further more, it has also been known that conventional benzodiazepine-type drugs, if the administration of them is discontinued, there may be considerable rebound in the amount and density of REM sleep, thus these drugs are not necessarily satisfactory from the practical viewpoints.

BACKGROUND ART

In JP54-135788, there is a description that a compound represented by the formula:

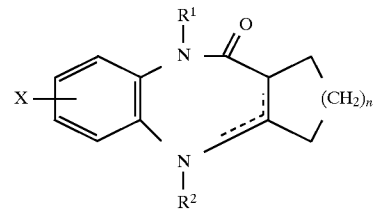

wherein X stands for H, halogen, lower alkyl or lower alkoxy; n denotes 1 or 2; $R^1$ and $R^2$ independently stand for H or a lower alkyl, either one of the two bonds shown by dotted line is a double bond, provided that, when $R^2$ is a lower alkyl, it is combined to a nitrogen atom which does not form double bond, and, when X and $R^1$ are H and n is 1, $R^2$ is a lower alkyl has an antianxiety action and an analgesic action. And, it is described that the diazepin derivative in WO94/17075 have an antiviral action.

Under the background as described above, studies aiming at synthesizing a therapeutic drug which is expected to have an excellent GnRH receptor antagonistic action or an action of improving sleeping disturbances and has no such undesirable side-effects as mentioned above, have been diligently conducted.

However, compounds, which have such an excellent GnRH receptor antagonistic action or action of improving sleeping disturbances as being a sufficiently satisfactory medicine, have not yet been found. Circumstances being such, development of a compound, which has a chemical structure different from that of the above-mentioned compound and has an excellent GnRH receptor antagonistic action or action of improving sleeping disturbances has been ardently desired.

DISCLOSURE OF INVENTION

The present inventors found that a compound having a characteristic feature of chemical structure in having 1,5-benzodiazepine as the basic skeleton and having substituent containing an aromatic group at the 1-position, which is represented by the formula:

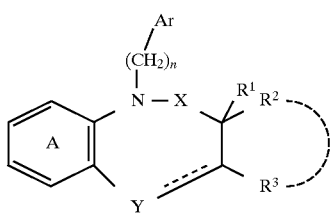

wherein ring A stands for an optionally substituted benzene ring; Ar stands for an optionally substituted aromatic group; $R^1$, $R^2$ and $R^3$ independently stands for a hydrogen atom, an acyl group, an optionally substituted hydrocarbon group or an optionally substituted heterocyclic group, or $R^2$ and $R^3$, taken together, may form a non-aromatic cyclic hydrocarbon group; X stands for a methylene group or a carbonyl group; ........ stands for a single bond or a double bond; when ........ is a single bond, Y stands for —$NR^4$— ($R^4$ stands for a hydrogen atom, an acyl group, an optionally substituted hydrocarbon group or an optionally substituted heterocyclic group) and, when ........ is a double bond, Y stands for a nitrogen atom; n denotes an integer of 1 to 3; provided that when X is a carbonyl group and, at the same time, $R^2$ and $R^3$, taken together, form a non-aromatic cyclic hydrocarbon, ........ is a double bond or $R^4$ stands for an optionally substituted heterocyclic group or —Z—$(CH_2)_m$—W (Z stands for a methylene group or a carbonyl group, W stands for an optionally substituted amino group and m denotes an integer of 0 to 5) or a salt thereof has an excellent GnRH receptor antagonistic action and is low in toxicity, thus being useful in the clinical field. Based on these findings, the present invention has been accomplished.

BEST MODE FOR CARRYING OUT THE INVENTION

Preferable examples of the compound (I) as described above are the following compounds.

A compound (I) as described above, wherein the optionally substituted benzene ring is a benzene ring which may be substituted by 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group.

A compound (I) as described above, wherein the optionally substituted aromatic group is (i) a $C_{6-14}$ aryl group or (ii) a 5- or 6-membered aromatic heterocyclic group containing, besides carbon atoms, 1 to 4 hetero-atoms selected from a nitrogen, oxygen and sulfur atom or a di- or tri-cyclic condensed heterocyclic group formed with a benzene ring, which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group, a phenyl group and an oxo group.

A compound (I) as described above, wherein the optionally substituted hydrocarbon group represented by $R^1$, $R^2$ and $R^3$ is a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group, which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group (o) a $C_{1-6}$ alkylmercapto group, (p) a $C_{6-14}$ aryl group and (q) a 5- or 6-membered heterocyclic group containing, besides carbon atoms, 1 to 4 hetero-atoms selected from a nitrogen, oxygen and sulfur atom or a di- or tri-cyclic condensed heterocyclic group formed with a benzene ring.

A compound (I) as described above, wherein the optionally substituted heterocyclic group is a 5- or 6-membered heterocyclic group containing, besides carbon atoms, 1 to 4 hetero-atoms selected from a nitrogen, oxygen and sulfur atom or a di- or tri-cyclic condensed heterocyclic group formed with a benzene ring, which may be substituted by 1 to 5 substituents selected from the group consisting of an amino group, a mono-$C_{1-6}$ alkylamino group, a di-$C_{1-6}$ alkylamino group, a halogen atom, nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group.

A compound (I) as described above, wherein the acyl group represented by $R^1$, $R^2$ and $R^3$ is a $C_{1-6}$ alkyl-carbonyl group, a $C_{6-14}$ aryl-carbonyl group, a $C_{7-16}$ aralkyl-carbonyl group, a $C_{1-3}$ alkylsulfonyl group or a $C_{6-14}$ arylsulfonyl group, A compound (I) as described above, wherein the non-aromatic cyclic hydrocarbon group is a 5- to 8-membered non-aromatic cyclic hydrocarbon group.

A compound (I) as described above, wherein the acyl group and the optionally substituted hydrocarbon group represented by $R^4$ are (1) a $C_{1-6}$ alkyl-carbonyl group, a $C_{6-14}$ aryl-carbonyl group, a $C_{7-16}$ aralkyl-carbonyl group, a $C_{1-3}$ alkylsulfonyl group or a $C_{6-14}$ arylsulfonyl group, (2) a $C_{1-6}$ alkyl, $C_{2-6}$ alkenyl, $C_{2-6}$ alkynyl, $C_{3-6}$ cycloalkyl, $C_{6-14}$ aryl or $C_{7-16}$ aralkyl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group, (o) a $C_{1-6}$ alkylmercapto group, (p) a $C_{6-14}$ aryl group, (q) a 5- or 6-membered heterocyclic group containing, besides carbon atoms, 1 to 4 hetero-atoms selected from a nitrogen, oxygen and sulfur atom or a di- or tri-cyclic condensed heterocyclic group formed with a benzene ring and (r) a $C_{1-6}$ acyloxy group, or (3) —Z—$(CH_2)_m$—W (Z stands for a methylene group or a carbonyl group, W stands for an optionally substituted amino group, and m denotes an integer of 0 to 5).

A compound (I) as described above, wherein the optionally substituted amino group is:

(i)

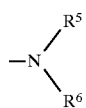

wherein $R^5$ and $R^6$ independently stands for (a) a hydrogen atom, (b) an optionally substituted hydrocarbon group or (c)

an optionally substituted 5- or 6-membered heterocyclic group or a di or tri-cyclic condensed ring with a benzene ring, and, (b) and (c) may bonded through a carbonyl group or a sulfonyl group, (ii)

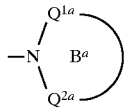

wherein ring B stands for an optionally substituted 5- or 6-membered non-aromatic heterocyclic ring or an optionally substituted 5- or 6-membered cyclic hydrocarbon group or a di- or tri-cyclic condensed heterocyclic group, $Q^1$ and $Q^2$ independently stands for —CO—,

—CH$_2$—, —CH(OH)— or

(iii)

wherein ring D stands for an optionally substituted 5- or 6-membered aromatic heterocyclic group or a di- or tri-cyclic condensed heterocyclic group or (iv)

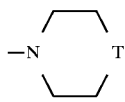

wherein T stands for an oxygen atom, >CH—$R^7$ or >N—$R^7$ ($R^7$ stands for an optionally substituted $C_{6-14}$ aryl group or an optionally substituted $C_{7-16}$ aralkyl group).

A compound (I) as described above, wherein ring A is non-substituted benzene ring.

A compound as described above, wherein Ar is a $C_{6-14}$ aryl group which may be substituted by 1 to 5 substituents selected from the group consisting of an amino group, a mono-$C_{1-6}$ alkylamino, a di-$C_{1-6}$ a alkylamino, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group, a phenyl group and an oxy group and n is 1.

A compound (I) as described above, wherein $R^1$ is (i) a hydrogen atom or (ii) a $C_{7-16}$ aralkyl group which may be substituted by 1 to 5 substituents selected from the group consisting of an amino group, a mono-$C_{1-6}$ alkylamino group, a di-$C_{1-6}$ alkylamino group, a halogen atom, a nitro group, sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group.

A compound (I) as described above, wherein $R^1$ is a hydrogen atom.

A compound (I) as described above, wherein $R^2$ is (i) a hydrogen atom or (ii) a $C_{7-16}$ aralkyl group which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group.

A compound (I) as described above, wherein $R^3$ is
(1) a hydrogen atom,
(2) a $C_{1-6}$ alkyl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group, (o) a $C_{1-6}$ alkylmercapto group, (p) a $C_{6-14}$ aryl group and (q) a 5- or 6-membered heterocyclic group containing, besides carbon atoms, 1 to 4 hetero-atoms selected from a nitrogen, oxygen and sulfur atom or a di- or tri-cyclic condensed heterocyclic group with a benzene ring,
(3) a $C_{2-6}$ alkenyl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group,(l) a $C_{1-6}$ alkoxy-carbonyl group, (m) a $C_{1-6}$ acyl group, (n) a mercapto group, (o) a $C_{1-6}$ alkylmercapto group, (p) a $C_{6-14}$ aryl group and (q) a 5- or 6-membered heterocyclic group containing, besides carbon atoms, 1 to 4 hetero-atoms selected from a nitrogen, oxygen and sulfur atom, or a di- or tri-cyclic condensed heterocyclic group with a benzene ring,
(4) a $C_{6-14}$ aryl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfon group, (g) a cyano group, (h) a hydroxy group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group and (o) a $C_{1-6}$ alkylmercapto,
(5) a $C_{7-16}$ aralkyl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group and (o) a $C_{1-6}$ alkylmercapto group, or
(6) a 5- or 6-membered heterocyclic group containing, besides carbon atoms, 1 to 4 hetero-atoms selected from a nitrogen, oxygen and sulfur or a di- or tri-cyclic condensed heterocyclic group with a benzene ring, which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a sulfo group, (g) a cyano group, (h) a hydroxyl group, (i) a $C_{1-6}$ alkyl group, (j) a $C_{1-6}$ alkoxy group, (k) a carboxyl group, (1) a $C_{1-6}$ alkoxy-carbonyl group, (m) a $C_{1-5}$ acyl group, (n) a mercapto group and (o) a $C_{1-6}$ alkylmercapto group.

A compound (I) as described above, wherein $R^2$ and $R^3$ form, taken together, a 5- to 8-membered cycloalkane.

A compound represented by the formula:

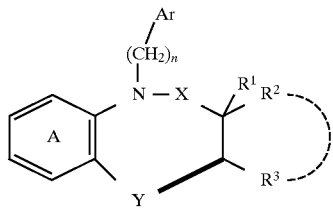

(I-A)

wherein ring A stands for an optionally substituted benzene ring; Ar stands for an optionally substituted aromatic group; $R^1$, $R^2$ and $R^3$ independently stands for a hydrogen atom, an acyl group, an optionally substituted hydrocarbon group or an optionally substituted heterocyclic group, or $R^2$ and $R^3$ may, taken together, form a non-aromatic cyclic hydrocarbon group; X stands for a methylene group or a carbonyl group, and n denotes an integer of 0 to 3, or a salt thereof.

A compound (I-A) as described above, wherein Ar is a 5- or 6-membered aromatic heterocyclic group which may be substituted by 1 to 4 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group and a phenyl group.

A compound represented by the formula:

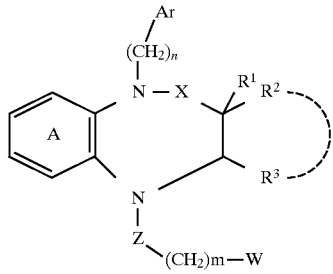

(I-B)

wherein ring A is an optionally substituted benzene ring; Ar stands for an optionally substituted aromatic group; $R^1$, $R^2$ and $R^3$ independently stands for a hydrogen atom, an acyl group, an optionally substituted hydrocarbon group or an optionally substituted heterocyclic group, or $R^2$ and $R^3$ may, taken together, form a non-aromatic cyclic hydrocarbon group; X stands for a methylene group or a carbonyl group, Z stands for a methylene group or a carbonyl group, W stands for an optionally substituted amino group; m denotes an integer of 0 to 5, and n denotes an integer of 0 to 3, or a salt thereof.

A compound (I-B) as described above, wherein the ring A is a benzene ring which may be substituted by 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group.

A compound (I-B) as described above, wherein the ring A is an unsubstituted benzene ring.

A compound (I-B) as described above, wherein Ar is (i) a $C_{6-14}$ aryl group or (ii) a 5- or 6-membered aromatic heterocyclic group containing, besides carbon atoms, 1 to 4 hetero-atoms selected from a nitrogen, oxygen and sulfur, which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group, a phenyl group and an oxo group.

A compound (I-B) as described above, wherein $R^1$ is (i) a hydrogen atom or (ii) a $C_{7-16}$ aralkyl group which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group;

$R^2$ is (i) a hydrogen atom or (ii) a $C_{7-16}$ aralkyl group which may be substituted by 1 to 5 substituents selected from the group consisting of an amino group, a mono-$C_{1-6}$ alkylamino, a di-$C_{1-6}$ alkylamino, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group;

$R^3$ is (1) a hydrogen atom, (2) a $C_{1-6}$ alkyl group which may be substituted by 1 to 5 substituents selected from (a) an amino group, (b) a mono-$C_{1-6}$ alkylamino group, (c) a di-$C_{1-6}$ alkylamino, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group, (o) a $C_{1-6}$ alkylmercapto group, (p) $C_{6-14}$ aryl group and (q) a 5- or 6-membered heterocyclic group containing, besides carbon atoms, 1 to 4 hetero-atoms selected from a nitrogen, oxygen and sulfur atom or a di- or tri-cyclic condensed heterocyclic group with a benzene ring, (3) a $C_{2-6}$ alkenyl group which may be substituted by 1 to 5 substituents selected from (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group, (o) a $C_{1-6}$ alkylmercapto group, (p) a $C_{6-14}$ aryl group and (q) a 5- or 6-membered heterocyclic ring group containing, besides carbon atoms, 1 to 4 hetero-atoms selected from a nitrogen, oxygen and sulfur atom or a di- or tri-cyclic condensed heterocyclic group with a benzene ring, (4) a $C_{6-14}$ aryl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group and (o) a $C_{1-6}$ alkylmercapto group or (5) a $C_{7-16}$ aralkyl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group and (o) a $C_{1-6}$ alkylmercapto group.

A compound (I-B) as described above, wherein $R^2$ and $R^3$, taken together, form a 5- to 8-membered cycloalkane.

A compound (I-B) as described above, wherein $R^1$ is a hydrogen atom.

A compound (I-B) as described above, wherein X is a carbonyl group.

A compound (I-B) as described above, wherein Z is a carbonyl group.

A compound (I-B) as described above, wherein n is 1.

A compound (I-B) as claimed in claim 19, wherein $R^1$ is a hydrogen atom, and $R^2$ and $R^3$, taken together, form a cyclopentane.

A compound (I-B) as described above, wherein W is (i)

($R^{5a}$ and $R^{6a}$ independently stands for (1) a hydrogen atom or (2) (a) $C_{1-6}$ alkyl, (b) phenyl, or (c) a 5- or 6-membered aromatic heterocyclic group containing, besides carbon atoms, 1 to 4 hetero-atoms selected from a nitrogen, oxygen and sulfur atom or a di- or tri-cyclic condensed heterocyclic group with a benzene ring, which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group and a $C_{1-6}$ acyloxy group, and, (a), (b) and (c) may bonded through a carbonyl group, (ii)

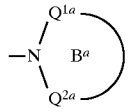

wherein $B^a$ ring stands for a 5- or 6-membered non-aromatic heterocyclic group or a di- or tri-cyclic condensed ring group with a 6-membered cyclic hydrocarbon group or a heterocyclic group; $B^a$ ring may be substituted by 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group; and $Q^{1a}$ and $Q^{2a}$ independently stands for —CO— or —C(OH)—, (iii)

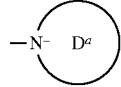

wherein $D^a$ ring stands for a 5- or 6-membered aromatic heterocyclic group containing, besides carbon atoms, 1 to 4 hetero-atoms selected from a nitrogen, oxygen and sulfur atom or a di- or tri-cyclic condensed heterocyclic group with a benzene ring, which may be substituted by 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group, or (iv)

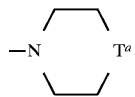

wherein $T^a$ stands for an oxygen atom, >CH—$R^{7a}$ or >N—$R^{7a}$ ($R^{7a}$ stands for a phenyl or benzyl group which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group.

A compound (I-B) as described above, wherein W is

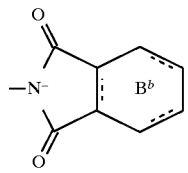

wherein $B^b$ ring stands for a 6-membered cyclic hydrocarbon group which may be substituted by 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxy group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkyl mercapto group, and ......... stands for single bond or a double bond.

A compound (I-B) as described above, wherein the 6-membered cyclic hydrocarbon is a benzene ring.

A compound (I-B) as described above, wherein W stands for —NH—$CH_2$—R, —NH—CO—R,

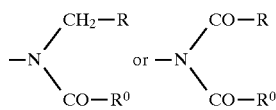

wherein R and $R^0$ independently stands for (1) a hydrogen atom or (2) (a) $C_{1-6}$ alkyl, (b) phenyl or (c) a 5- or 6-membered aromatic heterocyclic group containing, besides carbon atoms, 1 to 4 hetero-atoms selected from a nitrogen, oxygen and sulfur atom, which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group and a $C_{1-6}$ acyloxy group.

A process for producing a compound as described above, which comprises reacting a compound represented by the formula:

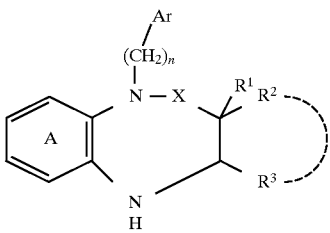

wherein all symbols are of the same meanings as defined in claim 1, or a salt thereof with a compound represented by the formula

Hal-R⁴ wherein Hal stands for a halogen atom, and $R^4$ is of the same meaning as defined above.

A process for producing a compound represented by the formula:

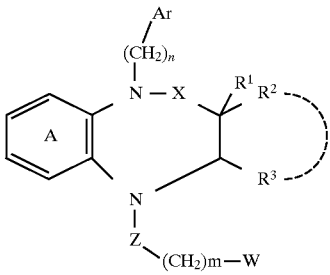

wherein all symbols are of the same meanings as defined above, or a salt thereof, which comprises reacting a compound represented by the formula:

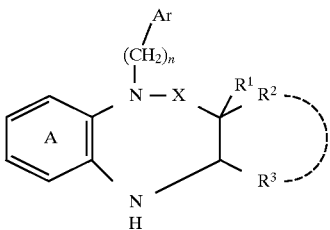

wherein all symbols are of the same meaning as defined above, or a salt thereof with a compound represented by the formula:

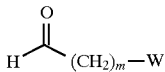

wherein all symbols are of the same meanings as defined above, or a salt thereof.

A process for producing a compound as described above, which comprises reacting a compound represented by the formula:

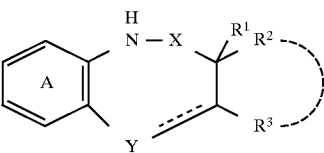

wherein all symbols are of the same meanings as defined above, or a salt thereof with a compound represented by the formula:

Ar—(CH₂)$_n$—Hal wherein Hal stands for a halogen atom and the other symbols are of the same meanings as defined above, or a salt thereof.

Examples of substituents which the benzene ring in the term "optionally substituted benzene ring" used in the present specification may have, include an amino group, a mono-$C_{1-6}$ alkylamino group (e.g. methylamino and ethylamino), a di-$C_{1-6}$ alkylamino group (e.g. dimethylamino and diethylamino), a halogen atom (e.g. fluorine, chlorine, bromine and iodine), a nitro group, a sulfo group, a cyano group, a hydroxyl group, a $C_{1-6}$ alkyl group (e.g. methyl, ethyl, propyl and isopropyl), a $C_{1-6}$ alkoxy group (e.g. methoxy, ethoxy, propoxy and isopropoxy), a carboxyl group, a $C_{1-6}$ alkoxy-carbonyl group (e.g. methoxycarbonyl, ethoxycarbonyl, propoxycarbonyl, isopropoxycarbonyl and butoxycarbonyl), a $C_{1-5}$ acyl group (e.g. formyl, acetyl and propionyl), a mercapto group and a $C_{1-6}$ alkylmercapto group (e.g. methylmercapto, ethylmercapto and propylmercapto).

These substituents may be substituted at any possible position on the benzene ring, and the number of these substituents ranges from 1 to 4, preferably 1 to 3, provided that when the number of those substituents is two or more, they may be the same one or different ones from each other.

The "aromatic group" in the term "optionally substituted aromatic group" used in the present specification means, for example, an aromatic hydrocarbon group or an aromatic heterocyclic group.

Examples of the "aromatic hydrocarbon group" include a monocyclic or condensed polycyclic aromatic hydrocarbon which have 6 to 18 carbon atoms. Preferable examples of them are a $C_{6-14}$ aryl group such as a phenyl, a 1-naphthyl, a 2-naphthyl, an indenyl and an anthryl. Especially, a phenyl group, a 1-naphthyl group and a 2-naphthyl group are preferable.

Examples of the "aromatic heterocyclic group" include a monocyclic or condensed polycyclic aromatic heterocyclic group. Preferable examples of the "monocyclic aromatic heterocyclic group" include a 5- or 6-membered monocyclic aromatic heterocyclic group containing, besides carbon atoms, one or two kinds of hetero atoms selected from a nitrogen, oxygen and sulfur atom, preferably 1 to 4 hetero atoms. And preferable examples of the "condensed polycyclic aromatic heterocyclic group" include a di- or tri-cyclic condensed heterocyclic group formed by condensation with an aromatic ring such as a benzene ring and the monocyclic aromatic heterocyclic group (e.g., pyridine). More specifically, mention is made of (1) a 5- or 6-membered monocyclic aromatic heterocyclic group such as a 2- or 3-thienyl, 2- or 3-furyl, 2- or 3-pyrrolyl, 2-, 4- or 5-imidazolyl, 4- or 5-pyrazolyl, 3-, 4- or 5-isothiazolyl, 3-, 4- or 5-isoxazolyl, 2, 3- or 4-pyridyl, 2-, 4- or 5-pyrimidinyl, 3- or 4-pyridazinyl, pyrazinyl and (2) a di- or tri-cyclic condensed ring group with a benzene ring and the monocyclic aromatic heterocyclic group such as a benzofuryl, benzothiazolyl, benzoxazolyl, benzoimidazolyl, 1-indolyl, 2- or 3-quinolyl, 1- or 3-isoquinolyl. More preferably, use is made of (1) a 5- or 6-membered monocyclic heterocyclic group containing, besides carbon atoms, 1 to 3 hetero-atoms selected from a nitrogen, oxygen and sulfur atom (e.g. 2- or 3-thienyl, 2- or 3-furyl, 2-, 4- or 5-imidazolyl, 2-, 3- or 4-pyridyl) or (2) di-cyclic condensed heterocyclic group with one benzene ring and the monocyclic aromatic heterocyclic group (e.g. 1-indolyl).

As the substituents which the "aromatic group" may have, use is made of, for example, similar ones to those which the above-mentioned "optionally substituted benzene ring" may have and a phenyl group and an oxo group. These substituents may be substituted on any possible position on the aromatic ring. The number of these substituents ranges from 1 to 5, preferably 1 to 3, provided that when the number is two or more, they are the same one or different from each other.

Examples of the term "5- or 6-membered heterocyclic group containing, besides carbon atoms, 1 to 4 hetero-atoms selected from a nitrogen, oxygen and sulfur atom or a di- or tri-cyclic condensed ring group with a benzene ring" used in the present specification include (1) a 5- or 6-membered monocyclic aromatic heterocyclic group as 2- or 3-thienyl, 2- or 3-furyl, 2- or 3-pyrrolyl, 2-, 4- or 5-imidazolyl, 4- or 5-pyrazolyl, 3-, 4- or 5-isothiazolyl, 3-, 4- or 5-isoxazolyl, 2-, 3- or 4-pyridyl, 2-, 4- or 5-pyrimidinyl, 3- or 4-pyridazinyl, pyrazinyl and (2) di- or tri-cyclic condensed heterocyclic group with a benzene ring and the monocyclic aromatic heterocyclic group such as benzofuryl, benzothiazolyl, benzoxazolyl, benzoimidazolyl, 1-indolyl, 2- or 3-quinolyl, 2- or 3-isoquinolyl.

The "hydrocarbon group" in the term "optionally substituted hydrocarbon group" used in the present specification include, for example, groups set forth in (1) or (2) hereinafter.

(1) Aliphatic hydrocarbon group:
   a) a $C_{1-6}$ alkyl group (e.g. methyl, ethyl, propyl, isopropyl, butyl, isobutyl, sec-butyl, tert-butyl, pentyl and hexyl),
   b) a $C_{2-6}$ alkenyl group (e.g. vinyl, allyl, isopropenyl, butenyl, isobutenyl and sec-butenyl),
   c) a $C_{2-6}$ alkynyl group (e.g. propargyl, ethynyl, butynyl and 1-hexyl),
(2) Cyclic hydrocarbon group:
   a) a $C_{3-6}$ cycloalkyl group (e.g. cyclopropyl, cyclobutyl, cyclopentyl and cyclohexyl), and the cyclohexyl may be condensed with an optionally substituted benzene ring,
   b) a $C_{6-14}$ aryl group (e.g. phenyl, tolyl, xylyl, 1-naphthyl, 2-naphthyl, biphenyl, 2-indenyl and 2-anthryl), especially a phenyl group,
   c) a $C_{7-16}$ aralkyl group (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl and 5-phenylpentyl), especially a benzyl group.

As the substituents which the "hydrocarbon group" may have, use is made of similar ones to those which the above-mentioned "optionally substituted benzene ring" may have, and further (i) a $C_{6-14}$ aryl group (e.g. phenyl, 1-naphthyl and 2-naphthyl), (ii) a 5- or 6-membered heterocyclic group containing, besides carbon atoms, 1 to 4 hetero-atoms selected from a nitrogen, oxygen and sulfur atom or di- or tri-cyclic condensed heterocyclic group with a benzene ring and (iii) a $C_{1-6}$ acyloxy group (e.g. formyloxy, acetoxy and propionyloxy). These substituents may be substituted at any possible position on the hydrocarbon group, and the number of the substituents ranges from 1 to 5, preferably 1 to 3, provided that when the number of substituents is two or more, they may be the same as or different from each other.

And, as the "optionally substituted hydrocarbon group", a group represented by —$(CH_2)_{m+1}$—W (W stands for an optionally substituted amino group and m denotes an integer of 0 to 5) are also preferable. The term "optionally substituted amino group" represented by W is shown hereinafter.

Examples of the "heterocyclic group" in the term "optionally substituted heterocyclic group" used in the present specification include (1) a 5- or 6-membered heterocyclic group containing, besides carbon atoms, 1 to 4 hetero-atoms selected from a nitrogen, oxygen and sulfur atom or (2) a di- or tri-cyclic condensed heterocyclic group with a benzene ring. Examples of them include the same one as the "aromatic heterocyclic group" described hereinabove and further a non-aromatic heterocyclic group such as a 2-pyrrolidinyl, pyrrolinyl, 2-imidazolidinyl, 2-pyrazolidinyl and 1-piperazinyl.

As substituents which the "heterocyclic group" may have, use is made of those similar to substituents which the above-mentioned "optionally substituted benzene ring" may have. These substituents may be substituted at any possible position on the heterocyclic ring. The number of these substituents ranges from 1 to 5, preferably 1 to 3, provided that when the number of the substituents is two or more, they may be the same as or different from each other.

The term "acyl group" used in the present specification includes, for example, a carboxylic acid acyl group derived from carboxylic acid and a sulfonic acid acyl group derived from sulfonic acid. Preferable examples are a $C_{1-6}$ alkyl-carbonyl group (e.g. acetyl), a $C_{6-14}$ aryl-carbonyl group (e.g. benzoyl), a $C_{1-3}$ alkylsulfonyl group (e.g. methylsulfonyl) and a $C_{6-14}$ arylsulfonyl group (e.g. phenylsulfonyl) and so on.

As substituents which the "acyl group" may have, use is made of those similar to substituents which the above-mentioned "optionally substituted benzene ring" may have. These substituents may be substituted at any possible position on the acyl group, and the number of them ranges from 1 to 5, preferably 1 to 3, provided that when the number of substituents is two or more, they may be the same as or different from each other.

As the "acyl group", a group of the formula, —CO—$CH_2)_m$—W (W stands for an optionally substituted amino group, and m denotes an integer of 1 to 5) is also preferable. The "optionally substituted amino group" represented by W is described hereinafter.

The term "non-aromatic cyclic hydrocarbon" used in the present specification means, for example, a 5- to 8-membered non-aromatic cyclic hydrocarbon. Examples of them include a $C_{5-8}$ cycloalkane (e.g. cyclopentane, cyclohexane and cycloheptane) and so on.

As the "optionally substituted amino group" used in the present specification, use is made of, for example, (i)

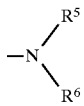

wherein $R^5$ and $R^6$ independently stands for (a) a hydrogen atom, (b) an optionally substituted hydrocarbon group or (c) an optionally substituted 5- or 6-membered heterocyclic or di- or tri-cyclic condensed heterocyclic group with a benzene ring, provided that (b) and (c) may be bonded through a carbonyl group or a sulfonyl group, (ii)

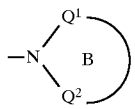

wherein ring B stands for an optionally substituted 5- or 6-membered non-aromatic heterocyclic group or a di- or tri-cyclic condensed ring group with an optionally substituted 5- or 6-membered cyclic hydrocarbon or heterocyclic ring; $Q^1$ and $Q^2$ each stands for —CO—, —CH$_2$—, —CH(OH)— or

(iii)

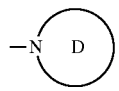

wherein ring D stands for an optionally substituted 5- or 6-membered aromatic heterocyclic group or a di- or tri-cyclic condensed heterocyclic group with a benzene group or (iv)

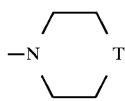

wherein T stands for an oxygen atom, >CH—$R^7$ or >N—$R^7$ ($R^7$ stands for an optionally substituted $C_{6-14}$ aryl group or an optionally substituted $C_{7-16}$ aralkyl group.

The terms used in the description concerning the "optionally substituted amino group" represented by W are explained in the following.

As the "optionally substituted hydrocarbon group" use is made of, for example, a group similar to the above-mentioned "optionally substituted hydrocarbon group", and the hydrocarbon group may be bonded through carbonyl group.

As the "5- or 6-membered heterocyclic group or di- or tri-cyclic condensed heterocyclic group with a benzene ring", use is made of, for example, those similar to the above-mentioned "5- or 6-membered heterocyclic group containing, besides carbon atoms, 1 to 4 hetero-atoms selected from a nitrogen, oxygen and sulfur atom or di- or tri-cyclic condensed heterocyclic group with a benzene ring". As substituents which these groups may have, use is made of those, in similar number, similar to the substituents which the above-mentioned "optionally substituted benzene ring" may have. And, these groups may be bonded through a carbonyl group or a sulfonyl group. The "5- or 6-membered non-aromatic heterocyclic group" means, for example,

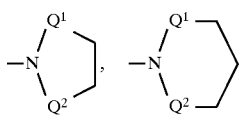

wherein $Q^1$ and $Q^2$ are the same meaning as defined above, respectively.

The "5- or 6-membered non-aromatic heterocyclic group" may have one or two "optionally substituted hydrocarbon group". As the "optionally substituted hydrocarbon group", use is made of, for example, a group similar to those described hereinabove.

Examples of the "5- or 6-membered cyclic hydrocarbon" include a benzene, cyclohexene and cyclohexane.

As the substituents which the "5- or 6-membered cyclic hydrocarbon" may have, use is made of a group similar to the substituents which the above-mentioned "optionally substituted benzene ring" may have.

Examples of the "5- or 6-membered heterocyclic group" include a 5- or 6-membered heterocyclic group containing, besides carbon atoms, 1 to 4 hetero-atoms selected from a nitrogen, oxygen and sulfur atom or a di- or tri-cyclic condensed heterocyclic group with a benzene ring. Examples of them includes a group similar to the "aromatic heterocyclic group". Preferable examples are a non-aromatic heterocyclic group such as a 2-pyrrolidinyl, pyrrolinyl, 2-imidazolidinyl, 2-pyrazolidinyl and 1-piperazinyl. Preferable example is a pyridine ring.

Examples of the "$C_{6-14}$ aryl" in the "optionally substituted $C_{6-14}$ aryl group" include a phenyl, 1-naphthyl and 2-naphthyl. As substituents which these groups may have, use is made of those similar to substituents which the "optionally substituted benzene ring" may have, in similar number to that of them.

Examples of the "$C_{7-16}$ aralkyl group" in the "optionally substituted $C_{7-16}$ aralkyl group" include a benzyl and a phenethyl. As substituents which these groups may have, use is made of a group similar to substituents which the "optionally substituted benzene ring" may have, in similar number to that of them.

In the following, when the same terms as used herein above, they have the same significances as those of the terms used herein above, unless otherwise specified.

In the above-mentioned formulae, ring A stands for an optionally substituted benzene ring. Preferable ring A is an unsubstituted benzene ring.

In the above-mentioned formulae, Ar stands for an optionally substituted aromatic group. Preferable examples of Ar include a $C_{6-14}$ aryl group (e.g. phenyl, 1-naphthyl and 2-naphthyl) which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group, a phenyl group and an oxo group, and so on.

In the above-mentioned formulae, n denotes 0 to 3, preferably 1.

In the above-mentioned formulae, $R^1$, $R^2$ and $R^3$ independently stands for a hydrogen atom, an acyl group, an optionally substituted hydrocarbon group or an optionally substituted heterocyclic group. And, $R^2$ and $R^3$, taken together, may form a non-aromatic cyclic hydrocarbon.

Preferable examples of $R^1$ include (i) a hydrogen atom or (ii) a $C_{7-16}$ aralkyl group (e.g. benzyl) which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, carboxyl group, a $C_{1-6}$ alkoxy-carbonyl group, a $C_{1-5}$ acyl group, a mercapto group and a $C_{1-6}$ alkylmercapto group, more preferably a hydrogen atom.

Preferable examples of $R^2$ include (i) a hydrogen atom or (ii) a $C_{7-16}$ aralkyl group (e.g. benzyl) which may be substituted by 1 to 5 substituents selected from an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group.

Preferable examples of $R^3$ include (1) a hydrogen atom,
(2) a $C_{1-6}$ alkyl group (e.g. methyl, ethyl, propyl and isopropyl) which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group, (o) a $C_{1-6}$ alkylmercapto group, (p) a $C_{6-14}$ aryl group and (q) a 5- or 6-membered heterocyclic group containing, besides carbon atoms, 1 to 4 hetero-atoms selected from a nitrogen, oxygen and sulfur atom or a di- or tri-cyclic condensed heterocyclic group with a benzene ring,
(3) a $C_{2-6}$ alkenyl group (e.g. vinyl) which may be substituted by 1 to 5 (preferably 1 to 3) substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-6}$ acyl group, (n) a mercapto group, (o) a $C_{1-6}$ alkylmercapto group, (p) a $C_{6-14}$ aryl group and (q) a 5-or 6-membered heterocyclic group containing, besides carbon atoms, 1 to 4 hetero-atoms selected from a nitrogen, oxygen and sulfur atom or a di- or tri-cyclic condensed heterocyclic group with a benzene ring,
(4) a $C_{6-14}$ aryl group (e.g. phenyl) which may be substituted by 1 to 5 (preferably 1 to 3) substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxy group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group and (o) a $C_{1-6}$ alkylmercapto group,
(5) a $C_{7-16}$ aralkyl group (e.g.benzyl) which may be substituted by 1 to 5 (preferably 1 to 3) substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group and (o) a $C_{1-6}$ alkylmercapto group, or
(6) a 5- or 6-membered heterocyclic group containing, besides carbon atoms, 1 to 4 hetero-atoms selected from a nitrogen, oxygen and sulfur atom or a di- or tri-cyclic condensed heterocyclic group with a benzene ring (e.g. 2- or 3-thienyl, 2- or 3-furyl, 2-, 4- or 5-imidazolyl, 2-, 3- or 4-pyridyl and 1-indolyl) which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group and (o) a $C_{1-6}$ alkylmercapto group.

It is preferable that $R^2$ and $R^3$, taken together, form a 5- to 8-membered cycloalkane (e.g. cyclopentane).

The case, where $R^1$ is a hydrogen atom and, $R^2$ and $R^3$, taken together, form cyclopentane, is also preferable.

In the above formulae, X stands for a methylene group or a carbonyl group.

In the above formulae, ......... means a single bond or a double bond. When ......... is a single bond, Y stands for —$NR^4$— ($R^4$ stands for a hydrogen atom, an acyl group, an optionally substituted hydrocarbon group or an optionally substituted heterocyclic group) and, when ......... is a double bond, Y stands for a nitrogen atom.

In the above formulae, preferable examples of $R^4$ include —Z—$(CH_2)_m$—W (Z stands for a methylene group or a carbonyl group, W stands for an optionally substituted amino group, and m denotes an integer of 0 to 5).

The symbol m denotes preferably 1 to 5.

Preferable examples of W include (1)

wherein $R^{5a}$ and $R^{6a}$ independently stands for (i) a hydrogen atom or (ii) (a) $C_{1-6}$ alkyl, (b) phenyl or (c) 5- or 6-membered aromatic heterocyclic group containing, besides carbon atoms, 1 to 4 hetero-atoms selected from a nitrogen, oxygen and sulfur atom or a di- or tri-cyclic condensed heterocyclic group with a benzene ring, which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group and a $C_{1-6}$ acyloxy group, and, (a), (b) and (c) may be bonded through a carbonyl group, (2)

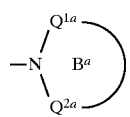

wherein ring $B^a$ stands for a 5- or 6-membered non-aromatic heterocyclic group or a di- or tri-cyclic condensed heterocyclic group with a 6-membered cyclic hydrocarbon or heterocyclic ring, the ring $B^a$ may have 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group, and, $Q^{1a}$ and $Q^{2a}$ independently stands for —CO— or —C(OH)—, (3)

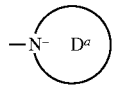

wherein ring $D^a$ stands for a 5- or 6-membered aromatic heterocyclic group containing, besides carbon atoms, 1 to 4 hetero-atoms selected from a nitrogen, oxygen and sulfur atom or a di- or tri-cyclic condensed heterocyclic group with a benzene ring, and, the ring $D^a$ may have 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group, and (4)

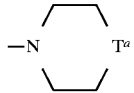

wherein $T^a$ stands for an oxygen atom, >CH—$R^{7a}$ or >N—$R^{7a}$ ($R^{7a}$ stands for a phenyl or benzyl group which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group). And, more preferable example of W is

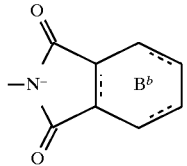

wherein ring $B^b$ stands for a 6-membered cyclic hydrocarbon which may be substituted by 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group, and ......... stands for a single bond or a double bond, etc.

Further, preferable examples of W include also —NH—CH$_2$—R, —NH—CO—R,

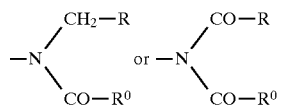

wherein R and $R^0$ independently stands for (i) a hydrogen atom or (ii) (a) a $C_{1-6}$ alkyl, (b) a phenyl or (c) a 5- or 6-membered aromatic heterocyclic group containing, besides carbon atoms, 1 to 4 hetero-atoms selected from a nitrogen, oxygen and sulfur atom, which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group and a $C_{1-6}$ acyloxy group.

Preferable examples of the compound (I) in the present invention include those represented by the following (A), (B) and (C).

(A) A compound represented by the formula:

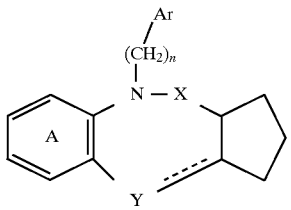

wherein ring A stands for an optionally substituted benzene ring; Ar stands for an optionally substituted aromatic group; X stands for a methylene group or a carbonyl group; ......... stands for a single bond or a double bond; when ......... is a single bond, $Y^a$ stands for —$NR^{4a}$— ($R^{4a}$ stands for a hydrogen atom, a $C_{1-6}$ alkyl-carbonyl group or a $C_{1-6}$ alkyl group), and, when ......... is double bond, $Y^a$ stands for a nitrogen atom, and n denotes an integer of 0 to 3, or a salt thereof.

Preferable examples of ring A include a benzene ring which may be substituted by 1 to 3 substituents selected from the group consisting of an amino group, a mono-$C_{1-6}$ alkylamino group, a di-$C_{1-6}$ alkylamino group, a halogen atom, a nitro group, a sulfo group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group.

Preferable example of n is 1.

(B) A compound represented by the formula:

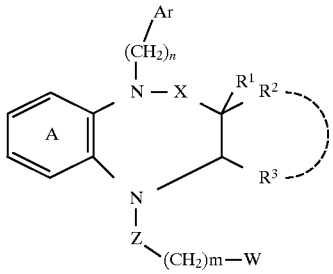

wherein ring A stands for an optionally substituted benzene ring; Ar stands for an optionally substituted aromatic group; $R^1$, $R^2$ and $R^3$ independently stands for a hydrogen atom, an acyl group, an optionally substituted hydrocarbon group or an optionally substituted heterocyclic group, or $R^2$ and $R^3$, taken together, may form a non-aromatic cyclic hydrocarbon; X stands for a methylene group or a carbonyl group; Z stands for a methylene group or a carbonyl group; W stands for an optionally substituted amino group; m denotes an integer of 0 to 5; and n denotes an integer of 0 to 3, or a salt thereof.

Preferable examples of ring A include a benzene ring which may be substituted by 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ mercapto group.

Preferable examples of Ar include (i) a $C_{6-14}$ aryl group or (ii) a 5- or 6-membered aromatic heterocyclic group containing, besides carbon atoms, 1 to 4 hetero atoms selected from a nitrogen, oxygen and sulfur atom, which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group, a phenyl group and an oxo group.

Preferable examples of $R^1$, $R^2$, $R^3$, X, Z and n are shown in the follow.

$R^1$ stands for (i) a hydrogen atom or (ii) a $C_{7-16}$ aralkyl group which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group; $R^2$ stands for (i) a hydrogen atom or (ii) a $C_{7-16}$ aralkyl group which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group and a $C_{1-6}$ alkylmercapto group; $R^3$ include (1) a hydrogen atom, (2) a $C_{1-6}$ alkyl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group, (o) a $C_{1-6}$ alkylmercapto group, (p) a $C_{6-14}$ aryl group and (q) a 5- or 6-membered heterocyclic group containing, besides carbon atoms, 1 to 4 hetero-atoms selected from a nitrogen, oxygen and sulfur atom or di- or tri-cyclic condensed heterocyclic group with a benzene ring, (3) a $C_{2-6}$ alkenyl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group, (o) a $C_{1-6}$ alkylmercapto group, (p) a $C_{6-14}$ aryl group and (q) a 5- or 6-membered heterocyclic group containing, besides carbon atoms, 1 to 4 hetero-atoms selected from a nitrogen, oxygen and sulfur atom, (4) a $C_{6-14}$ aryl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group and (o) a $C_{1-6}$ alkylmercapto group, or (5) a $C_{7-16}$ aralkyl group which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (i) a $C_{1-6}$ alkyl group, (j) a $C_{1-6}$ alkoxy group, (k) a carboxyl group, (l) a $C_{1-6}$ alkoxy-carbonyl group, (m) a $C_{1-5}$ acyl group, (n) a mercapto group and (o) a $C_{1-6}$ alkylmercapto group. And, a case where $R^2$ and $R^3$, taken together, form a 5- to 8-membered cycloalkane is also preferable.

X is preferably a carbonyl group.

Z is preferably a carbonyl group.

n is preferably 1.

(C) A compound represented by the formula:

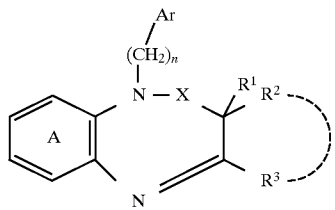

wherein ring A stands for an optionally substituted benzene ring; Ar stands for an optionally substituted aromatic group; $R^1$, $R^2$ and $R^3$ independently stands for a hydrogen atom, an acyl group, an optionally substituted hydrocarbon group or an optionally substituted heterocyclic group, or, $R^2$ and $R^3$, taken together, may form a non-aromatic cyclic hydrocarbon; X stands for a methylene group or a carbonyl group; and n denotes an integer of 0 to 3, or a salt thereof.

Preferable examples of Ar include (i) a $C_{6-14}$ aryl group or (ii) a 5- or 6-membered aromatic heterocyclic group containing, besides carbon atoms, 1 to 4 hetero-atoms selected from a nitrogen, oxygen and sulfur atom, which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group, a phenyl group and an oxo group. Especially preferable one is a pyridine ring which may be substituted by 1 to 4 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a $C_{1-5}$ acyl group, a mercapto group, a $C_{1-6}$ alkylmercapto group and a phenyl group.

The case, where $R^1$ stands for a hydrogen atom, and, $R^2$ and $R^3$, taken together, form a cyclopentane, is preferable.

Examples of more preferable compounds include (1) 9-(4-chlorobenzyl)-2,3,9,10a-tetrahydrobenzo[b]cyclopenta[e][1,4]diazepin-10(1H)-one, (2) 9-(2-fluorobenzyl)-2,3,9,10a-tetrahydrobenzo[b] cyclopenta[e][1,4]diazepin-10(1H)-one,
(3) 9-(4-pyridylmethyl)-2,3,9,10a-tetrahydrobenzo[b] cyclopenta[e][1,4]diazepin-10(1H)-one,
(4) 9-(4-aminobenzyl)-2,3,9,10a-tetrahydrobenzo[b] cyclopenta[e][1,4]diazepin-10(1H)-one,
(5) 9,10a-dibenzyl-2,3,3a,4,9,10a-hexahydrobenzo[b] cyclopenta[e][1,4]diazepin-10(1H)-one,
(6)(3aR*,10aR*)-9-benzyl-4-methyl-1,2,3,3a,4,9,10,10a-octahydrobenzo [b]cyclopenta[e][1,4]diazepin-10(1H)-one,
(7) (3aR*,10aS*)-9-benzyl-4-methyl-2,3,3a,4,9,10a-hexahydrobenzo [b]cyclopenta[e][1,4]diazepin-10(1H)-one,
(8) (3aR*,10aS*)-4-acetyl-9-benzyl-2,3,3a,4,9,10a-hexahydrobenzo [b]cyclopenta[e][1,4]diazepin-10(1H)-one,
(9) (3aR*,10aS*)-9-(2,4-dichlorobenzyl)-2,3,3a,4,9,10a-hexahydrobenzo [b]cyclopenta[e][1,4]diazepin-10(1H)-one,
(10) (3aR*,10aS*)-9-(1-naphthylmethyl)-4-(phthalimidacetyl)-2,3,3a,4,9,10a-hexahydrobenzo[b] cyclopenta[e][1,4]diazepin-10(1H)-one and
(11) (3aR*,10aS*)-9-(2-naphthylmethyl)-4-(phthalimidacetyl)-2,3,3a,4,9,10a-hexahydrobenzo[b] cyclopenta[e][1,4]diazepin-10(1H)-one.

And, the following compounds (a) and (b) are commonly used as, among others, intermediates for synthesizing the compound (I) of this invention. (a) A compound represented by the formula:

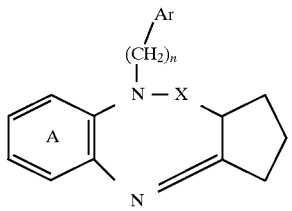

wherein each symbol is of the same meaning as defined above, or a salt thereof,
(b) A compound represented by the formula:

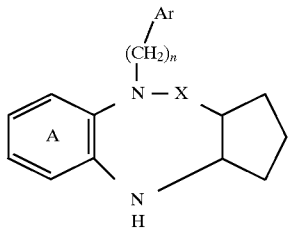

wherein each symbol is of the same meaning as defined above, or a salt thereof.

Preferable examples of the salts of the compound (I) of this invention include medically acceptable salts formed by the addition of acid. As such salts, use is made of, for example, inorganic acid salts such as hydrochloride, hydrobromide, hydroiodide, sulfate and phosphate, and, organic acid salts such as acetate, oxalate, succinate, ascorbate, maleate, lactate, citrate, methanesulfonate and benzoate.

Additionally stating, there exist optical isomers in the compounds included in the present invention, and, optically active compounds, which are the compounds obtained by optical resolution of the racemates, are of course included in this invention.

The optically active compounds can be produced by a per se known method. More specifically, they are produced from an optically active synthetic intermediate or by a conventionae optical resolution of the racemic final product.

As the method of optical resolution, mention is made of, for example, a method which comprises subjecting a salt formed with an optically active acid to fractional recrystallization; a method which comprises subjecting the racemate or a salt thereof to chromatography using a column for isolation of optically active compound (Chiral Column), for example ENANIO-OVM (Toso Co.,Ltd.) using water, various buffer solutions (e.g. phosphate buffer solution), various organic solvents including alcohol (e.g. methanol and ethanol), nitrile (e.g. acetonitrile), hexane and ethyl ether, singly or in a suitable mixture thereof as an eluent; and a method which comprises allowing a racemate to be condensed with, for example, MTPA [α-methoxy-α-(trifluoromethyl) phenylacetic acid] or menthoxyacetic acid, by a conventional method, for example, acid chloride method, to give a mixture of diastereomers of amide compound, which is subjected to a means of separation and purification such as fractional recrystallization or a silica gel chromatography, followed by subjecting the resultant to acid hydrolysis or basic hydrolysis.

While the condensed heterocyclic compounds (I) or salts thereof of this invention can be produced by various methods, they can be produced by, for example, the following methods.

The compound (I), when it is in a free form, can be made into a corresponding salt by a conventional method, while, when it is in a form of salt, it can be made into the free form by a conventional method. Thus-produced compound (I) or a salt thereof can be isolated and purified by means of a known method, for example, solvent extraction, pH change, phasic transfer, recrystallization and chromatography. In the case where the compound (I) or a salt thereof is an optically active compound, it can be isolated by means of the above-mentioned optical resolution.

The compound (I) of this invention can be produced by, for example, the following reaction schema 1 to 4. Compounds (Ia) to (Io) are all included in the compounds (I).

The reaction schema are shown below.
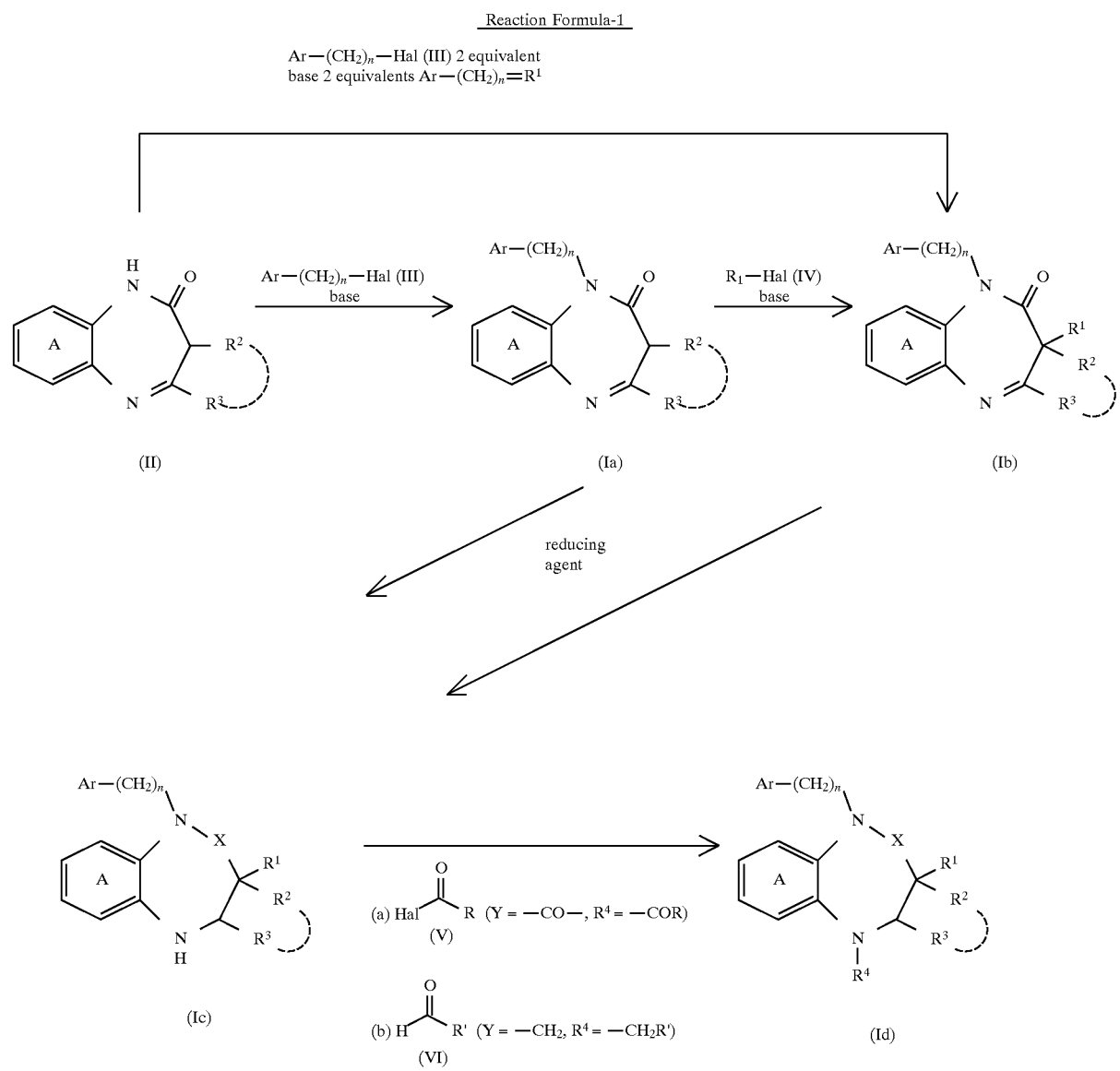

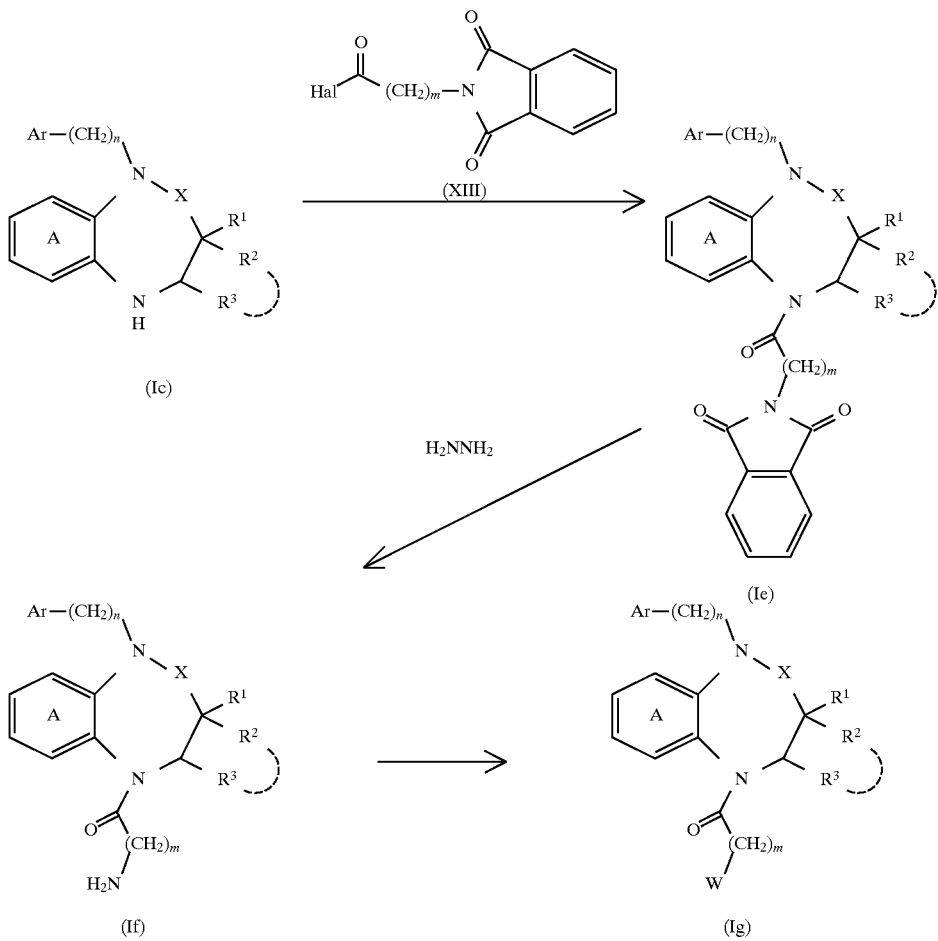
Hal and Hal' stand for halogen.
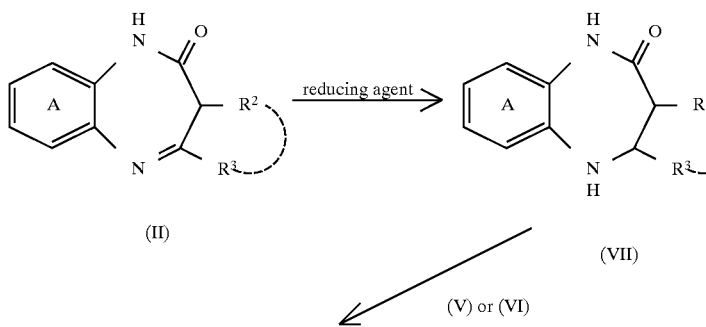

-continued
Reaction Formula-3
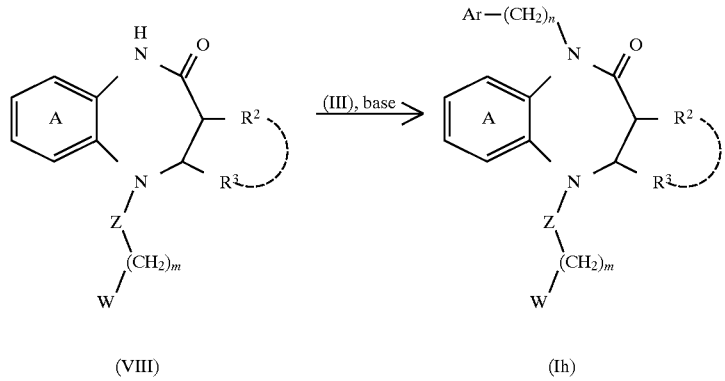
Reaction Formula-4
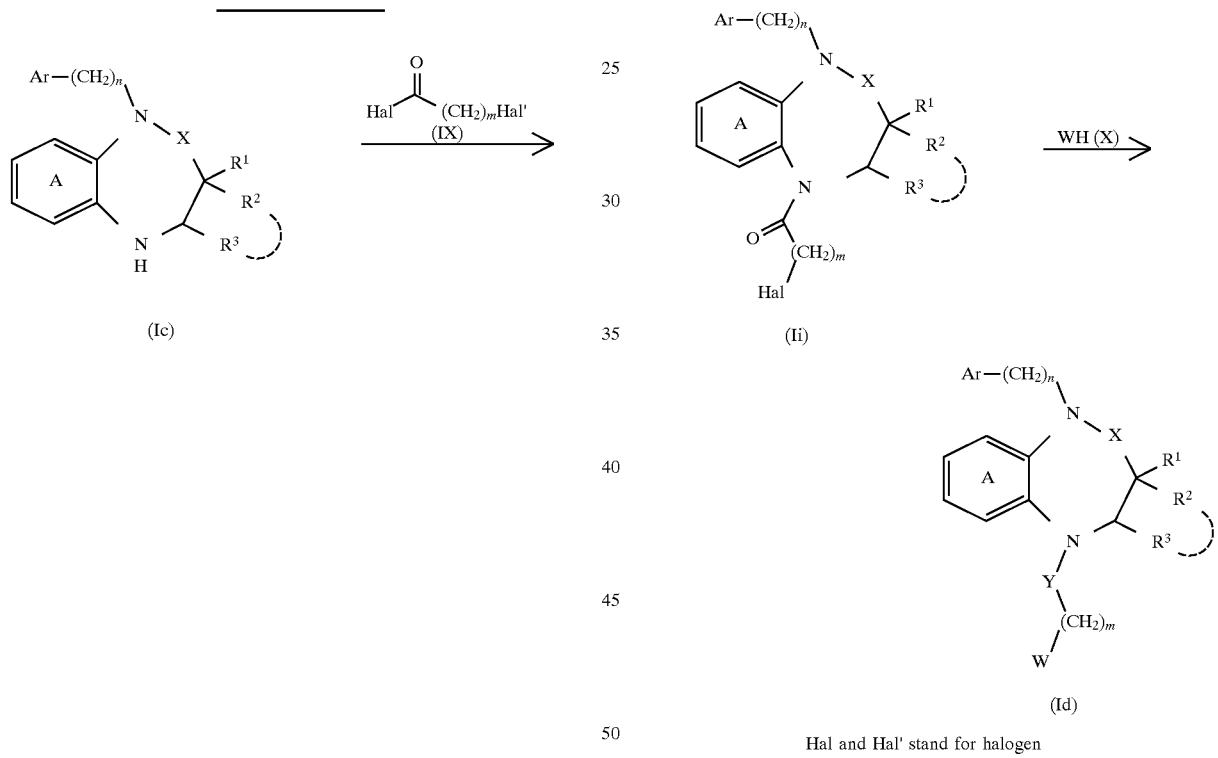
Hal and Hal' stand for halogen Reaction Formula-5

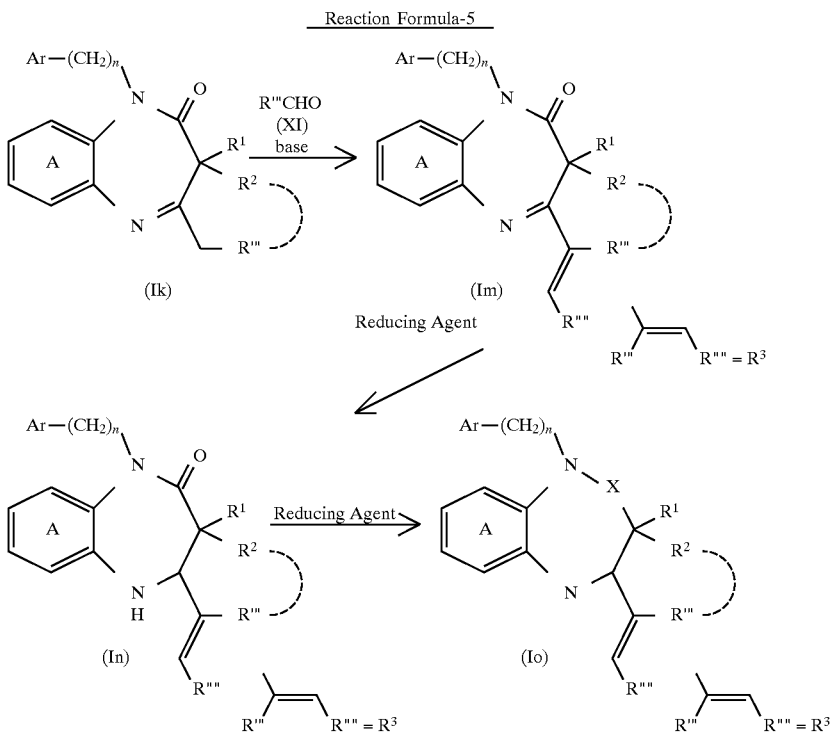

In the present invention, the compound (Ia) is produced by subjecting the compound (II) or a salt thereof disclosed in Journal of organic Chemistry, USSR, 1973, 9, 2080 to condensation with the compound (III) or a salt thereof. The condensation of the compound (II) or a salt thereof with the compound (III) or a salt thereof can be conducted in the absence of solvent or in an inert solvent. Examples of the inert solvents include halogenated hydrocarbons such as dichloroethane and chloroform, aliphatic hydrocarbons such as hexane and cyclohexane, aromatic hydrocarbons such as toluene and xylene, ethers such as diethyl ether, diisopropyl ether, amides such as dimethylformamide and dimethyl acetamide, or a mixture thereof. The volume of such solvent as above ranges usually from 0.2 to 50 ml, preferably 5 to 20 ml, relative 1 g of the compound (II). The reaction is conducted at temperatures ranging usually from −20° to 200° C., preferably from 0 to 150° C. The reaction time ranges usually from about 5 minutes to 72 hours, preferably from 10 minutes to 10 hours.

The compound (Ib) is produced by further subjecting the compound (Ia) to condensation with the compound(IV), and the reaction conditions are substantially the same as those for conversion from the compounds (II) to the compound (Ia). And, in the case where $R^1$ and $R^2$ are the same with each other, by using 2 equivalents or more, preferably 2 to 3 equivalents, of the compound (III), the compound (Ib) can be synthesized at one step.

The compound (Ic), in which X is carbonyl, is produced by subjecting the compound (Ia) or (Ib) to reduction or catalytic reduction with a reducing agent such as a metallic hydrogen complex compound. As the metallic hydrogen complex compound, use is made of, for example, sodium cyanoborohydride and sodium borohydride, and, as catalyst for the catalytic reduction, use is made of, for example, palladium carbon. For the reduction using sodium cyanoborohydride or sodium borohydride, alcohol such as methanol and ethanol or a mixture of the alcohol with any other inert organic solvent (e.g. diethyl ether and tetrahydrofuran), and, for controlling pH, protonic acid such as hydrochloric acid is used. The reducing agent is employed in an amount usually ranging from 1 to 3 equivalents, preferably 1 to 1.5 equivalent. The reaction temperatures range from −20° to 60° C. As the solvent employed for the catalytic reduction, mention is made of alcohols such as methanol and ethanol, carboxylic acids such as acetic acid and ethers such as diethyl ether and tetrahydrofuran, and, the amount of the catalyst ranges from 5 to 30% relative to the weight of the substrate. The reaction temperature ranges from 0° to 80° C., preferably 20° to 60° C. And, reduction form the carbonyl at the X portion to methylene, use is made of lithium aluminum hydride, and its amount ranges from 0.5 to 3 equivalents, preferably from 0.8 to 2 equivalents. As the solvent, use is made of usually ethers such as diethyl ether and tetrahydrofuran. The reaction temperature ranges from 0° to 100° C., preferably 20° to 80° C.

The compound (Id) can be produced, when Z is carbonyl, by subjecting the compound (Ic) to condensation with the compound (V) or a salt thereof, when desired, in the presence of a base, and, when Z is methylene, by subjecting the compound (Ic) or a salt thereof to condensation with the compound (VI) in the presence of a reducing agent.

The condensation of the compound (Ic) with the compound (V) or a salt thereof can be carried out in the absence of a solvent or in an inert solvent. As the inert solvent, use is made of, for example, halogenated hydrocarbons such as dichloroethane and chloroform, aliphatic hydrocarbons such as hexane and cyclohexane, ethers such as diethyl ether and diisopropyl ether, amides such as dimethylformamide and dimethyl acetamide, or a mixture of these solvent. The volume of solvent ranges usually from 0.2 to 50 ml, preferably form 5 to 20 ml, relative to one gram of the compound (Ic). The reaction is conducted at temperatures usually ranging from −5° to 200° C., preferably from 5° to 150° C. The reaction time ranges usually from about 5 minutes to 72 hours, preferably from about 10 minutes to about 10 hours.

The condensation of the compound (Ic) with the compound (VI) conducted in an inert solvent such as acetic acid in the presence of protonic acid such as hydrochloric acid, and the resulting adduct is subjected to reduction with a hydride type reducing agent, preferably a mild reagent, for example, sodium triacetoxyborohydride [Na(OAc)$_3$BH]. While the temperature range is not specifically restricted, it is, in general, preferably 0° to 100° C. The reaction time ranges from about 5 minutes to 10 hours, preferably from 10 minutes to 3 hours.

The compound (If) is produced by processing the compound (Ie), synthesized in accordance with the method of synthesizing the compound (Id), with for example hydrazine. The amount of hydrazine ranges from 1 to 5 times as much equivalents, preferably 2 to 3 equivalents, and, as the solvent, alcohols such as methanol, ethanol and propanol are preferable. The reaction temperature ranges from 20° C. to 120° C., preferably from 40° to 80° C.

The compound (Ig) is produced by subjecting the compound (If) to alkylation and acylation.

The alkylation is conducted by subjecting alkyl halide to condensation, when desired, in the presence of a base, in the absence of solvent or in an inert solvent, or by subjecting to reductive alkylation with aldehyde. As the inert solvent in the case of employing alkyl halide, use is made of substantially the same solvents as those employed for the condensation of the compound (II) with the compound (Ia). As the base which is employed when desired, mention is made of, for example, triethylamine, sodium hydride, sodium alkoxide, sodium hydroxide and potassium carbonate. The reaction temperature ranges from about –20° to 150° C., preferably 0° to 100° C. The reaction time ranges usually from 5 minutes to 24 hours, preferably from 10 minutes to 5 hours. For the reductive alkylation with aldehyde, as the reducing agent, use is made of a metallic hydrogen complex compound, for example, sodium cyanoborohydride and sodium triacetoxyborohydride [Na(OAc)$_3$BH], and, when desired, in the presence of a protonic acid e.g. hydrochloric acid. As the solvent, use is made of alcohols such as methanol and ethanol, carboxylic acids such as acetic acid and ethers such as diethyl ether and tetrahydrofuran. While the reaction temperature is not specifically restricted, it is, in general, in the range of from about 0° to 100° C. The reaction time ranges from about 5 minutes to 10 hours, preferably from 10 minutes to 3 hours. Acylation is conducted by using acyl halide or acid anhydride, when desired, in the presence of a base or an acid, in the absence of solvent or in an inert solvent for condensation. As the inert solvents, use is made of those similar to the solvents used for condensation of the compound(II) with the compound (III). As the base to be employed when desired, mention is made of,for example, triethylamine and pyridine, and, as the acid, mention is made of methanesulfonic acid, p-toluenesulfonic acid and camphorsulfonic acid. The reaction temperature ranges from about –20° to 150° C., preferably 0 to 100° C. The reaction time usually ranges from 5 minutes to 24 hours, preferably 10 minutes to 5 hours.

The compound (Ih) can be produced by subjecting the compound (VIII) with the compound (III). This condensation reaction is conducted under substantially the same conditions as in the condensation of the compound (II) with the compound (III). The compound (VIII) is synthesized by subjecting the compound (VII) to condensation with the compound (V) or the compound (VI), and the reaction conditions are substantially the same as those of the case where the compound (Id) is produced from the compound (Ic). And, the compound (VII) can be synthesized from the compound (II), and the reaction conditions are substantially the same as those of the case where the compound (Ic) is produced from the compound (III).

The compound (Id) is synthesized also by the reaction between the compound (Ii) and the compound (X). The condensation of the compound (Ii) and (X) can be conducted, when desired, in the presence of a base, in the absence of solvent or in an inert solvent. As the base, use is made of, for example triethylamine, sodium hydride, sodium alkoxide and lithium diisopropyl amide. As the inert solvent, use is made of, for example, halogenated hydrocarbons such as dichloroethane and chloroform, aliphatic hydrocarbons such as hexane and cyclohexane, aromatic hydrocarbons such as toluene and xylene, ethers such as diethyl ether and diisopropyl ether, amides such as dimethylformamide and dimethylacetamide, alcohols such as methanol and ethanol or a mixture of them. The volume of the solvent usually ranges from 0.2 to 50 ml, preferably 5 to 20 ml, relative to one gram of the compound (Ii). The reaction is conducted at temperatures usually ranging from –5° to 200° C., preferably from 5° to 150° C. The reaction time ranges usually from about 5 minutes to 72 hours, preferably from about 0.5 to 10 hours. The compound (Ii) can be synthesized by condensation of the compound (Ic) with the compound (IX). The reaction conditions are substantially the same as those in the case where the compound (Id) which has carbonyl group as a X part is synthesized from the compound (Ic).

The compound (Io) is produced by subjecting the compound (In) to catalytic reduction. As the catalyst for the catalytic reduction, use is made of,for example, platinum oxide, palladium carbon and Raney nickel, and, as the solvent, use is made of alcohols such as methanol and ethanol, amides such as dimethylformamide and dimethyl acetamide, or a mixture of them. The reaction temperature ranges from 0° C. to 100° C., preferably from 10° C. to 60° C. The amount of the catalyst usually ranges form 5 to 30% by weight relative to the weight of the substrate.

The compound (In) is produced by subjecting the compound (Im) to reduction. The conditions of the reduction reaction are substantially the same as those in the case where the compound (Ic) is produced from the compound (Ia).

The compound (Im) is produced by subjecting the compound (Ik) ((Ik) corresponds to (Ib) wherein R$^3$ stands for R''' CH$_2$) to condensation with the compound (XI). In this reaction, as the base, use is made of, for example, sodium hydride, lithium diisopropyl amide and sodium amide. As the solvent, use is made of, for example, alcohols such as methanol and ethanol, ethers such as tetrahydrofuran, amides such as dimethylformamide and dimethyl acetamide or a mixture of them. The reaction temperature ranges from –78° C. to 100° C., preferably 0° C. to 60° C.

In any of the above cases, by conducting, when desired, deprotection reaction, acylation, alkylation, hydrogenation, oxidation, reduction, carbon chain elongation reaction and substituent-exchange reaction singly or a combination of two or more of them, the compound (I) can be synthesized.

In the case where the object compound is obtained in the free form by the above reaction, it may optionally converted into a corresponding salt by a conventional method, and, in the case where the object compound is obtained as a salt, it can be converted into the free form or any other salt. Thus-obtained compound (I) or a salt thereof can be isolated from the reaction mixture and purified by a known means as exemplified by phasic transfer, concentration, solvent-extraction, fractional distillation, crystallization, recrystallization and chromatography.

Incidentally, in the case where the compound (I) is present as, for example, diastereomers and conformer, they can be isolated, when desired, respectively by the above-mentioned isolation and purification means. And, when the compound (I) is a racemic compound, it can be resolved into d-isomer and 1-isomer by a conventional means for optical resolution.

Additionally stating, in each of the reactions of this invention and in the respective reactions for synthesizing the starting compounds, when the starting compounds have amino group, carboxyl group or hydroxyl group, these groups may optionally be protected with protective groups commonly used in peptide chemistry, and, after completion of the reaction, the protective group is removed to give the object compound.

Examples amino-protective groups include $C_{1-6}$ alkyl-carbonyl group (e.g. formyl, acetyl and ethylcarbonyl), phenylcarbonyl group, $C_{1-6}$ alkyloxycarbonyl group (e.g. methoxycarbonyl and ethoxycarbonyl), benzoyl group, $C_{7-10}$ aralkyl-carbonyl group (e.g. benzyl carbonyl), trityl group, phthaloyl group and N,N-dimethyl amino methylene group. These groups may optionally substituted with 1 to 3 halogen atoms (e.g. fluorine, chlorine, bromine and iodine) and nitro group.

As carboxyl-protecting groups, use is made of, for example, $C_{1-6}$ alkyl group (e.g. methyl, ethyl, n-propyl, isopropyl, butyl and tert-butyl), phenyl group, trityl group and silyl group. These groups may optionally be substituted with, for example 1 to 3 halogen atoms (e.g. fluorine, chlorine, bromine and iodine), $C_{1-6}$ alkyl-carbonyl groups (e.g. formyl, acetyl, ethyl carbonyl and butyl carbonyl) and nitro group.

As hydroxyl-protecting groups, use is made of $C_{1-6}$ alkyl groups (e.g. methyl, ethyl, n-propyl, isopropyl, butyl and tert-butyl), phenyl group, $C_{7-10}$ aralkyl groups (e.g. benzyl), $C_{1-6}$ alkyl-carbonyl groups (e.g. formyl, acetyl and ethyl carbonyl), benzoyl group, $C_{7-10}$ aralkyl-carbonyl group (e.g. benzyl carbonyl), pyranyl group, furanyl group and silyl group. These groups may optionally be substituted with, for example, 1 to 3 halogen atoms (e.g. fluorine, chlorine, bromine and iodine), phenyl groups, $C_{7-10}$ aralkyl groups (e.g. benzyl) and nitro group.

And, for removing these protective groups, a per se known method or analogous methods thereto are employed, for example methods using acid, base, reduction, ultra-violet ray, hydrazine, phenyl hydrazine, sodium N-methyl dithiocarbamate, tetrabutyl ammonium fluoride and palladium acetate.

INDUSTRIAL APPLICABILITY

The compound (I) of this invention or a pharmaceutically acceptable salt thereof, by their GnRH receptor antagonistic action, suppress the secretion of gonadotropin releasing hormone and control the concentration of steroid hormone in blood, in humans and mammals (e.g. mouse, rat, rabbit, dog, cow and pig). Therefore, it can be used for ovulation inhibiting agent and prevention of implantation of ovum, or for prophylaxis and therapy of ammenorrhea, prostatic cancer, prostatic hypertrophy, endometriosis, hysteromyoma breast cancer, acne, precocious puberty, premenstrual syndrome, polycystic ovary syndrome and diseases caused by excess secretion of andorogen. And the compounds (I) of this invention or a pharmaceutically acceptable salt thereof can be used as therapeutic agents of insomnia caused by stress, poriomania at night and depression of activity in day time due to abnormal sarcadian rhythm often observed in aged people, jet lag caused by overseas travel and abnormal physical conditions caused by a three-shift labor system and as a preanesthetic medication. The compound (I) or a pharmaceutically acceptable salt thereof of this invention safly used for agents of various diseases which is low toxicity and side-effects. The compound (I) or a salt thereof can be also used for an estrus regulator in animals, an improvement of quality of the edible meats, a growth promotor in animals or an oviposition promotor in fishes.

The compound (I) or salts thereof of this invention can be safely administered orally or non-orally as they are or as medicinal preparations mixed with medicinally acceptable carriers in accordance with a per se known method, for example, tablets (including sugar-coated tablets and film-coated tablets), powdery preparations, granular preparations, liquid preparations, injectable preparations, suppository preparations and sustained release preparations. The daily dose varies with, for example, the subject to be administered, administration route and diseases to be treated, and, it is preferable, when administered to, for example, an adult patient suffering from prostatic hypertrophy, to administer once daily or severally divided dosages 0.1 to 20 mg/kg, preferably 0.2 to 10 mg/kg in terms of the effective component (the compound (I) or a salt thereof).

As pharmaceutically acceptable carriers, conventional various organic or inorganic carriers are used, and they are incorporated as excipients, lubricants, binders and disintegrants in solid compositions; and as solvents, solubilizers, suspending agents, isotonizing agent, buffering agents and pain-easing agents in liquid compositions. And, depending on necessity, further additives such as preservatives, antioxidants, coloring agents and sweeteners can also be supplemented. Preferable examples of excipients include lactose, sugar, D-mannitol, starch, crystalline cellulose and more volatile silicon dioxide. Preferable examples of lubricants include magnesium stearate, talc and colloid silica. Preferable examples of binders include crystalline cellulose, sugar, D-mannitol, dextrin, hydroxypropyl cellulose, hydroxypropylmethyl cellulose and polyvinyl pyrrolidone. Preferable examples of disintegrants include starch, carboxymethyl cellulose, carboxymethyl cellulose calcium, cross carmelose sodium and carboxymethyl starch sodium. Preferable examples of solvents include water for injection, alcohol, propylene glycol, macrogol, sesame oil and corn oil. Preferable examples of solubilizers include polyethylene glycol, propylene glycol, D-mannitol, benzyl benzoate, ethanol, tris-aminoethane, cholesterol, triethanolamine, sodium carbonate and sodium citrate. Preferable examples of suspending agents include surfactants such as stearyl triethanolamine, sodium lauryl sulfate, lauryl aminopropionic acid, lecithin, benzalkonium chloride, benzetonium chloride and monostearic glyceryl ester; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of isotonizing agents include sodium chloride, glycerin and D-mannitol. Preferable examples of buffering agents include buffering solutions such as phosphate, acetate, carbonate and citrate. Preferable examples of pain-easing agents include benzyl alcohol. Preferable examples of preservatives include parahydroxybenzoic acid esters, chlorobutanol, benzyl alcohol, phenethyl alcohol, dehydroacetic acid and sorbic acid. Preferable examples of antioxidants include sulfite and ascorbic acid.

EXAMPLES

This invention will be described in detail by the following Working Examples, Reference Examples and Experimental Examples, but they are not intended to limit the invention thereto, and may be modified within the range which does not deviate the scope of this invention.

In the following Working Examples, Reference Examples and Experimental Examples, "room temperatures" means 0° to 30° C., and other definitions have the following meanings.

s: singlet
d: doublet
t: triplet
q: quartet
quint: quintet
sext: sextet
m: multiplet
br: broad
J: coupling constant
Hz: Herz
CDCl$_3$: Deuterochloroform
THF: tetrahydrofuran
DMF: N,N-dimethylformamido
DMSO: dimethylsulphoxido
$^1$H-NMR: proton-nuclear magnetic resonance Working Example 1

9-Benzyl-2,3,9,10a-tetrahydrobenzo [b]cyclopenta [e][1,4]diazpin-10(1H)-one

A solution of 2,3,9,10a-tetrahydrobenzo[b]cyclopenta[e] [1,4]diazepin-10(1H)-one(100.1 g, 0.50 mol.) in N,N-dimethylformamide (750 ml) was cooled to 0° C. under nitrogen atmosphere. To the solution was added sodium hydride (60% liquid paraffin dispersion, 20.8 g, 0.52 mol.), and the mixture was stirred at the same temperature for 15 minutes, then at 25° C. for 10 minutes. This solution was cooled to 0° C., to which was added dropwise a solution of benzyl bromide (94.0 g, 0.55 mol.) in N,N-dimethyl formamide (50 mL) taking 15 minutes, and the mixture was stirred for 20 minutes at 25° C. The reaction solution was poured into a saturated aqueous solution of ammonium chloride (1.5 L), which was extracted with ethyl acetate. The organic layer was washed with water and a saturated aqueous solution of sodium chloride, then dried over sodium sulfate, which was subjected to filtration, and the filtrate was concentrated under reduced pressure. The concentrate was recrystallized from ethanol to give 81.3 g (yield 56%) of the titled compound. The sample for analytical experiment was recrystallized from ethanol-water. m.p. 152°–154° C.

$^1$H NMR(CDCl$_3$) δ: 1.85–2.2(3H,m), 2.6–2.9(3H,m), 3.0–3.1(1H, m), 5.12(2H,s), 7.05–7.35(9H,m).

Working Example 2

9(4-methoxybenzyl)-2,3,9,10a-tetrahydrobenzo[b] cyclopenta[e][1,4]diazepin-10(1H)-one Using 4-methoxybenzyl chloride, substantially the same procedure as in Working Example 1 was conducted to synthesize the titled compound. Yield 87%. m.p. 128°–131° C.(ethanol-diisopropyl ether)

$^1$H NMR(CDCl$_3$) δ: 1.85–2.15(3H,m), 2.6–2.9(3H,m), 3.0–3.1(1H, m), 3.76(3H,s), 5.01(1H,d,J=15.7 Hz), 5.10(1H, d,J=15.7 Hz), 6.79(2H,d,J=8.8 Hz), 7.03(2H,d,J=8.8 Hz), 7.1–7.35(4H,m).

Working Example 3

Methyl 4(7-chloro-10-oxo-1,2,3,9,10,10a-hexahydrobenzo [b]cyclopenta[e][1,4]diazepin-9-ylmethyl) benzoate Using 7-chloro-2,3,9,10a-tetrahydrobenzo[b]cyclopenta [e][1,4]diazepin-10(1H)-one and methyl 4-(bromomethyl) benzoate, the titled compound was synthesized by substantially the same procedure as in Working Example 1. Yield 52% m.p. 136°–138° C. (ethyl acetate-hexane).

$^1$H NMR(CDCl$_3$) δ: 1.9–2.1(3H,m), 2.6–2.85(3H,m), 3.0–3.1(1H, m), 3.89(3H,s), 5.06(1H,d,J=16.2 Hz), 5.22(1H, d,J=16.2 Hz), 7.1–7.4(5H,m), 7.9–8.0(2H,m).

Working Example 4

9-(4-chlorobenzyl)-2,3,9,10a-tetrahydrobenzo[b] cyclopenta[e][1,4]diazepin-10(1H)-one Using 4-chlorobenzyl chloride, substantially the same procedure was conducted, and the compound thus synthesized was refined by means of a silica-gel column chromatography (dichloromethane, then dichloromethane-methanol 100:1→50:1), followed by recrystallization from ethanol to give 5.826 g (yield 47%) of the titled compound, m.p. 155°–157° C.

$^1$H NMR(CDCl$_3$) δ: 1.85–2.15(3H,m), 2.6–2.85(3H,m), 3.0–3.1(1H, m), 5.02(1H,d,J=15.8 Hz), 5.14(1H,d,J=15.8 Hz), 7.0–7.05(2H,m), 7.1–7.35(6H,m).

Working Example 5

9-(2-Fluorobenzyl)-2,3,9,10a-tetrahydrobenzo[b] cyclopenta[e][1,4]diazepin-10(1H)-one Using 2-fluorobenzyl bromide, the titled compound was synthesized by substantially the same procedure as in Working Example 4. Yield 70% m.p. 135°–137° C. (ethyl acetate-hexane).

$^1$H NMR(CDCl$_3$) δ: 1.8–2.2(3H,m), 2.6–2.9(3H,m), 3.0–3.1(1H, m), 5.10(1H,d,J=16.4 Hz), 5.28(1H,d,J=16.4 Hz), 6.9–7.35(8H,m)

Working Example 6

9-(4-Fluorobenzyl)-2,3,9,10a-tetrahydrobenzo[b] cyclopenta[e][1,4]diazepin-10(1H)-one Using 4-fluorobenzyl bromide, the titled compound was synthesized by substantially the same procedure as in Working Example 4. Yield 80% m.p. 134°–137° C. (ethanol)

$^1$H NMR(CDCl$_3$) δ: 1.8–2.2(3H,m), 2.6–2.85(3H,m), 3.0–3.1(1H, m), 5.01(1H,d,J=15.8 Hz), 5.15(1H,d,J=15.8 Hz), 6.85–7.35(8H,m)

Working Example 7

9-(2,4-Dichlorobenzyl)-2,3,9,10a-tetrahydrobenzo[b] cyclopenta[e][1,4]diazepin-10(1H)-one Using 2,4-dichlorobenzyl chloride, the titled compound was synthesized by substantially the same procedure as in Working Example 4. Yield 77% m.p.144°–145° C. (ethanol)

$^1$H NMR(CDCl$_3$) δ: 1.85–2.15(3H,m), 2.65–2.85(3H,m), 3.05–3.15(1H, m), 5.09(1H,d,J=16.6 Hz), 5.22(1H,d,J=16.6 Hz), 6.85(1H,d,J=8.4 Hz), 7.1–7.35(6H,m)

Working Example 8

10-Benzyl-1,2,3,4,10,11a-hexahydro-11H-dibenzo [b,e][1,4]diazepin-11-one

Using 1,2,3,4,10,11a-hexahydro-11H-dibenzo [b,e][1,4] diazepin-11-one and benzyl bromide, the titled compound was synthesized in substantially the same procedure as in Working Example 4. Yield 66%. m.p. 123°–125° C. (ethanol-hexane).

¹H NMR(CDCl₃) δ: 1.5–2.1(5H,m), 2.25–2.55(2H,m), 2.75–2.95(1H, m), 3.01(1H,d,J=6.2 Hz), 5.03(1H,d,J=15.8 Hz), 5.19(1H,d,J=15.8 Hz), 7.0–7.35(9H,m)

Working Example 9

9-(4-Pyridylmethyl)-2,3,9,10a-tetrahydrobenzo[b]cyclopenta[e][1,4]diazepin-10(1H)-one 4-(chloromethyl)pyridine hydrochloride was suspended in dichloromethane, to which was added a saturated aqueous solution of sodium hydrogencarbonate to neutralize. The organic layer was separated, and the aqueous layer was subjected to extraction with dichloromethane. Organic layers were combined and dried over magnesium sulfate, which was subjected to filtration. The filtrate was concentrated under reduced pressure to give 4-(chloromethyl)pyridine. Using this compound, the titled compound was synthesized in accordance with the above process.

Yield 57%, m.p. 139°–141° C. (ethanol-ether)

'H NMR(CDCl₃) δ: 1.85–2.2(3H,m), 2.65–2.85(3H,m), 3.05–3.15(1H,m), 5.11(2H,S), 6.95–7.05(2H,m), 7.15–7.4(4H,m), 8.45–8.55(2H,m).

Working Example 10

9-(4-Nitrobenzyl)-2,3,9,10a-tetrahydrobenzo[b]cyclopenta[e][1,4]diazepin-10(1H)-one A suspension of 2,3,9,10a-tetrahydrobenzo[b]cyclopenta[e][1,4]diazepin-10(1H)-one (25.00 g, 0.125 mol.) in N,N-dimethylformamide (150 mL) was cooled to 0° C., to which was added sodium hydride (60% liquid paraffin dispersion, 5.00 g, 0.125 mol.). This mixture was stirred for 10 minutes at the same temperature and for 5 minutes at 20° C. This solution was cooled to 0° C., to which was added 4-nitrobenzyl bromide (28.32 g, 0.131 mol.), and the mixture was stirred for 10 minutes at 20° C. The reaction mixture was poured into a saturated aqueous solution of ammonium chloride (500 mL). Resulting precipitate was subjected to filtration, and washed with water, followed by recrystallization from dichloromethane-ethanol to give 29.76 g (yield 71%) of the titled compound. The sample for analylical experiment was prepared by recrystallization of the compound from chloroform-ethanol, m.p. 185°–188° C.

¹H NMR(CDCl₃) δ: 1.9–2.1(3H,m), 2.6–2.8(3H,m), 3.0–3.1(1H,m), 5.12(1H,d,J=16.0 Hz), 5.29(1H,d,J=16.4 Hz), 7.1–7.4(6H,m), 8.0–8.1(2H,m).

Working Example 11

Ethyl 4-(10-oxo-1,2,3,9,10,10a-hexahydrobenzo[b]cyclopenta[e][1,4]diazepin-9-ylmethyl)benzoate Using ethyl 4-(bromomethyl)benzoate, the titled compound was synthesized in accordance with the procedure of Working Example 1 as an oily product.

¹H NMR(CDCl₃) δ: 1.37(3H,t,J=71.Hz), 1.8–2.2(3H,m), 2.6–2.9(3H,m), 3.0–3.1(1H,m), 4.34(2H,q,J=7.1 Hz), 5.05–5.25(2H,m), 7.05–7.35(6H,m), 7.9–8.0(2H,m).

Working Example 12

9-(2,5-dimethoxy-3,4,6-trimethylbenzyl)-2,3,9,10a-tetrahydrobenzo [b]cyclopenta[e][1,4]diazepin-10(1H)-one Using 2,5-dimethoxy-3,4,6-trimethylbenzyl bromide, the titled compound was synthesized by substantially the same procedure as in Working Example 1. Yield 56%. m.p. 202°–204° C.

¹H NMR(CDCl₃) δ: 1.70–2.20(3H,m), 1.81(3H,s), 2.03(3H,s), 2.07(3H,s), 2.60–3.00(4H,m), 3.38(3H,s), 3.65(3H,s), 4.94(1H,d,J=14.6 Hz), 5.64(1H,d,J=14.6 Hz), 6.90–7.10(3H,m), 7.30–7.40(1H,m).

Working Example 13

1-Benzyl-4-methyl-1,3-dihydro-1,5-benzodiazepin-2(2H)-one

Using 4-methyl-1,3-dihydro-1,5-benzodiazepin-2(2H)-one, the titled compound was synthesized by substantially the same procedure as in Working Example 1. Yield 89%. m.p. 111°–113° C. (diethylether) 3.49(1H,d,J=11.0 Hz), 5.10(2H,s), 7.05–7.32(9H,m).

Working Example 14

1-Benzyl-4-phenyl-1,3-dihydro-1,5-benzodiazepin-2(2H)-one

The titled compound was synthesized by substantially the same procedure as in Working Example 1. Yield 68%. m.p. 122°–123° C.

¹H NMR(CDCl₃) δ: 3.17(1H,d,J=12.2 Hz), 4.24(1H,d,J-12.2 Hz), 5.13(2H,s), 7.00–7.60(12H,m), 8.15(2H,m).

Working Example 15

4-(10-oxo-1,2,3,9,10,10a-hexahydrobenzo[b]cyclopenta [e][1,4]diazepin-9-ylmethyl)benzoic acid In ethanol(15 mL) was dissolved ethyl 4-(10-oxo-1,2,3,9,10,10a-hexahydrobenzo[b]cyclopenta[e][1,4]diazepin-9-yl)benzoate. To the solution was added a 5N aqueous solution of sodium hydroxide (20 mL), and the mixture was stirred for 2 hours at 20° C. To the reaction mixture was added 3N HCl to adjust the pH of the solution to a range of 4–5. This mixture was subjected to extraction with ethyl acetate three times.

Organic layers were combined, washed with a saturated aqueous solution of sodium chloride, then dried over magnesium sulfate, which was subjected to filtration. The filtrate was concentrated under reduced pressure. The concentrate was purified by silica-gel column chromatography (dichloromethane-methanol 20:1) to afford 1.66 g of the titled compound (yield 50%, two steps). The sample for analylical experiment was prepared by recrystallization of the product from ethanol-water, m.p. 226°–228° C.

¹H NMR(CDCl₃) δ: 1.8–2.2(3H,m), 2.7–2.9(3H,m), 3.05–3.15(1H,m), 5.04(1H,d,J=15.8 Hz), 5.34(1H,d,J-16.2 Hz), 7.1–7.4(6H,m), 7.9–8.0(2H,m).

The proton signal of COOH could not be detected by broading.

Working Example 16

4-(7-chloro-10-oxo-1,2,3,9,10,10a-hexahydrobenzo[b]cyclopenta[e][1,4]diazepin-9-ylmethyl)benzoic acid A mixture of methyl 4-(7-chloro-10-oxo-1,2,3,9,10,10a-hexahydrobenzo[b]cyclopenta[e][1,4]diazepin-9-ylmethyl)benzoate(1.7 g, 4.4 mmol), a 20% aqueous solution of potassium carbonate (5 mL) and methanol (15 mL) was stirred for 1.5 hour at 20° C. and for 2 hours at 80° C. The pH of the reaction mixture was adjusted to 4, which was extracted with chloroform. Organic layers were combined and dried over magnesium sulfate, which was then subjected to filtration, followed by concentration of the filtrate under reduced pressure. The concentrate was recrystallized from ethanol-diisopropyl ether to give 0.49 g (yield 30%) of the titled compound, m.p. 251°–255° C.

$^1$H NMR(CD$_3$OD) δ: 1.9–2.1(3H,m), 2.6–2.8(3H,m), 5.04(1H,d,J=16.2 Hz), 5.44(1H,d,J=16.2 Hz), 7.12(2H,d,J=8.4 Hz), 7.20(1H,s), 7.21(1H,s), 7.50(1H,m), 7.85–7.95(2H,m).

Working Example 17

9-(4-Aminobenzyl)-2,3,9,10a-tetrahydrobenzo[b]cyclopenta[e][1,4]diazpin-10(1H)-one A mixture of 9-(4-nitrobenzyl)-2,3,9,10a-tetrahydrobenzo[b]cyclopenta[e][1,4]diazepin-10(1H)-one (2.82 g, 8.41 mmol) and 10% palladium-carbon(hydrous)(0.28%) was suspended in a mixture of tetrahydrofuran (25 mL) and ethyl acetate (25 mL). The suspension was stirred for 2 hours at 20° C. under hydrogen atmosphere. The catalyst was filtered off and the filtrate was concentrated under reduced pressure. The concentrate was purified by means of a silica-gel column chromatography (hexane-ethyl acetate 2:1→1:2) to give 1.04 g(yield 40%) of the titled compound. The sample for analytical experiment was recrystallized from ethyl acetate, m.p. 168°–171° C.

$^1$H NMR(CDCl$_3$) δ: 1.8–2.2(3H,m), 2.4–2.9(3H,m), 2.95–3.05(1H,m), 3.58(2H,br s), 4.99(2H,s), 6.5–6.6(2H,m), 6.85–6.95(2H,m), 7.1–7.4(4H,m).

Working Example 18

1,3-dibenzyl-4-trifluoromethyl-1,3-dihydro-1,5-benzodiazepin-2(2H)-one

To a solution of 4-trifluoromethyl-1,3-dihydro-1,5-benzodiazepin-2(2H)-one(3.0 g, 13.1 mmol) in N,N-dimethylformamide(20 mL) was added sodium hydride (content 60%, 1.1 g, 27.5 mmol), and the mixture was stirred for 15 minutes. To the mixture was added benzyl bromide (4.7 g, 27.5 mmol), which was stirred for further 30 minutes. The reaction mixture was diluted with water, which was extracted with ethyl acetate. The extract was washed with water, dried and concentrated. The concentrate was crystallized from ethyl acetate-hexane to give 3.3 g of the titled compound. Yield 61%. m.p. 150°–151° C.

$^1$H NMR(CDCl$_3$) δ: 2.89(1H,d,J=9.0 Hz), 3.34(2H,m), 4.91(1H,d,J=15.8 Hz), 5.28(1H,d,J=15.8 Hz), 6.90(2H,m), 7.10–7.50(12H,m).

Working Example 19

1,3-Dibenzyl-4-methyl-1,3-dihydro-1,5-benzodiazepin-2(2H)-one

The titled compound was synthesized by substantially the same procedure as in Working Example 18. Yield 71%. m.p. 140°–141° C.

$^1$H NMR(CDCl$_3$) δ: 2.31(3H,s), 3.22(2H,m), 3.69(1H,m), 5.00(1H,d,J=15.8 Hz), 5.19(1H,d,J=15.8 Hz), 6.95(2H,m), 7.10–7.40(12H,m).

Working Example 20

1,3-Dibenzyl-4-phenyl-1,3-dihydro-1,5-benzodiazepin-2(2H)-one

By substantially the same procedure as in Working Example 18, the titled compound was synthesized. Yield 74%. m.p. 173°–174° C.

$^1$H NMR(CDCl$_3$) δ: 3.01(1H,dd,J=14.2, 4.8 Hz)3.41(1H,dd,J=9.2, 4.8 Hz), 3.83(1H,dd,J=14.2, 9.2 Hz), 5.15(1H,d,J=15.8 Hz), 5.25(1H,d,J=15.8 Hz), 6.90–7.10(4H,m), 7.10–7.30(9H,m), 7.30–7.50(4H,m), 7.70–7.90(2H,m).

Working Example 21

1-Benzyl-3-(4-methoxybenzyl)-4-methyl-1,3-dihydro-1,5-benzodiazepin-2(2H)-one

To a solution of 1-benzyl-4-methyl-1,3-dihydro-1,5-benzodiazepin-2(2H)-one (3.0 g, 13.1 mmol) in N-dimethylformamide (20 mL) was added sodium hydride (content 60%, 0.51 g, 12.8 mmol). The mixture was stirred for 15 minutes, to which was added 4-methoxybenzylbromide (2.3 g, 11.5 mmol), and the mixture was stirred for further 30 minutes. The reaction mixture was diluted with water, which was extracted with ethyl acetate. The extract was washed with water, dried and concentrated. The concentrate was crystallized from ethyl acetate-hexane to give 3.3 g of the titled compound. Yield 76%. m.p. 136°–137° C.

$^1$H NMR(CDCl$_3$) δ: 2.30(3H,s), 3.15(2H,m), 3.62(1H,m), 3.78(3H,s), 5.00(1H,d,J=15.8 Hz), 5.18(1H,d,J=15.8 Hz), 6.79(2H,m), 6.91(2H,m), 7.10–7.40(9H,m).

Working Example 22

(3aR*, 10aS*)-9-(2,4-dichlorobenzyl)-2,3,3a,4,9,10a-hexahydrobenzo[b]cyclopenta[e][1,4]diazepin-10(1H)-one To a solution of 9-(2,4-dichlorobenzyl)-2,3,9,10a-tetrahydrobenzo[b]cyclopenta[e][1,4]diazepin-10(1H)-one (0.9 g, 2.5 mmol) in dichloromethane (3 mL) was added 2.5N HCl-ethanol solution (1.5 mL), and the mixture was immediately concentrated under reduced pressure. The concentrate was dissolved in methanol (10 mL), to which was added sodium lithium borohydride (250 mg, 6.6 mmol). The mixture was stirred for 20 minutes at room temperature. To the reaction mixture was added water, which was subjected to extraction with ethyl acetate three times. The organic layers were combined, washed with water and a saturated aqueous solution of sodium chloride, dried over magnesium sulfate, which was subjected to filtration. The filtrate was concentrated under reduced pressure, and the concentrate was purified by silica-gel column chromatography (hexane-ethyl acetate 6:1) to give 740 mg (yield 82%) of the titled compound. Amorphous.

$^1$H NMR(CDCl$_3$) δ: 1.4–2.1(5H,m), 2.3–2.5(1H,m), 2.9–3.05(1H,m), 3.4–3.7(1H, br), 3.95–4.2(1H,m), 5.01(1H,d,J-17.2 Hz), 5.26(1H,d,J=17.4 Hz), 6.9–7.2(5H,m), 7.30 (1H,d,J=2.2 Hz), 7.54(1H,d,J=8.4 Hz).

Working Example 23

(3aR*, 10aS*)-9-Benzyl-2,3,3a,4,9,10a-hexahydrobenzo[b]cyclopenta[e][1,4]diazepin-10(1H)-one A suspension of 9-benzyl-2,3,9,10a-tetrahydrobenzo[b]cyclopenta[e][1,4]diazepin-10(1H)-one (87.5 g, 0.30 mol) and bromocresol green (20 mg) in ethanol (300 mL) in a mixture of ethanol (300 mL) and tetrahydrofuran (300 mL) was cooled to 0° C., to which was added sodium cyanoborohydride (20.8 g, 0.33 mol). To the mixture was added dropwise slowly a 2.43N HCl-ethanol solution until the color of the solution does not change any more. To the reaction mixture was added water (800 mL), to which was added a saturated aqueous solution of sodium hydrogencarbonate to make the pH of the solution alkaline. Resulting crystalline precipitate was collected by filtratin, washed with water, and dried at 60° C. over diphosphorus pentoxide under reduced pressure to give 73.2 g (yield 83%) of the titled compound. The filtrate was concentrated under reduced pressure to distill off the organic solvent. The aqueous layer was subjected to extraction with ethyl acetate. The organic layer was washed with water and a saturated aqueous solution of sodium chloride, dried over magnesium sulfate, followed by filtration and concentration under reduced pressure. The concentrate was recrystallized from ethyl acetate-hexane to give additional 7.0 g (7%) of the titled compound, m.p. 172°–173° C.

$^1$H NMR(CDCl$_3$) δ: 1.5–2.1(5H,m), 2.4–2.5(1H,m), 2.96 (1H,td,J=7.6, 2.1 Hz), 3.44(1H,br s), 3.9–4.1(1H,m), 5.08 (2H,s), 6.9–7.3(9H,m).

Working Example 24

(3aR*,10aS*)-9-(4-Chlorobenzyl-2,3,3a,4,9,10a-hexahydrobenzo[b]cyclopenta[e][1,4]diazepin-10(1H)-one A suspension of 9-(4-chlorobenzyl)-2,3,9,10a-tetrahydrobenzo[b]cyclopenta[e][1,4]diazepin-10(1H)-one (4.62 g, 14.2 mmol) and bromocresol green (2 mg) in ethanol (40 mL) was cooled to 0° C., to which was added sodium cyanoborohydride (0.98 g, 15.6 mmol). To the mixture was added dropwise slowly until the color of the solution does not change any more. To the reaction mixture was added water (50 mL), which pH was made alkaline side with a saturated aqueous solution of sodium hydrogencarbonate. This mixture was subjected to extraction with ethyl acetate. The organic layer was washed with water and a saturated aqueous solution of sodium chloride, dried over magnesium sulfate, followed by filtration and concentration under reduced pressure to give the titled compound as an oily product.

$^1$H NMR(CDCl$_3$) δ: 1.5–2.1(5H,m), 2.3–2.5(1H,m), 2.9–3.0(1H,m), 3.3–3.5(1H,br), 3.9–4.1(1H,m), 4.90(1H,d,J=15.8 Hz), 5.17(1H,d,J=15.8 Hz), 6.9–7.3(8H,m).

Working Example 25

(3aR*,10aS*)-9-(4-Methoxybenzyl)-2,3,3a,4,9,10a-hexahydrobenzo[b]cyclopenta[e][1,4]diazepin-10(1H)-one Using 9-(4-methoxybenzyl)-2,3,9,10a-tetrahydrobenzo[b]cyclopenta[e][1,4]diazepin-10(1H)-one, the titled compound was synthesized by substantially the same procedure as in Working Example 24. Yield 96%. Amorphous.

$^1$H NMR(CDCl$_3$) δ: 1.45–2.1(5H,m), 2.3–2.5(1H,m), 2.93(1H,td,J=7.6,2.1 Hz), 3.39(1H,br s), 3.74(3H,s), 3.97 (1H,td,J=8.8,7.9 Hz), 4.95(1H,d,J=15.2 Hz), 5.06(1H,d,J= 15.2 Hz), 6.77(2H,d,J=8.8 Hz), 6.85–7.1(3H,m), 7.1–7.2 (1H,m), 7.21(2H,d,J=8.8 Hz).

Working Example 26

(3aR*,10aS*)-9-(4-Nitrobenzyl)-2,3,3a,4,9,10a-hexahydrobenzo[b]cyclopenta[e][1,4]diazepin-10(1H)-one Using 9-(4-nitrobenzyl)-2,3,9,10a-tetrahydrobenzo[b]cyclopenta[e][1,4]diazepin-10(1H)-one, synthesis was conducted by substantially the same procedure as in Working Example 24. The compound thus synthesized was purified by silica-gel column chromatography to afford the titled compound (yield 46%), m.p. 154°–155° C. (ethyl acetate-diethyl ether).

$^1$H NMR(CDCl$_3$) δ: 1.5–2.1(5H,m), 2.3–2.5(1H,m), 2.9–3.0(1H,m), 3.50(1H,br s), 3.9–4.1(1H,m), 4.91(1H,d,J= 16.0 Hz), 5.17(1H,d,J=16.6 Hz), 6.9–7.2(4H,m), 7.45–7.55 (2H,m), 8.0–8.15(2H,m).

Working Example 27

Methyl 4-((3aR*,10aS*)-7-chloro-10-oxo-1,2,3,3a,4,9,10,10a-octahydrobenzo[b]cyclopenta [e][1,4]diazepin-9-ylmethyl)benzoate Using methyl 4-(7-chloro-10-oxo-1,2,3,9,10,10a-hexahydrobenzo[b]cyclopenta[e][1,4]diazepin-9-ylmethyl)benzoate, synthesis was conducted in substantially the same manner as in Working Example 24. The compound thus synthesized was purified by silica-gel column chromatography (hexane-ethyl acetate 1:4) to give the titled compound as an oily product.

$^1$H NMR(CDCl$_3$) δ: 1.5–2.1(5H,m), 2.3–2.5(1H,m), 2.9–3.0(1H,m), 3.49(1H,br s), 3.88(3H,s), 3.9–4.1(1H,m), 4.91(1H,d,J=16.2 Hz), 5.30(1H,d,J=16.2 Hz), 6.84(1H,d,J= 8.2 Hz), 7.00(1H,dd,J=8.2,2.4 Hz), 7.13(1H,d,J=2.2 Hz), 7.3–7.4(2H,m), 7.85–7.95(2H,m).

Working Example 28

(3aR*,10aS*)-9-(2,5-Dimethoxy-3,4,6-trimethylbenzyl)-2,3,3a,4,9,10a-hexahydrobenzo[b]cyclopenta[e][1,4]-diazepin-10(1H)-one The titled compound was synthesized by substantially the same procedure as in Working Example 24. Yield 85%. m.p. 175°–176° C.

$^1$H NMR(CDCl$_3$) δ: 1.50–2.00(4H,m), 2.08(6H,s), 2.20 (3H,s), 2.40–2.60(1H,m), 2.80–2.90(1H,m), 3.32(1H,br s), 3.48(3H,s), 3.59(3H,s), 3.60–4.00(2H,m), 5.04(1H,d,J=14.8 Hz), 5.45(1H,d,J=14.8 Hz), 6.70–7.10(4H,m).

Working Example 29

9,10a-Dibenzyl-2,3,3a,4,9,10a-hexahydrobenzo[b]cyclopenta[e][1.4]diazepin-10(1H)-one Using 2,3,9,10a-tetrahydrobenzo[b]cyclopenta [e][1,4]diazepin-10(1H)-one and benzyl bromide, a crude product was obtained by substantially the same procedure as in Working Example 1. The crude product was, without further purification, subjected to substantially the same reaction as in Working Example 24 to produce simultaneously a dibenzyl compound and the compound of Working Example 23. The dibenzyl compound was purified by silica-gel column chromatography, followed by recrystallization from ethyl acetate-hexane to give the title compound in a yield of 4%, m.p. 144°–145° C.

$^1$H NMR(CDCl$_3$) δ: 1.3–2.1(5H,m), 2.48(1H,d,J=14.0 Hz), 2.7–2.8(1H,m), 2.85(1H,d,J=14.0 Hz), 3.38(1H, br s), 3.69(1H,t,J=7.4 Hz), 5.03(1H,d,J=15.8 Hz), 5.1691H,d,J= 15.4 Hz), 6.9–7.3(14H,m).

Working Example 30

1-Benzyl-4-methyl-1,3,4,5-tetrahydro-1,5-benzodiazepin-2(2H)-one

Using 1-benzyl-4-methyl-1,3-dihydro-1,5-benzodiazepin-2(2H)-one, the titled compound was synthesized by substantially the same procedure as in Working Example 24. Yield 89%. Oily product.

$^1$H NMR(CDCl$_3$) δ: 1.29(3H,d,J=6.4 Hz), 2.35(1H,dd,J=12.6, 7.4 Hz), 2.62(1H,dd,J=12.6, 5.4 Hz), 3.22(1H,br s), 4.02–4.20(1H,m), 4.99–5.18(2H,m), 6.80–7.32(9H,m).

Working Example 31

1-Benzyl-4-phenyl-1,3,4,5-tetrahydro-1,5-benzodiazepin-2(2H)-one

The titled compound was synthesized by substantially the same procedure as in Working Example 24. Yield 93%. m.p. 132°–133° C.

$^1$H NMR(CDCl$_3$) δ: 2.72(1H,dd,J=12.8, 5.2 Hz),2.90(1H, dd,J=12.8, 10.2 Hz), 3.65(1H,br s), 5.06(1H,dd,J=10.2, 5.2 Hz), 5.13(2H,s), 6.82(1H,dd,J=7.4, 1.6 Hz), 6.84(1H,dt,J=8.2, 1.8 Hz), 7.02(1H,dt,J=7.2, 1.8 Hz), 7.10–7.40(11H,m).

Working Example 32

1,3-Dibenzyl-4-methyl-1,3,4,5-tetrahydro-1,5-benzodiazepin-2(2H)-one

The titled compound was synthesized by substantially the same procedure as in Working Example 24. Yield 96%. m.p. 140°–141° C.

$^1$H NMR(CDCl$_3$) δ: 1.36(3H,d,J=5.8 Hz), 2.59(1H,m), 3.24(2H,m), 3.42(1H,br s), 3.92(1H,m), 4.86(1H,d,J=15.8 Hz), 5.25(1H,d,J=15.8 Hz), 6.08–7.30(14H,m).

Working Example 33

1,3-Dibenzyl-4-trifluoromethyl-1,3,4,5-tetrahydro-1,5-benzodiazepin-2(2H)-one

The titled compound was synthesized in substantially the same manner as in Working Example 24. Yield 77%. m.p. 150°–151° C.

$^1$H NMR(CDCl$_3$) δ: 2.89(1H,d,J=9.2 Hz), 3.34(2H,m), 3.83(1H,d,J=4.8 Hz), 4.32(1H,m), 5.00(1H,d,J=15.6 Hz), 5.15(1H,d,J=15.6 Hz), 6.80–7.40(14H,m).

Working Example 34

1,3-Dibenzyl-4-phenyl-1,3,4,5-tetrahydro-1,5-benzodiazepin-2(2H)-one

The titled compound was synthesized by substantially the same procedure as in Working Example 24. Yield 96%. m.p. 149°–150° C.

$^1$H NMR(CDCl$_3$) δ: 2.34(1H,dd,J=14.2 Hz, 4.8 Hz), 2.71(1H,dd,J=14.0 9.4 Hz), 3.40(1H,ddd,J=9.4, 6.6, 4.8 Hz), 3.62(1H,br s), 6.90–7.50(19H,m).

Working Example 35

1-Benzyl-3-(4-methoxybenzyl)-4-methyl-1,3,4,5-tetrahydro-1,5-benzodiazepin-2(2H)-one The titled compound was synthesized by substantially the same procedure as in Working Example 24. Yield 90%. m.p. 136°–137° C.

$^1$H NMR(CDCl$_3$) δ: 1.34(3H,d,J=6.2 Hz), 2.53(1H,m), 3.16(2H,m), 3.42(1H,br s), 3.78(3H,s), 3.91(1H, quintet, J=6.2 Hz), 4.83(1H,d,J=15.8 Hz), 5.25(1H,d,J=15.8 Hz), 6.70–7.30(13H,m).

Working Example 36

1-Benzyl-4-((E)-styryl)-1,3,4,5-tetrahydro-1,5-benzodiazepin-2(2H)-one

The titled compound was synthesized in substantially the same manner as in Working Example 24. Yield 64%. m.p. 186°–187° C.

$^1$H NMR(CDCl$_3$) δ: 2.68(2H,m), 3.46(1H,br s), 4.64(1H, m), 5.07(1H,d,J=14.2 Hz), 5.16(1H,d,J=14.2 Hz), 6.29(1H, dd,J=15.4, 8.2 Hz), 6.59(1H,d,J=15.4 Hz), 6.80–7.40(14H, m).

Working Example 37

(3aR*,10aS*)-9-(2,4-Dichlorobenzyl)-2,3,3a,4,9,10a-hexahydrobenzo[b]cyclopenta[e][1,4]diazepin-10(1H)-one hydrochloride In diethylether was dissolved (3aR*,10aS*)-9-(2,4-dichlorobenzyl)-2,3,3a,4,9,10a-hexahydrobenzo[b]cyclopenta[e][1,4]diazepin-10(1H)-one produced in Working Example 22. To the solution was added a 2.5N hydrogen chloride-ethanol solution, and the mixture was stirred. Resulting crystalline precipitate was collected by filtration to obtain the titled compound, m.p. 164°–167° C.

$^1$H NMR(DMSO-d$_6$) δ: 1.4–2.3(6H,m), 2.95–3.1(1H,m), 4.0–4.2(1H,m), 4.73(1H,br d,J=17.2 Hz), 5.18(1H,br d, J=18.4 Hz), 7.1–7.3(3H,m), 7.36(1H,dd,J=8.6, 2.2 Hz), 7.4–7.6(2H,m), 7.62(1H,d,J=2.2 Hz).

Working Example 38

(3aR*,10aS*)-9-Benzyl-2,3,3a,4,9,10a-hexahydrobenzo[b]cyclopenta[e][1,4]diazepin-10(1H)-one hydrochloride In ethanol was dissolved (3aR*,10aS*)-9-benzyl-2,3,3a, 4,9,10a-hexahydrobenzo[b]cyclopenta[e][1,4]diazepin-10 (1H)-one. To the solution was added dropwise a 2.5N HCl-ethanol solution, and the mixture was concentrated under reduced pressure. The concentrate was recrystallized from ethanol-ether to give the titled compound. m.p. 145°–148° C.

$^1$H NMR(DMSO-d$_6$) δ: 1.4–2.4(6H,m), 2.95–3.1(1H,m), 4.14(1H,q,J=8.1 Hz), 4.58(1H,d,J=16.2 Hz), 5.34(1H,d,J=16.4 Hz), 7.1–7.4(8H,m), 7.6–7.75(1H,m).

Working Example 39

(3aR*,10aS*)-9-(4-Chlorobenzyl)-2,3,3a,4,9,10a-hexahydrobenzo[b]cyclopenta[e][1,4]diazepin-10(1H)-one hydrochloride (3aR*,10aS*)-9-(4-Chlorobenzyl)-2,3,3a,4,9,10a-hexahydrobenzo[b]cyclopenta[e][1,4]diazepin-10(1H)-one produced in Working Example 24 was made into hydrochloride in accordance with the procedure described above. The hydrochloride was recrystallized from ethanol-ether to give the titled compound (yield 87%, two steps), m.p. 171°–178° C.

$^1$H NMR(CD$_3$OD) δ: 1.6–2.5(6H,m), 3.1–3.3(1H,m), 4.3–4.5(1H,m), 4.46(1H,d,J=16.2 Hz), 5.61(1H,d,J=16.0 Hz), 7.2–7.65(8H,m).

Working Example 40

(3aR*,10aS*)-9-(4-Nitrobenzyl)-2,3,3a,4,9,10a-hexahydrobenzo[b]cyclopenta[e][1,4]diazepin-10(1H)-one hydrochloride In ethanol was suspended (3aR*,10aS*)-9-(4-Nitrobenzyl)-2,3,3a,4,9,10a-hexahydrobenzo[b]cyclopenta[e][1,4]-diazepin-10(1H)-one produced in Working Example 26. To the suspension was added an HCl-ethanol solution, and the mixture was stirred. Resulting crystalline precipitate was collected by filtration, which was washed with ethanol to give the titled compound, m.p. 167°–170° C.

¹H NMR(DMSO-d₆) δ: 1.4–2.4(6H,m), 2.95–3.1(1H,m), 4.0–4.2(1H,m), 4.90(1H,d,J=16.6 Hz), 5.32(1H,d,J=17.4 Hz), 7.1–7.7(6H,m), 8.0–8.25(2H,m).

Working Example 41

Methyl 4-(3aR*,10aS*)-7-chloro-10-oxo-1,2,3,3a,4, 9,10,10a-octahydrobenzo[b]cyclopenta[e][1,4] diazepin-9-ylmethyl)benzoate hydrochloride In ethanol was dissolved methyl 4-(3aR*,10aS*)-7-chloro-10-oxo-1,2,3,3a,4,9,10,10a-octahydrobenzo[b]cyclopenta[e][1,4]diazepin-9-ylmethyl)benzoate. To the solution was gently added, at 0° C., a 2N HCl-ethanol solution. The mixture was left standing at the same temperature to cause crystallization to give 3.82 g (yield 90% two steps) of the titled compound. The sample of analytical experiment was prepared by recrystallization from methanol, m.p. 167°–182° C.

¹H NMR(DMSO-d₆) δ: 1.4–2.3(6H,m), 2.85–3.05(1H, m), 3.81(3H,s), 3.85–4.05(1H,m), 5.06(1H,d,J=17.2 Hz), 5.19(1H,d,J=17.2 Hz), 7.1–7.35(3H,m), 7.43(2H,d,J=8.2 Hz), 7.85(2H,d,J=8.2 Hz).

Working Example 42

(3aR*,10aS*)-9-Benzyl-1,2,3,3a,4,9,10,10a-octahydrobenzo[b]cyclopenta[e][1,4]diazepine To a solution of (3aR*,10aS*)-9-benzyl-2,3,3a,4,9,10a-hexahydrobenzo[b][e][1,4]diazepin-10(1H)-one (3.33 g, 11 mmol) in tetrahydrofuran (30 mL) was added lithium aluminium hydride (0.85 g, 22 mmol). The mixture was refluxed for one hour. The reaction mixture was cooled, to which was added celite, followed by dropwise addition of a small quantity of water. The mixture was subjected to filtration with celite, and washed with ethyl acetate. The filtrate was concentrated under reduced pressure, and the concentrate was purified by silica-gel column chromatography (hexane-ethyl acetate 20:1) to give 2.36 g (yield 77%) of the titled compound as an oily product.

¹H NMR(CDCl₃) δ: 1.2–2.4(7H,m), 2.7–3.0(1H,br s), 3.05(1H,dd,J=14.1, 2.6 Hz), 3.71(1H,dd,J=13.8, 11.0 Hz), 4.01(1H,td,J=6.2, 2.7 Hz), 4.39(1H,d,J=16.0 Hz), 4.48(1H, d,J=16.4 Hz), 6.5–6.7(4H,m), 7.2–7.4(5H,m).

Working Example 43

(3aR*,10aS*)-9-Benzyl-4-methyl-1,2,3,3a,4,9,10, 10a-octahydrobenzo[b]cyclopenta[e][1,4]diazepin Using (3aR*,10aS*)-9-benzyl-4-methyl-2,3,3a,4,9, 10a-hexahydrobenzo[b]cyclopenta[e][1,4]diazepin-10(1H)-one, the titled compound was synthesized in substantially the same manner as in Working Example 42. Yield 55%. Oily product.

¹H NMR(CDCl₃) δ: 1.2–2.4(7H,m), 2.83(3H,s), 2.89(1H, dd,J=11.6, 3.2 Hz), 3.05(1H,dt,J=9.2, 7.1 Hz), 3.60(1H,t,J= 11.4 Hz), 4.46(1H,d,J=16.6 Hz), 4.56(1H,d,J=16.8 Hz), 6.6–7.0(4H,m), 7.2–7.4(5H,m).

Working Example 44

(3aR*,10aS*)-9-Benzyl-1,2,3,3a,4,9,10,10a-octahydrobenzo[b]cyclopenta[e][1,4]diazepine hydrochloride In ethanol was dissolved (3aR*,10aS*)-9-benzyl-1,2,3, 3a,4,9,10,10a-octahydrobenzo[b]cyclopenta-[e][1,4] diazepine produced in Working Example 42. To the solution was added a 2.43N HCl-ethanol solution. This solution was concentrated under reduced pressure, and the concentrate was crystallized from ethanol to give the titled compound, m.p. 177°–179° C.

¹H NMR(DMSO-d₆) δ: 1.3–2.2(6H,m), 2.4–2.6(1H,m), 3.05–3.2(1H,m), 3.5–4.2(2H,m), 4.49(2H,s), 6.7–6.9(2H, m), 7.1–7.4(6H,m), 7.5–7.6(1H,m).

Working Example 45

(3aR*,10aS*)-9-Benzyl-4-methyl-1,2,3,3a,4,9,10, 10a-octahydrobenzo[b]cyclopenta[e][1,4]diazepine hydrochloride In ethanol was dissolved (3aR*,10aS*)-9-Benzyl-4-methyl- 1,2,3,3a,4,9,10,10a-octahydrobenzo[b]-cyclopenta [e][1,4]diazepine produced in Working Example 43. To the solution was added a 2.43N HCl-ethanol solution, which was concentrated under reduced pressure. The concentrate was dissolved in ethanol-ether, which was concentrated to dryness. Amorphous.

¹H NMR(DMSO-d₆/D₂O) δ: 1.1–2.4(7H,m), 2.9–3.2(2H, m), 3.25(3H,s), 3.6–3.8(1H,m), 4.43(2H,s), 7.0–7.6(9H,m).

Working Example 46

(3aR*,10aS*)-9-Benzyl-4-(phthalimidoacetyl)-2,3, 3a,4,9,10a-hexahydrobenzo[b]cyclopenta-[e][1,4] diazepin-10(1H)-one On a water-bath of 11° C., a solution of phthalimidoacetyl chloride (8.05 g, 36 mmol) in 1,2-dichloroethane (30 mL) was added dropwise to a solution of (3aR*,10aS*)-9-benzyl-4-2,3,3a,4,9,10a-hexahydrobenzo[b]cyclopenta[e][1,4] diazepin-10(1H)-one (9.06 g, 31 mmol) in 1,2-dichloroethane (40 mL). The mixture was stirred for 10 minutes at 12° C., to which was added an aqueous solution of sodium hydrogencarbonate (100 mL). The aqueous layer was seperated, and the organic layer was washed with water and a saturated aqueous solution of sodium chloride and dried over magnesium sulfate, which was them subjected to filtration. The filtrate was concentrated under reduced pressure, and the concentrate was recrystallized from chloroform-ethanol to give 9.82 g (yield 66%) of the titled compound, m.p. 247°–249° C.

¹H NMR(CDCl₃) δ: 1.1–1.5(3H,m), 1.6–1.9(2H,m), 2.0–2.25(1H,m), 3.24(1H,dt,J=12.2, 9.1 Hz), 3.39(1H,d,J= 16.6 Hz), 4.02(1H,d,J=16.6 Hz), 5.01(1H,d,J=15.3 Hz), 5.38 (1H,d,J=15.3 Hz), 5.7–5.85(1H,m), 7.2–7.5(9H,m), 7.65–7.9(4H,m).

Working Example 47

(3aR*,10aS*)-9-(4-Methoxybenzyl)-4-(phthalimidoacetyl)-2,3,3a,4,9,10a-hexahydrobenzo [b]cyclopenta[e][1,4]-diazepin- 10(1H)-one Using (3aR*,10aS*)-9-(4-methoxybenzyl)-4-2,3,3a,4,9, 10a-hexahydrobenzo[b]cyclopenta[e][1,4]-diazepin-10(1H) -one, the titled compound was synthesized in substantially the same manner as in Working Example 46. Yield 61%. m.p. 251°–253° C. (chloroform-ethanol)

¹H NMR(CDCl₃) δ: 1.1–1.5(3H,m), 1.5–1.9(2H,m), 2.0–2.25(1H,m), 3.16(1H,dt,J=12.0, 9.2 Hz), 3.33(1H,d,J= 16.5 Hz), 3.78(3H,s), 3.98(1H,d,J=16.5 Hz), 4.80(1H,d,J= 15.0 Hz), 5.46(1H,d,J=15.0 Hz), 5.77(1H,ddd,J=9.2, 8.2, 3.8 Hz), 6.87(2H,d,J=8.8 Hz), 7.1–7.5(5H,m), 7.6–7.9(5H,m).

Working Example 48

9,10a-Dibenzyl-4-(phthalimidoacetyl)-2,3,3a,4,9,10a-hexahydrobenzo[b]cyclopenta[e][1,4]diazepin-10(1H)-one Using 9,10a-dibenzyl-2,3,3a,4,9,10a-hexahydrobenzo[b]cyclopenta[e][1,4]diazepin-10(1H)-one, synthesis was conducted in substantially the same manner as in Working Example 46 to give a crude product, which was purified by silica-gel column chromatography (hexane-ethyl acetate 2:1→chloroform), followed by crystallization from chloroform-hexane to give the titled compound in a yield of 29%, m.p. 214°–215° C.

$^1$H NMR(CDCl$_3$) δ: 0.9–1.2(1H,m), 1.2–2.0(5H,m), 2.70 (1H,d,J=14.0 Hz), 3.38(1H,d,J=16.4 Hz), 3.57(1H,d,J=14.0 Hz), 3.99(1H,d,J=16.4 Hz), 5.23(2H,s), 6.58(1H,dd,J=7.9, 2.1 Hz), 7.1–7.5(14H,m), 7.65–7.8(2H,m), 7.8–7.9(2H,m).

Working Example 49

(3aR*,10aS*)-9-Benzyl-4-((4-nitrophthalimido)acetyl)-2,3,3a,4,9,10a-hexahydrobenzo[b]cyclopenta[e][1,4]-diazepin-10(1H)-one A mixture of (4-nitrophthalimido)acetic acid (2.17 g, 8.7 mmol) and thionyl chloride (5 mL) was refluxed for 80 minutes. The reaction mixture was cooled and, then, concentrated under reduced pressure to give a crude product of (4-nitrophthalimido)acetyl chloride. The crude product was dissolved, while heating, in 1,2-dichloroethane (10 mL). The solution was added (dropwise to a solution of (3aR*,10aS*)-9-benzyl-2,3,3a,4,9,10a-hexahydrobenzo[b]cyclopenta[e][1,4]-diazepin-10(1H)-one (2.30 g, 7.9 mmol) in 1,2-dichloroethane (10 mL). The mixture was stirred for 5 minutes at room temperatures, to which was added a saturated aqueous solution of sodium hydrogen carbonate (25 mL). The aqueous layer was separated. The organic layer was washed with water and a saturated aqueous solution of sodium chloride, which was dried over magnesium sulfate, and them subjected to filtration. The filtrate was concentrated under reduced pressure. The concentrate was crystallized from chloroform-ethanol-hexane to give 1.91 g (yield 46%) of the titled compound, m.p. 196.5°–197.5° C.

$^1$H NMR(CDCl$_3$) δ: 1.0–1.5(3H,m), 1.5–2.0(2H,m), 2.0–2.25(1H,m), 3.19(1H,dt,J=12.0, 9.1 Hz), 3.37(1H,d,J=16.5 Hz), 4.08(1H,d,J=16.5 Hz), 4.99(1H,d,J=15.4 Hz), 5.41 (1H,d,J=15.4 Hz), 5.7–5.85(1H,m), 7.2–7.5(9H,m), 8.04 (1H,d,J=8.0 Hz), 8.60(1H,dd,J=8.0, 1.8 Hz), 8.66(1H,d,J=2.0 Hz).

Working Example 50

(3aR*,10aS*)-9-Benzyl-4-(3-phthalimidopropionyl)-2,3,3a,4,9,10a-hexahydrobenzo[b]cyclopenta[e][1,4]-diazepin-10(1H)-one Using 3-phthalimidopropionic acid, the titled compound was synthesized by substantially the same procedure as in Working Example 49. Yield 80%. m.p. 242°–244° C. (dichloromethane-hexane).

$^1$H NMR(CDCl$_3$) δ: 1.0–1.9(6H,m), 2.0–2.2(1H,m), 2.2–2.4(1H,m), 3.14(1H,dt,J=12.0, 9.0 Hz), 3.6–3.9(2H,m), 4.78(1H,d,J=15.2 Hz), 5.36(1H,d,J=15.2 Hz), 5.75–5.9(1H, m), 7.05–7.45(9H,m), 7.65–7.85(4H,m).

Working Example 51

(3aR*,10aS*)-9-Benzyl-4-(4-phthalimidobutyryl)-2,3,3a,4,9,10a-hexahydrobenzo[b]cyclopenta[e][1,4]-diazepin-10(1H)-one Using 4-phthalimidobutyric acid, the titled compound was synthesized by substantially the same procedure as in Working Example 49. Yield 88%. m.p. 182°–184° C. (diisopropylether-hexane)

$^1$H NMR(CDCl$_3$) δ: 0.8–2.2(10H,m), 3.11(1H,dt,J=12.0, 8.8 Hz), 3.3–3.5(2H,m), 4.68(1H,d,J=15.0 Hz), 5.51(1H,d, J=15.0 Hz), 5.75–5.9(1H,m), 7.0–7.4(9H,m), 7.65–7.85(4H, m).

Working Example 52

(3aR*,10aS*)-9-Benzyl-4-(phthalimidoacetyl)-1,2,3,3a,4,9,10,10a-octahydrobenzo[b]cyclopenta[e][1,4]diazepin A crude product of (3aR*,10aS*)-9-benzyl-4-1,2,3,3a,4,9,10,10a-octahydrobenzo[b]cyclopenta-[e][1,4]diazepin synthesized from (3aR*,10aS*)-9-benzyl-2,3,3a,4,9,10a-hexahydrobenzo[b]cyclopenta [e][1,4]diazepin-10(1H)-one (2.92 g, 10 mmol) in substantially the same manner as in Working Example 42 was dissolved in 1,2-dichloroethane, to which was added phthalimidoacetyl chloride (2.24 g, 10 mmol). The mixture was stirred for 15 minutes at room temperature, which was refluxed for 15 minutes. To the reaction mixture was added a saturated aqueous solution of sodium hydrogencarbonate (15 mL). The aqueous layer was separated, and the organic layer was washed with water and, then, dried over magnesium sulfate, which was subject to filtration, followed by concentration under reduced pressure. To the concentrate was added ethanol-diethylether, and the solid matter was collected by filtration and recrystallized from chloroform-ethanol to give 1.72 g (yield 37%) of the titled compound, m.p. 232°–234° C.

$^1$H NMR(CDCl$_3$) δ: 1.3–1.8(5H,m), 1.8–1.95(1H,m), 2.35–2.55(1H,m), 3.02(1H,dd,J=14.3, 5.5 Hz), 3.95–4.1 (1H,m), 4.02(1H,d,J=16.6 Hz), 4.43(1H,d,J=16.6 Hz), 4.45 (1H,d,J=16.9 Hz), 4.66(1H,d,J=16.9 Hz), 5.2–5.35(1H,m), 6.7–6.8(2H,m), 7.0–7.2(2H,m), 7.2–7.4(5H,m), 7.65–7.9 (4H,m).

Working Example 53

(3aR*,10aS*)-9-(2,5-Dimethoxy-3,4,6-trimethylbenzyl)-4-(phathalimidoacetyl)-2,3,3a,4,9,10a-hexahydrobenzo[b]cyclopenta[e][1,4]diazepin-10(1H)-one In substantially the same manner as in Working Example 46, synthesis was conducted, and the product was purified by silica-gel column chromatography to give the corresponding (3aR*,10aS*) derivative. Yield 58%. m.p. 223°–224° C.

$^1$H NMR(CDCl$_3$) δ: 0.80–1.10(1H,m), 1.20–1.40(2H,m), 1.60–1.80(3H,m), 2.09(3H,s), 2.12(3H,s), 2.36(3H,s), 3.00–3.20(1H,m), 3.54(3H,s), 3.61(3H,s), 3.99(1H,d,J=16.6 Hz), 4.20(1H,d,J=16.6 Hz), 4.93(1H,d,J=14.4 Hz), 5.54(1H, d,J=14.4 Hz), 5.62(1H,m), 7.10–7.35(3H,m), 7.47(1H,d,J= 6.6 Hz), 7.60–7.90(4H,m).

Working Example 54

(3aR*,10aR*)-9-(2,5-Dimethoxy-3,4,6-trimethylbenzyl)-4-(phthalimidoacetyl)-2,3,3a,4,9,10a-hexahydrobenzo[b]cyclopenta[e][1,4]diazepin-10(1H)-one The (3aR*,10aR*) compound produced simultaneously in Working Example 53 was isolated by means of a silica-gel column chromatography. Yield 27%. m.p. 203°–204° C.

$^1$H NMR(CDCl$_3$) δ: 1.20–1.90(3H,m), 2.10(3H,s), 2.11 (3H,s), 2.10–2.40(1H,m), 2.34(3H,s), 2.70–3.00(2H,m), 3.59(3H,s), 3.62(3H,s), 3.82(1H,d,J=16.8 Hz), 4.00–4.20 (2H,m), 4.16(1H,d,J=16.8 Hz), 4.93(1H,d,J=14.2 Hz), 5.59 (1H,d,J=16.8 Hz), 7.10–7.30(3H,m), 7.40–7.60(1H,m), 7.60–7.90(4H,m).

Working Example 55

1-Benzyl-4-methyl-5-(phthalimidoacetyl)-1,3,4,5-tetrahydro-1,5-benzodiazepin-2(2H)-one The titled compound was synthesized from 1-benzyl-4-methyl-1,3,4,5-tetrahydro-1,5-benzodiazepin-2(2H)-one and phthalimidoacetyl chloride in substantially the same manner as in Working Example 46. Yield 61%. m.p. 248°–250° C. (diethyl ether).

$^1$H NMR(CDCl$_3$) δ: 1.17(3H,d,J=6.4 Hz), 2.17–2.39(1H, m), 2.56(1H,dd,J=13.0, 5.0 Hz), 3.21(1H,d,J=16.4 Hz), 3.93 (1H,d,J=16.4 Hz), 4.79(1H,d,J=15.0 Hz), 5.15–5.36(1H,m), 5.48(1H,d,J=15.0 Hz), 7.23–7.50(9H,m), 7.68–7.86(4H,m).

Working Example 56

1-Benzyl-4-phenyl-5-(phthalimidoacetyl)-1,3,4,5-tetrahydro-1,5-benzodiazepin-2(2H)-one The titled compound was synthesized in substantially the same procedure as in Working Example 46. Yield 89%. m.p. 127°–128° C.

$^1$H NMR(CDCl$_3$) δ: 2.81(1H,dd,J=13.8, 5.2 Hz), 3.00 (1H,t,J=3.8 Hz), 3.24(1H,d,J=16.6 Hz), 4.03(1H,d,J=16.6 Hz), 5.00(1H,d,J=15.2 Hz), 5.42(1H,d,J=15.2 Hz), 6.19(1H, dd,J=13.8, 5.2 Hz), 7.20–7.60(14H,m), 7.65–7.90(4H,m).

Working Example 57

1,3-Dibenzyl-4-methyl-5-(phthalimidoacetyl)-1,3,4,5-tetrahydro-1,5-benzodiazepin-2(2H)-one The titled compound was synthesized by substantially the same procedure as in Working Example 46. Yield 92%. m.p. 213°–214° C.

$^1$H NMR(CDCl$_3$) δ: 1.30(3H,d,J=6.8 Hz), 1.78(1H,dd,J= 14.6, 12.8 Hz), 2.65(1H,m), 3.41(1H,d,J=16.6 Hz), 3.52(1H, m), 4.05(1H,d,J=16.6 Hz), 4.92(1H,d,J=15.8 Hz), 5.02(1H, d,J=15.8 Hz), 5.56(1H,quintet,J=6.6 Hz), 6.90–8.00(18H, m).

Working Example 58

1,3-Dibenzyl-5-(phthalimidoacetyl)-4-trifluoromethyl-1,3,4,5-tetrahydro-1,5-benzodiazepin-2(2H)-one The titled compound was synthesized by substantially the same procedure as in Working Example 46. Yield 68%. m.p. 262°–263° C.

$^1$H NMR(CDCl$_3$) δ: 1.94(1H,t,J=14.2 Hz), 2.88(1H,dd, J=13.6, 6.6 Hz), 3.53(1H,d,J=16.6 Hz), 3.91(1H,dt,J=7.8, 6.6 Hz), 4.19(1H,d,J=6.6 Hz), 4.55(1H,d,J=15.6 Hz), 5.37 (1H,d,J=15.6 Hz), 6.10(1H,quintet,J=7.8 Hz), 6.70–8.00 (18H,m).

Working Example 59

1,3-Dibenzyl-4-phenyl-5-(phthalimidoacetyl)-1,3,4,5-tetrahydro-1,5-benzodiazepin-2(2H)-one The titled compound was synthesized in substantially the same procedure as in Working Example 46. Yield 97%. m.p. 255°–256° C.

$^1$H NMR(CDCl$_3$) δ: 1.82(1H,dd,J=15.0, 13.0 Hz), 2.27 (1H,dd,J=15.0, 5.4 Hz), 3.49(1H,d,J=16.6 Hz), 3.79(1H,dt, J=13.0, 5.4 Hz), 4.28(1H,d,J=6.6 Hz), 5.07(2H,s), 6.43(1H, d,J=5.4 Hz), 6.77(2H,m), 7.00–8.00(21H,m).

Working Example 60

1-Benzyl-3-(4-methoxybenzyl)-4-methyl-5-(phthalimidoacetyl)-1,3,4,5-tetrahydro-1,5-benzodiazepin-2(2H)-one The titled compound was synthesized in substantially the same manner as in Working Example 46. Yield 88%. m.p. 247°–248° C.

$^1$H NMR(CDCl$_3$) δ: 1.28(3H,d,J=6.6 Hz), 1.70(1H,dd,J= 14.2, 13.2 Hz), 2.58(1H,dd,J=14.6, 6.2 Hz), 3.43(1H,d,J= 16.4 Hz), 3.47(1H,m), 3.80(3H,s), 4.05(1H,d,J=16.4 Hz), 4.89(1H,d,J=15.4 Hz), 5.04(1H,d,J=15.4 Hz), 5.55(1H, quintet, J=6.6 Hz), 6.70–7.00(6H,m), 7.15–7.60(7H,m), 7.65–7.90(4H,m).

Working Example 61

1-Benzyl-5-(phthalimidoacetyl)-4-styryl-1,3,4,5-tetrahydro-1,5-benzodiazepin-2(2H)-one The titled compound was synthesized in substantially the same manner as in Working Example 46. Yield 89%. m.p. 183°–184° C.

$^1$H NMR(CDCl$_3$) δ: 2.64(1H,t,J=12.8 Hz), 2.74(1H,dd, J=12.8, 6.0 Hz), 3.24(1H,d,J=16.6 Hz), 3.99(1H,d,J=16.6 Hz), 4.88(1H,d,J=15.0 Hz), 5.48(1H,d,J=15.0 Hz), 5.85(1H, dt,J=12.0, 6.0 Hz), 6.02(1H,dd,J=15.6, 6.0 Hz), 6.59(1H,d, J=15.6 Hz), 7.10–7.60(14H,m), 7.60–7.90(4H,m).

Working Example 62

(3aR*,10aS*)-9-Benzyl-4-(2-phthalimidoethyl)-2,3,3a,4,9,10a-hexahydrobenzo[b]cyclopenta[e][1,4]-diazepin-10(1H)-one To a solution of phthalimidoacetaldehyde diethyl acetal (790 mg, 3.0 mmol) in acetic acid (2.5 mL) was added conc.HCl (0.1 mL). The mixture was stirred for 80 minutes at 50° C. The reaction mixture was cooled to room temperature, to which was added (3aR*,10aS*)-9-benzyl-2,3,3a,4,9,10a-hexahydrobenzo[b]cyclopenta [e][1,4] diazepin-10(1H)-one (877 mg, 3.0 mmol), and the mixture was stirred for 25 minutes at room temperatures. To this solution was added, sodium triacetoxyborohydride (805 mg, 3.9 mmol) portionwise, and the mixture was stirred for 40 minutes at 45° C. The reaction mixture was cooled to room temperatures, to which were added dichloromethane (10 mL) and water (10 mL). The aqueous layer was separated, and the organic layer was washed with water and a saturated aqueous solution of sodium hydrogencarbonate, dried over magnesium sulfate and subjected to filtration. The filtrate was concentrated under reduced pressure. The concentrate was purified by silica-gel column chromatography (chloroform-methanol 20:1), followed by crystallization from ethanol-hexane to give 0.80 g (yield 57%) the titled compound. The sample for analytical experiment was prepared by recrystallization from dichloromethane-ethanol-hexane. m.p. 142.0°–142.6° C.

$^1$H NMR(CDCl$_3$) δ: 1.4–1.8(3H,m), 1.9–2.2(2H,m), 2.25–2.45(1H,m), 2.78(1H,t,J=6.8 Hz), 3.2–3.6(5H,m), 4.85 (1H,d,J=15.4 Hz), 5.10(1H,d,J=15.4 Hz), 7.0–7.4(9H,m), 7.65–7.9(4H,m).

Working Example 63

(3aR*,10aS*)-9-Benzyl-4-methyl-2,3,3a,4,9,10a-hexahydrobenzo[b]cyclopenta[e][1,4]diazepin-10 (1H)-one To a solution of (3aR*,10aS*)-9-benzyl-2,3,3a,4,9,10a-hexahydrobenzo[b]cyclopenta[e][1,4]-diazepin-10(1H)-one (2.93 g, 10 mmol) in N,N-dimethylformamide (20 mL) were added sodium hydride (60% liquid paraffin dispersion, 0.41 g, 10 mmol) and methyl iodide (1.3 mL, 21 mmol). The mixture was stirred for 13 hours at 80° C. To the reaction mixture were added water and, then, a saturated aqueous solution of sodium hydrogencarbonate. The mixture was subjected extraction with ethyl acetate three times. Organic layers were combined and washed with water and, then, with a saturated aqueous solution of sodium hydrogencarbonate, which was dried over sodium sulfate, followed by filtration and concentration under reduced pressure. The concentrate was purified by silica-gel column chromatography (hexane-ethyl acetate 10:1) to give 2.52 g (yield 82%) of the titled compound. The sample for analytical experiment was prepared by recrystallization from methanol. m.p. 123°–125° C.

$^1$H NMR(CDCl$_3$) δ: 1.5–2.2(5H,m), 2.35–2.5(1H,m), 2.71(3H,s), 2.83(1H,t,J=7.0 Hz), 3.25–3.4(1H,m), 4.96(1H, d,J=15.8 Hz), 5.18(1H,d,J=15.8 Hz), 6.9–7.3(9H,m).

Working Example 64

(3aR*,10aS*)-4-Acetyl-9-benzyl-2,3,3a,4,9,10a-hexahydrobenzo[b]cyclopenta[e][1,4]diazepin-10(1H)-one A mixture of (3aR*,10aS*)-9-benzyl-2,3,3a,4,9,10a-hexahydrobenzo[b]cyclopenta[e][1,4]diazepin-10(1H)-one (1.47 g, 5.0 mmol) and acetic anhydride (5 mL) was stirred for 35 minutes at 100° C. Resulting crystalline precipitate was collected by filtration, which was washed with ethanol to give 1.29 g (yield 77%) of the titled compound, m.p. 209°–210° C.

$^1$H NMR(CDCl$_3$) δ: 1.1–1.3(1H,m), 1.22(3H,s), 1.3–1.4(2H,m), 1.5–1.7(1H,m), 1.7–1.9(1H,m), 2.0–2.2(1H,m), 3.14(1H,dt,J=12.0, 9.0 Hz), 4.62(1H,d,J=14.9 Hz), 5.62(1H, d,J=14.9 Hz), 5.86(1H,ddd,J=9.3, 8.6, 4.1 Hz), 6.95–7.0(1H, m), 7.15–7.25(6H,m), 7.4–7.45(2H,m).

Working Example 65

(3aR*,10aS*)-9-Benzyl-4-(2H-3-hydroxy-1-oxo-1,3-dihydroisoindole-2-acetyl)-2,3,3a,4,9,10a-hexahydrobenzo[b]cyclopenta[e][1,4]diazepin-10(1H)-one In a mixture of chloroform (8 mL) and methanol (8 mL) was dissolved (3aR*,10aS*)-9-benzyl-4-(phthalimidoacetyl)-2,3,3a,4,9,10a-hexahydrobenzo[b]cyclopenta[e][1,4]diazepin-10(1H)-one (623 mg, 1.3 mmol). The solution was cooled to 0° C. under nitrogen atmosphere. To this solution was added sodium borohydride (98 mg, 2.6 mmol), and the mixture was stirred for 25 min at the same temperature. The mixture was made acidic with 1N-hydrochloric acid then neutralized with a saturated aqueous solution of sodium hydrogen carbonate. This mixture was subjected to extraction twice with dichloromethane. Organic layers were combined, washed with water and dried over magnesium sulfate, which was subjected to filtration, and the filtrate was concentrated under reduced pressure. The concentrate was crystallized from chloroform-ethanol to give 461 mg (yield 73%) of the titled compound, m.p. 224°–228° C.

$^1$H NMR(CDCl$_3$) δ: 1.0–1.5(3H,m), 1.5–1.9(2H,m), 2.0–2.2(1H,m), 2.21(0.4H,d,J=17.0 Hz), 3.05–3.25(1H,m), 3.30 (0.6H,d,J=16.9 Hz), 3.51(0.6H,d,J=9.8 Hz), 3.97(0.6H,d,J=16.9 Hz), 4.16(0.4H,d,J=17.0 Hz), 4.60(0.4H,d,J=14.6 Hz), 4.89(0.4H,d,J=8.2 Hz), 5.15(1.2H,s), 5.53(0.4H,d,J=8.2 Hz), 5.67(0.4H,d,J=14.6 Hz), 5.7–5.9(1H,m), 5.92(0.6H,d, J=10.2 Hz), 7.2–7.8(13H,m).

Working Example 66

(3aR*,10aS*)-9-Benzyl-4-(2H-3-hydroxy-1-oxo-1,3-dihydroisoindole-2-acetyl)-1,2,3,3a,4,9,10,10a-octahydrobenzo[b]cyclopenta[e][1,4]diazepine Employing (3aR*,10aS*)-9-benzyl-4-(phthalimidoacetyl)-1,2,3,3a,4,9,10,10a-octahydrobenzo[b]cyclopenta[e][1,4]diazepine, the titled compound was synthesized by substantially the same procedure as in Working Example 65. Yield 81%. m.p. 184°–197° C.

$^1$H NMR(CDCl$_3$) δ: 1.1–2.0(6H,m), 2.3–2.5(1H,m), 2.95 (0.45H,dd,J=14.2, 6.2 Hz), 3.03(0.55H,dd,J=14.3, 5.1 Hz), 3.54(0.45H,d,J=17.2 Hz), 3.80(0.45H, dd, J=14.2, 2.6 Hz), 3.95(0.55H,d,J=16.8 Hz), 4.1–4.15(0.55H,m), 4.23(0.45H, d,J=10.6 Hz), 4.25–4.4(0.45H,m), 4.33(0.55H,d,J=16.8 Hz), 4.39(0.45H,d,J=16.5 Hz), 4.50(0.55H,d,J=16.8 Hz), 4.62 (0.45H,d,J=16.5 Hz), 4.67(0.55H,d,J=16.8 Hz), 4.83(0.55H, d,J=9.8 Hz), 5.15–5.35(1H,m), 5.80(0.55H,d,J=9.4 Hz), 5.84(0.45H,d,J=10.2 Hz), 6.7–7.8(13H,m).

Working Example 67

(3aR*,10aS*)-4-(phthalimidoacetyl)-9-(3,5,6-trimethyl-1,4-benzoquinon-2-ylmethyl)-2,3,3a,4,9,10a-hexahydrobenzo[b]cyclopenta[e][1,4]diazepin-10(1H)-one In a mixture of acetonitrile (3 mL) and water (2 mL) was suspended (3aR*,10aS*)-9-(2,5-dimethoxy-3,4,6-trimethylbenzyl)-4-(phthalimidoacetyl)-2,3,3a,4,9,10a-hexahydrobenzo[b]cyclopenta[e][1,4]diazepin-10(1H)-one (0.5 g, 0.86 mmol). To the suspension was added, while stirring, a solution of ammonium cerium (IV) nitrate (1.4 g, 2.55 mmol) in a mixture of acetonitrile (2 mL) and water (2 mL). The reaction mixture was stirred for one hour, which was diluted with water, followed by extraction with chloroform. The extract was washed with water and dried, then the solvent was distilled off. The residue was crystallized from ethyl acetate to give 300 mg (yield 63%) of the titled compound, m.p. 258°–260° C.

$^1$H NMR(CDCl$_3$) δ: 0.80–1.15(2H,m), 1.20–1.50(2H,m), 1.50–2.20(3H,m), 1.96(3H,s), 2.00(3H,s), 2.98(1H,dt,J=12.2, 9.2 Hz), 4.14(1H,d,J=16.6 Hz), 4.49(1H,d,J=16.6 Hz), 4.69(1H,d,J=14.2 Hz), 5.04(1H,d,J=14.2 Hz), 5.60(1H,dt,J=9.4, 3.8 Hz), 7.30–7.90(8H,m).

Working Example 68

(3aR*,10aS*)-4-(Aminoacetyl)-9-benzyl-2,3,3a,4,9,10a-hexahydrobenzo[b]cyclopenta[e][1,4]diazepin-10(1H)-one A suspension of (3aR*,10aS*)-9-benzyl-4-(phthalimidoacetyl)-2,3,3a,4,9,10a-hexahydrobenzo[b]cyclopenta[e][1,4]diazepin-10(1H)-one (9.82 g, 20 mmol) and hydrazine monohydrate (2.31 g, 46 mmol) in ethanol (200 mL) was refluxed for 3.5 hours. The reaction mixture was cooled, which was subjected to filtration. The filtrate was washed with chloroform, which was concentrated under reduced pressure. The concentrate was suspended in chloroform, which was again subjected to filtration. The filtrate was concentrated under reduced pressure. The concentrate was crystallized from dichloromethane-hexane to give 5.62 g (yield 80%). The sample for analytical experiment was prepared by recrystallization from dichloromethane-diisopropylether. m.p. 163°–165° C.

$^1$H NMR(CDCl$_3$) δ: 1.0–1.9(5H,m), 1.65(1H,s,J=17.2 Hz), 2.0–2.2(1H,m), 2.83(1H,s,J=17.2 Hz), 3.16(1H,dt,J=

12.0, 9.1 Hz), 4.56(1H,d,J=14.9 Hz), 5.65(1H,d,J=14.9 Hz), 5.87(1H,td,J=8.8, 4.0 Hz), 6.99(1H,d,J=7.8 Hz), 7.15– 7.3 (6H,m), 7.45(2H,d,J=4.2 Hz). The proton signal of NH$_2$ group was too broad to detect.

Working Example 69

(3aR*,10aS*)-9-Benzyl-4-((4-chlorophthalimido) acetyl)-2,3,3a,4,9,10a-hexahydrobenzo[b]cyclopenta [e][1,4]-diazepin-10(1H)-one A suspension of (3aR*,10aS*)-4-(aminoacetyl)-9-benzyl-2,3,3a,4,9,10a-hexahydrobenzo[b]cyclopenta-[e][1,4] diazepin-10(1H)-one (0.58 g, 1.7 mmol) and 4-chlorophthalic anhydride (0.31 g, 1.7 mmol) in toluene (10 mL) was refluxed for 3.5 hours using a Dean-Stark water separator. The reaction mixture was left standing for cooling at room temperatures, to which was added hexane. The resulting solid was collected by filtration, which was recrystallized from chloroform-hexane to give 0.66 g (yield 75%) of the titled compound, m.p. 237°–238° C.

$^1$H NMR(CDCl$_3$) δ: 1.0–1.5(3H,m), 1.5–2.0(2H,m), 2.0–2.25(1H,m), 3.18(1H,dt,J=12.4, 8.9 Hz), 3.35(1H,d,J=17.3 Hz), 4.02(1H,d,J=17.3 Hz), 5.00(1H,d,J=15.2 Hz), 5.38 (1H,d,J=15.2 Hz), 5.78(1H,ddd,J=9.3, 8.2, 4.2 Hz), 7.2–7.5 (9H,m), 7.67(1H,dd,J=8.1, 1.9 Hz), 7.75–7.85(2H,m).

Working Example 70

(3aR*,10aS*)-9-Benzyl-4-((4-fluorophthalimido) acetyl)-2,3,3a,4,9,10a-hexahydrobenzo[b]cyclopenta [e][1,4]-diazepin-10(1H)-one A suspension of (3aR*,10aS*)-4-(aminoacetyl)-9-benzyl-2,3,3a,4,9,10a-hexahydrobenzo[b]cyclopenta-[e][1,4] diazepin-10(1H)-one (490 mg, 1.4 mmol) and 4-fluorophthalic acid anhydride (233 mg, 1.4 mmol) in xylene (3 mL) was stirred for 30 minutes at 140° C. The reaction mixture was left standing for cooling at room temperature, to which was added hexane (5 mL). The resulting solid was collected by filtration, followed by recrystallization from dichloromethane-hexane to give 436 mg (yield 62%) of the titled compound, m.p. 235°–236° C.

$^1$H NMR(CDCl$_3$) δ: 1.1–1.5(3H,m), 1.5–1.9(2H,m), 2.0–2.25(1H,m), 3.18(1H,dt,J=12.0, 9.1 Hz), 3.35(1H,d,J=16.6 Hz), 4.02(1H,d,J=16.6 Hz), 5.00(1H,d,J=15.2 Hz), 5.38 (1H,d,J=15.2 Hz), 5.78(1H,ddd,J=9.2, 8.2, 3.8 Hz), 7.2–7.5 (10H,m), 7.52(1H,dd,J=7.1, 2.3 Hz), 7.85(1H,dd,J=8.0, 4.4 Hz).

Working Example 71

(3aR*,10aS*)-9-Benzyl-4-((4-methylphthalimido) acetyl)-2,3,3a,4,9,10a-hexahydrobenzo[b]cyclopenta [e][1,4]diazepin-10(1H)-one Using 4-methylphthalic anhydride, the titled compound was synthesized by substantially the same procedure as in Working Example 70. Yield 78%. m.p. 237.4°–237.9° C. (chloroform-hexane)

$^1$H NMR(CDCl$_3$) δ: 1.1–1.5(3H,m), 1.5–2.0(2H,m), 2.0–2.25(1H,m), 2.50(3H,s), 3.18(1H,dt,J=12.0, 9.1 Hz), 3.38(1H,d,J=16.6 Hz), 4.00(1H,d,J=16.6 Hz), 5.02(1H,d,J=15.4 Hz), 5.36(1H,d,J=15.4 Hz), 5.7–5.85(1H,m), 7.2–7.6 (10H,m), 7.64(1H,d,J=0.8 Hz), 7.72(1H,d,J=7.6 Hz).

Working Example 72

(3aR*,10aS*)-9-Benzyl-4-((3-nitrophthalimido) acetyl)-2,3,3a,4,9,10a-hexahydrobenzo[b]cyclopenta [e][1,4]-diazepin-10(1H)-one Using 3-nitrophthalic acid anhydride, the titled compound was synthesized in substantially the same manner as in Working Example 70. Yield 61%. m.p. 238.5°–239.5° C. (chloroform-ethanol).

$^1$H NMR(CDCl$_3$) δ: 1.0–1.5(3H,m), 1.5–1.95(2H,m), 2.0–2.25(1H,m), 3.17(1H,dt,J=12.0, 9.1 Hz), 3.32(1H,d,J=16.6 Hz), 4.03(1H,d,J=16.6 Hz), 4.91(1H,d,J=15.2 Hz), 5.47 (1H,d,J=15.2 Hz), 5.75(1H,ddd,J=9.4, 8.0, 4.1 Hz), 7.2–7.5 (9H,m), 7.85–7.95(1H,m), 8.1–8.15(2H,m).

Working Example 73

(3aR*,10aS*)-9-Benzyl-4-((3-hydroxyphthalimido) acetyl)-2,3,3a,4,9,10a-hexahydrobenzo[b]cyclopenta [e][1,4)-diazepin-10(1H)-one Using 3-hydroxyphthalic anhydride, the titled compound was synthesized by substantially the same procedure as in Working Example 70. Yield 64%. m.p. 271.5°–272.0° C. (chloroform-ethanol-diethyl ether).

$^1$H NMR(CDCl$_3$) δ: 1.05–1.95(5H,m), 2.0–2.25(1H,m), 3.19(1H,d,J=11.8, 9.2 Hz), 3.31(1H,d,J=16.7 Hz), 3.99(1H, d,J=16.7 Hz), 5.00(1H,d,J=15.2 Hz), 5.38(1H,d,J=15.2 Hz), 5.79(1H,ddd,J=9.1, 8.3, 3.9 Hz), 7.16(1H,d,J=8.6 Hz), 7.1–7.8(11H,m), 7.58(1H,dd,J=8.0, 7.4 Hz).

Working Example 74

(3aR*,10aS*)-9-Benzyl-4-(naphthalene-2,3-dicarboximidoacetyl)-2,3,3a,4,9,10a-hexahydrobenzo[b]cyclopenta[e][1,4]diazepin-10 (1H)-one Using naphthalene-2,3-dicarboxylic acid anhydride, the titled compound was synthesized by substantially the same procedure as in Working Example 70. Yield 40%. m.p. 297.7°–298.4° C. (chloroform-hexane).

$^1$H NMR(CDCl$_3$) δ: 1.1–1.5(3H,m), 1.5–2.0(2H,m), 2.0–2.3(1H,m), 3.19(1H,dt,J=12.4, 9.2 Hz), 3.48(1H,d,J=16.5 Hz), 4.10(1H,dt,J=16.5 Hz), 5.04(1H,d,J=15.4 Hz), 5.38(1H,d,J=15.4 Hz), 5.81(1H,ddd,J=9.3, 8.3, 4.1 Hz), 7.2–7.5(9H,m), 7.65–7.75(2H,m), 8.0–8.1(2H,m), 8.34(2H, s).

Working Example 75

(3aR*,10aS*)-9-Benzyl-4-(naphthalene-1,8-dicarboximidoacetyl)-2,3,3a,4,9,10a-hexahydrobenzo[b]cyclopenta[e][1,4]diazepin-10 (1H)-one Using naphthalene-1,8-dicarboxylic acid anhydride, the titled compound was synthesized by substantially the same procedure as in Working Example 70. Yield 64%. m.p. 287°–288° C. (dichloromethane-hexane).

$^1$H NMR(CDCl$_3$) δ: 1.1–1.5(3H,m), 1.5–2.0(2H,m), 2.0–2.3(1H,m), 3.20(1H,dt,J=11.6, 9.3 Hz), 4.25(1H,d,J=16.0 Hz), 4.63(1H,d,J=16.0 Hz), 5.16(1H,d,J=15.8 Hz), 5.32 (1H,d,J=15.8 Hz), 5.87(1H,ddd,J=9.2, 8.4, 4.0 Hz), 7.2–7.5 (8H,m), 7.59(1H,d,J=8.2 Hz), 7.7–7.8(2H,m), 8.22(2H,dd, J=8.2, 1.0 Hz), 8.60(2H,dd,J=7.1, 0.9 Hz).

Working Example 76

9-Benzyl-4-(2H-1,3-dioxo-1,3,4,5,6,7-hexahydroisoindole-2-acetyl)-2,3,3a,4,9,10a-hexahydrobenzo[b]cyclopenta[e][1,4]diazepin-10 (1H)-one Using 3,4,5,6-tetrahydrophthalic anhydride, synthesis was carried out in substantially the same manner as in Working Example 70 to give a mixture of cis-compound and trans-compound (2:1). Yield 64%. m.p. 194.6°–195.0° C. (ethanol-hexane).

¹H NMR(CDCl₃) δ: 1.0–2.4(14H,m), 2.8–3.0(0.33H,m), 3.02(0.33H,d,J=17.0 Hz), 3.05–3.25(0.67H,m), 3.17(0.67H, d,J=16.8 Hz), 3.72(0.33H,d,J=17.0 Hz), 3.81(0.67H,d,J=16.8 Hz), 4.05–4.2(0.33H,m), 4.57(0.33H,d,J=14.6 Hz), 4.96(0.67H,d,J=15.6 Hz), 5.37(0.67H,d,J=15.6 Hz), 5.7–5.8 (0.67H,m), 5.75(0.33H,d,J=14.6 Hz), 7.15–7.5(9H,m).

Working Example 77

(3aR*,10aS*)-9-Benzyl-4-(1,3-dioxo-1,2,3,4-tetrahydroisoquinoline-2-acetyl)-2,3,3a,4,9,10a-hexahydrobenzo[b]cyclopenta[e][1,4]diazepin-10 (1H)-one Using homophthalic anhydride, the titled compound was synthesized by substantially the same procedure as in Working Example 70. Yield 35%. m.p. 237°–238° C. (chloroform-ethanol).

¹H NMR(CDCl₃) δ: 1.1–1.5(3H,m), 1.5–2.0(2H,m), 2.0–2.3(1H,m), 3.19(1H,dt,J=11.8, 9.2 Hz), 4.00(1H,d,J=6.0 Hz), 4.07(2H,s), 4.41(1H,dt,J=16.0 Hz), 5.13(1H,d,J=15.6 Hz), 5.26(1H,d,J=15.6 Hz), 5.75–5.9(1H,m), 7.2–7.65(12H, m), 8.19(1H,dd,J=7.9, 1.3 Hz).

Working Example 78

(3aR*,10aS*)-9-Benzyl-4(pyridine-2,3-dicarboxyimidoacetyl)-2,3,3a,4,9,10a-hexahydrobenzo [b]cyclopenta[e][1,4]diazepin-10 (1H)-one A mixture of (3aR*,10aS*)-4-(aminoacetyl)-9-benzyl-2, 3,3a,4,9,10a-hexahydrobenzo[b]cyclopenta [e][1,4] diazepin-10(1H)-one (420 mg, 1.2 mmol), pyridine-2,3-dicarboxylic acid anhydride (179 mg, 1.2 mmol) and xylene (3 mL) was stirred for 2.5 hours at 140° C. The reaction mixture was left standing for cooling at room temperature, to which was added hexane (5 mL). The resulting solid matter was collected by filtration, which was dissolved in dichloromethane. The solution was washed with 1N aqueous solution of NaOH, water and a saturated aqueous solution of sodium chloride, which was dried over magnesium sulfate and subjected to filtration, and the filtrate was concentrated under reduced pressure. The concentrate was purified by silica-gel column chromatography (hexane-ethyl acetate 1:3), followed by crystallization from chloroform-hexane to give 131 mg (yield 23%) of the titled compound, m.p. 246.5°–247.5° C.

¹H NMR(CDCl₃) δ: 1.1–2.0(5H,m), 2.0–2.25(1H,m), 3.18(1H,dt,J=12.2, 9.1 Hz), 3.40(1H,d,J=16.5 Hz), 4.10(1H, d,J=16.5 Hz), 5.41(1H,d,J=15.4 Hz), 5.78(1H,ddd,J=9.1, 8.4, 4.1 Hz), 7.2–7.5(9H,m), 7.61(1H,dd,J=7.7, 4.7 Hz), 8.17(1H,dd,J=7.6, 1.4 Hz), 8.97(1H,dd,J=4.8, 1.4 Hz).

Working Example 79

2-(2-((3aR*,10aS*)-9-Benzyl-10-oxo-1,2,3,3a,4,9, 10,10a-octahydrobenzo[b]cyclopenta[e][1,4] diazepin-4-yl)-2-oxoethyl)-2H-1,3-dioxo-1,3-dihydroisoindole-5-carboxylic acid A mixture of (3aR*,10aS*)-4-(aminoacetyl)-9-benzyl-2, 3,3a,4,9,10a-hexahydrobenzo[b]cyclopenta [e][1,4] diazepin-10(1H)-one (1.26 g, 3.6 mmol), trimellitic acid anhydride (692 mg, 3.6 mmol) and N,N-dimethylformamide (3 mL) was stirred for 30 minutes at room temperature and for one hour at 145° C. The reaction mixture was concentrated under reduced pressure. The concentrate was crystallized from methanol-diethylether to give 736 mg (yield 39%) of the titled compound, m.p. 295°–297° C.

¹H NMR(DMSO-d₆) δ: 1.0–1.5(3H,m), 1.5–1.9(2H,m), 1.9–2.2(1H,m), 3.0–3.2(1H,m), 3.44(1H,d,J=16.6 Hz), 4.16 (1H,d,J=16.6 Hz), 5.08(1H,d,J=16.2 Hz), 5.20(1H,d,J=16.2 Hz), 5.55–5.7(1H,m), 7.0–7.6(9H,m), 8.04(1H,d,J=8.0 Hz), 8.27(1H,d,J=0.8 Hz), 8.39(1H,dd,J=7.9, 1.3 Hz).

The proton signal of COOH was too broad to detect.

Working Example 80

(3aR*,10aS*)-9-Benzyl-4-(cis-2H-1,3-dioxo-1,3,3a, 4,7,7a-hexahydroisoindole-2-acetyl)-2,3,3a,4,9,10a-hexahydrobenzo[b]cyclopenta[e][1,4]-diazepin-10 (1H)-one To a solution of (3aR*,10aS*)-4-(aminoacetyl)-9-benzyl-2,3,3a,4,9,10a-hexahydrobenzo[b]cyclopenta [e][1,4] diazepin-10(1H)-one (420 mg, 1.2 mmol) in dichloromethane (5 mL) was added dropwise a solution of cis-1, 2,3,6-tetraphthalic anhydride (183 mg, 1.1 mmol) in dichloromethane (2 mL). The mixture was stirred for 10 minutes at room temperature, to which were added sodium acetate (99 mg, 1.2 mmol) and acetic anhydride (3 mL), then dichloromethane was distilled off under atmospheric pressure, and the residue was stirred for 25 minutes at 100° C. The reaction mixture was left standing for cooling at room temperature, to which was added water (5 mL), and the mixture was stirred vigorously. The reaction mixture was subjected to extraction twice with dichloromethane. Organic layers were combined and washed with water, a saturated aqueous solution of sodium hydrogencarbonate and a saturated aqueous solution of sodium chloride, dried over magnesium sulfate, which was then subjected to filtration, followed by concentration under reduced pressure. The concentrate was crystallized from ethanol-diisopropylether to give 400 mg (yield 69%) of the titled compound, m.p. 183°–185° C.

¹H NMR(CDCl₃) δ: 1.0–1.5(3H,m), 1.5–2.0(2H,m), 2.0–2.4(3H,m), 2.45–2.65(2H,m), 3.05–3.25(3H,m), 3.25 (1H,d,J=16.3 Hz), 3.84(1H,d,J=16.3 Hz), 5.04(1H,d,J=15.4 Hz), 5.24(1H,d,J=15.4 Hz), 5.7–5.85(1H,m), 5.85–5.95(2H, m), 7.15–7.45(9H,m).

Working Example 81

(3aR*,10aS*)-9-Benzyl-4-(benzamidoacetyl)-2,3,3a, 4,9,10a-hexahydrobenzo[b]cyclopenta[e][1,4]-diazepin-10(1H)-one On a water bath kept at 15° C., to a solution of (3aR*, 10aS*)-4-(aminoacetyl)-9-benzyl-4-2,3,3a,4,9,10a-hexahydrobenzo[b]cyclopenta[e][1,4]-diazepin-10(1H)-one (0.88 g, 2.5 mmol) in 1,2-dichloroethane (3 mL) was added dropwise a solution of benzoyl chloride (0.39 g, 2.8 mmol) of 1,2-dichloroethane (2 mL). The mixture was stirred for 5 minutes at the same temperature, to which was added a saturated aqueous solution of sodium hydrogencarbonate (3 mL), and the mixture was stirred for further 5 minutes. The aqueous layer was separated, and the organic layer was washed with water, dried over magnesium sulfate, subjected to filtration and concentrated under reduced pressure. The concentrate was crystallized from diethylether-hexane to give 1.08 g (yield 95%) of the titled compound, m.p. 201°–203° C.

¹H NMR(CDCl₃) δ: 1.0–1.9(5H,m), 2.0–2.25(1H,m), 2.24(1H,dd,J=18.3, 3.3 Hz), 3.18(1H,dt,J=12.2, 8.9 Hz), 3.88(1H,dd,J=17.9, 5.1 Hz), 4.65(1H,d,J=14.8 Hz), 5.55 (1H,d,J=14.8 Hz), 5.8–6.0(1H,m), 6.7–6.9(1H,m), 7.0–7.35 (7H,m), 7.4–7.6(5H,m), 7.7–7.8(2H,m).

Working Example 82

9-Benzyl-4-((2-methoxybenzamido)acetyl)-2,3,3a,4, 9,10a-hexahydrobenzo[b]cyclopenta[e][1,4] diazepin-10(1H)-one Using 2-methoxybenzoyl chloride, synthesis was conducted in substantially the same manner as in Working Example 81 to give a mixture of cis-compound and trans-compound (4:1). Yield 64%. m.p. 187°–188° C. (ethyl acetate-hexane).

$^1$H NMR(CDCl$_3$) δ: 1.0–1.5(3H,m), 1.5–2.0(2H,m), 2.0–2.35(1H,m), 2.35–2.5(0.2H,m), 2.45(0.8H,dd,J=18.3, 3.3 Hz), 2.8–2.9(0.2H,m), 3.18(0.8H,dt,J=12.2, 9.1 Hz), 3.9–4.2(0.4H,m), 3.98(0.8H,dd,J=18.5, 4.9 Hz), 4.03(0.6H, s), 4.07(2.4H,s), 4.57(0.2H,d,J=14.6 Hz), 4.75(0.8H,d,J= 15.0 Hz), 5.42(0.8H,d,J=15.0 Hz), 5.63(0.2H,d,J=14.6 Hz), 5.93(0.8H,ddd,J=9.3, 8.2, 4.2 Hz), 6.95–7.5(12H,m), 8.05–8.15(1H,m), 8.3–8.4(0.2H,m), 8.55–8.65(0.8H,m).

Working Example 83

(3aR*,10aS*)-9-Benzyl-4-((3-methoxybenzamido) acetyl)-2,3,3a,4,9,10a-hexahydrobenzo[b]cyclopenta [e][1,4]-diazepin-10(1H)-one Using 3-methoxybenzoyl chloride, the titled compound was synthesized in substantially the same manner as in Working Example 81. Yield 68%. m.p. 160°–161° C. (diethylether)

$^1$H NMR(CDCl$_3$) δ: 1.00–1.45(3H,m), 1.50–1.89(2H,m), 2.05–2.22(1H,m), 2.23(1H,dd,J=18.0, 3.3 Hz), 3.18(0.18H, dt,J=12.0, 8.8 Hz), 3.85(3H,s), 3.88(1H,dd,J=18.0, 5.0 Hz), 4.65(1H,d,J=14.6 Hz), 5.55(1H,d,J=14.6 Hz), 5.86–5.95 (1H,m), 6.80(1H,br s), 7.02–7.58(13H,m).

Working Example 84

(3aR*,10aS*)-9-Benzyl-4-((4-methoxybenzamido) acetyl)-2,3,3a,4,9,10a-hexahydrobenzo[b]cyclopenta [e][1,4]-diazepin-10(1H)-one Using 4-methoxybenzoyl chloride, the titled compound was synthesized in substantially the same manner as in Working Example 81. Yield 93%. m.p. 160°–161° C. (ethyl acetate-hexane).

$^1$H NMR(CDCl$_3$) δ: 1.0–1.9(5H,m), 2.0–2.25(1H,m), 2.25(1H,dd,J=18.3, 3.3 Hz), 3.18(1H,dt,J=12.4, 9.0 Hz), 3.86(3H,s), 3.88(1H,dd,J=18.3, 5.1 Hz), 4.67(1H,d,J=14.9 Hz), 5.52(1H,d,J=14.9 Hz), 5.8–6.0(1H,m), 6.6–6.8(1H,m), 6.9–7.0(2H,m), 7.0–7.35(7H,m), 7.4–7.55(2H,m), 7.7–7.8 (2H,m).

Working Example 85

(3aR*,10aS*)-9-Benzyl-4-((2,6-dimethoxybenzamido) acetyl)-2,3,3a,4,9,10a-hexahydrobenzo[b]cyclopenta [e][1,4]diazepin-10 (1H)-one Using 2,6-dimethoxybenzoyl chloride, the titled compound was synthesized in substantially the same manner as in Working Example 81. Yield 53%. m.p. 182°–184° C. (diethylether).

$^1$H NMR(CDCl$_3$) δ: 1.05–1.44(3H,m), 1.56–1.92(2H,m), 2.03–2.25(1H,m), 2.57(1H,dd,J=18.4, 3.4 Hz), 3.17(1H,dt, J=12.4, 8.6 Hz), 3.82(6H,s), 4.00(1H,dd,J=18.4, 5.0 Hz), 4.85(1H,d,J=15.0 Hz), 5.37(1H,d,J=15.0 Hz), 5.84–5.94 (1H,m), 6.50–6.65(3H,m), 7.11–7.47(10H,m).

Working Example 86

(3aR*,10aS*)-9-Benzyl-4-((3,4-dimethoxybenzamido) acetyl)-2,3,3a,4,9,10a-hexahydrobenzo[b]cyclopenta [e][1,4]diazepin-10 (1H)-one Using 3,4-dimethoxybenzoyl chloride, the titled compound was synthesized in substantially the same manner as in Working Example 81. Yield 84%. m.p. 174°–176° C. (diethylether).

$^1$H NMR(CDCl$_3$) δ: 1.10–1.47(3H,m), 1.50–1.93(2H,m), 2.03–2.32(2H,m), 3.10–3.27(1H,m), 3.81–3.99(1H,m), 3.95 (6H,s), 4.68(1H,d,J=14.6 Hz), 5.54(1H,d,J=14.6 Hz), 5.83–5.93(1H,m), 6.75(1H,br s), 6.89(1H,d,J=8.4 Hz), 7.04–7.54(11H,m).

Working Example 87

(3aR*,10aS*)-9-Benzyl-4-((3,5-dimethoxybenzamido) acetyl)-2,3,3a,4,9,10a-hexahydrobenzo[b]cyclopenta [e][1,4]diazepin-10 (1H)-one Using 3,5-dimethoxybenzoyl chloride, the titled compound was synthesized in substantially the same manner as in working Example 81. Yield 64%. m.p. 113°–115° C. (diethylether)

$^1$H NMR(CDCl$_3$) δ: 1.03–1.45(3H,m), 1.56–1.91(2H,m), 2.05–2.26(2H,m), 3.18(1H,dt,J=12.2, 8.8 Hz), 3.83(6H,s), 3.85(1H,dd,J=18.2, 5.2 Hz), 4.65(1H,d,J=14.8 Hz), 5.55 (1H,d,J=14.8 Hz), 5.84–5.95(1H,m), 6.58(1H,t,J=2.2 Hz), 6.77(1H,br s), 6.88(2H,d,J=2.2 Hz), 7.11–7.28(7H,m), 7.39–7.55(2H,m).

Working Example 88

(3aR*,10aS*)-9-Benzyl-4-((3,4-methylenedioxybenzamido) acetyl)-2,3,3a,4,9,10a-hexahydrobenzo[b]cyclopenta[e][1,4]diazepin-10 (1H)-one Using 3,4-methylenedioxybenzoyl chloride, the titled compound was synthesized in substantially the same manner as in Working Example 81. Yield 92%. m.p. 174°–176° C. (diethyl ether).

$^1$H NMR(CDCl$_3$) δ: 1.05–1.50(3H,m), 1.53–1.91(2H,m), 2.05–2.23(1H,m), 2.21(1H,dd,J=18.2, 3.4 Hz), 3.11–3.25 (1H,m), 3.85(1H,dd,J=18.2, 5.0 Hz), 4.65(1H,d,J=14.6 Hz), 5.54(1H,d,J=14.6 Hz), 5.83–5.95(1H,m), 6.04(2H,s), 6.66 (1H,br s), 6.85(1H,d,J=8.0 Hz), 7.07–7.50(11H,m).

Working Example 89

(3aR*,10aS*)-4-((2-Acetoxybenzamido)acetyl)-9-benzyl-2,3,3a,4,9,10a-hexahydrobenzo[b]cyclopenta [e(l1,4]-diazepin-10 (1H)-one Using O-acetylsalicyloyl chloride, the titled compound was synthesized in substantially the same manner as in Working Example 81. Yield 48%. Amorphous.

$^1$H NMR(CDCl$_3$) δ: 1.03–1.45(3H,m), 1.53–1.90(2H,m), 2.05– 2.31(1H,m), 2.26(1H,dd,J=18.6, 3.2 Hz), 2.50(3H,s), 3.18(1H,dt,J=12.2, 8.8 Hz), 3.85(1H,dd,J=18.6, 4.8 Hz), 4.63(1H,d,J=14.8 Hz), 5.54(1H,d,J=14.8 Hz), 5.84–5.94 (1H,m), 7.00–7.54(13H,m), 7.94(1H,dd,J=7.8, 1.8 Hz).

Working Example 90

(3aR*,10aS*)-9-Benzyl-4-((2-nitrobenzamido)
acetyl)-2,3,3a,4,9,10a-hexahydrobenzo[b]cyclopenta
[e][1,4]-diazepin-10(1H)-one Using 2-nitrobenzoyl chloride, the titled compound was synthesized in substantially the same manner as in Working Example 81. Yield 62%. m.p. 132°–135° C. (diethylether).

$^1$H NMR(CDCl$_3$) δ: 1.05–1.45(3H,m), 1.50–1.90(2H,m), 2.04–2.18(1H,m), 2.28(1H,dd,J=18.0,3.4 Hz), 3.12(1H,dt, J=12.0, 8.0 Hz), 3.96(1H,dd,J=18.0,5.2 Hz), 4.70(1H,d,J= 14.8 Hz), 5.52(1H,d,J=14.8 Hz), 5.80–5.90(1H,m), 6.59(1H, br s), 7.14–7.46(7H,m), 7.42–7.73(5H,m), 8.02–8.06(1H, m).

Working Example 91

(3aR*,10aS*)-9-Benzyl-4-((3-nitrobenzamino)
acetyl)-2,3,3a,4,9,10a-hexahydrobenzo[b]cyclopenta
[e][1,4]-diazepin-10(1H)-one Using 3-nitrobenzoyl chloride, the titled compound was synthesized in substantially the same manner as in Working Example 81. Yield 77%. m.p. 206°–208° C. (diethylether).

$^1$H NMR(CDCl$_3$) δ: 1.01–1.46(3H,m), 1.57–1.90(2H,m), 2.05–2.32(2H,m), 3.21(1H,dt,J=11.8,8.8 Hz), 3.90(1H,dd,J= 18.0,5.0 Hz), 4.66(1H,d,J=14.6 Hz), 5.58(1H,d,J=14.6 Hz), 5.84–5.96(1H,m), 7.00–7.67(11H,m), 8.07(1H,d,J=7.8 Hz), 8.34–8.38(1H,m), 8.61(1H,br s).

Working Example 92

(3aR*,10aS*)-9-Benzyl-4-((4-nitrobenzamido)
acetyl)-2,3,3a,4,9,10a-hexahydrobenzo[b]cyclopenta
[e][1,4]-diazepin-10(1H)-one Using 4-nitrobenzoyl chloride, the titled compound was synthesized in substantially the same manner as in Working Example 81. Yield 82%. m.p. 231°–233° C. (diethylether).

$^1$H NMR(CDCl$_3$) δ: 1.02–1.43(3H,m), 1.52–1.91(2H,m), 2.10–2.27(2H,m), 3.20(1H,dt,J=12.2,8.8 Hz), 3.85(1H,dd, J=18.4,5.0 Hz), 4.63(1H,d,J=14.6 Hz), 5.58(1H,d,J=14.6 Hz), 5.84–5.94(1H,m), 6.88–7.34(8H,m), 7.46–7.53(2H,m), 7.90–7.96(2H,m), 8.28–8.34(2H,m).

Working Example 93

(3aR*,10aS*)-9-Benzyl-4-((2-pyridinecarboxamide)
acetyl)-2,3,3a,4,9,10a-hexahydrobenzo[b]cyclopenta
[e][1,4]diazepin-10(1H)-one Using picolinoyl chloride hydrochloride, the titled compound was synthesized in substantially the same manner as in Working Example 81. Yield 37%. m.p. 169°–171° C.(diethylether).

$^1$H NMR(CDCl$_3$) δ: 1.01–1.42(3H,m), 1.53–1.90(2H,m), 2.05–2.31(2H,m), 3.18(1H,dt,J=12.0,8.8 Hz), 3.95(1H,dd, J=18.0,6.4 Hz), 4.58(1H,d,J=14.2 Hz), 5.58(1H,d,J=14.2 Hz), 5.86–5.95(1H,m), 6.95–7.50(10H,m), 7.82(1H,dt,J= 7.8,1.6 Hz), 8.09(1H,d,J=7.8 Hz), 8.38(1H,br s), 8.62(1H, d,J=8.8 Hz).

Working Example 94

(3aR*,10aS*)-9-Benzyl-4-((3-pyridinecarboxamido)
acetyl)-2,3,3a,4,9,10a-hexahydrobenzo[b]cyclopenta
[e][1,4]diazepin-10(1H)-one Using Nicotinoylchloride hydrochloride, the titled compound was synthesized in substantially the same manner as in Working Example 81. Yield 68%. m.p.189°–191° C.(diethyether).

$^1$H NMR(CDCl$_3$) δ: 1.03–1.43(3H,m), 1.56–1.91(2H,m), 2.05–2.26(2H,m), 3.19(1H,dt,J=12.6,9.0 Hz), 3.87(1H,dd, J=18.2,5.2 Hz), 4.63(1H,d,J=14.8 Hz), 5.58(1H,d,J=14.8 Hz), 5.84–5.95(1H,m), 6.85(1H,br s), 7.05–7.55(10H,m), 8.04–8.10(1H,m), 8.76(1H,br s), 9.02(1H,br s).

Working Example 95

(3aR*,10aS*)-9-Benzyl-4-((4-pyridinecarboxamido)
acetyl)-2,3,3a,4,9,10a-hexahydrobenzo[b]cyclopenta
[e][1,4]diazepin-10(1H)-one Using isonicotinoyl chloride hydrochloride, the titled compound was synthesized in substantially the same manner as in Working Example 81. Yield 42%. m.p. 196°–199° C. (diethylether).

$^1$H NMR(CDCl$_3$) δ: 1.00–1.51(3H,m), 1.55–1.91(2H,m), 2.05–2.27(2H,m), 3.14–3.29(1H,m), 3.83(1H,dd,J=18.4,5.0 Hz), 4.61(1H,d,J=14.8 Hz), 5.60(1H,d,J=14.8 Hz), 5.84–5.95(1H,m), 6.88–7.63(12H,m), 8.77(2H,d,J=5.2 Hz).

Working Example 96

(3aR*,10aS*)-9-Benzyl-4-((4-
trifluoromethylbenzamido) acetyl)-2,3,3a,4,9,10a-
hexahydrobenzo[b]cyclopenta[e][1,4]diazepin-10
(1H)-one Using 4-(trifluoromethyl)benzoyl chloride, the titled compound was synthesized in substantially the same manner as in Working Example 81. Yield 57%. m.p. 218°–220° C. (diethylether).

$^1$H NMR(CDCl$_3$) δ: 1.02–1.58(3H,m), 1.51–1.90(2H,m), 2.05–2.39(2H,m), 3.19(1H,dt,J=12.4,8.8 Hz), 3.86(1H,dd, J=18.0,4.8 Hz), 4.64(1H,d,J=14.8 Hz), 5.57(1H,d,J=14.8 Hz), 5.84–5.95(1H,m), 6.90(1H,br s), 6.99–7.23(7H,m), 7.40–7.50(2H,m), 7.72(2H,d,J=8.0 Hz), 7.88(2H,d,J=8.0 Hz).

Working Example 97

(3aR*,10aS*)-9-Benzyl-4-((2,6-dimethylbenzamido)
acetyl)-2,3,3a,4,9,10a-hexahydrobenzo[b]cyclopenta
[e][1,4]diazepin-10(1H)-one Using 2,6-dimethyl benzoyl chloride, the titled compound was synthesized in substantially the same manner as in Working Example 81. Yield 38%. m.p. 208°–209° C. (diethylether).

$^1$H NMR(CDCl$_3$) δ: 1.03–1.50(3H,m), 1.51–1.90(2H,m), 2.05–2.39(8H,m), 3.17(1H,dt,J=12.4,8.6 Hz), 4.10(1H,dd, J=18.0,6.2 Hz), 4.75(1H,d,J=14.8 Hz), 5.48(1H,d,J=14.8 Hz), 5.81–5.92(1H,m), 6.23(1H,br s), 7.00–7.52(12H,m).

Working Example 98

(3aR*,10aS*)-9-Benzyl-4-(furan-2-
carboxamidoacetyl)-2,3,3a,4,9,10a-hexahydrobenzo
[b]cyclopenta[e][1,4]diazepin-10(1H)-one Using 2-furoyl chloride, the titled compound was synthesized in substantially the same manner as in Working Example 81. Yield 94%. m.p. 169°–170° C. (ethyl acetate-hexane).

$^1$H NMR(CDCl$_3$) δ: 1.0–1.5(3H,m), 1.5–1.9(2H,m), 2.0–2.2(1H,m), 2.16(1H,dd,J=17.9,3.3 Hz), 3.17(1H,dt,J= 12.4,8.9 Hz), 3.85(1H,dd,J=18.1,5.7 Hz), 4.62(1H,d,J=14.7

Hz), 5.57(1H,d,J=14.7 Hz), 5.89(1H,ddd,J=9.0,8.2,4.0 Hz), 6.49(1H,dd,J=3.5,1.7 Hz), 6.8–6.95(1H,m), 7.0–7.6(11H, m).

Working Example 99

(3aR*,10aS*)-9-Benzyl-4-(thiophene-2-carboxamidoacetyl) -2,3,3a,4,9,10a-hexahydrobenzo[b]cyclopenta[e][1,4]diazepin-10(1H)-one Using 2-thiophene carbonyl chloride, the titled compound was synthesized in substantially the same manner as in Working Example 81. Yield 80%. m.p. 222.7°–223.1° C. (dichloromethane-hexane).

$^1$H NMR(CDCl$_3$) δ: 1.0–1.5(3H,m), 1.5–1.9(2H,m), 2.0–2.2(1H,m), 2.18(1H,dd,J=18.2,3.4 Hz), 3.18(1H,dt,J=12.0,9.0 Hz), 3.84(1H,dd,J=18.4,5.2 Hz), 4.62(1H,d,J=14.6 Hz), 5.57(1H,d,J=14.6 Hz), 5.89(1H,ddd,J=9.2,8.4,4.0 Hz), 6.5 . 6.7(1H,m), 7.0–7.4(8H,m), 7.4–7.6(4H,m).

Working Example 100

(Z)-3-(2-((3aR*,10aS*)-9-Benzyl-10-oxo-1,2,3,3a,4,9, 10,10a-octahydrobenzo[b]cyclopenta [e][1,4]diazepin-4-yl)-2-oxoethylcarbamoyl)acrylic acid A mixture of (3aR*,10aS*)-4-(aminoacetyl)-9-benzyl-2,3,3a,4,9,10a-hexahydrobenzo[b]cyclopenta [e][1,4]diazepin-10(1H)-one (420 mg, 1.2 mmol) and maleic anhydride (118 mg, 1.2 mmol) was stirred for 30 minutes in xylene at 140° C. The reaction mixture was left standing for cooling at room temperature, to which was added hexane (5 mL). The resulting solid was collected by filtration, which was recrystallized from chloroform-ethanol-diethyl ether to give 420 mg (yield 78%) of the titled compound, m.p. 207°–209° C.

$^1$H NMR(DMSO-d$_6$) δ: 1.0–1.9(5H,m), 1.9–2.1(1H,m), 2.1–2.35(1H,m), 3.12(1H,dt,J=11.4,9. 1 Hz), 3.65–3.85(1H, m), 4.80(1H,d,J=15.2 Hz), 5.37(1H,d,J=15.2 Hz), 5.65–5.8 (1H,m), 6.28(1H,d,J=12.4 Hz), 6.53(1H,d,J=12.4 Hz), 7.0–7.65(9H,m), 8.9–9.0(1H,m).

The proton signal of COOH was too broad to detect.

Working Example 101

3-(2-((3aR*,10aS*)-9-Benzyl-10-oxo-1,2,3,3a,4,9,10,10a-octahydrobenzo[b]cyclopenta[e][1,4]diazepin-4-yl)-2-oxoethylcarbamoyl)propionic acid Using succinic anhydride, the titled compound was synthesized in substantially the same manner as in Working Example 100. Yield 54%. m.p. 148°–151° C. (chloroform-hexane).

$^1$H NMR(CDCl$_3$) δ: 1.0–1.5(3H,m), 1.5–1.9(2H,m), 1.95–2.25(1H,m), 2.04(1H,dd,J=18.1,3.5 Hz), 2.4–2.7(4H, m), 3.17(1H,dt,J=12.0,9.1 Hz), 3.72(1H,dd,J=18.1,5.3 Hz), 4.64(1H,d,J=15.0 Hz), 5.53(1H,d,J=15.0 Hz), 5.8–5.9(1H, m), 6.4–6.5(1H,m), 7.0–7.3(7H,m), 7.4–7.55(2H,m).

The proton signal of COOH was too broad to detect.

Working Example 102

(3aR*,10aS*)-4-((2-aminobenzamido)acetyl)-9-benzyl-2,3,3a,4,9,10a-hexahydrobenzo[b]cyclopenta [e][1,4]diazepin-10(1H)-one A mixture of (3aR*,l0aS*)-4-(aminoacetyl)-9-benzyl-2,3,3a,4,9,10a-hexahydrobenzo[b]cyclopenta [e][1,4]diazepin-10(1H)-one (420 mg, 1.2 mmol) and isatoic anhydride (196 mg, 1.2 mmol) was stirred for 30 minutes in xylene at 140° C. The reaction mixture was left standing for cooling at room temperature, to which was added hexane (5 mL). The resulting solid was collected by filtration, which was recrystallized from ethanol-hexane to give 345 mg (yield 58%) of the titled compound. This compound was in good agreement in $^1$H-NMR spectrum with the compound produced in substantially the same manner as in Working Example 106 starting from (3aR*,10aS*)-9-benzyl-4-((2-nitrobenzamido)acetyl)-2,3,3a,4,9,10a-hexahydrobenzo [b]cyclopenta[e][1, 4]diazepin-10(1H)-one. m.p. 179.2°–179.7° C.

$^1$H NMR(CDCl$_3$) δ: 1.0–1.5(3H,m), 1.5–1.9(2H,m), 2.0–2.25(1H,m), 2.15(1H,dd,J=18.1,3.5 Hz), 3.18(1H,dt,J=12.4,8.5 Hz), 3.82(1H,dd,J=18.0,5.2 Hz), 4.61(1H,d,J=14.7 Hz), 5.45(2H,br s), 5.60(1H,d,J=14.7 Hz), 5.8–6.0(1H,m), 6.6–6.75(3H,m), 7.0–7.6(11H,m).

Working Example 103

(3aR*,10aS*)-9-Benzyl-4-((diacetylamino)acetyl)-2,3,3a,4,9,10a-hexahydrobenzo[b]cyclopenta[e][1,4]diazepin-10a(1H)-one]

A solution of (3aR*,10aS*)-4-(aminoacetyl)-9-benzyl-2,3,3a,4,9,10a-hexahydrobenzo[b]cyclopenta [e][1,4]diazepin-10(1H)-one (420 mg, 1.2 mmol) in acetic anhydride was stirred for 10 min at room temperature, followed by refluxing for 4 hours. The reaction mixture was cooled, to which was added water, followed by stirring. The mixture was subjected to extraction twice with chloroform. The organic layers were combined and washed with water, and, then, with a saturated aqueous solution of sodium hydrogencarbonate, which was dried over magnesium sulfate and subjected to filtration. The filtrate was concentrated under reduced pressure. The concentrate was purified by silica-gel column chromatography (chloroform-ethyl acetate 4:1), followed by crystallization from dichloromethane-ethanol-petroleum ether to give 265 mg (yield 51%) of the titled compound, m.p. 142.5°–143.4° C.

$^1$H NMR(CDCl$_3$) δ: 1.05–1.5(3H,m), 1.5–1.95(2H,m), 2.0–2.3(1H,m), 2.27(6H,s), 2.92(1H,d,J=17.1 Hz), 3.16(1H, dt,J=12.2,9.2 Hz), 4.30(1H,d,J=17.1 Hz), 4.99(1H,d,J=15.2 Hz), 5.23(1H,d,J=15.2 Hz), 5.78(1H,ddd,J=9.5,8.2,4.4 Hz), 7.2–7.5(9H,m).

Working Example 104

(3aR*,10aS*)-9-Benzyl-4(2H-1,3-dihydroisoindole-2-acetyl)-2,3,3a,4,9,10a-hexahydrobenzo[b]cyclopenta [e][1,4]diazepin-10(1H)-one A mixture of (3aR*,10aS*)-4-(aminoacetyl)-9-benzyl-2,3,3a,4,9,10a-hexahydrobenzo[b]cyclopenta [e][1,4]diazepin-10(1H)-one(0.87 g, 2.5 mmol), α,α'-dibromo-o-xylene (0.66g, 2.5 mmol), potassium carbonate (1.04 g, 7.5 mmol), tetrahydrofuran (5 mL) and water (4 mL) was refluxed for 6 hours. The reaction mixture was cooled, which was subjected to extraction with ethyl acetate. The extract was washed with water, dried over magnesium sulfate, which was subjected to filtration, and the filtrate was concentrated under reduced pressure. The concentrate was purified by silica-gel column chromatography (hexane-ethyl acetate 1:1→1:2), followed by crystallization from diisopropylether-hexane to give 0.31 g (yield 27%) of the titled compound, m.p. 130°–134° C.

$^1$H NMR(CDCl$_3$) δ: 1.0–1.9(5H,m), 2.0–2.25(1H,m), 2.77(1H,d,J=14.5 Hz), 2.98(1H,d,J=14.5 Hz), 3.1–3.3(1H, m), 3.6–3.85(4H,m), 4.67(1H,d,J=15.4 Hz), 4.92(1H,d,J=15.4 Hz), 5.8–6.0(1H,m), 6.8–7.5(13H,m).

Working Example 105

(3aR*,10aS*)-9-Benzyl-4-(2H-1,3-dihydroisoindole-2-acetyl)-2,3,3a,4,9,10a-hexahydrobenzo[b]cyclopenta [e][1,4]diazepin-10(1H)-one hydrochloride (3aR*,10aS*)-9-Benzyl-4(2H-1,3-dihydroisoindole-2-acetyl)- 2,3,3a,4,9,10a-hexahydrobenzo[b]cyclopenta [e][1,4]diazepin-10(1H)-one produced in Working Example 104 was dissolved in methanol, to which was added a 10% solution of hydrogen chloride-methanol. the solution was concentrated under reduced pressure, and the concentrate was crystallized from ethanol-diethyl ether to give the titled compound, m.p. 170°–177° C.

$^1$H NMR(DMSO-d$_6$) δ: 1.0–1.5(3H,m), 1.5–1.9(2H,m), 1.95–2.2(1H,m), 2.66(1H,d,J=15.8 Hz), 3.05–3.25(1H,m), 4.0–5.2(4H,m), 4.25(1H,d,J=15.8 Hz), 4.96(1H,d,J=15.2 Hz), 5.24(1H,d,J=15.2 Hz), 5.65–5.8(1H,m), 7.15–7.6(13H,m).

Working Example 106

(3aR*,10aS*)-4-((3-Aminophthalimido)acetyl)-9-benzyl-2,3,3a,4,9,10a-hexahydrobenzo[b]cyclopenta [e][1,4]diazepin-10(1H)-one To a suspension of (3aR*,10aS*)-9-benzyl-4-((3-nitrophthalimido)acetyl-2,3,3a,4,9,10a-hexahydrobenzo[b]cyclopenta[e][1,4]diazepin-10(1H)-one (424 mg, 0.81 mmol) and platinum oxide (22 mg) in methanol was added a 10% solution of hydrogen chloride-methanol (0.6 mL). The mixture was stirred for 8 hours at room temperature under hydrogen atmosphere. To the reaction mixture was added N,N-dimethylformamide, and the catalyst was removed by filtration. The filtrate was concentrated under reduced pressure. The concentrate was dissolved in chloroform, which was washed with a IN aqueous solution of sodium hydroxide, water and a saturated aqueous solution of sodium chloride, followed by drying over magnesium sulfate, filtration and concentration under reduced pressure. The concentrate was purified by silica-gel column chromatography (hexane-ethylacetate 2:3→1:2), followed by recrystallization from chloroform-hexane to give 110 mg (yield 27%) of the titled compound, m.p. 25°5–262° C.

$^1$H NMR(CDCl$_3$) δ: 1.1–1.5(3H,m), 1.5–1.9(2H,m), 2.0–2.25(1H,m), 3.18(1H,dt,J=12.4,9.0 Hz), 3.37(1H,d,J=16.5 Hz), 3.97(1H,d,J=16.5 Hz), 5.03(1H,d,J=15.4 Hz), 5.21 (2H,br s), 5.33(1H,d,J=15.4 Hz), 5.7–5.9(1H,m), 6.82(1H,d,J=8.4 Hz), 7.12(1H,d,J=6.8 Hz), 7.2–7.5(10H,m).

Working Example 107

(3aR*,10aS*)-9-Benzyl-4-((3-methoxyphthalimido) acetyl)-2,3,3a,4,9,10a-hexahydrobenzo[b]cyclopenta [e][1,4]diazepin-10(1H)-one To a suspension of (3aR*,10aS*)-9-benzyl-4-((3-hydroxyphthalimido)acetyl)-2,3,3a,4,9,10a-hexahydrobenzo[b]cyclopenta[e][1,4]diazepin-10(1H)-one (343 mg, 0.69 mmol) in N,N-dimethylformamide (3 mL) were added potassium carbonate (115 mg, 0.83 mmol) and methyl iodide (0.10 mL, 1.6 mmol). The mixture was stirred for 4.5 hours at room temperature, to which was added water. The resulting solid was separated by filtration, and the filtrate was subjected to extraction with chloroform. In this organic layer was dissolved the solid previously separated by filtration. The solution was dried over magnesium sulfate, which was subjected to filtration. The filtrate was concentrated under reduced pressure. The concentrate was recrystallized from chloroform-diethylether to give 340 mg (yield 96%) of the titled compound, m.p. 247°–248° C.

$^1$H NMR(CDCl$_3$) δ: 1.05–1.45(3H,m), 1.55–1.9(2H,m), 2.0–2.2(1H,m), 3.16(1H,dt,J=12.0,9.0 Hz), 3.33(1H,d,J=16.4 Hz), 3.89(1H,d,J=16.4 Hz), 4.02(3H,s), 4.90(1H,d,J=15.0 Hz), 5.46(1H,d,J=15.0 Hz), 5.7–5.85(1H,m), 7.19(1H,d,J=8.4 Hz), 7.2–7.55(10H,m), 7.66(1H,dd,J=8.4,7.4 Hz).

Working Example 108

2-(2-((3aR*,10aS*)-9-benzyl-10-oxo-1,2,3,3a,4,9,10,10a-octahydrobenzo[b]cyclopenta[e][1,4] diazepin-4-yl)-2-oxoethyl)-2H-1,3-dioxo-1,3-dihydroisoindole-5-carboxylate To a solution of 2-(2-((3aR*,10aS*)-9-benzyl-10-oxo-1,2,3,3a,4,9,10,10a-octahydrobenzo[b]cyclopenta [e][1,4]diazepin-4-yl)-2-oxoethyl)-2H-1,3,-dioxo-1,3-dihydroisoindole-5-carboxylic acid (1.15 g, 2.2 mmol) in N,N-dimethylformamide (10 mL) were added potassium carbonate (0.6 g, 4.3 mmol) and methyl iodide (1 mL, 16 mmol). The mixture was stirred for one hour at room temperature. To the reaction mixture were added chloroform and water. The aqueous layer was separated. The organic layer was washed with water and a saturated aqueous solution of sodium chloride, which was dried over magnesium sulfate and subjected to filtration, then the filtrate was concentrated under reduced pressure. The concentrate was purified by silica-gel column chromatography (hexane-ethyl acetate 2:1→1:1), which was crystallized from diethylether-hexane to give 293 mg (yield 24%) the titled compound, m.p. 201°–202° C.

$^1$H NMR(CDCl$_3$) δ: 1.1–1.5(3H,m), 1.5–2.0(2H,m), 2.0–2.25(1H,m), 3.18(1H,dt,J=12.4,9.1 Hz), 3.38(1H,d,J=16.4 Hz), 3.99(3H,s), 4.05(1H,d,J=16.4 Hz), 5.00(1H,d,J=15.1 Hz), 5.40(1H,d,J=15.1 Hz), 5.78(1H,ddd,J=9.1,8.2,3.8 Hz), 7.2–7.5(9H,m), 7.92(1H,dd,J=7.7,0.7 Hz), 8.41(1H,dd,J=7.7,1.5 Hz), 8.48(1H,d,J=0.6 Hz).

Working Example 109

(3aR*,10aS*)-4-((N-Acetylbenzamido)acetyl)-9-benzyl-2,3,3a,4,9,10a-hexahydrobenzo[b]cyclopenta [e][1,4]diazepin-10(1H)-one To a solution of (3aR*,10aS*)-9-benzyl-4-(benzamidoacetyl)-2,3,3a,4,9,10a-hexahydrobenzo[b]cyclopenta[e][1,4]diazepin-10(1H)-one (0.18 g, 0.4 mmol) in acetic anhydride (20 mL) was added 10 mg of p-toluenesulfonic acid monohydrate. The mixture was refluxed for two hours. To the reaction mixture was added a saturated aqueous solution of sodium hydrogencarbonate, which was subjected to extraction with dichloromethane. The extract was washed with water, which was dried, followed by distilling off the solvent. The residue was purified silica-gel column chromatography (dichloromethane), followed by crystallization from diethylether to give 0.11 g (yield 58%) of the titled compound, m.p. 164–°166° C.

$^1$H NMR(CDCl$_3$) δ: 1.08–1.50(3H,m), 1.53–1.95(2H,m), 2.01–2.30(5H,m), 3.18(1H,dt,J=11.8,9.0 Hz), 3.58(1H,d,J=16.4 Hz), 4.24(1H,d,J=16.4 Hz), 4.91–5.12(2H,m), 5.79–5.92(1H,m), 7.05–7.63(12H,m), 7.77(1H,dd,J=6.6,1.6 Hz).

Working Example 110

9-(2-Methoxybenzyl)-4-(phthalimidoacetyl)-2,3,3a, 4,9,10a-hexahydrobenzo[b]cyclopenta[e][1,4] diazepin-10(1H)-one To a suspension of 4-(phthalimidoacetyl)-2,3,3a,4,9,10a-hexahydrobenzo[b]cyclopenta[e][1,4]diazepin-10(1H)-one (389 mg, 1.0 mmol) in N,N-dimethylformamide (3 mL) was added sodium hydride (60% liquid paraffin dispersion, 44 mg, 1.1 mmol). The mixture was stirred for 10 minutes at room temperature. To this mixture was added 2-methoxybenzyl bromide (241 mg, 1.2 mmol), which was stirred for 90 minutes at room temperature. To the reaction mixture was added a saturated aqueous solution of ammonium chloride (3 mL), which was diluted with water. The resulting solid was collected by filtration, which dissolved in chloroform. The solution was dried over magnesium sulfate, which was subjected to filtration, and the filtrate was concentrated under reduced pressure. The concentrate was recrystallized from chloroform-ethanol to give 234 mg (yield 46%) of a mixture of cis-compound and trans-compound. m.p. 261°–272° C.

$^1$H NMR(CDCl$_3$) δ: 1.1–1.25(6H,m), 2.5–2.7(0.4H,m), 3.17(0.6H,dt,J=12.6,9.1 Hz), 3.37(0.4H,d,J=16.6 Hz), 3.60 (0.6H,d,J=16.8 Hz), 3.81(1.8H,s), 3.83(1.2H,s), 4.10(0.6H, d,J=16.8 Hz), 4.16(0.4H,d,J=16.6 Hz), 4.5–4.7(0.4H,m), 4.71(0.4H,d,J=15.2 Hz), 5.15(0.6H,d,J=15.9 Hz), 5.27 (0.6H,d,J=15.9 Hz), 5.7–5.85(0.6H,m), 5.74(0.4H,d,J=15.2 Hz), 6.8–7.1(2H,m), 7.1–7.5(6H,m), 7.65–7.8(2H,m), 7.8–7.9(2H,m).

Working Example 111

9-(3-Methoxybenzyl)-4-(phthalimidoacetyl)-2,3,3a, 4,9,10a-hexahydrobenzo[b]cyclopenta[e][1,4] diazepin-10(1H)-one Using 3-methoxybenzyl chloride, the titled compound was synthesised in substantially the same manner as in Working Example 110 as a mixture of cis-compound and trans-compound (1:1). Yield 42%. m.p. 193°–194° C. (chloroform-ethanol).

$^1$H NMR(CDCl$_3$) δ: 1.1–2.4(6H,m), 2.5–2.7(0.5H,m), 3.18(0.5H,dt,J=11.6,9.2 Hz), 3.41(0.5H,d,J=16.6 Hz), 3.50 (0.5H,d,J=16.6 Hz), 3.77(3H,s), 4.05(0.5H,d,J=16.6 Hz), 4.17(0.5H,d,J=16.6 Hz), 4.55–4.75(0.5H,m), 4.74(0.5H,d,J= 15.0 Hz), 5.10(0.5H,d,J=15.0 Hz), 5.20(0.5H,d,J=15.0 Hz), 5.44(0.5H,d,J=15.0 Hz), 5.80(0.5H,ddd,J=9.3,8.2,4.0 Hz), 6.75–6.95(3H,m), 7.2–7.6(5H,m), 7.65–7.9(4H,m).

Working Example 112

9-(4-Methoxybenzyl)-4-(phthalimidoacetyl)-2,3,3a, 4,9,10a-hexahydrobenzo[b]cyclopenta[e][1,4] diazepin-10(1H)-one Using 4-methoxybenzyl chloride, the titled compound was synthesized in substantially the same manner as in Working Example 110 as a mixture of cis-compound and trans-compound (11:9). Yield 43%. m.p. 237°–238° C. (chloroform-ethanol).

$^1$H NMR(CDCl$_3$) δ: 1.0–2.4(6H,m), 2.5–2.7(0.45H,m), 3.16(0.55H,dt,J=11.6,8.9 Hz), 3.33(0.45H,d,J=16.4 Hz), 3.36(0.55H,d,J=16.4 Hz), 3.78(1.35H,s), 3.79(1.65H,s), 3.98(0.45H,d,J=16.4 Hz), 4.20(0.55H,d,J=16.4 Hz), 4.55–4.75(0.45H,m), 4.60(0.55H,d,J=15.0 Hz), 4.80(0.45H, d,J=15.0 Hz), 5.46(0.45H,d,J=15.0 Hz), 5.65(0.55H,d,J= 15.0 Hz), 5.7–5.85(0.55H,m), 6.8–6.95(2H,m), 7.15–7.5 (6H,m), 7.65–7.9(4H,m).

Working Example 113

(3aR*,10aS*)-9-(1-Naphthylmethyl)-4-(phthalimidoacetyl) -2,3,3a,4,9,10a-hexahydrobenzo [b]cyclopenta[e][1,4]diazepin-10(1H)-one To a suspension of (3aR*,10aS*)-4-(phthalimidoacetyl)-2,3,3a,4,9,10a-hexahydrobenzo[b]cyclopenta[e][1,4] diazepin-10(1H)-one (391 mg, 1.0 mmol) in N,N-dimethylformamide (3 mL) was added sodium hydride (60% liquid paraffin dispersion, 44 mg, 1.1 mmol). The mixture was stirred for 10 minutes at 28° C., to which was added 1-(chloromethyl) naphthalene(213 mg, 1.2 mmol), followed by stirring for 20 minutes at the same temperature. To the reaction mixture was added water (5 mL), and the mixture was subjected to extraction twice with chloroform. The organic layers were combined and washed with water, dried over magnesium sulfate, followed by filtration and concentration under reduced pressure. The concentrate was crystallized from ethanol to give 177 mg (yield 33%) of the titled compound, m.p. 266°–270° C.

$^1$H NMR(CDCl$_3$) δ: 1.15–1.55(3H,m), 1.55–2.0(2H,m), 2.0–2.3(1H,m), 3.17(1H,d,J=16.1 Hz), 3.15–3.35(1H,m), 3.82(1H,d,J=16.1 Hz), 5.66(2H,s), 5.80(1H,td,J=8.6,3.9 Hz), 7.2–8.0(14H,m), 8.0–8.2(1H,m).

Working Example 114

(3aR*,10aS*)-9-(2-Naphthylmethy)-4-(phthalimidoacetyl)-2,3,3a,4,9,10a-hexahydrobenzo [b]cyclopenta[e][1,4]diazepin-10(1H)-one Using 2-(bromomethyl)naphthalene, the titled compound was synthesized in substantially the same manner as in Working Example 113. Yield 53%. m.p. 238°–239° C.

$^1$H NMR(CDCl$_3$) δ: 1.1–1.5(3H,m), 1.6–2.0(2H,m), 2.0–2.3(1H,m), 3.23(1H,dt,J=11.8,9.1 Hz), 3.54(1H,d,J= 16.4 Hz), 4.04(1H,d,J=16.4 Hz), 5.31(1H,d,J=15.8 Hz), 5.41 (1H,d,J=15.8 Hz), 5.75–5.9(1H,m), 7.2–7.6(6H,m), 7.6–8.0 (9H,m).

Working Example 115

(3aR*,10aS*)-4-(Phthalimidoacetyl)-9-(2-pyridylmethyl)-2,3,3a,4,9,10a-hexahydrobenzo[b] cyclopenta[e][1,4]diazepin-10(1H)-one In a mixture of water (0.5 mL) and ethyl acetate (1 mL)was dissolved 2-(chloromethyl)pyridine hydrochloride (246 mg, 1.5 mmol). This solution was neutralized with the addition of sodium hydrogencarbonate. The organic layer was separated, and the remaining aqueous layer was subjected to extraction twice with ethyl acetate. The organic layers were combined and dried over magnesium sulfate, followed by concentration under reduced pressure to give 2-(chloromethyl)pyridine. To a suspension of (3aR*,10aS*) -4-(phthalimidoacetyl)-2,3,3a,4,9,10a-hexahydrobenzo[b] cyclopenta[e][1,4]diazepin-10(1H)-one (389 mg, 1.0 mmol) in N,N-dimethylformamide (3 mL), which was cooled to 0° C., was added sodium hydride (60% liquid paraffin dispersion, 44 mg, 1.1 mmol). The mixture was stirred for 3 minutes at the same temperature and for 10 minutes at room temperature. To this mixture was added a solution of the 2-(chloromethyl)pyridine, which was produce by the above-mentioned procedure, in N,N-dimethylformamide (0.5 mL). The mixture was stirred for 3 hours at room temperature. To the reaction mixture was added water, and resulting precipitate was collected by filtration, which was recrystallized from chloroform-ethanol-diisopropylether to give 232 mg (yield 48%) of the titled compound, m.p. 227°–229° C.

¹H NMR(CDCl₃) δ: 1.1–1.5(3H,m), 1.6–1.9(2H,m), 2.0–2.5(1H,m), 3.14(1H,dt,J=11.6,9.1 Hz), 3.84(1H,d,J=16.4 Hz), 4.27(1H,d,J=16.4 Hz), 5.20(1H,d,J=15.7 Hz), 5.29 (1H,d,J=15.7 Hz), 5.82(1H,td,J=8.7,4.2 Hz), 7.1–7.9(11H, m), 8.57(1H,d,J=4.8 Hz).

Working Example 116

(3aR*,10aS*)-4-(Phthalimidoacetyl)-9-(3-pyridylmethyl)-2,3,3a,4,9,10a-hexahydrobenzo[b]cyclopenta[e][1,4]diazepin-10(1H)-one Using 3-(chloromethyl)pyridine hydrochloride, the titled compound was synthesized in substantially the same manner as in Working Example 115. Yield 51%. m.p. 220°–223° C. (chloroform-ethanol-diisopropylether).

¹H NMR(CDCl₃) δ: 1.05–1.5(3H,m), 1.55–1.95(2H,m), 2.0–2.25(1H,m), 3.18(1H,dt,J=11.8,9.2 Hz), 3.31(1H,d,J=16.6 Hz), 4.10(1H,d,J=16.6 Hz), 5.09(1H,d,J=15.4 Hz), 5.31 (1H,d,J=15.4 Hz), 5.7–5.9(1H,m), 7.25–7.55(5H,m), 7.65–7.9(5H,m), 8.44(1H,d,J=1.8 Hz), 8.53(1H,dd,J=4.9,1.3 Hz).

Working Example 117

(3aR*,10aS*)-4-(Phthalimidoacetyl)-9-(4-pyridylmethyl)-2,3,3a,4,9,10a-hexahydrobenzo[b]cyclopenta[e][1,4) diazepin-10(1H)-one Using 4-(chloromethyl)pyridine hydrochloride, the titled compound was synthesized in substantially the same manner as in Working Example 115. Yield 48%. m.p. 211°–212° C. (chloroform-ethanol-diisopropylether).

¹H NMR(CDCl₃) δ: 1.1–2.0(5H,m), 2.05–2.3(1H,m), 3.1–3.3(1H,m), 3.63(1H,d,J=16.5 Hz), 4.26(1H,d,J=16.5 Hz), 4.97(1H,d,J=16.5 Hz), 5.39(1H,d,J=16.5 Hz), 5.75–5.95(1H,m), 7.2–7.5(6H,m), 7.7–7.9(4H,m), 8.61(2H, d,J=6.2 Hz).

Working Example 118

(3aR*,10aS*)-4-(Phthalimidoacetyl)-9-(2-pyridylmethyl)-2,3,3a,4,9,10a-hexahydrobenzo[b]cyclopenta[e][1,4]diazepin-10(1H)-one hydrochloride In dichloromethane was dissolved (3aR*,10aS*)-4-phthalimidoacetyl)-9-(2-pyridylmethyl)-2,3,3a,4,9,10a-hexahydrobenzo[b]cyclopenta[e][1,4]diazepin-10(1H)-one synthesized in Working Example 115, to which was added dropwise a 10% hydrogen chloride-methanol solution. The solution was concentrated under reduced pressure, and the concentrate was crystallized from ethanol-diethylether, m.p. 225.7°–226.3° C.

¹H NMR(DMSO-d₆) δ: 1.0–1.5(3H,m), 1.6–1.9(2H,m), 1.9–2.2(1H,m), 2.95–3.2(1H,m), 3.82(1H,d,J=16.6 Hz), 4.31(1H,d,J=16.6 Hz), 5.05(1H,d,J=16.4 Hz), 5.44(1H,d,J=16.4 Hz), 5.6–5.75(1H,m), 7.35–7.7(6H,m), 7.8–8.0(4H,m), 8.05–8.2(1H,m), 8.65–8.75(1H,m).

Working Example 119

(3aR*,10aS*)-4-(Phthalimidoacetyl)-9-(3-pyridylmethyl)-2,3,3a,4,9,10a-hexahydrobenzo[b]cyclopenta[e][1,4]diazepin-10(1H)-one hydrochloride The (3aR*,10aS*)-4-(phthalimidoacetyl)-9-(3-pyridylmethyl)-2,3,3a,4,9,10a-hexahydrobenzo[b]cyclopenta[e][1,4]diazepin-10(1H)-one, which was obtained in Working Example 116, was made into the corresponding hydrochloride in substantially the same manner as in Working Example 118. m.p. 192°–197° C. (ethanol-diethylether).

¹H NMR(DMSO-d₆) δ: 1.0–1.5(3H,m), 1.5–1.9(2H,m), 1.9–2.1(1H,m), 3.0–3.25(1H,m), 3.45(1H,d,J=16.8 Hz), 4.29(1H,d,J=16.8 Hz), 5.15(1H,d,J=16.0 Hz), 5.35(1h,d,J=16.0 Hz), 5.55–5.7(1H,m), 7.35–7.7(4H,m), 7.8–8.0(5H,m), 8.2–8.3(1H,m), 8.7–8.8(2H,m).

Working Example 120

(3aR*,10aS*)-4-(Phthalimidoacetyl)-9-(4-pyridylmethyl)-2,3,3a,4,9,10a-hexahydrobenzo[b]cyclopenta[e][1,4]diazepin-10(1H)-one The (3aR*,10aS*)-4-(phthalimidoacetyl)-9-(4-pyridylmethyl)-2,3,3a,4,9,10a-hexahydrobenzo[b]cyclopenta[e][1,4]diazepin-10(1H)-one, which was synthesized in Working Example 117, was made into the corresponding hydrochloride in substantially the same manner as in Working Example 118, m.p. 223°–225° C. (ethanol-diethylether).

¹H NMR(DMSO-d₆) δ: 1.1–1.5(3H,m), 1.6–1.9(2H,m), 1.95–2.2(1H,m), 3.05–3.25(1H,m), 3.63(1H,d,J=16.6 Hz), 4.36(1H,d,J=16.6 Hz), 5.14(1H,d,J=17.4 Hz), 5.54(1H,d,J=17.4 Hz), 5.6–5.75(1H,m), 7.35–7.6(3H,m), 7.70(1H,dd,J=7.2, 1.4 Hz), 7.8–8.0(6H,m), 8.84(2H,d,J=5.8 Hz).

Working Example 121

9-Phenyl-4-(phthalimidoacetyl)-2,3,3a,4,9,10a-hexahydrobenzo[b]cyclopenta[e][1,4]diazepin-10(1H)-one To a suspension of 4-(phthalimidoacetyl)-2,3,3a,4,9,10a-hexahydrobenzo[b]cyclopenta[e][1,4]diazepin-10(1H)-one (584 mg, 1.5 mmol) and potassium carbonate (228 mg, 1.6 mmol) in bromobenzene (3 mL) was added copper (I) iodide (57 mg, 0.3 mmol), and the mixture was heated for 90 minutes under reflux. To the reaction mixture was added chloroform, which was subjected to filtration, and the filtrate was concentrated under reduced pressure. The concentrate was recrystallized from chloroform-ethanol-hexane to give 440 mg (yield 63%) of a mixture of cis-compound and trans-compound (3:2), m.p. 272°–273° C.

¹H NMR(CDCl₃) δ: 1.1–2.5(6H,m), 2.7–2.9(0.4H,m), 3.15–3.3(0.6H,m), 3.98(0.8H,m,J=16.8 Hz), 4.10(0.6H,d,J=16.4 Hz), 4.47(0.6H,d,J=16.4 Hz), 4.76(0.4H,ddd,J=12.6, 10.8,6.8 Hz), 5.8–6.0(0.6H,m), 6.98(0.6H,dd,J=7.6,1.8 Hz), 7.0–7.1(0.6H,m), 7.2–7.6(7.8H,m), 7.7–7.95(4H,m).

Working Example 122

(3aR*,10aS*)-9-Benzyl-4-(chloroacetyl)-2,3,3a,4,9,10a-hexahydrobenzo[b]cyclopenta[e][1,4]diazepin-10(1H)-one On a water-bath kept at 14° C., to a solution of (3aR*,10aS*)-9-benzyl-2,3,3a,4,9,10a-hexahydrobenzo[b]cyclopenta[e][1,4]diazepin-10(1H)-one (5.85 g, 20 mmol) in 1,2-dichloroethane (20 mL) was added dropwise a solution of chloroacetyl chloride (2.5 g, 22 mmol) in 1,2-dichloroethane (15 mL), and the mixture was stirred for 10 minutes. The aqueous layer of this mixture was separated, and the organic layer was washed with water and a saturated aqueous solution of sodium chloride, dried over magnesium sulfate, which was subjected to filtration, and the filtrate was concentrated under reduced pressure. The concentrate was recrystallized from dichloromethane-hexane to give 6.49 g (yield 88%) of the titled compound, m.p. 154°–156° C.

$^1$H NMR(CDCl$_3$) δ: 1.0–1.5(3H,m), 1.5–1.9(2H,m), 2.0–2.3(1H,m), 2.76(1H,d,J=13.2 Hz), 3.05–3.25(1H,m), 3.19(1H,d,J=13.2 Hz), 4.59(1H,d,J=15.0 Hz), 5.63(1H,d,J=15.0 Hz), 5.75–5.9(1H,m), 7.0–7.35(7H,m), 7.4–7.55(2H, m).

Working Example 123

(3aR*,10aS*)-9-Benzyl-4-(bromoacetyl)-2,3,3a,4,9, 10a-hexahydrobenzo[b]cyclopenta[e][1,4]diazepin-10(1H)-one Using bromoacetyl bromide, the titled compound was synthesized in substantially the same manner as in Working Example 122. Yield 45%. m.p. 177°–179° C. (dichloromethane-diisopropylether).

$^1$H NMR(CDCl$_3$) δ: 1.0–1.5(3H,m), 1.5–1.9(2H,m), 2.0–2.25(1H,m), 2.82(1H,d,J=11.4 Hz), 2.88(1H,d,J=11.4 Hz), 3.16(1H,dt,J=12.2,9.1 Hz), 4.67(1H,d,J=15.0 Hz), 5.55 (1H,d,J=15.0 Hz), 5.82(1H,ddd,J=9.3,8.3,4.1Hz), 7.2–7.35 (7H,m), 7.35–7.5(2H,m).

Working Example 124

(3aR*,10aS*)-9-Benzyl-4-(3-chloropropionyl)-2, 3,3a,4,9,10a-hexahydrobenzo[b]cyclopenta[e][1,4] diazepin-10(1H)-one The titled compound was synthesized in substantially the same manner as in Working Example 122. Yield 82%, m.p. 182°–184° C.

$^1$H NMR(CDCl$_3$) δ: 1.00–1.45(4H,m), 1.50–1.90(2H,m), 2.00–2.30(2H,m), 3.00–3.35(2H,m), 3.62(1H,dt,J=10.8,7.4 Hz), 4.62(1H,d,J=14.6 Hz), 5.56(1H,d,J=14.6 Hz), 5.85(1H, ddd,J=9.2,8.2,4.0 Hz), 7.03(1H,dd,J=7.4,1.0 Hz), 7.10–7.30 (6H,m), 7.35–7.50(2H,m).

Working Example 125

(3aR*,10aS*)-9-Benzyl-4-(4-chlorobutyryl)-2,3,3a, 4,9,10a-hexahydrobenzo[b]cyclopenta[e][1,4] diazepine-10(1H)-one The titled compound was synthesized in substantially the same manner as in Working Example 122. Yield 92%. m.p. 169°–170° C.

$^1$H NMR(CDCl$_3$) δ: 0.90–1.45(4H,m), 1.50–2.20(6H,m), 3.05–3.50(3H,m), 4.75(1H,d,J=15.0 Hz), 5.44(1H,d,J=15.0 Hz), 5.87(1H,ddd,J=9.4,8.0,4.0 Hz), 7.02(1H,dd,J=8.0,1.0 Hz), 7.10–7.30(6H,m), 7.35–7.50(2H,m).

Working Example 126

(3aR*,10aS*)-9-Benzyl-4-(5-bromovaleryl)-2,3,3a, 4,9,10a-hexahydrobenzo[b]cyclopenta[e][1,4] diazepin-10(1H)-one The titled compound was synthesized in substantially the same manner as in Working Example 122. Yield 80%. m.p. 134°–135° C.

$^1$H NMR(CDCl$_3$) δ: 0.90–1.90(11H,m), 2.00–2.20(1H, m), 3.00–3.30(3H,m), 4.72(1H,d,J=14.8 Hz), 5.45(1H,d,J=14.8 Hz), 5.85(1H,ddd,J=9.0,8.0,4.0 Hz), 6.97(1H,dd,J=8.0, 1.0 Hz), 7.00–7.50(8H,m).

Working Example 127

(3aR*,10aS*)-9-Benzyl-4-(6-bromohexanoyl)-2,3, 3a,4,9,10a-hexahydrobenzo[b]cyclopenta[e][1,4] diazepin-10(1H)-one The titled compound was synthesized in substantially the same manner as in Working Example 122. Yield 62%. m.p. 111°–112° C.

$^1$H NMR(CDCl$_3$) δ: 0.90–1.90(13H,m), 2.10–2.20(1H, m), 3.00–3.20(1H,m), 3.33(2H,t,J=6.8 Hz), 4.73(1H,d,J=15.0 Hz), 5.43(1H,d,J=15.0 Hz), 5.86(1H,ddd,J=9.0,8.0,4.0 Hz), 6.97(1H,dd,J=8.0,1.0 Hz), 7.00–7.59(8H,m).

Working Example 128

(3aR*,10aS*)-9-Benzyl-4-(pyridine-3,4-dicarboximidoacetyl)-2,3,3a,4,9,10a-hexahydrobenzo[b]cyclopenta[e][1,4]diazepin-10(1H)-one On a water-bath kept at 20° C., to a solution of pyridine-3,4-carboximide (178 mg, 1.2 mmol) in N,N-dimethylformamide (1.5 mL) was added sodium hydride (60% liquid paraffin dispersion, 48 mg, 1.2 mmol), and the mixture was stirred for 3 minutes. To this mixture was added (3aR*,10aS*)-9-benzyl-4-(chloroacetyl)-2,3,3a,4,9,10a-hexahydrobenzo[b]cyclopenta[e][1,4]diazepin-10(1H)-one (443 mg, 1.2 mmol), which was stirred for 10 minutes at 20° C. and for one hour at 90° C. The reaction mixture was cooled, to which was added water. The resulting precipitate was collected by filtration, which was dissolved in chloroform. The solution was dried over magnesium sulfate, which was subjected to filtration, and the filtrate was concentrated under reduced pressure. The concentrate was crystallized from chloroform-ethanol to give 319 mg (yield 55%) of the titled compound, m.p. 215.5°–215.9° C.

$^1$H NMR(CDCl$_3$) δ: 1.1–1.5(3H,m), 1.5–1.95(2H,m), 2.0–2.5(1H,m), 3.18(1H,dt,J=12.2,9.1 Hz), 3.35(1H,d,J=16.8 Hz), 4.04(1H,d,J=16.8 Hz), 4.98(1H,d,J=15.3 Hz), 5.41 (1H,d,J=15.3 Hz), 5.7–5.85(1H,m), 7.2–7.5(9H,m), 7.75 (1H,dd,J=4.8,1.0 Hz), 9.07(1H,d,J=4.8 Hz), 9.15(1H,d,J=1.2 Hz).

Working Example 129

(3aR*,10aS*)-9-Benzyl-4-(succinimidoacetyl)- 2,3, 3a,4,9,10a-hexahydrobenzo[b]cyclopenta[e][1,4] diazepin-10(1H)-one Using succinimide, synthesis was conducted in substantially the same manner as in Working Example 128 to give a crude product, which was purified by silica-gel column chromatography (hexane-ethylacetate 2:3, 1:2→1:3), followed by crystallization from ethanol-diisopropylether to give the titled compound in a yield of 57%. m.p. 212°–213° C.

$^1$H NMR(CDCl$_3$) δ: 1.05–1.5(3H,m), 1.55–1.95(2H,m), 2.0–2.25(1H,m), 2.75(4H,s), 3.17(1H,dt,J=12.2,9.1 Hz), 3.27(1H,d,J=16.4 Hz), 3.86(1H,d,J=16.4 Hz), 5.02(1H,d,J=15.4 Hz), 5.29(1H,d,J=15.4 Hz), 5.7–5.85(1H,m), 7.1–7.5 (9H,m).

Working Example 130

(3aR*,10aS*)-9-Benzyl-4-((1-imidazolyl)acetyl)-2, 3,3a,4,9,10a-hexahydrobenzo[b]cyclopenta[e][1,4] diazepin-10(1H)-one The titled compound was synthesized in substantially the same manner as in Working Example 128. Yield 61%. m.p. 183°–184° C.

$^1$H NMR(CDCl$_3$) δ: 1.00–1.50(2H,m), 1.50–1.90(2H,m), 1.90–2.35(2H,m), 3.11(1H,d,J=16.2 Hz), 3.18(1H,m), 3.98 (1H,d,J=16.2 Hz), 4.59(1H,d,J=14.8 Hz), 5.57(1H,d,J=14.8 Hz), 5.78(1H,m), 6.68(1H,s), 7.00(3H,m), 7.10–7.40(6H, m), 7.51(2H,m).

Working Example 131

(3aR*,10aS*)-9-Benzyl-4-(3-(1-imidazolyl) propionyl)-2,3,3a,4,9,10a-hexahydrobenzo[b] cyclopenta[e][1,4]diazepin-10(1H)-one The titled compound was synthesized in substantially the same manner as in Working Example 128. Yield 29%. m.p. 150°–152° C.

¹H NMR(CDCl₃) δ: 1.00–2.30(8H,m), 3.13(1H,dt,J=11.8, 8.8 Hz), 3.55–3.80(1H,m), 4.10–4.30(1H,m), 4.53(1H,d,J= 14.8 Hz), 5.60(1H,d,J=14.8 Hz), 5.80–6.00(1H,m), 6.44(1H, d,J=7.8 Hz), 6.73(1H,s), 6.99(1H,s), 7.10–7.50(9H,m).

Working Example 132

(3aR*,10aS*)-9-Benzyl-4-(4-(1-imdazaolyl)butyryl) -2,3,3a,4,9,10a-hexahydrobenzo[b]cyclopenta[e][1, 4]diazepin-10(1H)-one The titled compound was synthesized in substantially the same manner as in Working Example 128. Yield 14%. m.p. 135°–136° C.

¹H NMR(CDCl₃) δ: 0.65–0.85(1H,m), 1.00–2.00(8H,m), 2.00–2.20(1H,m), 3.15(1H,dt,J=11.8,8.8 Hz), 3.60–3.95 (2H,m), 4.66(1H,d,J=14.8 Hz), 5.50(1H,d,J=14.8 Hz), 5.86 (1H,ddd,J=9.4,8.0,4.0 Hz), 6.70–6.90(2H,m), 7.02(1H,s), 7.10–7.50(9H,m).

Working Example 133

(3aR*,10aS*)-9-Benzyl-4-(6-(1-imidazolyl) hexanoyl)-2,3,3a,4,9,10a-hexahydrobenzo[b] cyclopenta[e][1,4]-diazepin-10(1H)-one The titled compound was synthesized in substantially the same manner as in Working Example 128. Yield 81%. m.p. 133°–134° C.

¹H NMR (CDCl₃) δ: 0.70–1.90(11H,m), 1.90–2.20(3H, m), 3.13(1H,dt,J=11.6,9.2 Hz), 3.86(2H,t,J=7.0 Hz), 4.71 (1H,d,J=15.0 Hz), 5.41(1H,d,J=15.0 Hz), 5.86(1H,dt,J=8.0, 4.0 Hz), 6.80–7.50(12H,m).

Working Example 134

(3aR*,10aS*)-9-Benzyl-4-((1-benzimidazolyl) acetyl)-2,3,3a,4,9,10a-hexahydrobenzo[b]cyclopenta [e][1,4]-diazepin-10(1H)-one The titled compound was synthesized in substantially the same manner as in Working Example 128. Yield 57%. m.p. 188°–189° C.

¹H NMR (CDCl₃) δ: 1.00–1.50(3H,m), 1.50–1.90(2H,m), 2.11(1H,m), 3.15(1H,m), 3.58(1H,d,J=16.6 Hz), 4.26(1H,d, J=16.6 Hz), 4.48(1H,d,J=15.0 Hz), 4.99(1H,d,J=15.0 Hz), 5.82(1H,m), 7.00– 7.60(13H,m),7.76(1H,m).

Working Example 135

(3aR*,10aS*)-9-Benzyl-4-((4-phenylpiperazino) acetyl)-2,3,3a,4,9,10a-hexahydrobenzo[b]cyclopenta [e][1,4]-diazepin-10(1H)-one The titled compound was synthesized in substantially the same manner as in Working Example 128. Yield 25%. m.p. 164°–165° C.

¹H NMR (CDCl₃) δ: 1.00–1.50(3H,m), 1.50–1.90(2H,m), 2.00–2.60(7H,m), 3.0–3.25(5H,m), 4.04(1H,d,J=15.0 Hz), 5.32(1H,d,J=15.0 Hz), 5.85(1H,m), 6.75–7.00(3H,m), 7.10–7.50(11H,m).

Working Example 136

(3aR*,10aS*)-9-Benzyl-4-(1H-2-oxo-2,3-dihydroindole-1-acetyl)-2,3,3a,4,9,10a-hexahydrobenzo[b]cyclopenta [e][1,4]diazepin-10 (1H)-one On a water-bath kept at 22° C., to a solution of oxyindole (160 mg, 1.2 mmol) in N,N-dimethylformamide (1.5 mL) was added sodium hydride (60% liquid paraffim dispersion, 48 mg, 1.2 mmol), and the mixture was stirred for 3 minutes. To this mixture was added (3aR*, 10aS*)-9-benzyl-4-(chloroacetyl)-2,3,3a,4,9,10a-hexahydrobenz[b]cyclopenta [e][1,4]diazepin-10(1H)-one (443 mg, 1.2 mmol), which was stirred for one hour at 23° C. To the reaction mixture was added water, and resulting precipitate was collected by filtration and dissolved in chloroform. The chloroform solution was dried over magnesium sulfate, which was subjected to filtration, and the filtrate was concentrated under reduced pressure. The concentrate was purified by means of a silica-gel column chromatography (hexane-ethyl acetate 1:1→1:2), followed by recrystallization from dichloromethane-hexane to give 46 mg (yield 8%) of the titled compound, m.p. 203°–205° C.

¹H NMR (CDCl₃) δ: 1.1–1.5(3H,m), 1.5–1.95(2H,m), 2.0–2.25(1H,m), 3.05–3.25(1H,m), 3.12(1H,d,J=17.0 Hz), 3.39(1H,d,J=22.1 Hz), 3.52(1H,d,J=22.1 Hz), 4.34(1H,d,J= 17.0 Hz), 4.98(1H,d,J=15.2 Hz), 5.12(1H,d,J=15.2 Hz), 5.80 (1H,td,J=8.8,4.3 Hz), 6.51(1H,d,J=7.8 Hz), 7.02(1H,t,J=7.6 Hz), 7.1–7.5(11H,m).

Working Example 137

(3aR*,10aS*)-9-Benzyl-4-((0-sulfobenzoic acid cyclic imido)acetyl)-2,3,3a,4,9,10a-hexahydrobenzo [b]-cyclopenta[e][1,4]diazepin-10(1H)-one A mixture of (3aR*,10aS*)-9-benzyl-4-(chloroacetyl)-2, 3,3a,4,9,10a-hexahydrobenzo[b]-cyclopenta[e]cyclopenta [e][1,4]diazepin-10(1H)-one (516 mg, 1.4 mmol), saccharin sodium dihydrate (355 mg, 1.5 mmol) and sodium iodide (220 mg, 1.5 mmol) was refluxed for 24 hours in a mixture of 2-butanone (2 mL) and water (1 mL). The reaction mixture was cooled, then the resulting solid was collected by filtration, followed by recrystallization from dichloromethane-hexane to give 270 mg (yield 37%) of the titled compound, m.p. 229–230° C. H NMR (CDCl₃) δ: 1.0–1.5(3H,m), 1.5–2.0(2H,m), 2.0–2.25(1H,m), 3.12(1H,d, J=17.0 Hz), 3.17(1H,dt,J=12.0,9.0 Hz), 3.93(1H,d,J=17.0 Hz), *4.81(1H,d,J=15.0 Hz), 5.53(1H,d,J=15.0 Hz), 5.79 (1H,ddd,J=9.2,8.1,4.1 Hz), 7.2–7.55(9H,m), 7.75–7.95(3H, m), 8.0–8.1(1H,m).

Working Example 138

(3aR*,10aS*)-9-Benzyl-4-((benzylamino)acetyl)-2, 3,3a,4,9,10a-hexahydrobenzo[b]cyclopenta[e][1,4]-diazepin-10(1H)-one To a solution of (3aR*,10aS*)-9-benzyl-4-(chloroacetyl) -2,3,3a,4,9,10a-hexahydrobenzo[b]-cyclopenta[e][1,4] diazepin-10(1H)-one (1.0 g, 2.7 mmol) and benzylamine (1.45 g, 13.6 mmol) in ethanol (30 mL) was added potassium carbonate (560 mg, 4.1 mmol), and the mixture was refluxed for 17 hours. The solvent was distilled off. To the residue was added water, which was subjected to extraction with dichloromethane. The extract was washed with water, dried and, then, the solvent was distilled off. The residue was purified by silica-gel column chromatography (ethyl acetate-hexane 1:1), followed by crystallization from diethyl-ether to give 0.36 g (yield 30%), m.p. 95–98° C.

¹H NMR (CDCl₃) δ: 1.05–1.45(3H,m), 1.52–1.91(2H,m), 2.10(1H,d,J=16.1 Hz), 2.05–2.21(2H,m), 2.96(1H,d,J=16.1 Hz), 3.09–3.22(1H,m), 3.45–3.60(2H,m), 4.82(1H,d,J=15.2 Hz), 5.22(1H,d,J=15.2 Hz), 5.84–5.95(1H,m), 6.96–7.01 (1H,m), 7.12–7.43(13H,m).

Working Example 139

(3aR*,10aS*)-9-Benzyl-4-((N-benzyl-N-methylamino) acetyl)-2,3,3a,4,9,10a-hexahydrobenzo[b]cyclopenta [e][1,4]diazepin-10 (1H)-one Using N-benzyl-N-methylamine, the titled compound was synthesized in substantially the same manner as in Working Example 138. Yield 38%. m.p. 75°–78° C. (diethyl ether)

¹H NMR (CDCl₃) δ: 1.10–1.50(3H,m), 1.52–1.91(2H,m), 2.05–2.31(4H,m), 2.39–2.91(2H,m), 3.04–3.52(3H,m), 4.72–5.15(2H,m), 5.82–5.93(1H,m), 6.91–7.50(14H,m).

Working Example 140

(3aR*,10aS*)-9-Benzyl-4-((N,N-dibenzylamino) acetyl)-2,3,3a,4,9,10a-hexahydrobenzo[b]cyclopenta [e][1,4]-diazepin-10(1H)-one A solution of (3aR*,10aS*)-9-benzyl-4-(chloroacetyl)-2, 3,3a,4,9,10a-hexahydrobenzo[b]-cyclopenta[e][1,4]diazepin-10(1H)-one (1.0 g, 2.7 mmol) and dibenzylamine (5.36 g, 27.1 mmol) in 1,2-dichloroethane (30 mL) was refluxed for 17 hours, to which was added a saturated aqueous solution of sodium hydrogencarbonate, followed by extraction with dichloromethane. The extract solution was washed with water and dried, followed by distilling off the solvent. The residue was purified by silica-gel column chromatography (ethyl acetate-hexane 1:1) to give 0.40 g (yield 28%) as an oily product.

¹H NMR (CDCl₃) δ: 1.01–1.41(3H,m), 1.55–1.91(2H,m), 1.91–2.23(1H,m), 2.25(1H,d,J=16.8 Hz), 3.00(1H,d,J=16.8 Hz), 3.05–3.23(1H,m), 3.68(2H,d,J=13.6 Hz), 3.85(2H,d,J=13.6 Hz), 4.66(1H,d,J=15.0 Hz), 4.81(1H,d,J=15.0 Hz), 5.83–5.95(1H,m), 6.50(1H,d,J=7.6 Hz), 6.88–6.97(1H,m), 7.02–7.43(17H,m).

Working Example 141

(3aR*,10aS*)-9-Benzyl-4-((N-benzylbenzamido) acetyl)-2,3,3a,4,9,10a-hexahydrobenzo[b]cyclopenta [e][1,4]diazepin-10(1H)-one A solution of (3R*,10aS*)-9-benzyl-4-((benzylamino) acetyl)-2,3,3a,4,9,10a-hexahydrobenzo[b]cyclopenta[e][1, 4]diazepin-10(1H)-one (0.2 g, 0.46 mmol) and benzoylchloride (0.17 g, 1.2 mmol) in 1,2-dichloroethane (10 mL) was stirred for 30 minutes at room temperature. To the reaction mixture was added a saturated aqueous solution of sodium hydrogencarbonate, which was subjected extraction with dichloromethane. The extraction solution was washed with water and dried, followed by distilling off the solvent. The residue was purified by silica-gel column chromatography (dichloromethane), which was crystallized from diethyl ether to give 70 mg (yield 28%), m.p. 166°–168° C.

¹H NMR (CDCl₃) δ: 1.00–1.43(3H,m), 1.53–1.95(2H,m), 2.05–2.28(1H,m), 2.45–2.92(1H,m), 3.65–3.85(1H,m), 4.05–5.15(5H,m), 5.78–6.09(1H,m), 6.52–7.63(19H,m).

Working Example 142

(3aR*,10aS*)-9-Benzyl-4-((N-benzylacetamido) acetyl)-2,3,3a,4,9,10a-hexahydrobenzo[b]cyclopenta [e][1,4]diazepin-10(1H)-one Using acetyl chloride, the titled compound was synthesized in substantially the same manner as in Working Example 141. Yield 22%. m.p. 179°–181° C. (diethyl ether).

¹H NMR (CDCl₃) δ: 1.05–1.47(3H,m), 1.55–1.90(2H,m), 2.01–2.20(5H,m), 3.01–3.22(1H,m), 4.11–4.82(4H,m), 5.30 (1H,d,J=15.0 Hz), 5.86–5.95(1H,m), 6.43–6.75(1H,m), 6.90 (1H,d,J=6.4 Hz), 7.04–7.51(12H,m).

Working Example 143

(3aR*,10aS*)-9-Benzyl-4-((N-benzylformamide) acetyl)-2,3,3a,4,9,10a-hexahydrobenzo[b]cyclopenta [e][1,4]diazepin-10(1H)-one A mixture of formic acid (3.8 mL) and acetic anhydride (2.1 mL) was stirred for 20 minutes at room temperature. To the reaction mixture was added a solution of (3aR*,10aS*)-9-benzyl-4-((benzylamino) acetyl)-2,3,3a,4,9,10a-hexahydrobenzo[b]cyclopenta [e][1,4]diazepin-10(1H)-one (0.2 g, 0.46 mmol) in dichloromethane (10 mL), which was stirred for 20 minutes at room temperature. To the reaction mixture was added a saturated aqueous solution of sodium hydrogencarbonate, which was subjected to extraction with dichloromethane. The extract was washed with water and dried, followed by distilling off the solvent. The residue was purified by silica-gel column chromatography (dichloromethane) to give 60 mg (yield 28%) of the titled compound as an amorphous product.

¹H NMR (CDCl₃) δ: 1.05–1.48(3H,m), 1.52–1.91(2H,m), 2.01–2.25(1H,m), 2.40(0.3H,d,J=16.4 Hz), 2.46(0.7H,d,J=16.4 Hz), 3.07–3.26(1H,m), 4.00(1H,d,J=16.4 Hz), 4.24–4.90(4H,m), 6.39–7.48(14H,m), 7.57(0.3H,s), 8.23 (0.7H,s).

Working Example 144

1-Benzyl-4-((E)-styryl)-1,3-dihydro-1,5-benzodiazepin-2(2H)-one

To a solution of 1-benzyl-4-methyl-1,3-dihydro-1,5-benzodiazepin-2(2H)-one (3.0 g, 11.4 mmol) in N,N-dimethylformamide (20 mL) was added sodium hydride (content 60%, 0.51 g, 12.8 mmol), and the mixture was stirred for 15 minutes at room temperature. To the reaction mixture was added benzaldehyde (1.45 g, 13.7 mmol), which was stirred for further 30 minutes at the same temperature. The reaction mixture was diluted with water, which was subjected to extraction with ethyl acetate. The extract solution was washed with water and dried, followed by concentration. The concentrate was crystallized from ethylacetate-hexane to give 1.9 g of the titled compound. Yield 75%. m.p. 150°–151° C.

¹H NMR (CDCl₃) δ: 3.00(1H,d,J=11.8 Hz), 4.06(1H,d, J=11.8 Hz), 5.08(1H,d,J=14.2 Hz), 5.19(1H,d,J=14.2 Hz), 7.00–7.70(16H,m).

Working Example 145

9-(1-Naphthylmethyl)-2,3,9,10a-tetrahydrobenzo[b]-cyclopenta[e][1,4]diazepin-10(1H)-one Using 1-(chloromethyl)naphthalene, the titled compound was synthesized in substantially the same manner as in Working Example 4. Yield 50%. m.p. 145°–147° C. (ethyl ether-petroleum ether).

¹H NMR (CDCl₃) δ: 1.9–2.2(3H,m), 2.6–2.75(2H,m), 2.75–2.9(1H,m), 3.1–3.2(1H,m), 5.52(2H,d,J=16.4 Hz), 5.63(2H,d,J=16.4 Hz), 7.0–7.2(3H,m), 7.2–7.4(3H,m), 7.4–7.55(2H,m), 7.72(1H,d,J=8.4 Hz), 7.8–7.95(2H,m).

Working Example 146

9-(2-Naphthylmethyl)-2,3,9,10a-tetrahydrobenzo[b]-cyclopenta[e][1,4]diazepin-10(1H)-one Using 2-(bromomethyl)naphthalene, the titled compound was synthesized in substantially the same procedure as in Working Example 4. Yield 59%. m.p. 164°–167° C. (ethyl acetate-petroleum ether).

¹H NMR (CDCl₃) δ: 1.9–2.2(3H,m), 2.65–2.9(3H,m), 3.05–3.15(1H,m), 5.22(2H,d,J=16.0 Hz), 5.31(2H,d,J=16.0 Hz), 7.0–7.35(5H,m), 7.35–7.5(2H,m), 7.55(1H,s). 7.7–7.8 (3H,m).

Working Example 147

9-Benzyl-7-chloro-2,3,9.10a-tetrahydrobenzo[b]-cyclopenta[e][1,4]diazepin-10(1H)-one Using 7-chloro-2,3,9,10a-tetrahydrobenzo[b]-cyclopenta [e][1,4]diazepin-10(1H)-one, the titled compound was synthesized in substantially the same procedure as in Working Example 4. Yield 68%. m.p. 134°–136° C. (diisopropyl ether).

¹H NMR (CDCl₃) δ: 1.8–2.2(3H,m), 2.6–2.9(3H,m), 2.95–3.05(1H,m), 5.03(2H,d,J=15.8 Hz), 5.16(2H,d,J=15.8 Hz), 7.0–7.4(8H,m).

Working Example 148

9,10a-Bis(2-naphthylmethyl)-2,3,9,10a-tetrahydrobenzo[b]cyclopenta[e][1,4]diazepin-10(1H)-one The bis-naphthylmethyl compound produced simultaneously with the compound of Working Example 146 was purified by silica-gel column chromatography (chloroform), which was recrystallized from chloroform-petroleum ether to give the titled compound in a yield of 8%. m.p. 191°–193° C.

¹H NMR (CDCl₃) δ: 1.6–1.8(2H,m), 2.08(1H,dt,J=12.8, 8.8 Hz), 2.4–2.8(2H,m), 2.70(2H,d,J=14.0 Hz), 2.82(2H,d, J=14.0 Hz), 3.0–3.2(1H,m), 5.07(2H,d,J=15.8 Hz), 5.51(2H, d,J=15.8 Hz), 7.0–7.85(18H,m).

Working Example 149

9,10a-Dibenzyl-7-chloro-2,3,9,10a-tetrahydrobenzo[b]-cyclopenta[e][1,4]diazepin-10(1H)-one The dibenzyl compound produced simultaneously with the compound of Working Example 147 was purified by silica-gel column chromatography (hexane-ethyl acetate 4:1→2:1), followed by crystallization from diisopropyl ether to give the titled compound in a yield of 8%, m.p. 139°–141° C.

¹H NMR (CDCl₃) δ: 1.55–1.8(2H,m), 1.98(1H,ddd,J= 12.7,10.0,7.4 Hz), 2.4–2.8(2H,m), 2.50(2H,d,J=14.3 Hz), 2.63(2H,d,J=14.3 Hz), 2.9–3.1(1H,m), 5.00(2H,d,J=16.0 Hz), 5.25(2H,d,J=16.0 Hz), 6.8–6.9(2H,m), 7.0–7.15(2H, m), 7.15–7.4(8H,m), 7.37(1H,d,J=8.4 Hz).

Working Example 150

1,3-Dibenzyl-4-((E)-styryl)-1,3-dihydro-1,5-benzodiazepin-2(2H)-one

Using 1-benzyl-4-((E)-styryl)-1,3-dihydro-1,5-benzodiazepin-2(2H)-one, synthesis was conducted in substantially the same manner as in Working Example 21 to give the titled compound as an oily product. Yield 89%.

¹H NMR (CDCl₃) δ: 3.26–3.35(2H,m), 3.90(1H,dd,J= 13.0,11.0 Hz), 5.03(1H,d,J=16.2 Hz), 5.20(1H,d,J=16.2 Hz), 6.91–7.75(21H,m).

Working Example 151

1-Benzyl-4-methyl-3-(2-propen-1-yl)-1,3-dihydro-1,5-benzodiazepin-2(2H)-one

Using 1-benzyl-4-methyl-1,3-dihydro-1,5-benzodiazepin-2(2H)-one and 3-bromopropene, the titled compound was synthesized in substantially the same manner as in Working Example 21 as an oily product in a yield of 85%.

¹H NMR (CDCl₃) δ: 2.25(3H,s), 2.58–2.75(1H,m), 2.90–3.07(2H,m), 5.03–5.20(2H,m), 5.12(2H,s), 5.71–5.93(1H,m), 7.03–7.31(9H,m).

Working Example 152

1-Benzyl-4-methyl-3((E)-3-phenyl-2-propen-1-yl)-1,3-dihydro-1,5-benzodiazepin-2(2H)-one Using 1-benzyl-4-methyl-1,3-dihydro-1,5-benzodiazepin-2(2H)-one, the title compound was synthe-sized in substantially the same manner as in Working Example 21 in a yield of 69%, m.p. 152°–154° C. (diethyl ether).

¹H NMR (CDCl₃) δ: 2.30(3H,s), 2.70–3.31(3H,m), 5.07 (1H,d,J=15.8 Hz), 5.19(1H,d,J=15.8 Hz), 6.12–6.28(1H,m), 6.48(1H,d,J=15.8 Hz), 7.03–7.72(14H,m).

Working Example 153

(3aR*,10aS*)-9-(1-naphthylmethyl)-2,3,3a,4,9,10a-hexahydrobenzo[b]cyclopenta[e][1,4]diazepin-10(1H)-one Using 9-(1-naphthylmethyl)-2,3,9,10a-tetrahydrobenzo[b]cyclopenta[e][1,4]diazepin-10(1H)-one, the titled compound was synthesized in substantially the same manner as in Working Example 24 in a yield of 67%, m.p. 126°–128° C. (ethyl acetate-hexane).

¹H NMR (CDCl₃) δ: 1.4–2.2(5H,m), 2.35–2.6(1H,m), 3.0–3.1(1H,m), 3.47(1H,br s), 4.04(1H,ddd,J=9.9,7.7,7.0 Hz), 5.48(2H,d,J=16.4 Hz), 5.64(2H,d,J=16.4 Hz), 6.85–7.1 (3H,m), 7.1–7.2(1H,m), 7.3–7.55(4H,m), 7.70(1H,d,J=8.4 Hz), 7.75–7.9(1H,m), 7.95–8.05(1H,m).

Working Example 154

(3aR*,10aS*)-9-(2-naphthylmethyl)-2,3,3a,4,9,10a-hexahydrobenzo[b]cyclopenta[e][1,4]diazepin-10(1H)-one Using 9-(2-naphthylmethyl)-2,3,9,10a-tetrahydrobenzo[b]cyclopenta[1,4]diazepin-10(1H)-one, the titled compound was synthesized in substantially the same manner as in yield of 81%, m.p. 148.0°–148.5° C. (ethyl acetate-hexane).

¹H NMR (CDCl₃) δ: 1.4–2.2(5H,m), 2.4–2.6(1H,m), 2.95–3.05(1H,m), 3.3–3.6(1H,br), 4.02(1H,ddd,J=9.9,7.7, 6.7 Hz), 5.19(2H,d,J=15.7 Hz), 5.29(2H,d,J=15.7 Hz), 6.85–7.1(3H,m), 7.15–7.25(1H,m), 7.35–7.5(3H,m), 7.65–7.8(4H,m).

Working Example 155

(4aR*,11aS*)-10-Benzyl-1,2,3,4,4a,5,10,11a-octahydro-11H-dibenzo[b,e][1,4]diazepin-11-one Using 10-benzyl-1,2,3,4,10,11a-hexahydro-11H-dibenzo[b,e][1,4]diazepin-11-one, synthesis was conducted in substantially the same manner as in Working Example 24 to give a crude product, which was purified by silica-gel column chromatography (hexane-ethyl acetate 1:1), followed by crystallization from ethyl acetate-hexane to give the titled compound in a yield of 79%, m.p. 164°–166° C.

¹H NMR (CDCl₃) δ: 1.0–1.4(2H,m), 1.4–2.0(4H,m), 2.0–2.35(2H,m), 2.94(1H,t,J=5.2 Hz), 3.37(1H,br s), 3.6–3.75(1H,m), 5.03(2H,d,J=15.9 Hz), 5.13(2H,d,J=15.9 Hz), 6.8–7.35(9H,m).

Working Example 156

(3aR*,10aS*)-9-(4-Fluorobenzyl)-2,3,3a,4,9,10a-hexahydrobenzo[b]cyclopenta[e][1,4]diazepin-10(1H-one Using 9-(4-fluorobenzyl)-2,3,9,10a-tetrahydrobenzo[b]cyclopenta[e][1,4]diazepin-10(1H)-one, the titled compound was synthesized in substantially the same manner as in Working Example 24 as an oily product.

¹H NMR (CDCl₃) δ: 1.4–2.1(5H,m), 2.3–2.5(1H,m), 2.94 (1H,td,J=7.5,1.9 Hz), 3.2–3.6(1H,br), 3.98(1H,ddd,J=10.0, 7.8,6.6 Hz), 4.90(2H,d,J=15.5 Hz), 5.18(2H,d,J=15.5 Hz), 6.8–7.3(8H,m).

Working Example 157

(3aR*,10aS*)-9-(2-Fluorobenzyl)-2,3,3a,4,9,10a-hexahydrobenzo[b]cyclopenta[e[(1,4]diazepin-10 (1H)-one Using 9-(2-fluorobenzyl)-2,3,9,10a-tetrahydrobenzo[b]cyclopenta[e][1,4]diazepin-10(1H)-one, the titled compound was synthesized in substantially the same manner as in Working Example 24 in a yield of 93%, m.p. 154°–155° C. (ethyl acetate-hexane)

$^1$H NMR (CDCl$_3$) δ: 1.45–2.15(5H,m), 2.35–2.55(1H,m), 2.9–3.05(1H,m), 3.3–3.7(1H,m), 4.01(1H,ddd,J=9.9,7.7,6.6 Hz), 5.06(2H,d,J=16.4 Hz), 5.24(2H,d,J=16.4 Hz), 6.85–7.25(7H,m), 7.50(1H,td,J=7.7,1.6 Hz).

Working Example 158

(3aR*,10aS*)-9-Benzyl-7-chloro-2,3,3a,4,9,10a-hexahydrobenzo[b]cyclopenta[e][1,4]diazepin-10 (1H)-one Using 9-benzyl-7-chloro-2,3,9,10a-tetrahydrobenzo[b]cyclopenta[e][1,4]diazepin-10(1H)-one, the titled compound was synthesized in substantially the same manner as in Working Example 26 in a yield of 53%, m.p. 160°–163° C. (ethylacetate-hexane).

$^1$H NMR (CDCl$_3$) δ: 1.5–2.1(5H,m), 2.3–2.55(1H,m), 2.9–3.0(1H,m), 3.3–3.6(1H,br), 3.9–4.05(1H,m), 4.96(2H,d,J=15.7 Hz), 5.15(2H,d,J=15.7 Hz), 6.82(2H,d,J=8.4 Hz), 6.99(1H,dd,J=8.3,2.3 Hz), 7.15(1H,d,H=2.2 Hz), 7.15–7.3 (5H,m).

Working Example 159

1,3-dibenzyl-4-((E)-styryl)-1,3,4,5-tetrahydro-1,5-benzodiazepin-2)2H)-one

Using 1,3-dibenzyl-4-((E)-styryl)-1,3-dihydro-1,5-benzodiazepin-2(2H)-one, the titled compound was synthesized in substantially the same manner as in Working Example 24 as an amorphous product in a yield of 89%.

$^1$H NMR (CDCl$_3$) δ: 2.60(1H,dd,J=13.8,5.4 Hz), 3.13–3.35(2H,m), 3.49(1H,br s), 4.35(1H,dd,J=8.0,5.4 Hz), 4.93(1H,d,J=15.8 Hz), 5.22(1H,d,J=15.8 Hz), 6.40(1H,dd, J=15.6,8.0 Hz), 6.54(1H,d,J=15.6 Hz), 6.86–7.48(19H,m).

Working Example 160

1-Benzyl-4-methyl-3-(2-propen-1-yl)-1,3,4,5-tetrahydro-1,5-benzodiazepin-2(2H)-one Using 1-benzyl-4-methyl-3-(2-propen-1-yl)-1,3-dihydro-1,5-benzodiazepin-2(2H)-one, the titled compound was synthesized in substantially the same manner as in Working Example 24 in a yield of 85%, m.p. 81°–83° C. (diethylether).

$^1$H NMR (CDCl$_3$) δ: 1.27(3H,d,J=6.2 Hz), 1.99–2.13(1H, m), 2.54–2.69(1H,m), 2.94(1H,d,J=11.2 Hz), 3.48(1H,br s), 3.79–3.91(1H,m), 4.94–5.07(2H,m), 5.08(2H,s), 5.60–5.81 (1H,m), 6.78–7.32(9H,m).

Working Example 161

1-Benzyl-4-methyl-3-((E)-3-phenyl-2-propen-1-yl)-1,3,4,5-tetrahydro-1,5-benzodiazepin-2(2H)-one Using 1-benzyl-4-methyl-3((E)-3-phenyl-2-propen-1-yl)-1,3-dihydro-1,5-benzodiazepin-2(2H)-one, the titled compound was synthesized by substantially the same procedure as in Working Example 24 in a yield of 77%, m.p. 119°–120° C. (diethyl ether).

$^1$H NMR (CDCl$_3$) δ: 1.30(3H,d,J=6.2 Hz), 2.12–2.28(1H, m), 2.70–2.85(1H,m), 2.96–3.05(1H,m), 3.55(1H,br s), 3.85–4.00(1H,m), 4.97(1H,d,J=15.4 Hz), 5.20(1H,d,J=15.4 Hz), 6.07–6.19(1H,m), 6.42(1H,d,J=15.8 Hz), 6.82–7.50 (13H,m), 7.68–7.88(1H,m).

Working Example 162

9,10a-Bis(4-Nitrobenzyl)-2,3,3a,4,9,10a-hexahydrobenzo[b]cyclopenta[e][1,4]diazepin-10 (1H)-one Using 2,3,9,10a-tetrahydrobenzo[b]cyclopenta-[e][1,4]diazepin-10(1H)-one and 4-nitrobenzyl bromide, a crude product was produced by substantially the same procedure as in Working Example 10. The crude product was, without further purification, subjected to substantially the same reaction as in Working Example 24, and the dibenzyl compound produced simultaneously with the compound of Working Example 26 was purified by silica-gel column chromatography (hexane-ethylacetate 2:1), followed by crystallization from ethyl acetate-hexane to give the titled compound in a yield of 7.7%, m.p. 226°–230° C.

$^1$H NMR (CDCl$_3$) δ: 1.4–2.2(5H,m), 2.55(2H,d,J=14.3 Hz), 2.6–2.8(1H,m), 2.96(2H,d,J=14.3 Hz), 3.47(1H,br s), 3.73(1H,t,J=7.1 Hz), 4.86(2H,d,J=15.9 Hz), 5.47(2H,d,J= 15.9 Hz), 6.9–7.3(6H,m), 7.43(2H,d,J=8.8 Hz), 8.06(2H,d, J=8.8 Hz), 8.09(2H,d,J=8.8 Hz).

Working Example 163

(3aR*,10aS*)-9-(4-Aminobenzyl)-2,3,3a,4,9,10a-hexahydrobenzo[b]cyclopenta[e][1,4]diazepin-10 (1H)-one (3aR*,10aS*)-9-(4-Nitrobenzyl)-2,3,3a,4,9,10a-hexahydrobenzo[b]cyclopenta[e][1,4]diazepin-10(1H)-one (5.06 g, 15 mmol) and 10% palladium-carbon (hydrous) (0.5 g) were suspended in a mixture of tetrahydrofuran (15 mL) and methanol (15 mL). The suspension was stirred for 4.5 hours at room temperature. The catalyst was filtered off, and the filtrate was concentrated under reduced pressure. The concentrate was crystallized from ethyl acetate-hexane to give 3.27 g (yield 71%) of the titled compound, m.p. 149.1°–149.6° C.

$^1$H NMR (CDCl$_3$) δ: 1.4–2.1(5H,m), 2.35–2.6(1H,m), 2.85–3.0(1H,m), 3.96(1H,ddd,J=10.1,7.9,6.6 Hz), 4.95(2H, s), 6.56(2H,d,J=8.4 Hz), 6.8–7.2(6H,m).

Working Example 164

1-Benzyl-4-phenethyl-1,3,4,5-tetrahydro-1,5-benzodiazepin-2(2H)-one

A suspension of 1-benzyl-4-((E)-styryl)-1,3,4,5-tetrahydro-1,5-benzodiazepin-2(2H)-one (0.51 g, 0.69 mmol) and platinum oxide (50 mg) in methanol (20 ml) was stirred for 3 hours at room temperature under hydrogen atmosphere. The reaction mixture was subjected to filtration. The solvent of the filtration was distilled off, and the residue was crystallized from diethyl ether to give 500 mg (yield 98%) of the titled compound, m.p. 135°–137° C.

$^1$H NMR (CDCl$_3$) δ: 1.86–1.97(2H,m), 2.43(1H,dd,J= 12.4,7.6 Hz), 2.62–2.77(3H,m), 3.36(1H,brs), 3.83–4.02 (1H,m), 5.02(1H,d,J=15.8 Hz), 5.12(1H,d,J=15.8 Hz), 6.74 (1H,dd,J=7.4,1.6 Hz), 6.87–7.38(13H,m).

Working Example 165

1-Benzyl-4-phenethyl-5-(phthalimidoacetyl)-1,3,4,5-tetrahydro-1,5-benzodiazepin-2(2H)-one

Using 1-benzyl-4-phenethyl-1,3,4,5-tetrahydro-1,5-benzodiazepin-2(2H)-one, the titled compound was synthesized in substantially the same manner as in Working Example 46 in a yield of 46% as an amorphous product.

$^1$H NMR (CDCl$_3$) δ: 1.52–1.67(1H,m), 1.81–2.07(1H,m), 2.34(1H,t,J=12.8 Hz), 2.54–2.77(3H,m), 3.20(1H,d,J=16.4 Hz), 3.89(1H,d,J=16.4 Hz), 4.91(1H,d,J=15.4 Hz), 5.21–5.44(1H,m), 5.37(1H,d,J=15.4 Hz), 7.06–7.59(14H,m), 7.60–7.91(4H,m).

Working Example 166

1-Benzyl-4-methyl-5-(phthalimidoacetyl)-3-(2-propen-1-yl)-1,3,4,5-tetrahydro-1,5-benzodiazepin-2(2H)-one

Using 1-benzyl-4-methyl-3-(2-propen-1-yl)-1,3,4,5-tetrahydro-1,5-benzodiazepin-2(2H)-one, the titled compound was synthesized in substantially the same manner as in Working Example 46 in a yield of 46%, m.p. 218°–219° C. (diethyl ether).

$^1$H NMR (CDCl$_3$) δ: 1.18(3H,d,J=7.0 Hz), 1.28–1.46(1H,m), 1.88–2.07(1H,m), 3.02–3.19(1H,m), 3.26(1H,d,J=16.4 Hz), 3.94(1H,d,J=16.4 Hz), 4.73–5.00(2H,m), 4.83(1H,d,J=15.0 Hz), 5.42(1H,d,J=15.0 Hz), 5.48–5.81(2H,m), 7.18–7.51(9H,m), 7.70–7.91(4H,m).

Working Example 167

1-Benzyl-4-methyl-3-((E)-3-phenyl-2-propen-1-yl)-5-(phthalimidoacetyl)-1,3,4,5-tetrahydro-1,5-benzodiazepin-2(2H)-one

Using 1-benzyl-4-methyl-3-((E)-3-phenyl-2-propen-1-yl)-1,3,4,5-tetrahydro-1,5-benzodiazepin-2(2H)-one, the titled compound was synthesized in substantially the same manner as in Working Example 46 in a yield of 71%, m.p. 262°–264° C. (diethyl ether).

$^1$H NMR (CDCl$_3$) δ: 1.24(3H,d,J=6.8 Hz), 1.31–1.52(1H,m), 2.21–2.24(1H,m), 3.17–3.31(1H,m), 3.42(1H,d,J=16.4 Hz), 4.04(1H,d,J=16.4 Hz), 5.09(2H,s), 5.40–5.58(1H,m), 5.95–6.10(2H,m), 7.04–7.53(14H,m), 7.69–7.91(4H,m).

Working Example 168

**(4aR*,11aS*)-10-Benzyl-5-(phthalimidoacetyl)- 1,2,3,4,4a,5,10,11a-octahydro-11H-dibenzo[b,e][1,4]-diazepin-11-one**

To a solution of (4aR*,11aS*)-10-benzyl-1,2,3,4,4a,5,10,11a-octahydro-11H-dibenzo[b,e][1,4]-diazepin-11-one (200 mg, 0.65 mmol) in 1,2-dichloroethane (2 mL) was added phthalimidoacetyl chloride (175 mg, 0.78 mmol), and the mixture was stirred for 15 minutes at room temperature. To this solution was added pyridine (0.08 mL), and the mixture was stirred for 15 minutes at room temperature. To the reaction mixture was added a saturated aqueous solution of sodium hydrogencarbonate. The aqueous layer was separated, and the organic layer was washed with water and a saturated aqueous solution of sodium chloride, which was dried over magnesium sulfate, followed by filtration and concentration under reduced pressure. The concentrate was crystallized from ethanol to give 138 mg (yield 43%) of the titled compound, m.p. 241°–242.5° C.

$^1$H NMR (CDCl$_3$) δ: 0.6–0.9(1H,m), 1.0–1.3(2H,m), 1.3–1.7(4H,m), 2.15–2.3(1H,m), 3.02(1H,dt,J=14.6,5.7 Hz), 3.37(2H,d,J=16.6 Hz), 4.15(2H,d,J=16.6 Hz), 4.90(2H,d,J=15.4 Hz), 5.15–5.3(1H,m), 5.45(2H,d,J=15.4 Hz), 7.2–7.45 (8H,m), 7.55–7.65(1H,m), 7.65–7.9(4H,m).

Working Example 169

**(3aR*,10aS*)-9-(4-Chlorobenzyl)-4-(phthalimidoacetyl)-2,3,3a,4,9,10a-hexahydrobenzo[b]cyclopenta[e][1,4]-diazepine-10(1H)-one**

(3aR*,10aS*)-9-(4-Chlorobenzyl)-2,3,3a,4,9,10a-hexahydrobenzo[b]cyclopenta[e][1,4]diazepin-10(1H)-one hydrochloride (426 mg, 1.2 mmol) and phthalimidoacetyl chloride (389 mg, 1.7 mmol) were suspended in toluene (4 mL). The suspension was refluxed for 16 hours. To the reaction mixture was added a saturated aqueous solution of sodium hydrogencarbonate, which was subjected to extraction with chloroform. The extract solution was washed with water and a saturated aqueous solution of sodium hydrogencarbonate, which was dried and subjected to filtration. The filtrate was concentrated under reduced pressure. The concentrate was crystallized from ethanol-hexane to give 91 mg (yield 15%) of the titled compound, m.p. 205°–206° C.

$^1$H NMR (CDCl$_3$) δ: 1.1–1.5(3H,m), 1.5–1.9(2H,m), 2.0–2.25(1H,m), 3.18(1H,dt,J=11.9,9.1 Hz), 3.46(2H,d,J=16.7 Hz), 4.14(2H,d,J=16.7 Hz), 5.07(2H,d,J=15.4 Hz), 5.25 (2H,d,J=15.4 Hz), 5.7–5.9(1H,m), 7.2–7.5(8H,m), 7.65–7.9 (4H,m).

Working Example 170

**(3aR*,10aS*)-4-(2H-1,3-Dioxo-1,3,4,5,6,7-hexahydroisoindole-2-acetyl)-9-(1-naphthylmethyl)-2,3,3a,4,9,10a-hexahydrobenzo[b]cyclopenta[e][1,4]-diazepin-10(1H)-one**

Using (3aR*,10aS*)-9-(1-naphthylmethyl)-2,3,3a,4,9,10a-hexahydrobenzo[b]cyclopenta[e][1,4]-diazepin-10(1H)-one and 2H-1,3-dioxo-1,3,4,5,6,7-hexahydroisoindole-2-acetic acid, synthesis was conducted in substantially the same manner as in Working Example 49 to give a crude product, which was purified by silica-gel column chromatography (hexane-ethyl acetate 2:1→1:1), followed by crystallization from ethylacetate-hexane to give the titled compound in a yield of 50%, m.p. 220°–222° C.

$^1$H NMR (CDCl$_3$) δ: 1.1–1.5(3H,m), 1.6–2.0(2H,m), 1.74 (4H,s), 2.0–2.3(1H,m), 2.32(4H,s), 2.91(2H,d,J=16.5 Hz), 3.21(1H,dt,J=11.8,9.2 Hz), 3.58(2H,d,J=16.5 Hz), 5.56(2H,d,J=15.8 Hz), 5.70(2H,d,J=15.8 Hz), 5.7–5.85(1H,m), 7.15–7.5(6H,m), 7.5–7.6(2H,m), 7.75(1H,d,J=8.0 Hz), 7.8–7.9(1H,m), 8.0–8.1(1H,m).

Working Example 171

**(3aR*,10aS*)-4(2H-1,3-Dioxo-1,3,4,5,6,7-hexahydroisoindole- 2-acetyl)-9-(naphthylmethyl)-2,3,3a,4,9,10a-hexahydrobenzo[b]cyclopenta[e][1,4]-diazepin-10(1H)-one**

Using (3aR*,10aS*)-9-(2-naphthylmethyl)-2,3,3a,4,9,10a-hexahydrobenzo[b]cyclopenta[e][1,4]-diazepin-10(1H)-one, the titled compound was synthesized in substantially the same manner as in Working Example 170 in a yield of 32% m m.p. 225°–226° C. (ethyl acetate-hexane).

$^1$H NMR (CDCl$_3$) δ: 1.1–1.5(3H,m), 1.5–2.0(2H,m), 1.74 (4H,s), 2.0–2.25(1H,m), 2.32(4H,s), 3.22(1H,dt,J=11.8,9.2

Hz), 3.33(2H,d,J=16.4 Hz), 3.83(2H,d,J=16.4 Hz), 5.28(2H, d,J=15.6 Hz), 5.38(2H,d,J=15.6 Hz), 5.81(1H,td,J=8.6,3.9 Hz), 7.15–7.55(7H,m), 7.62(1H,s), 7.7–7.85(2H,m), 7.88 (1H,d,J=8.6 Hz).

Working Example 172

9-Benzyl-4-(2,3-diphenylmaleimidoacetyl)-2,3,3a,4, 9,10a-hexahydrobenzo[b]cyclopenta[e][1,4]- diazepin-10(1H)-one Using 2,3-diphenyl maleic anhydride, synthesis was conducted in substantially the same manner as in Working Example 70 to give a mixture of cis-compound and trans-compound (13:7) in a yield of 78%, m.p. 207°–208° C. (chloroform-ethanol-diethyl ether).

$^1$H NMR (CDCl$_3$) δ: 1.0–2.0(4.3H,m), 2.0–2.4(1.35H,m), 2.8–3.05(0.7H,m), 3.05–3.3(0.65H,m), 3.19(0.7H,d,J=17.1 Hz), 3.29(1.3H,d,J=16.7 Hz), 3.85(0.7H,d,J=17.1 Hz), 3.92 (1.3H,d,J=16.7 Hz), 4.1–4.25(0.35H,m), 4.54(0.7H,d,J=14.4 Hz), 4.87(1.3H,d,J=15.2 Hz), 5.48(1.3H,d,J=15.2 Hz), 5.7–5.9(0.65H,m), 5.81(0.7H,d,J=14.4 Hz), 7.1–7.6(19H, m).

Working Example 173

(3aR*,10aS*)-9-Benzyl-4-(2,3- dimethylmaleimidoacetyl)-2,3,3a,4,9,10a- hexahydrobenzo[b]cyclopenta[e][1,4]-diazepin-10 (1H)-one Using maleic anhydride, the titled compound was synthesized in substantially the same manner as in Working Example 70 in a yield of 46%, m.p. 196°–200° C. (chloroform-ethanol-diisopropyl ether).

$^1$H NMR (CDCl$_3$) δ: 1.0–1.5(3H,m), 1.5–2.3(3H,m), 1.96 (6H,s), 3.05–3.25(1H,m), 3.17(2H,d,J=16.9 Hz), 3.82(2H,d, J=16.9 Hz), 4.96(2H,d,J=15.3 Hz), 5.37(2H,d,J=15.3 Hz), 5.75(1H,td,J=8.6,3.9 Hz), 7.1–7.5(9H,m).

Working Example 174

9-Benzyl-4-(cis-cyclohexane-1,2- dicarboximidoacetyl)-2,3,3a,4,9,10a- hexahydrobenzo[b]cyclopenta[e][1,4]-diazepin 10 (1H)-one Synthesis was conducted in substantially the same manner as in Working Example 80 from (3aR*,10aS*)-4- (aminoacetyl)-9-benzyl-2,3,3a,4,9,10a-hexahydrobenzo[b] cyclopenta[e][1,4]diazepin-10(1H)-one and cis-cyclohexane-1,2-dicarboxylic anhydride to give a crude product, which was purified by silica-gel column chromatography (ethyl acetate), followed by crystallization from ethyl acetate-hexane to give a mixture of cis-compound and trans-compound (7:3) on H between 3a- and 10a-positions in a yield of 74%, m.p. 180°–184° C.

$^1$H NMR (CDCl$_3$) δ: 1.0–2.0(12.4H,m), 2.0–2.4(1.3H,m), 2.8–3.0(2.6H,m), 3.05–3.3(0.7H,m), 3.08(0.6H,d,J=16.9 Hz), 3.24(1.4H,d,J=16.5 Hz), 3.72(0.6H,d,J=16.9 Hz), 3.84 (1.4H,d,J=16.5 Hz), 4.05–4.25(0.3H,m), 4.57(0.6H,d,J=15.0 Hz), 5.01(1.4H,d,J=15.4 Hz), 5.30(1.4H,d,J=15.4 Hz), 5.7–5.85(0.7H,m), 5.75(0.6H,d,J=15.0 Hz), 7.15–7.5(9H, m).

Working Example 175

(3aR*,10aS*)-9-benzyl-4-(trans-cyclohexane-1,2- dicarboxyimidoacetyl)-2,3,3a,4,9,10a- hexahydrobenzo[b]cyclopenta[e][1,4]diazepine-10 (1H)-one The diasteromer mixture was obtained by reacting (3aR*, 10aS*)-4-(aminoacetyl)-9-benzyl-2,3,3a,4,9,10a- hexahydrobenzo[b]cyclopenta[e][1,4]diazepine-10(1H)-one and (±)-trans-cyclohexane-1,2-dicarboxylic anhydride as the same manner as in Working Example 70 in yield 46%. m.p. 182°–184° C. (ethylacetate-hexane).

$^1$H NMR (CDCl$_3$) δ: 1.0–2.5(16H,m), 3.05–3.3(2H,m), 3.7–3.8(1H,m), 4.9–5.05(1H,m), 5.2–5.4(1H,m), 5.76(1H, td,J=8.6,3.6 Hz), 7.1–7.5(9H,m).

Working Example 176

(3aR*,10aS*)-9-Benzyl-4-(cyclopenten-1,2- dicarboximidoacetyl)-2,3, 3a,4,9,10a- hexahydrobenzo[b]cyclopenta[e][1,4]diazepin-10 (1H)-one A mixture of (3aR*,10aS*)-4-(aminoacetyl)-9-benzyl-2, 3,3a,4,9,10a-hexahydrobenzo[b]cyclopenta-[e][1,4] diazepin-10(1H)-one (349 mg, 1 mmol), cyclopentane-1,2- dicarboxylic anhydride (138 mg, 1 mmol) and xylene (3 mL) was stirred for 75 minutes at 140° C. The reaction mixture was cooled, to which was added hexane (5 mL). Resulting precipitate was collected by filtration, to which were added sodium acetate (99 mg, 1.2 mmol) and acetic anhydride (3 mL), and the mixture was stirred for two hours at 100° C. To the reaction mixture was added water, which was viborourly stirred and, then, subjected to extraction twice with dichloromethane. Organic layers were combined and washed with water (twice), a saturated aqueous solution of sodium hydrogencarbonate and a saturated aqueous solution of sodium chloride, which was dried over magnesium sulfate and subjected to filtration, and the filtrate was concentrated under reduced pressure. The concentrate was purified by silica-gel column chromatography (hexane-ethyl acetate 2:1→1:1), followed by crystallization from ethyl acetate-diethyl ether to give 200 mg (yield 47%) of the titled compound, m.p. 178°–179° C.

$^1$H NMR (CDCl$_3$) δ: 1.0–1.5(3H,m), 1.55–1.9(2H,m), 2.0– 2.2(1H,m), 2.3–2.5(2H,m), 2.67(4H,t,J=7.0 Hz), 3.17 (1H,dt,J=11.8,9.0 Hz), 3.17(2H,d,J=16.8 Hz), 3.83(2H,d,J= 16.8 Hz), 5.00(2H,d,J=15.4 Hz), 5.33(2H,d,J=15.4 Hz), 5.7–5.85(1H,m), 7.1–7.5(9H,m).

Working Example 177

(3aR*,10aS*)-9-Benzyl-4-((phenylacetamido)acetyl) -2,3,3a,4,9,10a-hexahydrobenzo[b]cyclopenta[e][1, 4]-diazepin-10(1H)-one Using phenylacetyl chloride, the titled compound was synthesized in substantially the same manner as in Working Example 81 in a yield of 69%, m.g. 237°–238° C. (diethyl ether).

$^1$H NMR (CDCl$_3$) δ: 1.00–1.42(3H,m), 1.45–1.89(2H,m), 1.85(1H,dd,J=18.0,3.4 Hz), 1.98–2.18(1H,m), 3.12(1H,dt, J=12.2,8.4 Hz), 3.53(2H,s), 3.70(1H,dd,J=18.2,5.8 Hz), 4.57 (1H,d,J=14.8 Hz), 5.53(1H,d,J=14.8 Hz), 5.74–5.87(1H,m), 5.90–6.00(1H,m), 6.85–7.50(14H,m).

Working Example 178

(3aR*,10aS*)-9-Benzyl-4-((3-phenyl propionamido) acetyl)-2,3,3a,4,9,10a-hexahydrobenzo[b]cyclopenta [e][1,4]-diazepin-10(1H)-one Using 3-phenyl propionyl chloride, the titled compound was synthesized in substantially the same manner as in Working Example 81 in a yield of 49%, m.p. 205°–207° C. (diethyl ethyl).

$^1$H NMR (CDCl$_3$) δ: 1.01–1.44(3H,m), 1.51–1.91(2H,m), 2.03–2.20(2H,m), 2.44–2.52(2H,m), 2.93(2H,t,J=8.0 Hz), 3.16(1H,dt,J=12.4,8.8 Hz), 3.73(1H,dd,J=18.0,5.4 Hz), 4.68 (1H,d,J=14.8 Hz), 5.46(1H,d,J=14.8 Hz), 5.79–5.91(1H,m), 6.00–6.11(1H,m), 7.02–7.52(14H,m).

Working Example 179

(3aR*,10aS*)-9-Benzyl-4-((4-phenylbutyramido) acetyl)-2,3,3a,4,9,10a-hexahydrobenzo[b]cyclopenta [e][1,4]-diazepin-10(1H)-one Using 4-phenyl butyryl chloride, the titled compound was synthesized in substantially the same manner as in Working Example 81 in a yield of 48%, m.p. 219°–221° C. (diethyl ether).

$^1$H NMR (CDCl$_3$) δ: 1.01–1.48(3H,m), 1.50–2.29(8H,m), 2.64(2H,t,J=7.4 Hz), 3.16(1H,dt,J=12.2,8.8 Hz), 3.76(1H, dd,J=18.2,5.6 Hz), 4.70(1H,d,J=14.8 Hz), 5.45(1H,d,J=14.8 Hz), 5.80–5.91(1H,m), 6.05(1H,br s), 7.01–7.52(14H,m).

Working Example 180

(3aR*,10aS*)-4-((Benzenesulfonamido)acetyl)-9-benzyl-2,3,3a,4,9,10a-hexahydrobenzo[b]cyclopenta [e][1,4]-diazepin-10(1H)-one To a solution of (3aR*,10aS*)-4-aminoacetyl-9-benzyl-2, 3,3a,4,9,10a-hexahydrobenzo[b]cyclopenta-[e][1,4] diazepin-10(1H)-one (0.2 g, 0.57 mmol) and benzenesulfonyl chloride (0.12 g, 0.69 mmol) in dichloromethane (10 mL) was added triethylamine (70 mg, 0.69 mmol). The mixture was stirred for 30 minutes at room temperature. To the reaction mixture was added a saturated aqueous solution of sodium hydrogencarbonate, which was subjected to extraction with dichloromethane. The extract was washed with water and dried, then, the solvent was distilled off. The residue was purified by silica-gel column chromatography (dichloromethane), which was crystallized from diethyl ether to give 170 mg (yield 61%) of the titled compound, m.p. 185°–187° C.

$^1$H NMR (CDCl$_3$) δ: 1.00–1.60(4H,m), 1.70–1.89(1H,m), 1.95–2.11(1H,m), 2.15(1H,dd,J=16.8,3.6 Hz), 3.11(1H,dt,J= 12.0,8.8 Hz), 3.33(1H,dd,J=16.8,5.8 Hz), 4.69(1H,d,J=15.0 Hz), 5.30(1H,d,J=15.0 Hz), 5.28–5.41(1H,br s), 5.64–5.75 (1H,m), 6.82(1H,dd,J=7.8,1.4 Hz), 7.12–7.63(11H,m), 7.73–7.78(2H,m).

Working Example 181

(3aR*,10aS*)-4-(N-Acetyl-N-(3-phenylpropionyl) aminoacetyl)-9-benzyl-2,3,3a,4,9,10a-hexahydrobenzo[b]cyclopenta[e][1,4]diazepin-10 (1H)-one Using (3aR*,10aS*)-9-benzyl-4-((3-phenylpropionamido)acetyl)-2,3,3a,4,9,10a-hexahydrobenzo[b]cyclopenta[e][1,4]diazepin-10(1H)-one, the titled compound was synthesized in substantially the same manner as in Working Example 109 in a yield of 76%, m.p. 138°–140° C. (diethyl ether).

$^1$H NMR (CDCl$_3$) δ: 1.05–1.90(5H,m), 2.02–2.21(1H,m), 2.28(3H,s), 2.63–2.98(5H,m), 3.08–3.23(1H,m), 4.25(1H,d, J=17.2 Hz), 4.92(1H,d,J=15.2 Hz), 5.18(1H,d,J=15.2 Hz), 5.73–5.84(1H,m), 7.09–7.50(14H,m).

Working Example 182

(3aR*,10aS*)-9-(4-Biphenylmethyl)-4-(phthalimidoacetyl)-2,3,3a,4,9,10a-hexahydrobenzo [b]cyclopenta[e][1,4]-diazepin-10(1H)-one Using 4-(chloromethyl)biphenyl, the titled compound was synthesized in substantially the same manner as in Working Example 113 in a yield of 49%, m.p. 207.0°–207.5° C. (ethanol).

$^1$H NMR (CDCl$_3$) δ: 1.1–1.5(3H,m), 1.6–2.0(2H,m), 2.0–2.5(1H,m), 3.21(1H,dt,J=11.6,9.1 Hz), 3.53(2H,d,J= 16.4 Hz), 4.14(2H,d,J=16.4 Hz), 5.18(2H,d,J=15.6 Hz), 5.30 (2H,d,J=15.6 Hz), 5.82(1H,td,J=8.7,4.1 Hz), 7.2–7.5(9H,m), 7.5–7.65(4H,m), 7.65–7.9(4H,m).

Working Example 183

(3aR*,10aS*)-4-(Phthalimidoacetyl)-9-(2-quinolylmethyl) -2,3,3a,4,9,10a-hexahydrobenzo[b] cyclopenta[e][1,4]-diazepin-10(1H)-one 2-(Chloromethyl)quinoline hydrochloride (321 mg, 1.5 mmol) was dissolved in water (0.5 mL) and ethyl acetate (1 mL), which was neutralized with sodium hydrogencarbonate. The organic layer was separated, and the aqueous layer was subjected to extraction twice with ethyl acetate. The organic layers were combined and dried over magnesium sulfate, which was concentrated under reduced pressure. To the concentrate were added (3aR*,10aS*)-4-(phthalimidoacetyl)-2,3,3a,4,9,10a-hexahydrobenzo[b]-cyclopenta[e][1,4]diazepin-10(1H)-one (390 mg, 1.0 mmol) and N,N-dimethylformamide (3 mL). To this suspension was added, at 0° C., sodium hydride (60% liquid paraffin dispersion, 48 mg, 1.2 mmol), and the mixture was stirred for 20 minutes at room temperature. To the reaction mixture was added water, which was subjected to extraction twice with chloroform. Organic layers were combined, washed with water, dried over magnesium sulfate, subjected to filtration and, then, concentrated under reduced pressure. The concentrate was crystallized from ethanol-hexane to give 243 mg (yield 46%) of the titled compound, m.p. 258°–260° C.

$^1$H NMR (CDCl$_3$) δ: 1.1–1.5(3H,m), 1.6–1.95(2H,m), 2.05–2.25(1H,m), 3.1–3.3(1H,m), 3.74(2H,d,J=16.5 Hz), 4.23(2H,d,J=16.5 Hz), 5.32(2H,d,J=15.8 Hz), 5.59(2h,d,J= 15.8 Hz), 5.87(1H,td,J=8.7,4.1 Hz), 7.2–7.9(12H,m), 8.00 (1H,d,J=8.4 Hz), 8.25(1H,d,J=8.4 Hz).

Working Example 184

(3aR*,10aS*)-4-(Phthalimidoacetyl)-9-(2-quinolylmethyl)-2,3,3a,4,9,10a-hexahydrobenzo[b]-cyclopenta[e][1,4]diazepin-10(1H)-one hydrochloride (3aR*,10aS*)-4-(Phthalimidoacetyl)-9-(2-quinolylmethyl)-2,3,3a,4,9,10a-hexahydrobenzo[b]-cyclopenta[e][1,4]diazepin-10(1H)-one, which was produced in Working Example 183, was made into the corresponding hydrochloride in substantially the same manner as in Working Example 118, m.p. 256°–259° C. (ethanol-diethyl ether).

$^1$H NMR (DMSO-d$_6$) δ: 1.2–1.5(3H,m), 1.6–1.9(2H,m), 1.9–2.2(1H,m), 3.0–3,2(1H,m), 3.76(2H,d,J=16.4 Hz), 4.33 (2H,d,J=16.4 Hz), 5.0–5.25(1H,m), 5.6–5.8(2H,m), 7.3–7.8 (6H,m), 7.8–8.2(7H,m), 8.5–8.7(1H,m).

Working Example 185

(3aR*,10aS*)-4-(Bromoacetyl)-9-(4-fluorobenzyl)-2,3,3a,4,9,10a-hexahydro[b]cyclopenta[e][1,4] diazepin-10(1H)-one Using (3aR*,10aS*)-9-(4-fluorobenzyl)-2,3,3a,4,9,10a-hexahydrobenzo[b]cyclopenta[e][1,4]-diazepin-10(1H)-one and bromoacetyl chloride, synthesis was conducted in substantially the same manner as in Working Example 122 to give a crude product, which was purified by silica-gel column chromatography (hexane-ethyl acetate 2:1→1:1), followed by crystallization from ethyl acetate-hexane to give the titled compound in a yield of 9%, m.p. 145°–147° C.

$^1$H NMR (CDCl$_3$) δ: 1.0–1.5(3H,m), 1.5–1.9(2H,m), 2.0–2.25(1H,m), 2.85(2H,d,J=13.2 Hz), 3.16(1H,dt,J=11.8, 9.1 Hz), 3.32(2H,d,J=13.2 Hz), 4.61(2H,d,J=14.7 Hz), 5.34 (2H,d,J=14.7 Hz), 5.82(1H,td,J=8.8,3.9 Hz), 6.95(2H,t,J= 8.6 Hz), 7.05–7.35(4H,m), 7.35–7.55(2H,m).

Working Example 186

(3aR*,10aS*)-9-Benzyl-4-(bromoacetyl)-7-chloro-2, 3,3a,4,9,10a-hexahydrobenzo[b]cyclopenta[e][1,4]-diazepin-10(1H)-one Using (3aR*,10aS*)-9-benzyl-7-chloro-2,3,3a,4,9,10a-hexahydrobenzo[b]cyclopenta[e][1,4]-diazepin-10(1H)-one and bromoacetyl bromide, the titled compound was synthesized in substantially the same manner as in Working Example 122 in a yield of 50%, m.p. 163°–164° C. (ethyl acetate-hexane).

$^1$H NMR (CDCl$_3$) δ: 1.05–1.7(4H,m), 1.7–1.95(1H,m), 2.0–2.25(1H,m), 2.78(2H,d,J=11.1 Hz), 2.86(2H,d,J=11.1 Hz), 3.17(1H,dt,J=11.7,9.0 Hz), 4.62(2H,d,J=15.0 Hz), 5.55 (2H,d,J=15.0 Hz), 5.80(1H,td,J=8.7,3.9 Hz), 7.1–7.35(7H, m), 7.42(1H,d,J=2.2 Hz).

Working Example 187

(3aR*,10aS*)-4-(Bromoacetyl)-9-(2-fluorobenzyl)-2,3,3a,4,9,10a-hexahydrobenzo[b]cyclopenta[e][1,4]-diazepin- 10(1H)-one Using (3aR*,10aS*)-9-(2-fluorobenzyl)-2,3,3a,4,9,10a-hexahydrobenzo[b]cyclopenta[e][1,4]-diazepin-10(1H)-one and bromoacetyl bromide, the titled compound was synthesized in substantially the same manner as in Working Example 122 in a yield of 62%, m.p. 198.5°–199.6° C. (ethyl acetate-hexane).

$^1$H NMR (CDCl$_3$) δ: 1.0–1.5(3H,m), 1.5–1.9(2H,m), 2.05–2.25(1H,m), 3.02(2H,d,J=11.4 Hz), 3.09(2H,d,J=11.4 Hz), 3.16(1H,dt,J=12.1,9.0 Hz), 4.96(2H,d,J=15.3 Hz), 5.41 (2H,d,J=15.3 Hz), 5.82(1H,ddd,J=9.2,8.4,4.0 Hz), 6.95(1H, ddd,J=10.0,8.2,1.6 Hz), 7.0–7.55(7H,m).

Working Example 188

4-((3aR*,10aS*)-4-(bromoacetyl)-7-chloro-10-oxo-1,2,3,3a,4,9,10,10a-octahydrobenzo[b]cyclopenta-[e][1,4]diazepin-9-ylmethyl)benzoate Using 4-((3aR*,10aS*)-7-chloro-10-oxo-1,2,3,3a,4,9,10, 10a-octahydrobenzo[b]cyclopenta-[e][1,4]diazepin-9-ylmethyl)benzoate and bromoacetyl chloride, the titled compound was synthesized in substantially the same manner as in Working Example 185 in a yield of 16%, m.p. 169.5°–170.1° C. (ethyl acetate-hexane).

$^1$H NMR (CDCl$_3$) δ: 1.1–1.75(4H,m), 1.8–2.0(1H,m), 2.05–2.3(1H,m), 3.05(2H,s), 3.20(1H,dt,J=11.9,9.1 Hz), 3.90(3H,s), 4.91(2H,d,J=15.8 Hz), 5.33(2H,d,J=15.8 Hz), 5.82(1H,td,J=8.8,3.9 Hz),7.1–7.4(5H,m), 7.98(2H,d,J=8.4 Hz).

Working Example 189

(3aR*,10aS*)-4-(Bromoacetyl)-9-(4-nitrobenzyl)-2, 3,3a,4,9,10a-hexahydrobenzo[b]cyclopenta[e][1,4]-diazepin-10(1H)-one Using (3aR*,10aS*)-9-(4-nitrobenzyl)-2,3,3a,4,9,10a-hexahydrobenzo[b]cyclopenta[e][1,4]-diazepin-10(1H)-one and bromoacetyl bromide, the titled compound was synthesized in substantially the same manner as in Working Example 185 in a yield of 37%, m.p. 160.5°–161.5° C. (ethyl acetate-hexane).

$^1$H NMR (CDCl$_3$) δ: 1.1–1.5(3H,m), 1.55–2.0(2H,m), 2.05–2.3(1H,m), 3.1–3.3(1H,m), 3.21(2H,d,J=10.2 Hz), 3.33(2H,d,J=10.2 Hz), 5.17(2H,s), 5.86(1H,td,J=8.8,4.0 Hz), 7.15–7.5(6H,m), 8.19(2H,d,J=8.8 Hz).

Working Example 190

(3aR*,10aS*)-9-(Benzyl-4-(glutarimidoacetyl)-2,3, 3a,4,9,10a-hexahydrobenzo[b]cyclopenta[e][1,4]-diazepin-10(1H)-one To a solution of glutarimide (136 mg, 1.2 mmol) in N,N-dimethylformamide (2 mL) was added, at 0° C., sodium hydride (60% liquid paraffin dispersion, 44 mg, 1.1 mmol), and the mixture was stirred for 5 minutes. To this mixture was added (3aR*,10aS*)-9-benzyl-4-(bromoacetyl) -2,3,3a,4,9,10a-hexahydrobenzo[b]-cyclopenta[e][1,4] diazepin-10(1H)-one (413 mg, 1 mmol), and the mixture was stirred for 30 minutes at room temperature. The reaction mixture was poured into a saturated aqueous solution of ammonium chloride (4 mL), which was subjected to extraction twice with chloroform. Organic layers were combined, washed with water and dried over magnesium sulfate, which was subjected to filtration, and the filtrate was concentrated under reduced pressure. The concentrate was crystallized from ethyl acetate-diethyl ether to give 305 mg (yield 68%) of the titled compound, m.p. 220°–221° C.

$^1$H NMR (CDCl$_3$) δ: 1.1–1.5(3H,m), 1.5–2.2(5H,m), 2.67 (4H,t,J=6.6 Hz), 3.17(1H,dt,J=11.8,9.2 Hz), 3.77(2H,d,J= 15.8 Hz), 4.18(2H,d,J=15.8 Hz), 5.07(2H,d,J=15.8 Hz), 5.23 (2H,d,J=15.8 Hz), 5.7–5.9(1H,m), 7.15–7.45(9H,m).

Working Example 191

(3aR*,10aS*)-9-(4-Fluorobenzyl)-4-(phthalimidoacetyl)- 2,3,3a,4,9,10a-hexahydrobenzo[b]cyclopenta[e][1,4]-diazepin-10(1H)-one (3aR*,10aS*)-4-(Bromoacetyl)-9-(4-fluorobenzyl)-2,3,3a,4,9,10a-hexahydrobenzo[b]cyclopentate)[1,4] -diazepin-10(1H)-one (388 mg, 0.9 mmol) and potassium phthalimide (167 mg, 0.9 mmol) were suspended in N,N-dimethylformamide (2 mL), and the suspension was stirred for 14 hours. To the reaction mixture was added water, which was subjected to extraction three times with chloroform. Organic layers were combined, washed with water and a saturated aqueous solution of sodium chloride and dried over magnesium sulfate, which was subjected to filtration, and the filtrate was concentrated under reduced pressure. The concentrate was crystallized from ethanol-hexane to give 322 mg (yield 72%) of the titled compound, m.p. 206°–207° C.

$^1$H NMR (CDCl$_3$) δ: 1.0–1.5(3H,m), 1.6–1.9(2H,m), 2.0–2.25(1H,m), 3.18(1H,dt,J=11.9,9.1 Hz), 3.38(2H,d,J= 16.4 Hz), 4.09(2H,d,J=16.4 Hz), 4.97(2H,d,J=15.4 Hz), 5.36 (2H,d,J=15.4 Hz), 5.7–5.9(1H,m), 7.04(2H,t,J=8.6 Hz), 7.2–7.5(6H,m), 7.65–7.9(4H,m).

Working Example 192

Methyl 4-((3aR*,10aS*)-7-chloro-10-oxo-4-(phthalimidoacetyl)-1,2,3,3a,4,9,10,10a-octahydrobenzo[b]cyclopenta[e][1,4]diazepin-9-ylmethyl)benzoate Using methyl 4-((3aR*,10aS*)-4-(bromoacetyl)-7-chloro-10-oxo-1,2,3,3a,4,9,10,10a-octahydrobenzo[b]

cyclopenta[e][1,4]diazepin-9-ylmethyl) benzoate, the titled compound was synthesized in substantially the same manner as in working Example 191 in a yield of 88%, m.p. 234.4–235.3C. (ethanol-hexane).

$^1$H NMR (CDCl$_3$) δ: 1.2–1.8(4H,m), 1.8–2.0(1H,m), 2.0–2.25(1H,m), 3.21(1H,dt,J=11.6,9.0 Hz), 3.46(2H,d,J=16.4 Hz), 3.89(3H,s), 4.06(2H,d,J=16.4 Hz), 5.21(2H,s), 5.7–5.9(1H,m), 7.2–7.45(5H,m), 7.65–7.9(4H,m), 8.05(2H, d,J=8.4 Hz).

Working Example 193

(3aR*,10aS*)-9-Benzyl-7-chloro-4-(phthalimidoacetyl)-2,3,3a,4,9,10a-hexahydrobenzo[b]cyclopenta[e][1,4]-diazepin-10(1H)-one Using (3aR*,10aS*)-9-benzyl-4-(bromoacetyl)-7-chloro-2,3,3a,4,9,10a-hexahydrobenzo[b]cyclopenta-[e][1,4]diazepin-10(1H)-one, the titled compound was synthesized in substantially the same manner as in Working Example 191 in a yield of 88%, m.p. 241.4°–242.7° C. (chloroform-hexane).

$^1$H NMR (CDCl$_3$) δ: 1.1–1.75(4H,m), 1.75–1.95(1H,m), 2.0–2.25(1H,m), 3.19(1H,dt,J=11.9,9.2 Hz), 3.37(2H,d,J=16.6 Hz), 3.93(2H,d,J=16.6 Hz), 4.89(2H,d,J=15.4 Hz), 5.44 (2H,d,J=15.4 Hz), 5.76(1H,ddd,J=9.0,8.2,3.9 Hz), 7.2–7.4 (8H,m), 7.65–7.9(4H,m).

Working Example 194

(3aR*,10aS*)-9-(2-Fluorobenzyl)-4-(phthalimidoacetyl)-2,3,3a,4,9,10a-hexahydrobenzo[b]cyclopenta[e][1,4]-diazepin-10(1H)-one Using (3aR*,10aS*)-4-(bromoacetyl)-9-(2-fluorobenzyl)-2,3,3a,4,9,10a-hexahydrobenzo-[b]cyclopenta[e][1,4]diazepin-10(1H)-one, the titled compound was synthesized in a yield of 70%, m.p. 250°–253° C. (dichloromethane-hexane).

$^1$H NMR (CDCl$_3$) δ: 1.1–1.5(3H,m), 1.6–1.95(2H,m), 2.0–2.25(1H,m), 3.17(1H,dt,J=11.8,9.0 Hz), 3.51(2H,d,J=16.4 Hz), 4.11(2H,d,J=16.4 Hz), 5.15(2H,d,J=15.6 Hz), 5.37 (2H,d,J=15.6 Hz), 5.79(1H,td,J=8.6,4.0 Hz), 6.9–7.1(1H,m), 7.15–7.55(7H,m), 7.65–7.9(4H,m).

Working Example 195

(3aR*,10aS*)-9-(4-Nitrobenzyl)-4-(phthalimidoacetyl)-2,3,3a,4,9,10a-hexahydrobenzo[b]cyclopenta [e][1,4]-diazepin- 10(1H)-one Using (3aR*,10aS*)-4-(bromoacetyl)-9-(4-nitrobenzyl)-2,3,3a,4,9,10a-hexahydrobenzobenzo-[b]cyclopenta[e][1,4]diazepin-10(1H)-one, the titled compound was synthesized in substantially the same manners as in Working Example 191 in a yield of 88%, m.p. 224°–225° C. (ethanol).

$^1$H NMR (CDCl$_3$) δ: 1.1–1.6(3H,m), 1.6–2.0(2H,m), 2.05–2.3(1H,m), 3.21(1H,dt,J=11.8,9.1 Hz), 3.47(2H,d,J=16.4 Hz), 4.20(2H,d,J=16.4 Hz), 5.22(2H,d,J=16.1 Hz), 5.34 (2H,d,J=16.1 Hz), 5.75–5.9(1H,m), 7.2–7.55(4H,m), 7.50 (2H,d,J=8.8 Hz), 8.25(2H,d,J=8.8 Hz).

Working Example 196

(3aR*,10aS*)-9-(Benzyl-4-(phenethylaminoacetyl)-2,3,3a,4,9,10a-hexahydrobenzo[b]cyclopenta[e][1,4]-diazepin-10(1H)-one Using (3aR*,10aS*)-9-benzyl-4-bromoacetyl-2,3,3a,4,9,10a-hexahydrobenzo[b]cyclopent[e][1,4]-diazepin-10(1H)-one and phenethylamine, the titled compound was synthesized in substantially the same manner as in Working Example 138 in a yield of 48%, m.p. 108°–109° C. (diethyl ether).

$^1$H NMR (CDCl$_3$) δ: 1.09–1.44(3H,m), 1.51–1.88(2H,m), 1.95–2.20(2H,m), 2.40–2.78(4H,m), 2.92(1H,d,J=16.6 Hz), 3.15(1H,dt,J=14.8 Hz,9.0 Hz), 4.76(1H,d,J=15.0 Hz), 5.36 (1H,d,J=15.0 Hz), 5.80–5.92(1H,m), 7.02(1H,d,J=7.8 Hz), 7.08–7.44(14H,m).

Working Example 197

1-Benzyl-4((E)-2-(4-pyridyl)vinyl)-1,3-dihydro-1,5-benzodiazepin-2(2H)-one

Using 1-benzyl-4-methyl-1,3-dihydro-1,5-benzodiazepin-2(2H)-one and isonicotinaldehyde, the titled compound was synthesized in substantially the same manner as in Working Example 144 in a yield of 36%, m.p. 208°–210° C. (diethyl ether).

$^1$H NMR (CDCl$_3$) δ: 3.02(1H,d,J=11.4 Hz), 4.02(1H,d, J=11.4 Hz), 5.05(1H,d,J=15.8 Hz), 5.16(1H,d,J=15.8 Hz), 7.06–7.47(13H,m), 8.66(2H,d,J=6.0 Hz).

Working Example 198

9-(3-Nitrobenzyl)-2,3,9,10a-tetrahydrobenzo[b]cyclopenta[e][1,4]diazepin-10(1H)-one Employing 3-nitrobenzyl chloride, the titled compound was synthesized in substantially the same manner as in Working Example 1. Yield 71%. m.p.123.5°–125.5° C. (ethyl acetate - diisopropyl ether).

$^1$H NMR(CDCl$_3$) δ: 1.9–2.2(3H,m), 2.6–2.85(3H,m), 3.05–3.15(1H,m), 5.11(1H,d,J=16.2 Hz), 5.30(1H,d,J=16.2 Hz), 7.1–7.4(5H,m), 7.45(1H,t,J=7.5 Hz), 7.98(1H,t,J=1.6 Hz), 8.07(1H,dt,J=7.7,1.8 Hz).

Working Example 199

9-Benzyl-7-methoxy-2,3,9,10a-tetrahydrobenzo[b]cyclopenta[e][1,4]diazepin-10(1H)-one Employing 7-methoxy-2,3,9,10a-tetrahydrobenzo[b]cyclopent[e][1,4]diazepin-10(1H)-one, the titled compound was synthesized in substantially the same manner as in Working Example 4. Yield 43%. m.p.105°–107° C. (diethyl ether).

$^1$H NMR(CDCl$_3$) δ: 1.86–2.15(3H,m), 2.66(2H,t,J=8.0 Hz), 2.75–2.95(1H,m), 3.03–3.11(1H,m), 3.67(3H,s), 5.01 (1H,d,J=15.6 Hz), 5.18(1H,d,J=15.6 Hz), 6.76(2H,dd,J=6.6, 2.4 Hz), 7.16–7.37(6H,m).

Working Example 200

9-Benzyl-7-fluoro-2,3,9,10a-tetrahydrobenzo[b]cyclopenta[e][1,4]diazepin-10(1H)-one Employing 7-fluoro-2,3,9,10a-tetrahydrobenzo[b][1,4]diazepin-10(1H)-one, the titled compound was synthesized in substantially the same manner as in Working Example 4.

Yield 43%. m.p.158°–159° C. (diethyl ether).

$^1$H NMR(CDCl$_3$) δ: 1.89–2.22(3H,m), 2.64–2.72(2H,m), 2.75–2.96(1H,m), 3.02–3.08(1H,m), 5.09(2H,s), 6.84–7.31 (8H,m).

Working Example 201

9-Benzyl-6-nitro-2,3,9,10a-tetrahydrobenzo[b]-cyclopenta[e][l,4]diazepin-10(1H)-one Employing 6-nitro-2,3,9,10a-tetrahydrobenzo[b]-cyclopenta[e][1,4]diazepin-10(1H)-one, the titled compound was synthesized in substantially the same manner as in Working Example 4. Yield 46%. Oily 10 product.

$^1$H NMR(CDCl$_3$) δ: 1.91–2.25(3H,m), 2.75(2H,t,J=7.8 Hz), 2.78–2.91(1H,m), 3.02–3.09(1H,m), 5.17(2H,s), 7.04–7.10(2H,m), 7.22–7.42(4H,m), 7.95(1H,dt,J=9.0,2.8 Hz), 8.18(1H,d,J=2.6 Hz).

Working Example 202

9-(4-Cyanobenzyl)-2,3,9,10a-tetrahydrobenzo[b]-cyclopenta[e][1,4]diazepin-10(1H)-one Employing 4-cyanobenzyl bromide, the titled compound was synthesized in substantially the same manner as in Working Example 4. Yield 85%. Oily product.

$^1$H NMR(CDCl$_3$) δ: 1.86–2.25(3H,m), 2.56–2.83(3H,m), 3.03–3.11(1H,m), 5.06(1H,d,J=16.4 Hz), 5.25(1H,d,J=16.4 Hz), 7.08–7.67(8H,m).

Working Example 203

9-(3-Cyanobenzyl)-2,3,9,10a-tetrahydrobenzo[b]-cyclopenta[e][1,4]diazepin-10(1H)-one Employing 3-cyanobenzyl bromide, the titled compound was synthesized in substantially the same manner as in Working Example 4. Yield 100%. Oily product.

$^1$H NMR(CDCl$_3$) δ: 1.98–2.23(3H,m), 2.64–2.93(3H,m), 3.07–3.12(1H,m), 5.11(1H,d,J=16.2 Hz), 5.30(1H,d,J=16.2 Hz), 7.10–7.67(8H,m)

Working Example 204

9-((4-Methylthio)benzyl)-2,3,9,10a-tetrahydrobenzo[b]cyclopenta[e][1,4]diazepin-10(1H)one Employing 4-(methylthio)benzylbromide, the titled compound was synthesized in substantially the same manner as in Working Example 4. Yield 56%. m.p.124°–126° C. (diethyl ether).

$^1$H NMR(CDCl$_3$) δ: 1.82–2.20(3H,m), 2.43(3H,s), 2.67–2.74(2H,m), 2.76–2.93(1H,m), 3.00–3.07(1H,m), 5.07 (2H,s), 7.01(2H,d,J=8.4 Hz), 7.05–7.34(6H,m).

Working Example 205

9-(2-Phenylethyl)-2,3,9,10a-tetrahydrobenzo[b]-cyclopenta[e][1,4]diazepin-10(1H)-one A solution of 2,3,9,10a-tetrahydrobenzo[b]-cyclopenta[e] [1,4]diazepin-10(1H)-one (5.01 g, 25 mmol) in N,N-dimethylformamide (30 mL) was cooled to 0° C. To the solution was added sodium hydride (60% liquid paraffin dispersion, 1.0 g, 25 mmol). The mixture was stirred for 5 minutes at the same temperature and for 10 minutes at room temperature. To this solution was added a solution of 2-(bromoethyl)benzene (5.09 g, 27.5 mmol) in N,N-dimethylformamide (1 mL), and the mixture was stirred for 2.5 hours at room temperature. The reaction mixture was poured into a saturated aqueous solution of ammonium chloride (40 mL), which was diluted with water, followed by extraction twice with ethyl acetate. Organic layers were combined and washed with water and a saturated aqueous solution of sodium chloride, which was dried by allowing to pass through magnesium sulfate and silica-gel, followed by concentration under reduced pressure. Unreacted diazepinone was allowed to crystallize, and most portion of which was removed. The remainder was purified by silica-gel column chromatography (hexane-ethyl acetate 20:1, later 5:1), followed by recrystallization from ethyl acetate-hexane to afford the titled compound (2.37 g, 31%), m.p.101°–102° C.

$^1$H NMR(CDCl$_3$) δ: 1.75–2.05(3H,m), 2.4–2.95(6H,m), 3.90(1H,ddd,J=13.7,8.7,5.1 Hz), 4.52(1H,ddd,J=13.8,8.9, 7.6 Hz), 7.05–7.4(9H,m).

Working Example 206

(3aR*,10aS*)-9-Benzyl-7-methoxy-4-(phthalimidoacetyl)-2,3,3a,4,9,10a-hexahydrobenzo [b]cyclopenta-[e][1,4]diazepin-10(1H)-one Employing (3aR,10aS*)-9-Benzyl-7-methoxy-2,3,3a,4,9, 10a-hexahydrobenzo(b)cyclopenta-[e][1,4]diazepin-10(1H) -one, the titled compound was synthesized in substantially the same manner as in Working Example 46. Yield 43%. m.p.244°–245° C. (diethyl ether).

$^1$H NMR(CDCl$_3$) δ: 1.15–1.55(3H,m), 1.61–1.93(2H,m), 2.02–2.23(1H,m), 3.18(1H,dt,J=12.2,8.6 Hz), 15 3.45(1H,d, J=16.6 Hz), 3.71(3H,s), 4.04(1H,d,J=16.6 Hz), 5.01(1H,d, J=15.2 Hz), 5.29(1H,d,J=15.2 Hz), 5.70–5.82(1H,m), 6.77–6.90(2H,m), 7.20–7.42(6H,m), 7.66–7.91(4H,m).

Working Example 207

(3aR,10aS*)-9-Benzyl-7-fluoro-4-(phthalimidoacetyl)-2,3,3a,4,9,10a-hexahydrobenzo [b]cyclopenta-[e][1,4]diazepin-10(1H)-one Employing (3aR*,10aS*)-9-benzyl-7-fluoro-2,3,3a,4,9, 10a-hexahydrobenzo[b]cyclopenta-[e][1,4]diazepin-10(1H) -one, the titled compound was synthesized by substantially the same procedure as in Working Example 46. Yield 30%. m.p.266°–268° C. (diethyl ether).

$^1$H NMR(CDCl$_3$) δ: 1.13–1.51(3H,m), 1.58–1.95(2H,m), 2.05–2.25(1H,m), 3.20(1H,dt,J=11.6,8.4 Hz), 3.39(1H,d,J= 15.6 Hz), 3.95(1H,d,J=15.6 Hz), 4.95(1H,d,J=15.4 Hz), 5.38 (1H,d,J=15.4 Hz), 5.71–5.84(1H,m), 6.95–7.15(2H,m), 7.20–7.48(6H,m), 7.68–7.91(4H,m).

Working Example 208

(3aR*,10aS*)-9-Benzyl-6-nitro-4-(phthalimidoacetyl)- 2,3,3a,4,9,10a-hexahydrobenzo [b]cyclopenta[e][1,4]diazepin-10(1H)-one Employing (3aR*,10aS*)-9-benzyl-6-nitro-2,3,3a,4,9, 10a-hexahydrobenzo[b]cyclopenta-[e][1,4]diazepin-10(1H) -one, the titled compound was synthesized by substantially the same procedure as in Working Example 46. Yield 64%. Amorphous.

$^1$H NMR(CDCl$_3$) δ: 1.11–1.59(3H,m), 1.61–2.01(2H,m), 2.10–2.31(1H,m), 3.28(1H,dt,J=11.6,9.4 Hz), 3.46(1H,d,J= 16.2 Hz), 3.94(1H,d,J=16.2 Hz), 5.09(1H,d,J=15.8 Hz), 5.39 (1H,d,J=15.8 Hz), 5.75–5.91(1H,m), 7.21–7.59(6H,m), 7.79–7.92(4H,m), 8.22–8.40(2H,m).

Working Example 209

(3aR*,10aS*)-9-(3-Nitrobenzyl)-4-(phthalimidoacetyl)-2,3,3a,4,9,10a-hexahydrobenzo [b]cyclopenta-[e][1,4]diazepin-10(1H)-one Employing (3aR*,10aS*)-9-(3-nitrobenzyl)-2,3,3a,4,9, 10a-hexahydrobenzo[b]cyclopenta-[e][1,4]diazepin-10(1H) -one, the titled compound was synthesized by substantially the same procedure as in Working Example 46. Yield 39%. m.p.250°–252° C. (diethyl ether).

¹H NMR(CDCl₃) δ: 1.17–1.56(3H,m), 1.60–1.98(2H,m), 2.03–2.31(1H,m), 3.23(1H,dt,J=11.4,8.4 Hz), 3.49(1H,d,J=16.6 Hz), 4.19(1H,d,J=16.6 Hz), 5.19(1H,d,J=16.0 Hz), 5.36(1H,d,J=16.0 Hz), 5.74–5.90(1H,m), 7.10–7.55(4H,m), 7.59–7.90(6H,m), 8.07–8.20(2H,m).

Working Example 210

(3aR*,10aS*)-9-(4-Cyanobenzyl)-4-(phthalimidoacetyl)-2,3,3a,4,9,10a-hexahydrobenzo[b]cyclopenta[e][1,4]diazepin-10(1H)-one Employing (3aR*,10aS*)-9-(4-cyanobenzyl)-2,3,3a,4,9,10a-hexahydrobenzo[b]cyclopenta-[e][1,4]diazepin-10(1H)-one, the titled compound was synthesized by substantially the same procedure as in Working Example 46. Yield 40%. m.p.222°–224° C. (diethyl ether).

¹H NMR(CDCl₃) δ: 1.13–1.55(3H,m), 1.59–1.98(2H,m), 2.01–2.29(1H,m), 3.20(1H,dt,J=11.6,8.8 Hz), 3.49(1H,d,J=16.6 Hz), 4.22(1H,d,J=16.6 Hz), 5.24(2H,s), 5.75–5.90(1H,m), 7.15–7.60(6H,m), 7.63–7.95(6H,m).

Working Example 211

(3aR*,10aS*)-9-(3-Cyanobenzyl)-4-(phthalimidoacetyl)-2,2,3a,4,9,10a-hexahydrobenzo[b]cyclopenta[e][1,4]diazepin-10(1H)-one Employing (3aR*,10aS*)-9-(3-cyanobenzyl)-2,3,3a,4,9,10a-hexahydrobenzo[b]cyclopenta-[e][1,4]diazepin-10(1H)-one, the titled compound was synthesized by substantially the same procedure as in Working Example 46. Yield 40%. m.p.270°–271° C. (diethyl ether).

¹H NMR(CDCl₃) δ: 1.10–1.52(3H,m), 1.58–1.96(2H,m), 2.02–2.23(1H,m), 3.19(1H,dt,J=11.4,8.6 Hz), 3.44(1H,d,J=16.0 Hz), 4.15(1H,d,J=16.0 Hz), 5.13(1H,d,J=15.8 Hz), 5.26(1H,d,J=15.8 Hz), 5.74–5.88(1H,m), 7.20–7.91(12H,m).

Working Example 212

(3aR*,10aS*)-9-(4-methylthio)benzyl-4-(phthalimidoacetyl)-2,3,3a,4,9,10a-hexahydrobenzo-[b]cyclopenta[e][1,4]diazepin-10(1H)-one Employing (3aR*,10aS*)-9-(4-methylthio)benzyl-2,3,3a,4,9,10a-hexahydrobenzo[b]cyclopenta[e][1,4]diazepin-10(1H)-one, the titled compound was synthesized by substantially the same procedure as in Working Example 46. Yield 61%. m.p.223°–224° C. (diethyl ether).

¹H NMR(CDCl₃) δ: 1.06–1.49(3H,m), 1.58–1.90(2H,m), 2.02–2.25(1H,m), 2.44(3H,s), 3.17(1H,dt,J=11.8,8.8 Hz), 3.43(1H,d,J=16.4 Hz), 4.07(1H,d,J=16.4 Hz), 4.96(1H,d,J=15.4 Hz), 5.33(1H,d,J=15.4 Hz), 5.74–5.85(1H,m), 7.19–7.48(8H,m), 7.64–7.90(4H,m).

Working Example 213

(3aR*,10aS*)-9-(4-Aminobenzyl)-4-(phthalimidoacetyl)-2,3,3a,4,9,10a-hexahydrobenzo[b]cyclopenta[e][1,4]diazepin-10(1H)-one A suspension of (3aR*,10aS*)-9-(4-nitrobenzyl)-4-(phthalimidoacetyl)-2,3,3a,4,9,10a-hexahydrobenzo[b]cyclopenta[e][1,4]diazepin-10(1H)-one (110 mg, 0.21 mmol) and platinum oxide (20 mg) in methanol (20 mL) was stirred for 12 hours at room temperature under hydrogen atmosphere. The reaction mixture was subjected to filtration, and the filtrate was concentrated under reduced pressure, which was crystallized from diethyl ether to give 72 mg (yield 81%) of the object compound, m.p.286°–289° C.

¹H NMR(CDCl₃) δ: 1.0–1.45(3H,m), 1.5–1.9(2H,m), 2.0–2.2(1H,m), 3.13(1H,dt,J=11.9,9.1 Hz), 3.30(1H,d,J=16.5 Hz), 3.65(2H,brs), 3.90(1H,d,J=16.5 Hz), 4.58(1H,d,J=14.8 Hz), 5.56(1H,d,J=14.8 Hz), 5.74(1H,td,J=8.6,3.7 Hz), 6.64(2H,d,J=8.0 Hz), 7.07(2H,d,J=8.4 Hz), 7.2–7.35(1H,m), 7.2–7.35(1H,m), 7.35–7.5(3H,m), 7.65–7.9(4H,m).

Working Example 214

(3aR*,10aS*)-9-(4-Hydroxybenzyl)-4-(phthalimidoacetyl)-2,3,3a,4,9,10a-hexahydrobenzo[b]cyclopenta-[e][1,4]diazepin-10(1H)-one A suspension of (3aR*,10aS*)-9-(4-benzyloxybenzyl)-4-(phthalimidacetyl)-2,3,3a,4,9,10a-hexahydrobenzo[b]cyclopenta[e][1,4]diazepin-10(1H)-one (1.1 g, 1.88 mmol) and platinum oxide (100 mg) in methanol (50 mL) was stirred for 1.5 hour. The reaction mixture was subjected to filtration, and the filtrate was concentrated under reduced pressure, which was crystallized from diethyl ether to give 410 mg (yield 44%) of the object compound, m.p.264°–267° C.

¹H NMR(CDCl₃) δ: 1.01–1.49(3H,m), 1.52–1.93(2H,m), 2.01–2.25(1H,m), 3.02–3.25(1H,m), 3.15(1H,d,J=16.6 Hz), 3.88(1H,d,J=16.6 Hz), 4.61(1H,d,J=14.8 Hz), 5.60(1H,d,J=14.8 Hz), 5.70–5.85(1H,m), 6.01(1H,s), 6.80(2H,d,J=8.6 Hz), 7.14(2H,d,J=8.6 Hz), 7.23–7.51(4H,m), 7.61–7.79(4H,m).

Working Example 215

(3aR*,10aS*)-9-(3-Hydroxybenzyl)-4-(phthalimidoacetyl)-2,3,3a,4,9,10a-hexahydrobenzo[b]cyclopenta[e][1,4]diazepin-10(1H)-one Employing (3aR*,10aS*)-9-(3-benzyloxybenzyl)-4-(phthalimidoacetyl)-2,3,3a,4,9,10a-hexahydrobenzo[b]cyclopenta[e][1,4]diazepin-10(1H)-one, the titled compound was synthesized by substantially the same procedure as in Working Example 214. Yield 77%. m.p.259°–262° C. (decomp.) (diethyl ether).

¹H NMR(CDCl₃) δ: 1.02–1.51(3H,m), 1.58–1.91(2H,m), 2.05–2.27(1H,m), 3.19(1H,dt,J=11.4,9.0 Hz), 3.57(1H,d,J=17.0 Hz), 4.31(1H,d,J=17.0 Hz), 4.34(1H,d,J=15.4 Hz), 4.75(1H,d,J=15.4 Hz), 5.67–5.87(1H,m), 6.50(1H,br), 6.63–6.92(3H,m), 7.10–7.48(5H,m), 7.70–7.92(4H,m).

Working Example 216

(3aR*,10aS*)-9-Benzyl-4-((benzylsulfonamide)acetyl)-2,3,3a,4,9,10a-hexahydrobenzo[b]cyclopenta[e][1,4]diazepin-10(1H)-one Employing benzylsulfonyl chloride,the titled compound was synthesized by substantially the same procedure as in Working Example 180. Yield 65%. m.p.175°–176° C. (diethyl ether).

¹H NMR(CDCl₃) δ: 0.98–1.20(3H,m), 1.25–1.45(2H,m), 1.47–1.98(3H,m), 2.02–2.23(1H,m), 3.06–3.23(2H,m), 4.17(1H,d,J=13.6 Hz), 4.29(1H,d,J=13.6 Hz), 4.62(1H,d,J=14.8 Hz), 4.67–4.74(1H,br), 5.48(1H,d,J=14.8 Hz), 5.74–5.87(1H,m), 6.72(1H,dt,J=7.8,1.2 Hz), 7.07–7.48(13H,m).

Working Example 217

(3aR*,10aS*)-9-(2-Phenylethyl)-4-(phthalimidoacetyl)-2,3,3a,4,9,10a-hexahydrobenzo[b]cyclopenta-[e][1,4]diazepin-10(1H)-one Employing (31R*,10aS*)-4-(bromoacetyl)-9-(2-phenylethyl)-2,3,3a,4,9,10a-hexahydrobenzo[b]cyclopenta-[e][1, 4]diazepin-10-one, the titled compound was synthesized by substantially the same procedure as in Working Example 191. Yield 63%. m.p.178°–179° C. (ethanol-hexane).

$^1$H NMR(CDCl$_3$) δ: 1.0–1.5(3H,m), 1.6–1.9(2H,m), 2.0–2.25(1H,m), 2.94(1H,ddd,J=12.9,10.6,4.9 Hz), 3.05–3.35(2H,m), 3.85(1H,d,J=16.5 Hz), 3.95–4.3(2H,m), 4.35(1H,d,J=16.5 Hz), 5.82(1H,td,J=8.7,4.1 Hz), 7.1–7.55 (9H,m), 7.6–7.9(4H,m).

Working example 218

(3aR*,10aS*)-9-(3-Phenylpropyl)-4-(phthalimidoacetyl)-2,3,3a,4,9,10a-hexahydrobenzo [b]cyclopenta-[e][1,4]diazepin-10(1H)-one Employing (3aR*,10aS*)-4-(bromoacetyl)-9-(3-phenylpropyl)-2,3,3a,4,9,10a-hexahydrobenzo-[b] cyclopenta[e][1,4]diazepin-10(1H)-one, the titled compound was synthesized by substantially the same procedure as in Working Example 191. Yield 73%.

m.p.192.3°–193.3° C. (ethanol).

$^1$H NMR(CDCl$_3$) δ: 0.9–1.2(1H,m), 1.2–1.5(2H,m), 1.55–1.85(2H,m), 1.9–2.3(3H,m), 2.6–2.8(2H,m), 3.08(1H, dt,J=12.3,9.0 Hz), 3.65–3.85(1H,m), 3.87(1H,d,J=16.5 Hz), 4.14(1H,ddd,J=13.7,10.8,5.5 Hz), 4.34(1H,d,J=16.5 Hz), 5.79(1H,td,J=8.7,4.0 Hz), 7.1–7.5(9H,m), 7.65–7.9(4H,m).

Working Example 219

4-(Aminomethyl)-1-benzyl-5-(phthalimidoacetyl)-1, 3,4,5-tetrahydro-1,5-benzodiazepin-2(2H)-one hydrobromide To a solution of 1-benzyl-4-(benzyloxy-carbonylamino methyl)-5-(phthalimidoacetyl)-1,3,4,5-tetrahydro-1,5-benzodiazepin-2(2H)-one (1.51 g, 2.5 mol) in chloroform (20 mL) was added 25% hydrogen bromide-acetic acid solution (5 mL). The mixture was stirred for 25 minutes at room temperature, which was concentrated under reduced pressure. The concentrate was crystallized from ethanol-diethyl ether, followed by recrystallization from dichloromethane-ethanol-diethyl ether to afford the object compound (1.13 g, 82%), m.p.232°–234° C.

$^1$H NMR(DMSO-d$_6$) δ: 2.4–3.0(4H,m), 3.34(1H,d,J=16.6 Hz), 4.27(1H,d,J=16.6 Hz), 4.84(1H,d,J=15.9 Hz), 5.2–5.4 (1H,m), 5.31(1H,d,J=15.9 Hz), 7.2–7.6(8H,m), 7.7–8.1(8H, m)

Working Example 220

1-Benzyl-5-(phthalimidoacetyl)-4-(propylaminomethyl)-1,3,4,5-tetrahydro-1,5-benzodiazepin-2(2H)-one hydrochloride To a suspension of 4-aminomethyl-1-benzyl-5-(phthalimidoacetyl)-1,3,4,5-tetrahydro-1,5-benzodiazepin-2 (2H)-one hydrobromide (200 mg, 0.41 mmol), bromocresol green (3 mg) and propionaldehyde (28 mg, 0.49 mmol) in methanol (30 mL) was added, under ice-cooling, sodium cyanoborohydride (26 mg, 0.41 mmol). To the mixture was then added slowly a 10% HCl-methanol solution until no more color change of the solution was observed. The mixture was stirred for 4 hours at room temperature, to which was added water.

The mixture was made alkaline with a saturated aqueous solution of sodium hydrogencarbonate. The alkaline solution was subjected to extraction with ethylacetate. The extract was washed with brine which was dried over magnesium sulfate, followed by concentration under reduced pressure. To the concentrate was added a 10% HCl-methanol solution, which was concentrated under reduced pressure to give 126 mg (yield 57%) of the object compound. Amorphous.

$^1$H NMR(CDCl$_3$,free base) δ: 0.81(3H,t,J=7.2 Hz), 1.21–1.50(2H,m), 2.13–2.52(4H,m), 2.63(1H,dd,J=13.0,5.0 Hz), 2.99(1H,dd,J=12.4,4.2 Hz), 3.20(1H,d,J=16.4 Hz), 3.96(1H, d,J=16.4 Hz), 4.86(1H,d,J=15.2 Hz), 5.12–5.28(1H,m), 5.44 (1H,t,J=15.2 Hz), 7.18–7.52(10H,m), 7.64–7.83(4H,m)

The chemical structures of the Working Examples are shown hereinafter.

Chemical Structures

Working Example 1

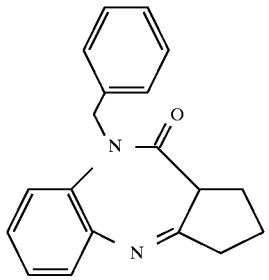

Working Example 2

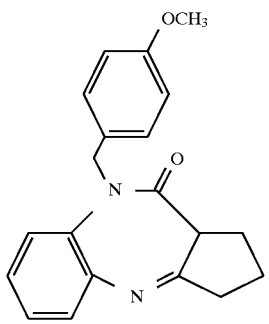

Working Example 3

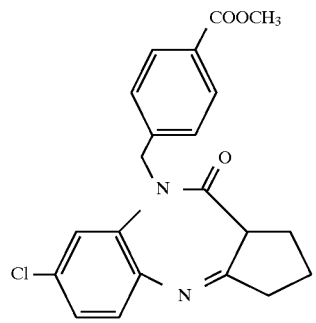

-continued
Working Example 4
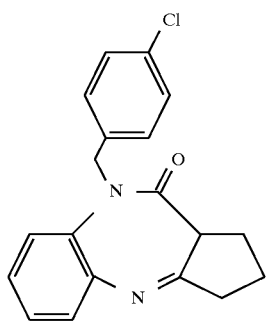
Working Example 5
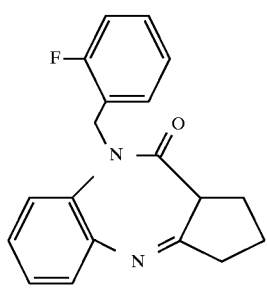
Working Example 6
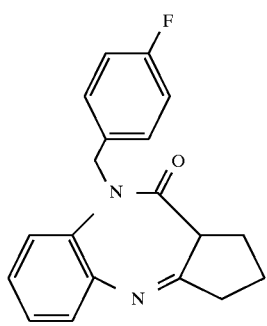
Working Example 7
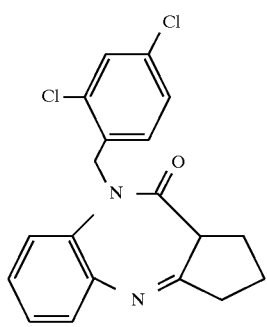
-continued
Working Example 8
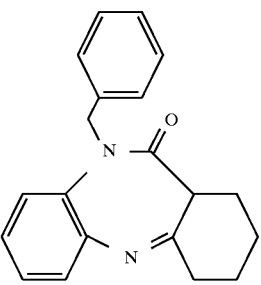
Working Example 9
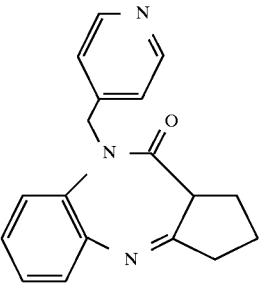
Working Example 10
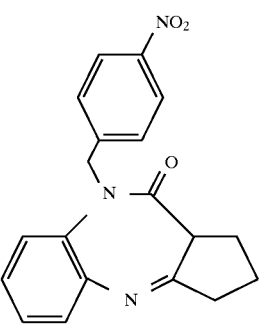
Working Example 11
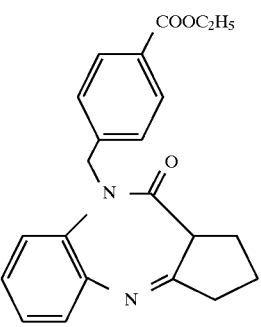

-continued
Working Example 12
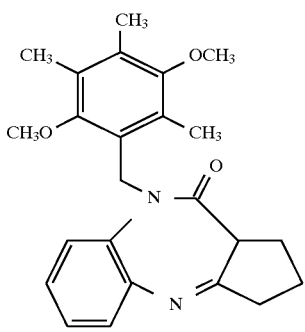
Working Example 13
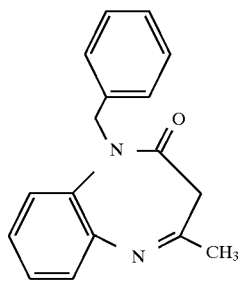
Working Example 14
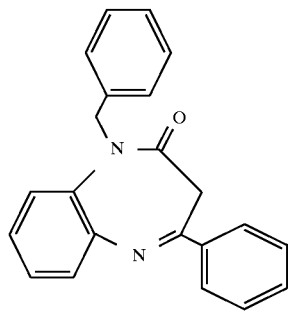
Working Example 15
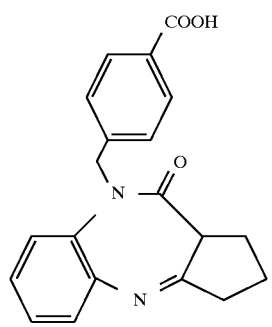
-continued
Working Example 16
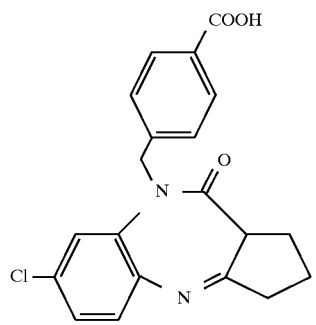
Working Example 17
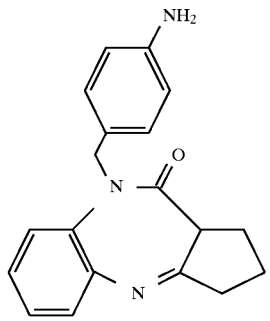
Working Example 18
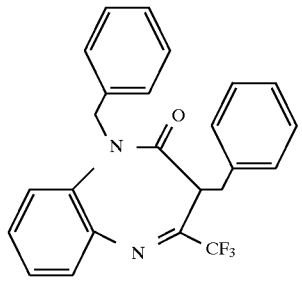
Working Example 19
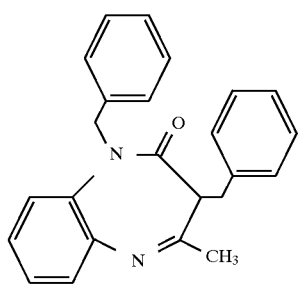

-continued
Working Example 20
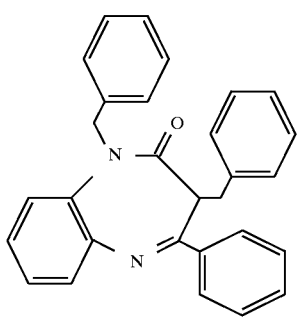
Working Example 21
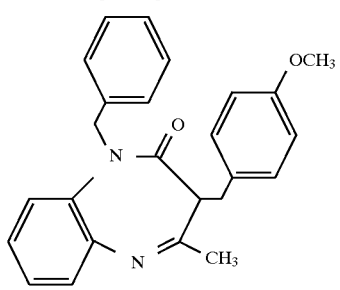
Working Example 22
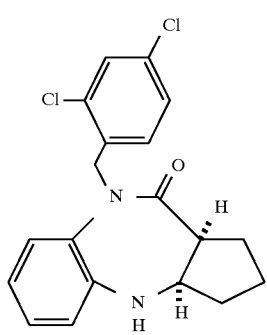
Working Example 23
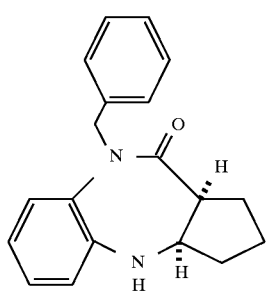
-continued
Working Example 24
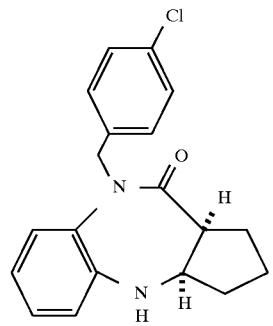
Working Example 25
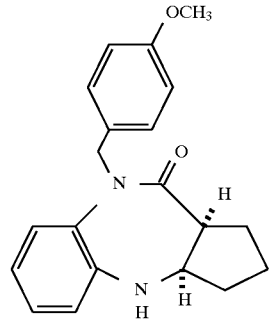
Working Example 26
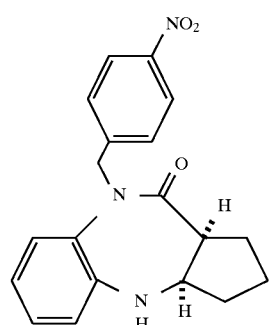
Working Example 27
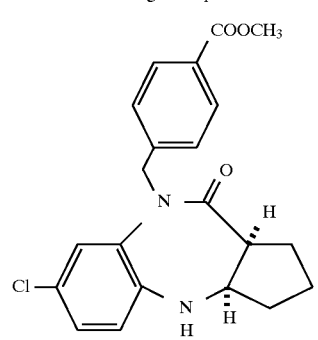

-continued
Working Example 28
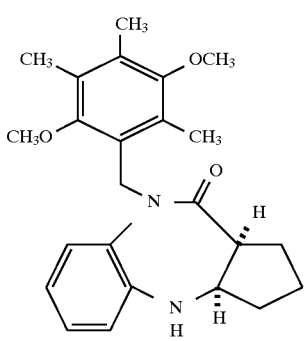
Working Example 29
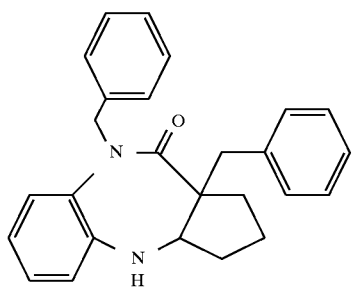
Working Example 30
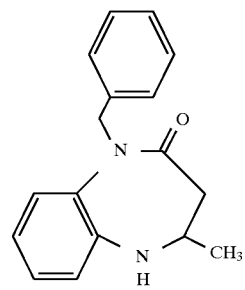
Working Example 31
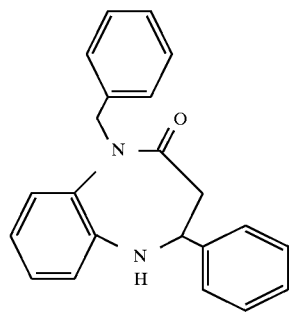
-continued
Working Example 32
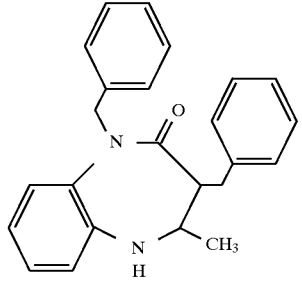
Working Example 33
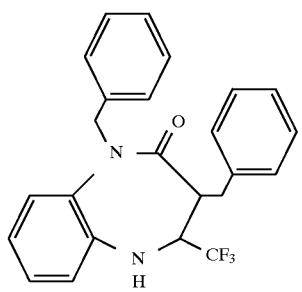
Working Example 34
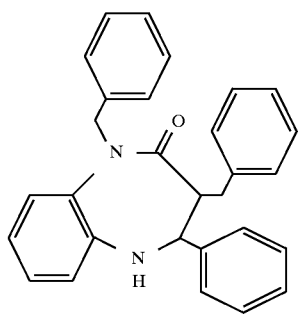
Working Example 35
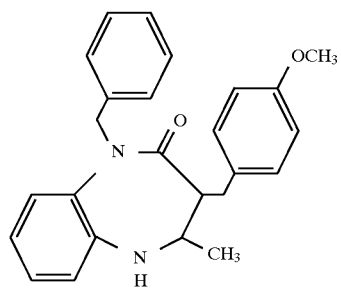
Working Example 36
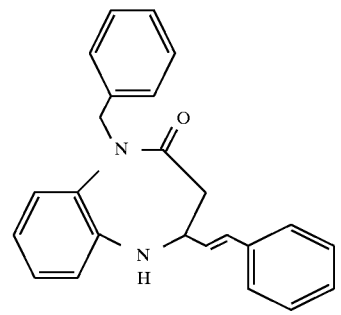

-continued
Working Example 37
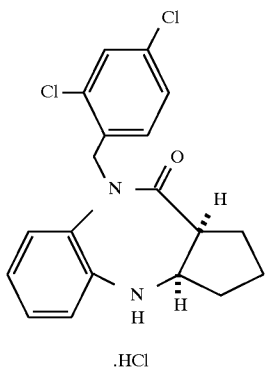
.HCl
Working Example 38
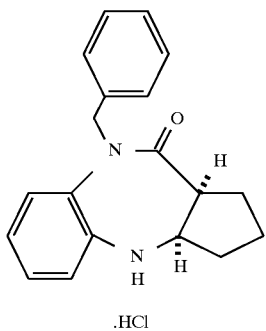
.HCl
Working Example 39
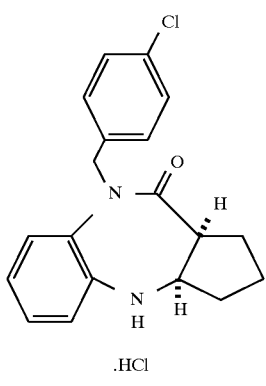
.HCl
Working Example 40
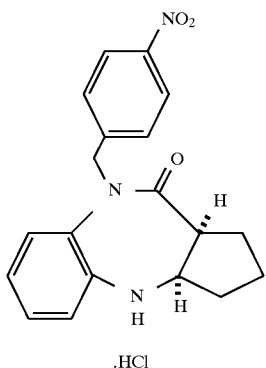
.HCl
-continued
Working Example 41
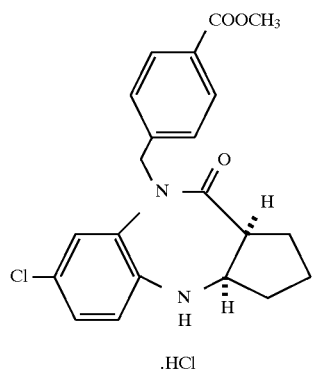
.HCl
Working Example 42
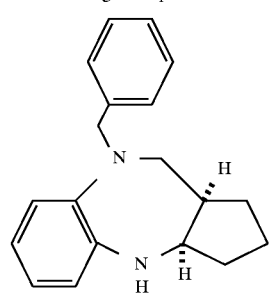
Working Example 43
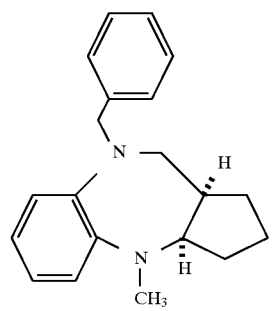
Working Example 44
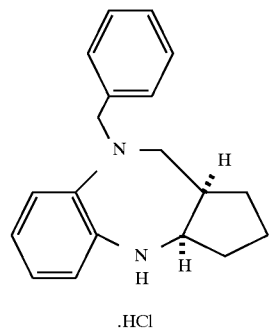
.HCl -continued
Working Example 45
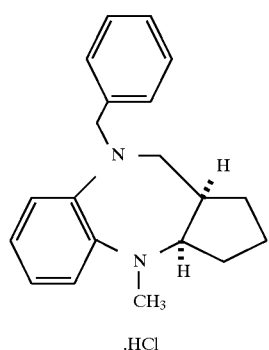
.HCl
Working Example 46
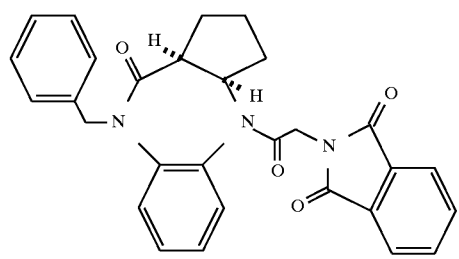
Working Example 47
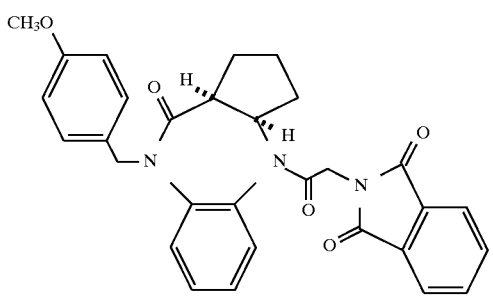
Working Example 48
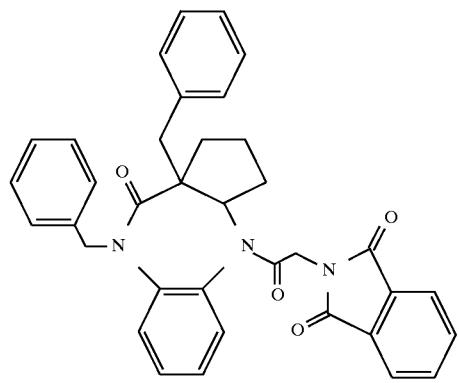
-continued
Working Example 49
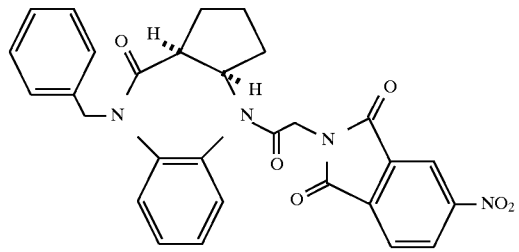
Working Example 50
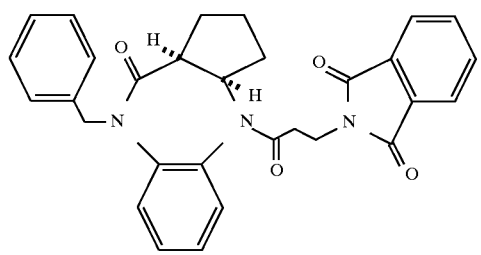
Working Example 51
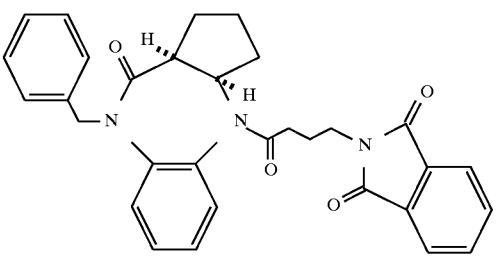
Working Example 52
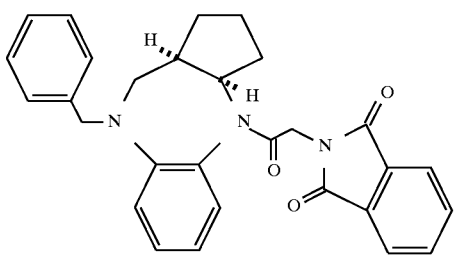
Working Example 53
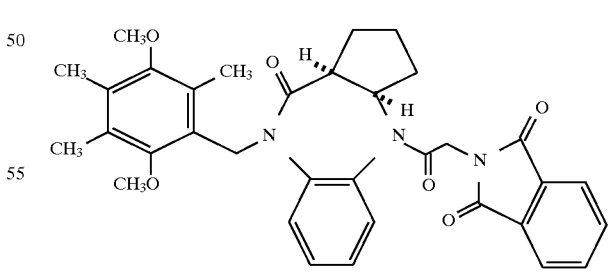

-continued
Working Example 54
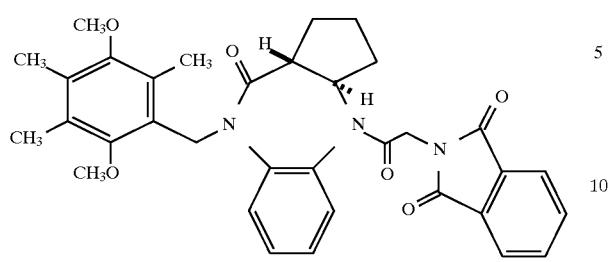
Working Example 55
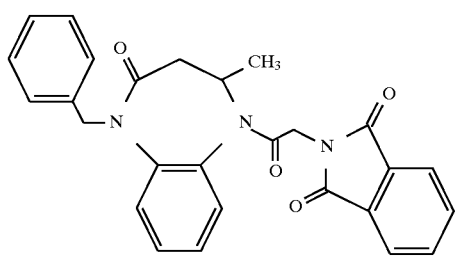
Working Example 56
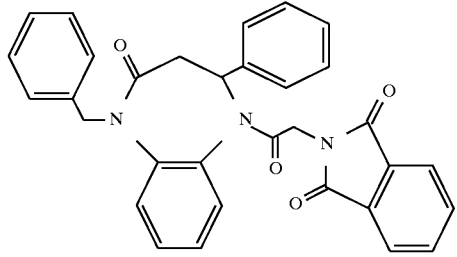
Working Example 57
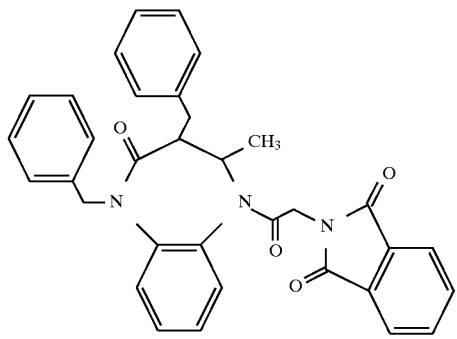
Working Example 58
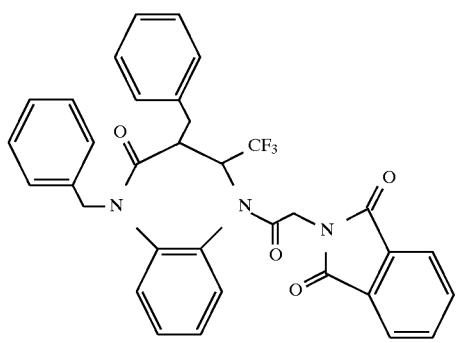
-continued
Working Example 59
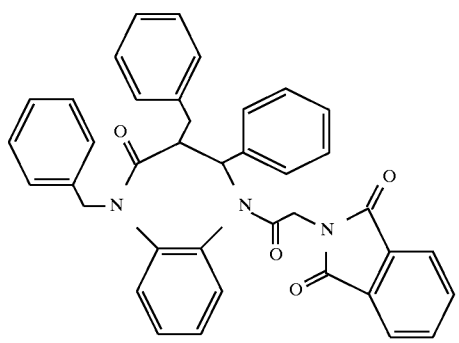
Working Example 60
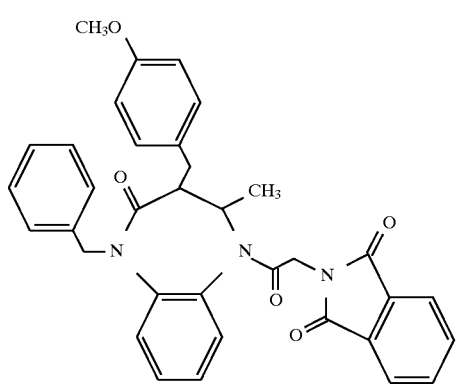
Working Example 61
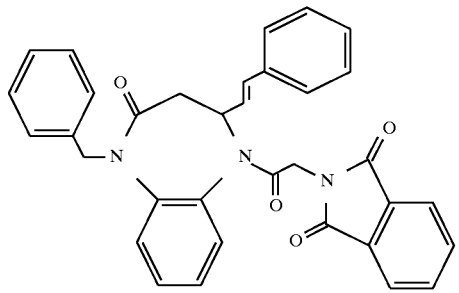
Working Example 62
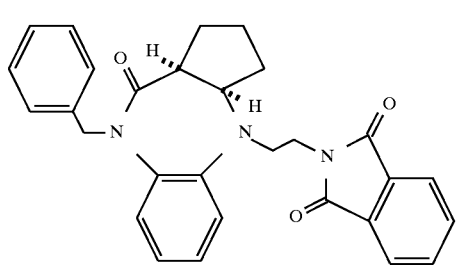

-continued
Working Example 63
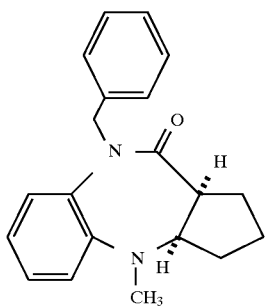
Working Example 64
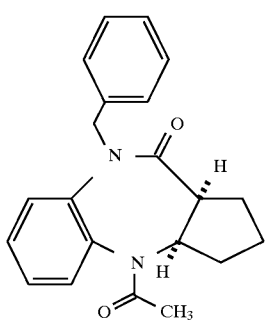
Working Example 65
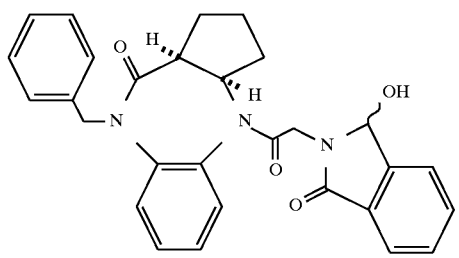
Working Example 66
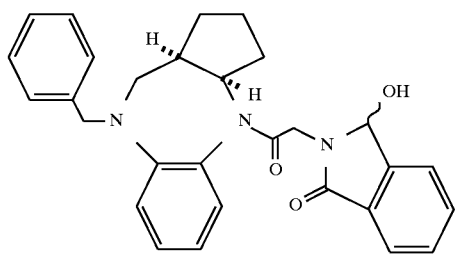
Working Example 67
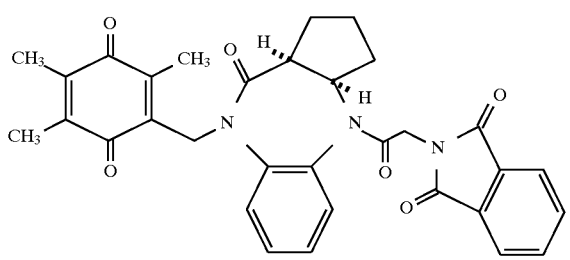
-continued
Working Example 68
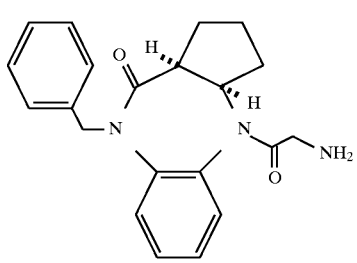
Working Example 69
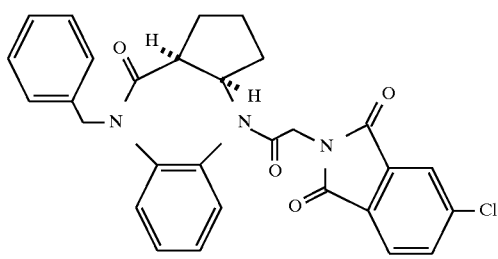
Working Example 70
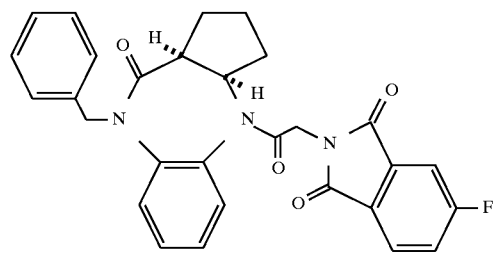
Working Example 71
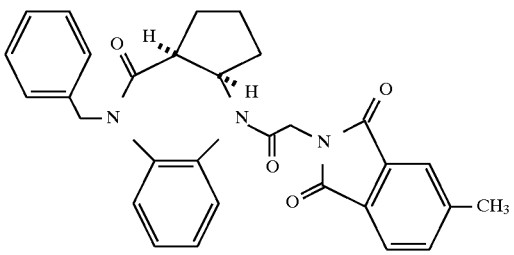
Working Example 72
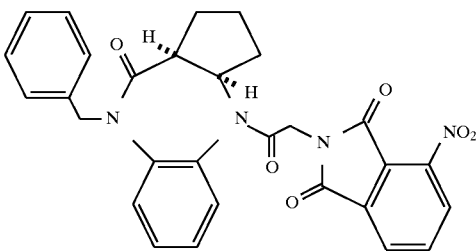

113
-continued
Working Example 73
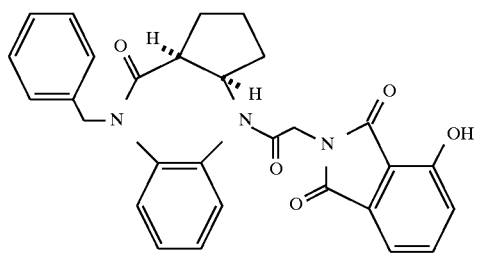
Working Example 74
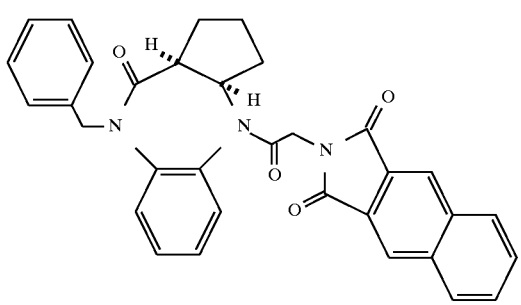
Working Example 75
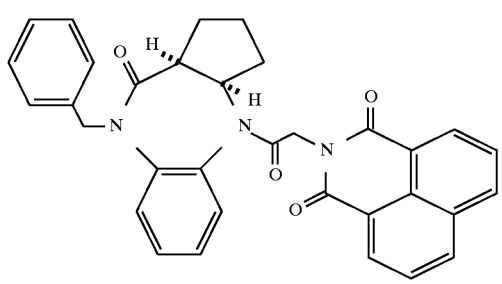
Working Example 76
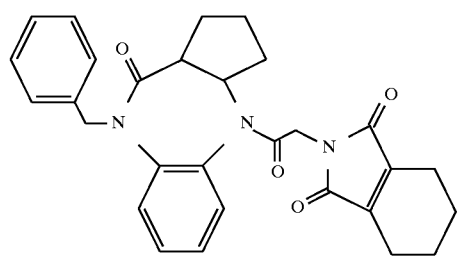
Working Example 77
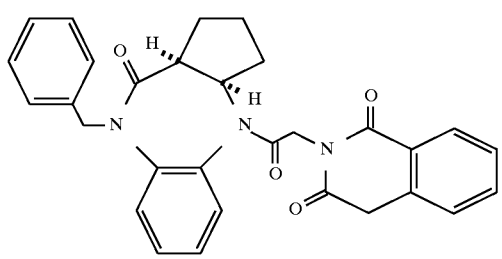
114
-continued
Working Example 78
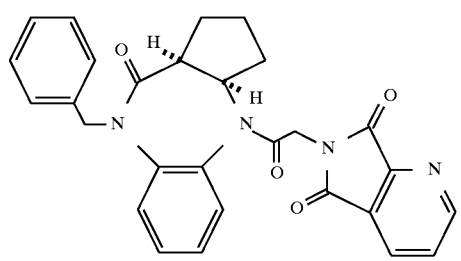
Working Example 79
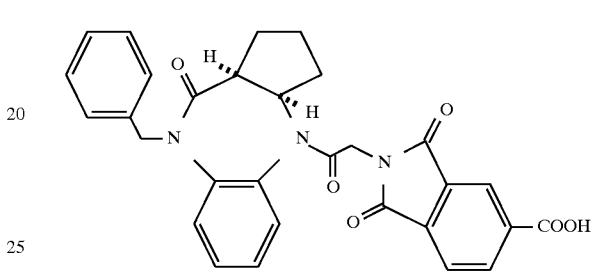
Working Example 80
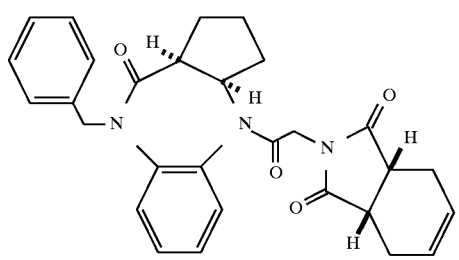
Working Example 81
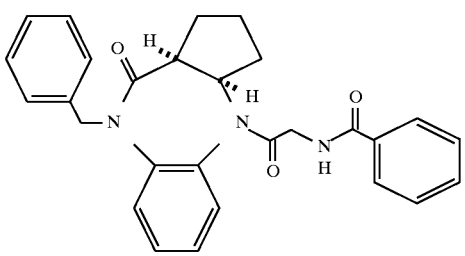
Working Example 82
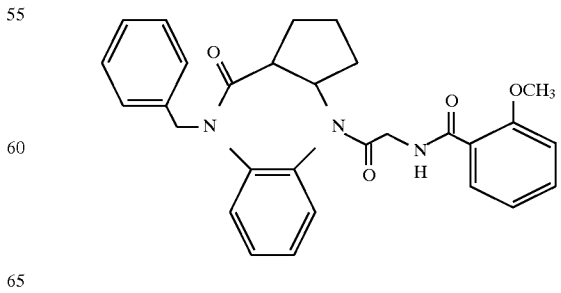

-continued
Working Example 83
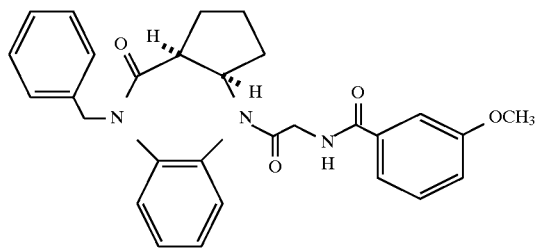
Working Example 84
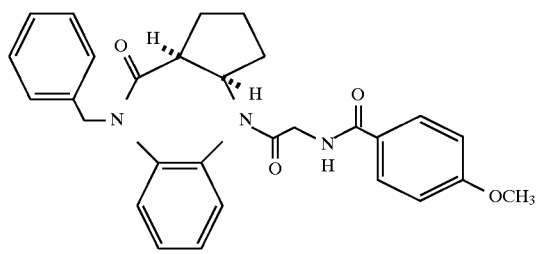
Working Example 85
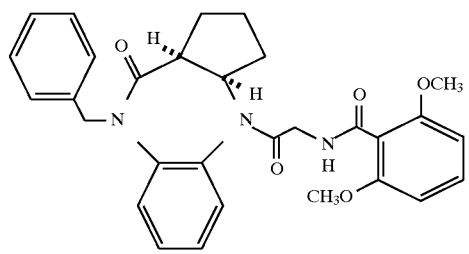
Working Example 86
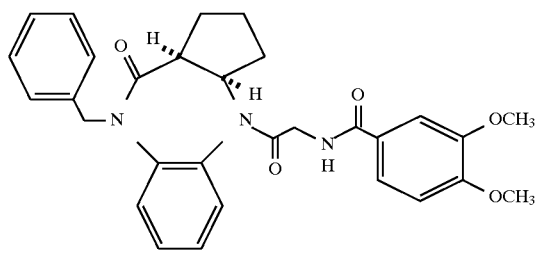
Working Example 87
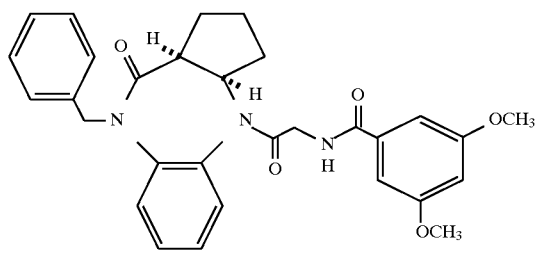
-continued
Working Example 88
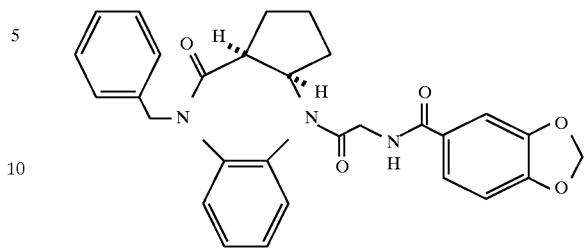
Working Example 89
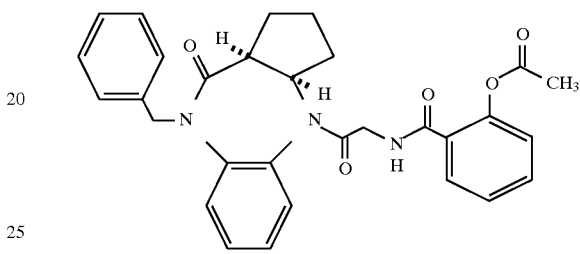
Working Example 90
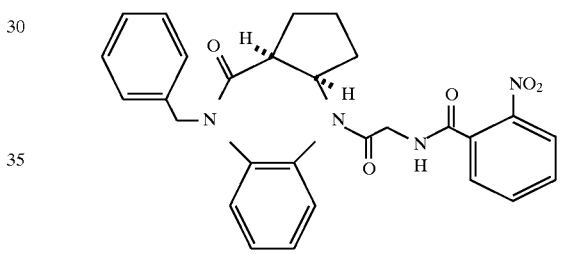
Working Example 91
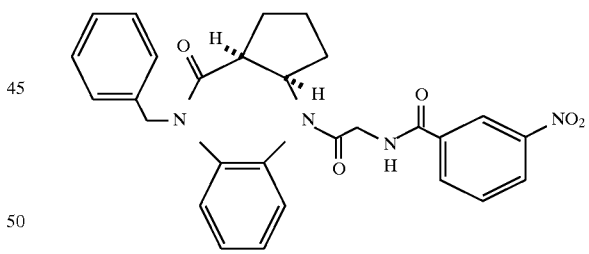
Working Example 92
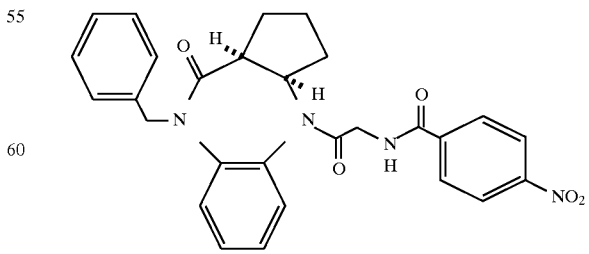

-continued
Working Example 93
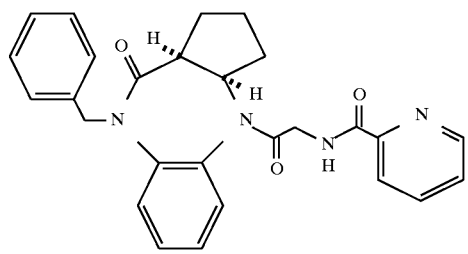
Working Example 94
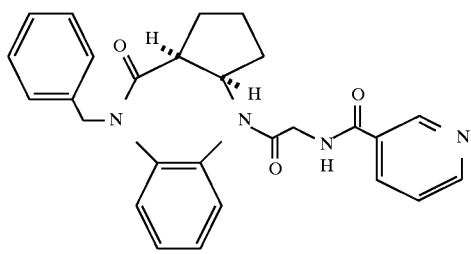
Working Example 95
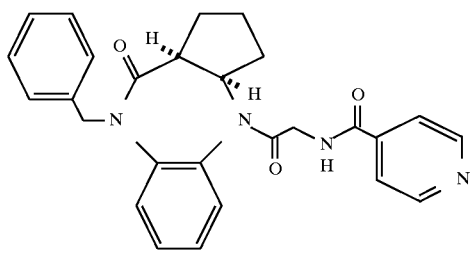
Working Example 96
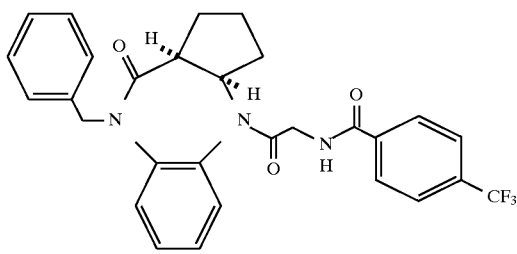
Working Example 97
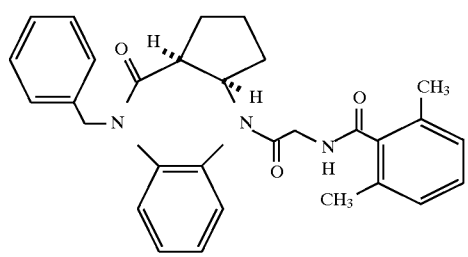
-continued
Working Example 98
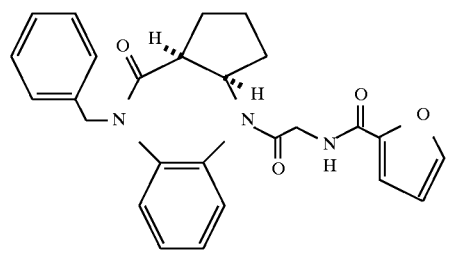
Working Example 99
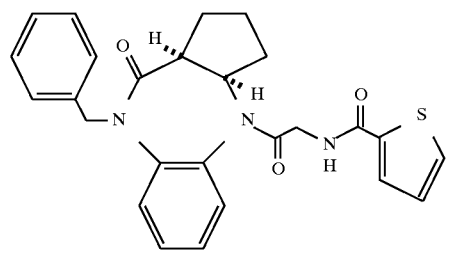
Working Example 100
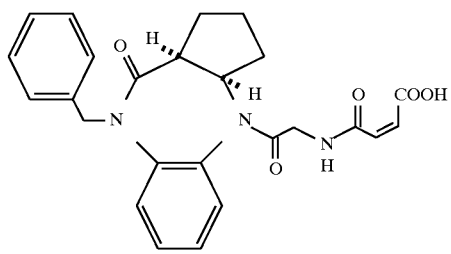
Working Example 101
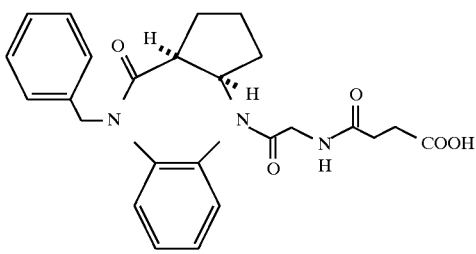
Working Example 102
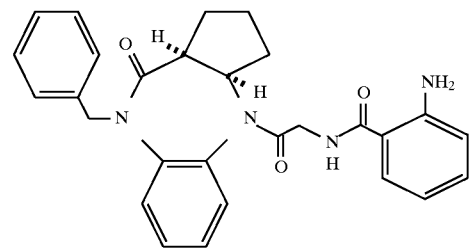

-continued
Working Example 103
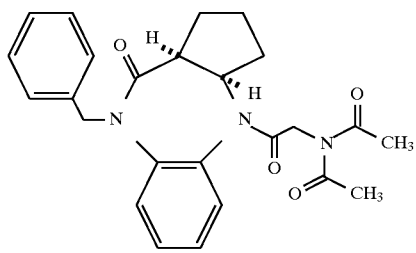
Working Example 104
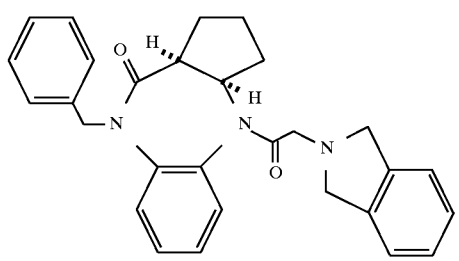
Working Example 105
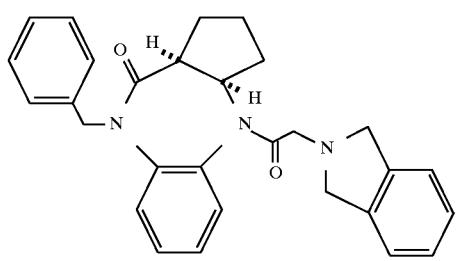
.HCl
Working Example 106
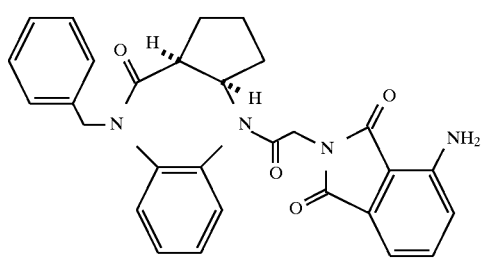
Working Example 107
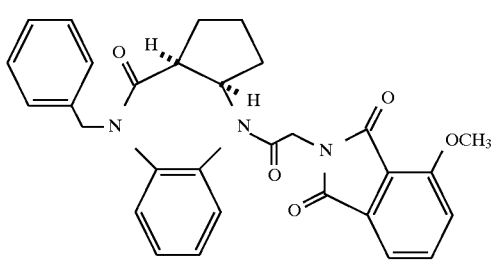
-continued
Working Example 108
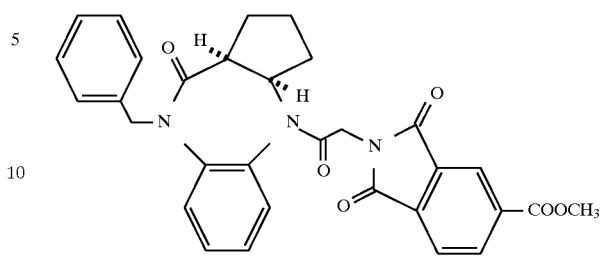
Working Example 109
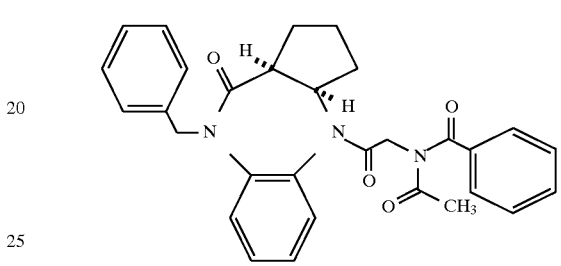
Working Example 110
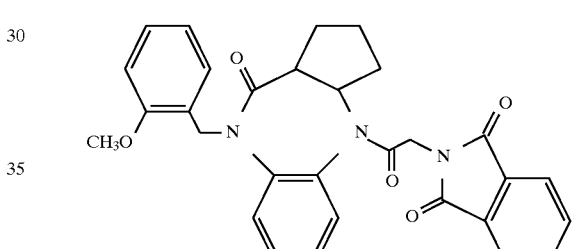
Working Example 111
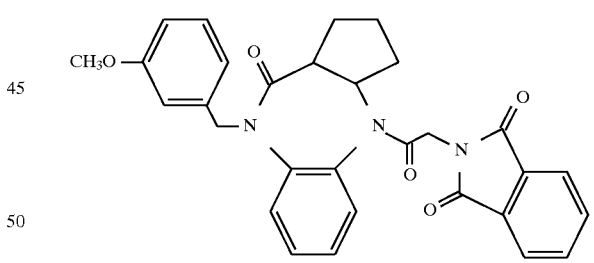
Working Example 112
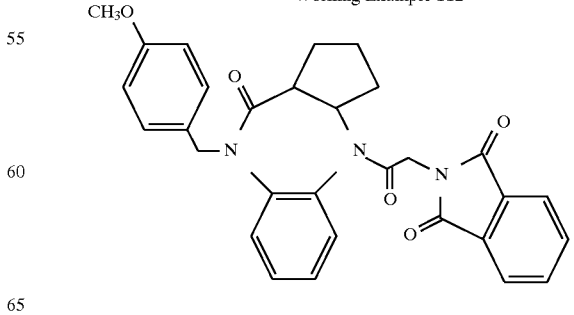

Working Example 113
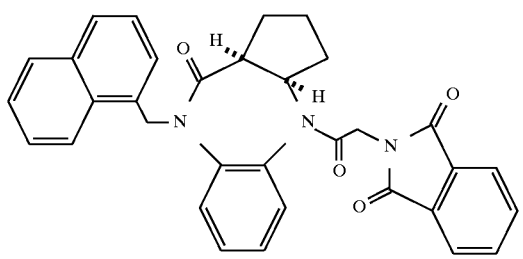
Working Example 114
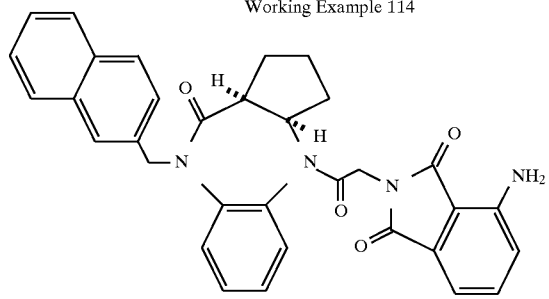
Working Example 115
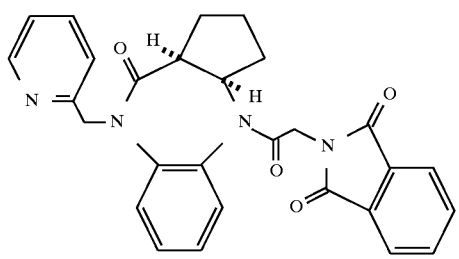
Working Example 116
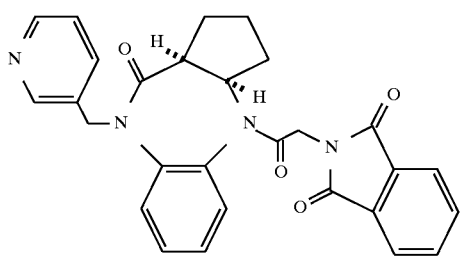
Working Example 117
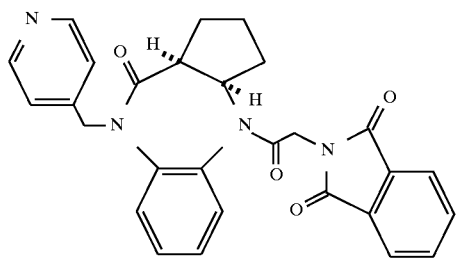
Working Example 118
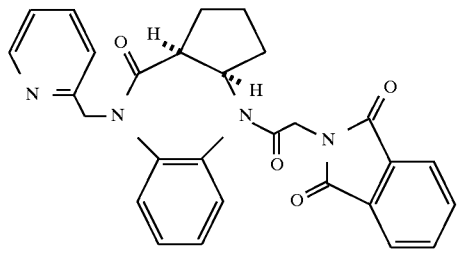
.HCl
Working Example 119
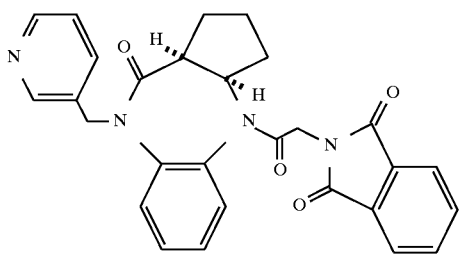
.HCl
Working Example 120
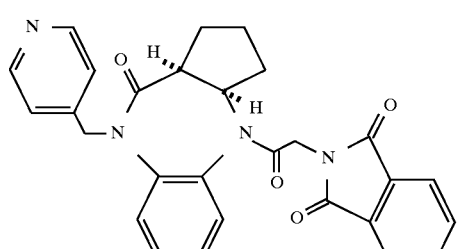
.HCl
Working Example 121
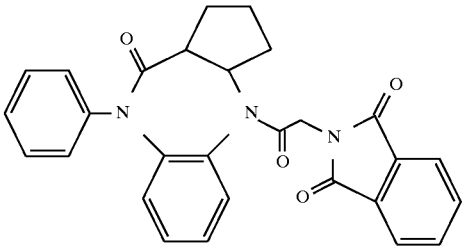
Working Example 122
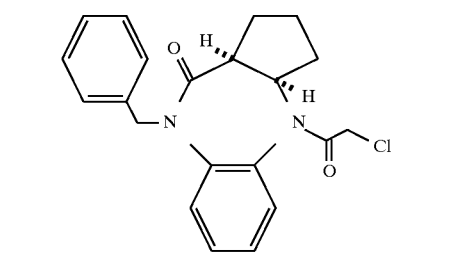

-continued
Working Example 123
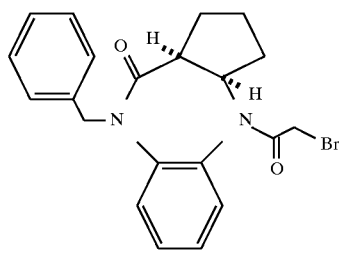
Working Example 124
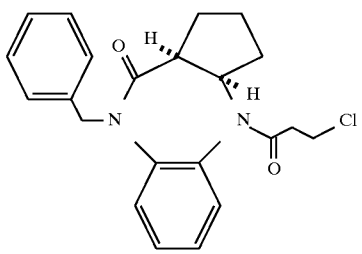
Working Example 125
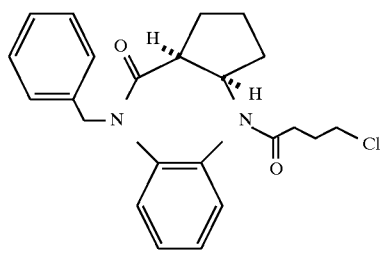
Working Example 126
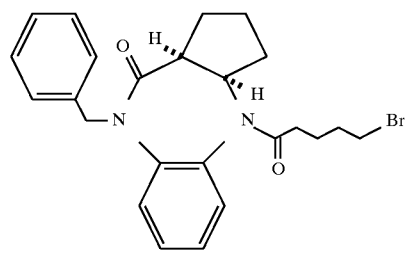
Working Example 127
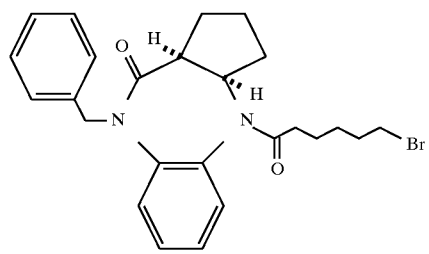
-continued
Working Example 128
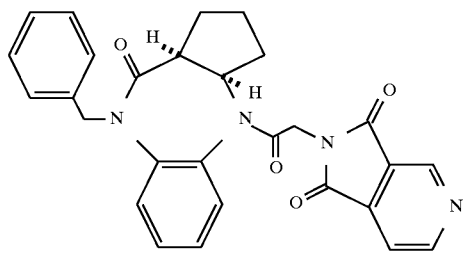
Working Example 129
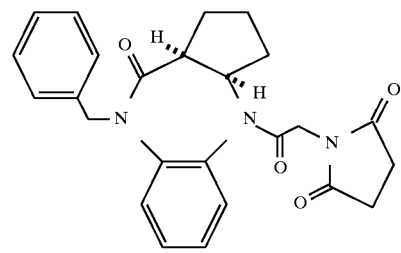
Working Example 130
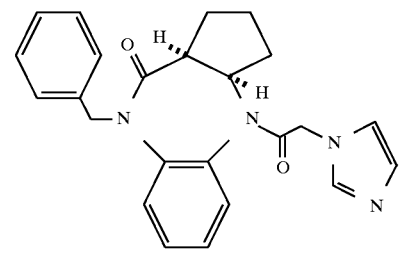
Working Example 131
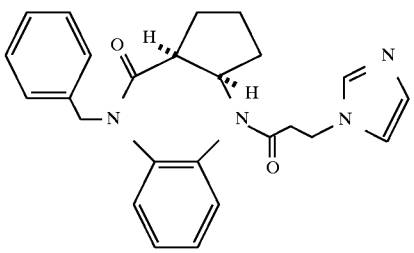
Working Example 132
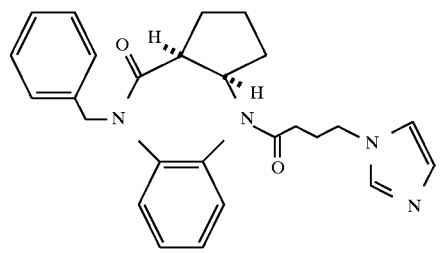

-continued
Working Example 133
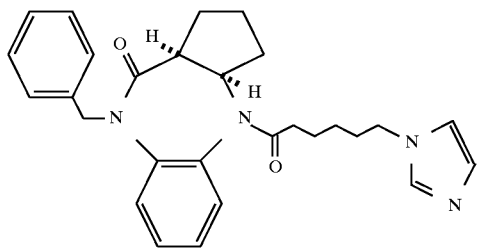
Working Example 134
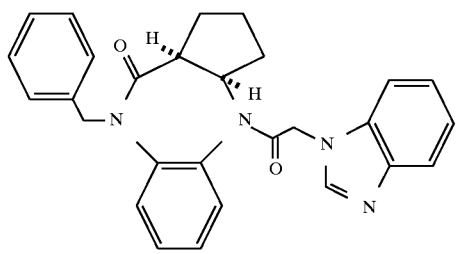
Working Example 135
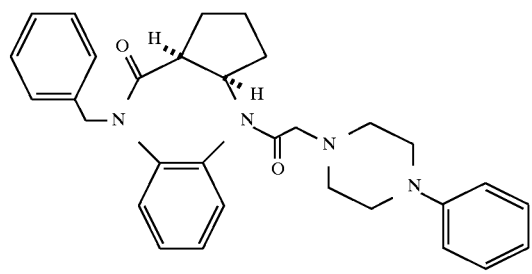
Working Example 136
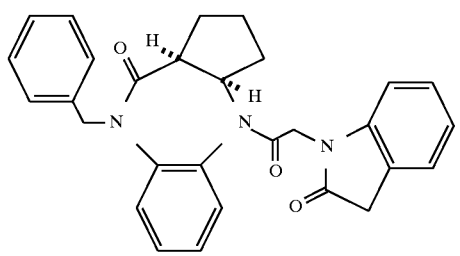
Working Example 137
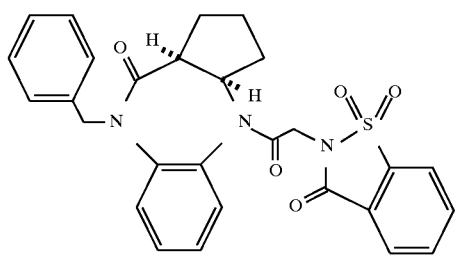
-continued
Working Example 138
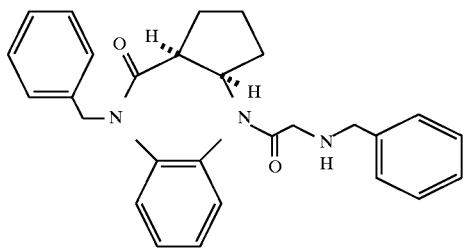
Working Example 139
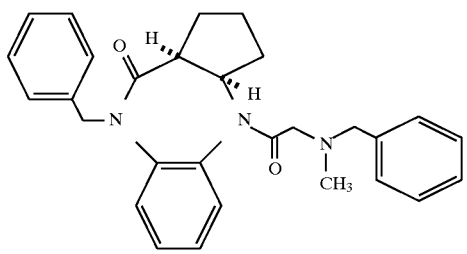
Working Example 140
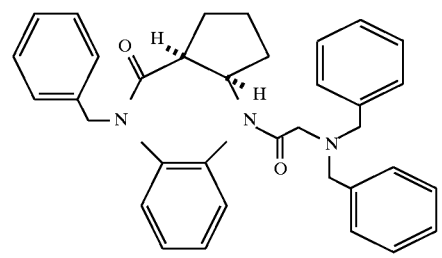
Working Example 141
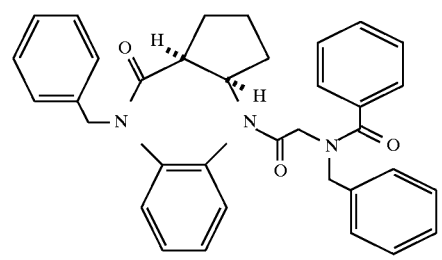
Working Example 142
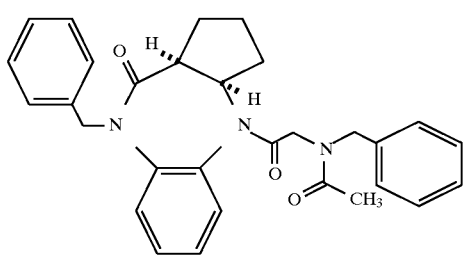

-continued
Working Example 143
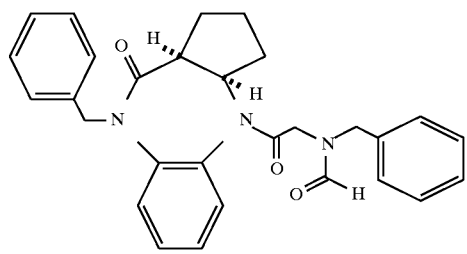
Working Example 144
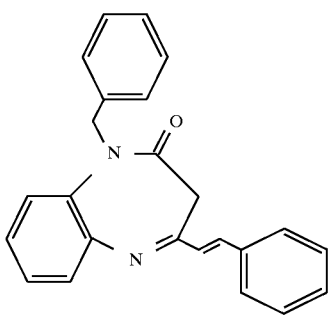
Working Example 145
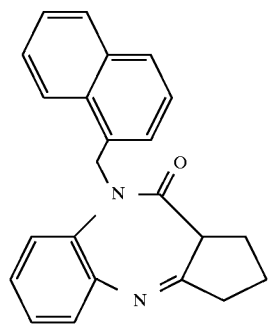
Working Example 146
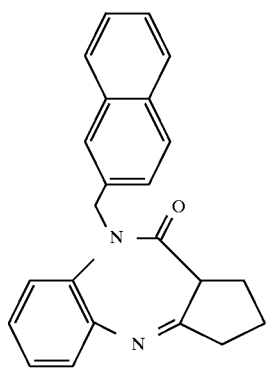
-continued
Working Example 147
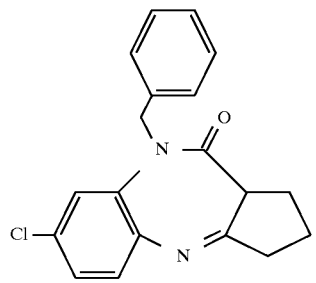
Working Example 148
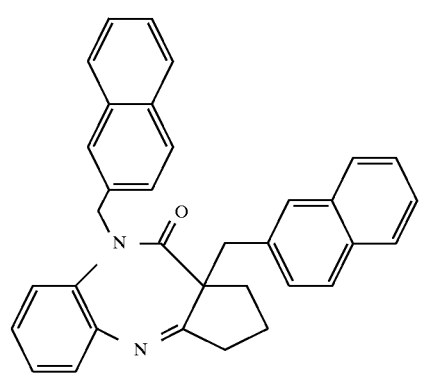
Working Example 149
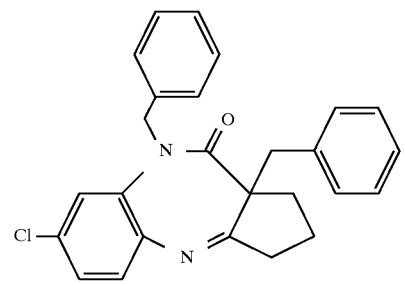
Working Example 150
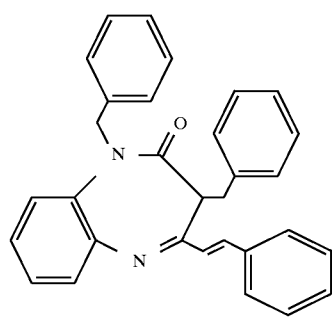

-continued
Working Example 151
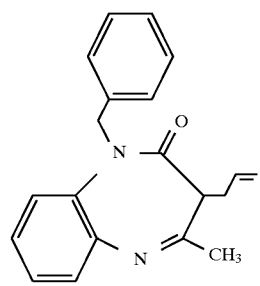
Working Example 152
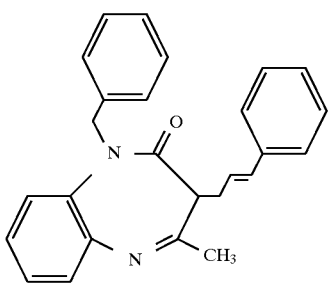
Working Example 153
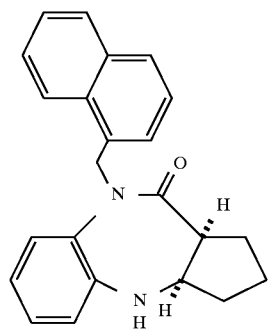
Working Example 154
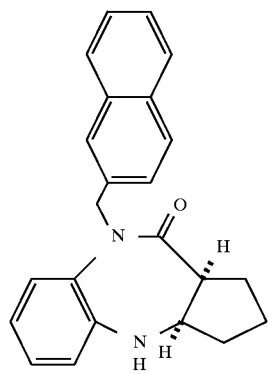
-continued
Working Example 155
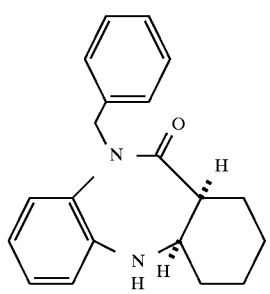
Working Example 156
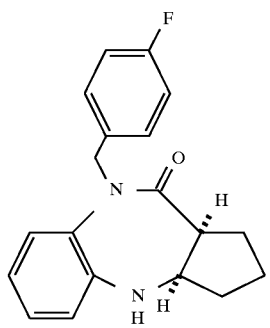
Working Example 157
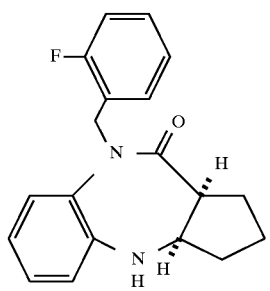
Working Example 158
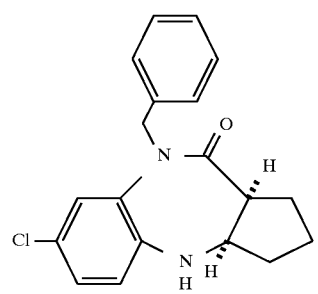

Working Example 159
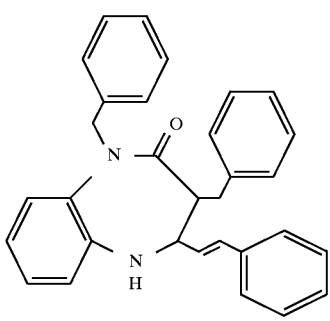
Working Example 160
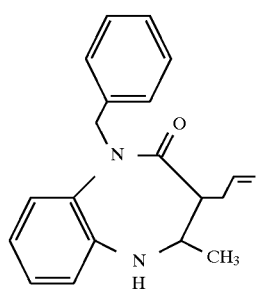
Working Example 161
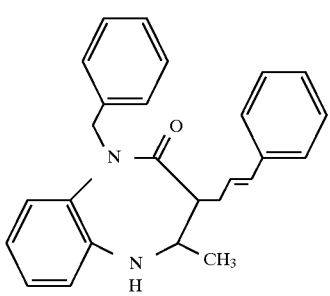
Working Example 162
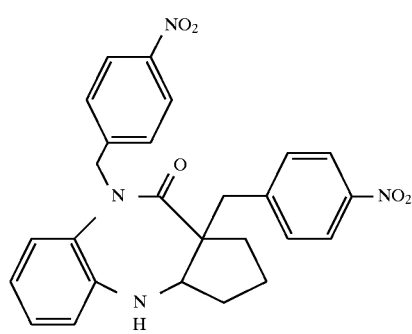
Working Example 163
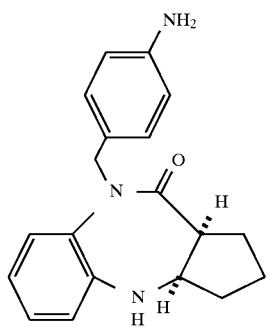
Working Example 164
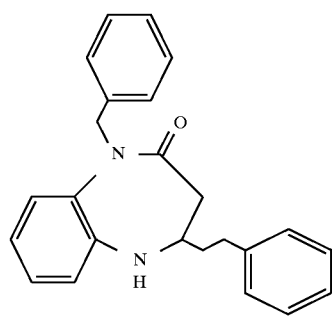
Working Example 165
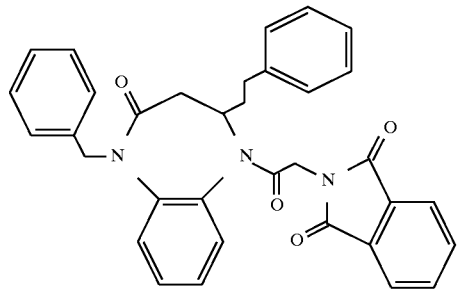
Working Example 166
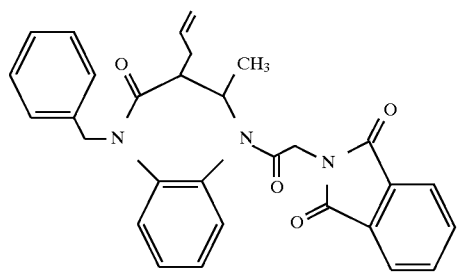

-continued
Working Example 167
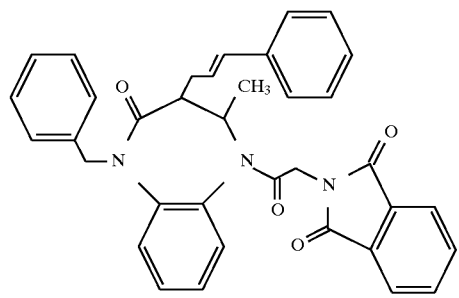
Working Example 168
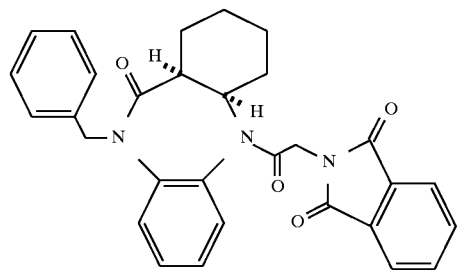
Working Example 169
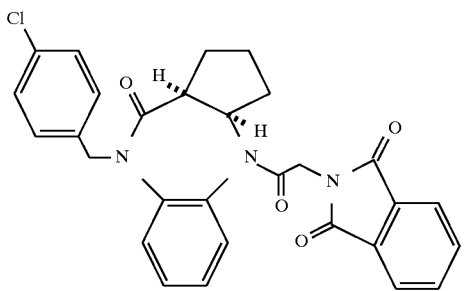
Working Example 170
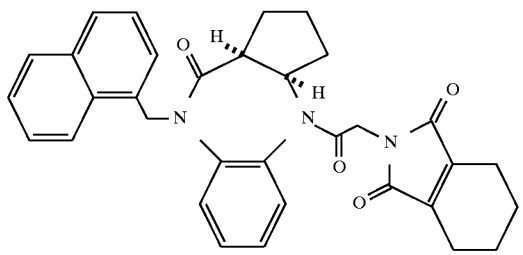
Working Example 171
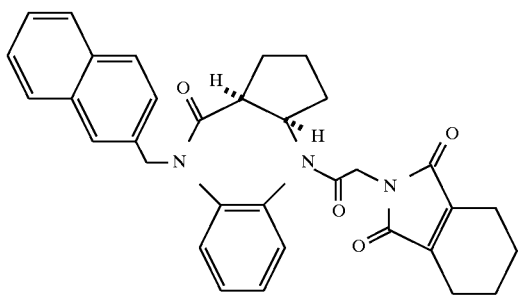
-continued
Working Example 172
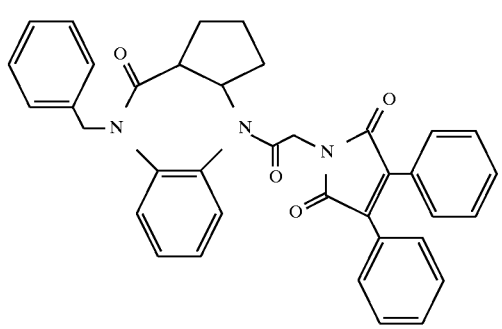
Working Example 173
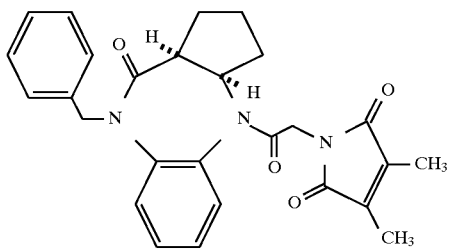
Working Example 174
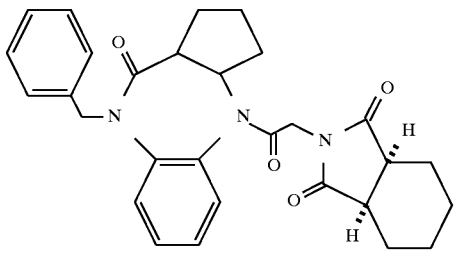
Working Example 175
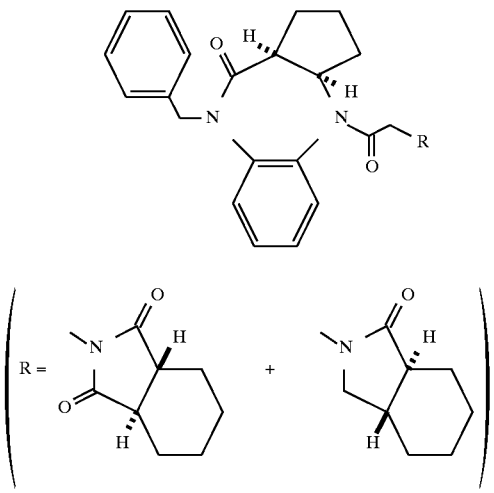

-continued
Working Example 176
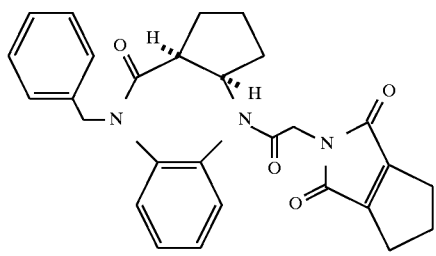
Working Example 177
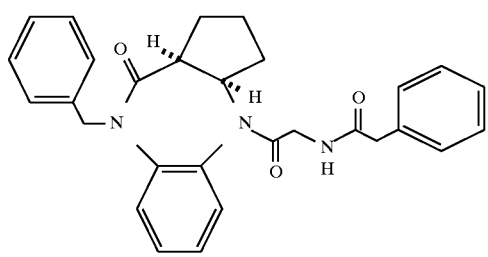
Working Example 178
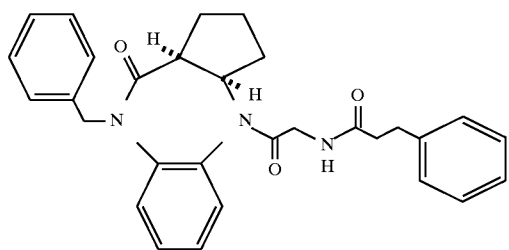
Working Example 179
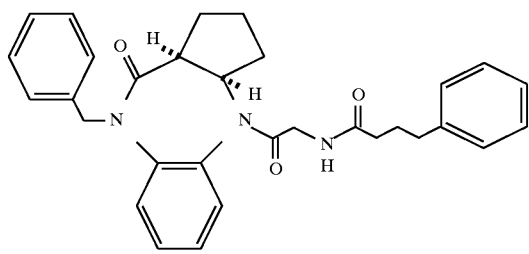
Working Example 180
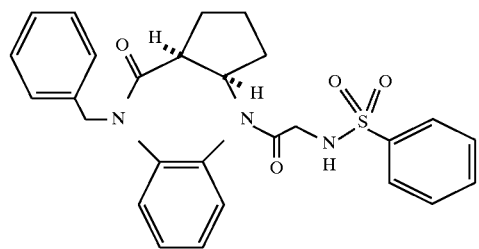
-continued
Working Example 181
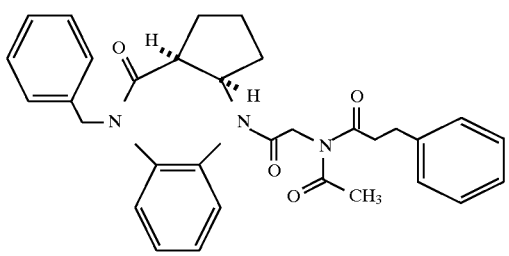
Working Example 182
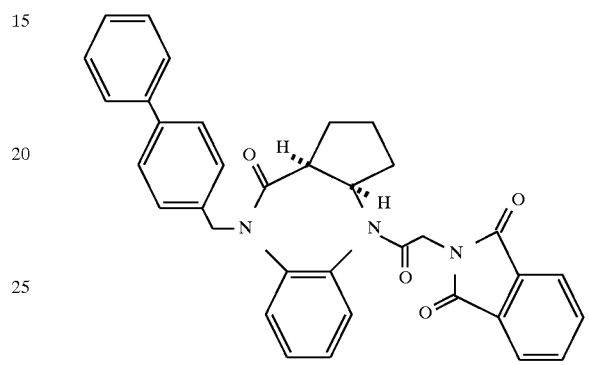
Working Example 183
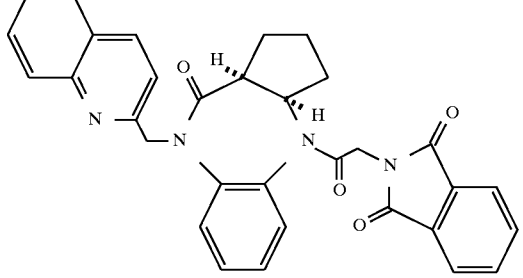
Working Example 184
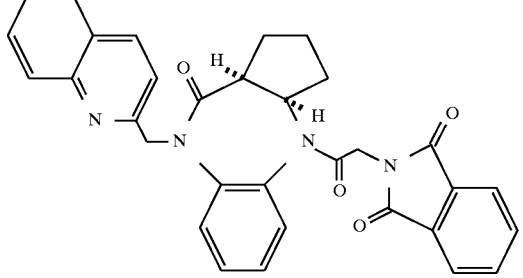
.HCl -continued
Working Example 185
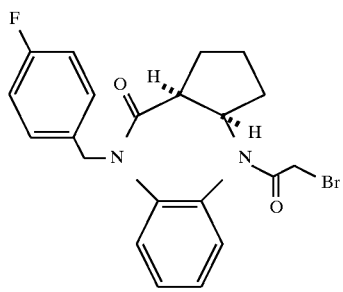
Working Example 186
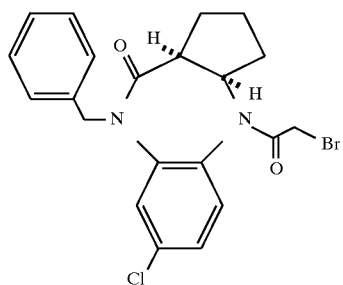
Working Example 187
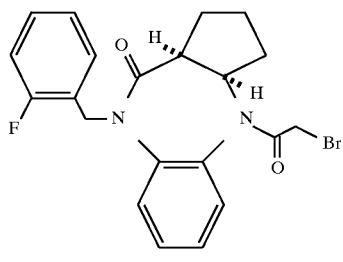
Working Example 188
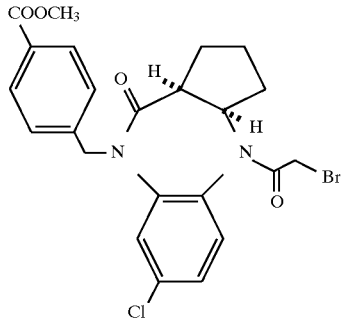
Working Example 189
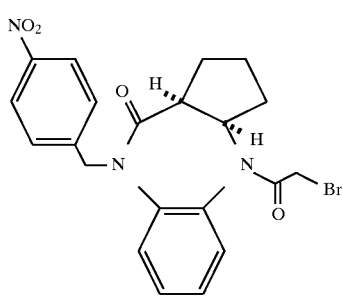
-continued
Working Example 190
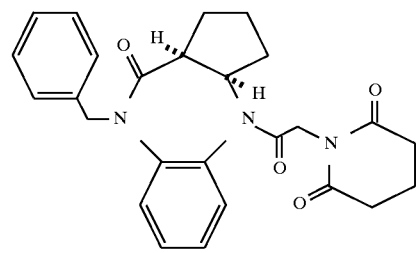
Working Example 191
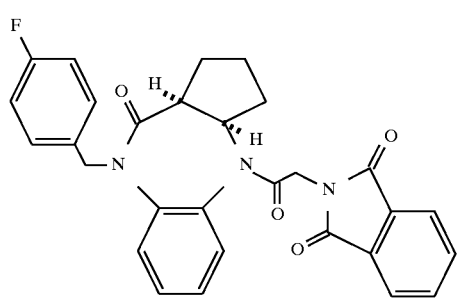
Working Example 192
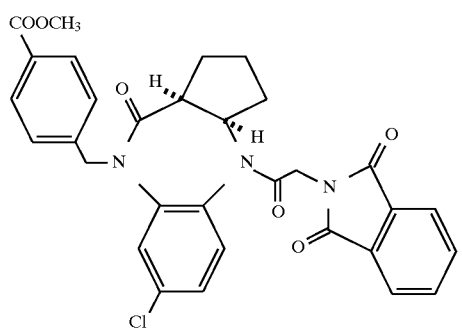
Working Example 193
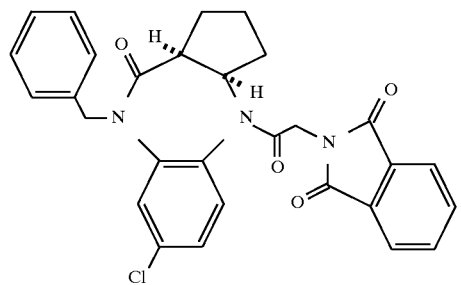
Working Example 194
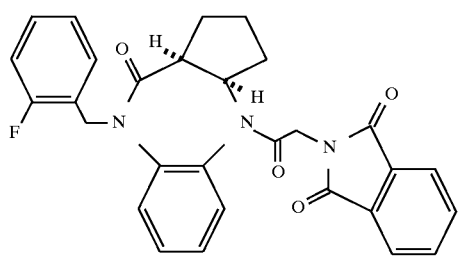

-continued
Working Example 195
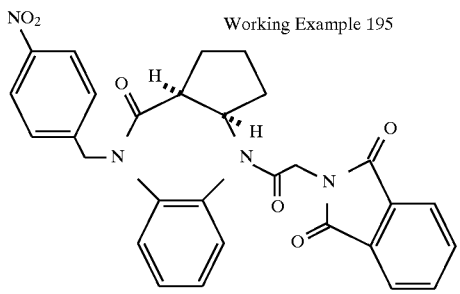
Working Example 196
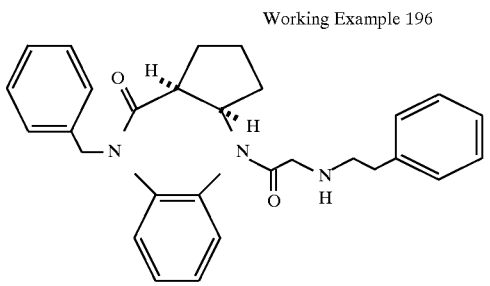
Working Example 197
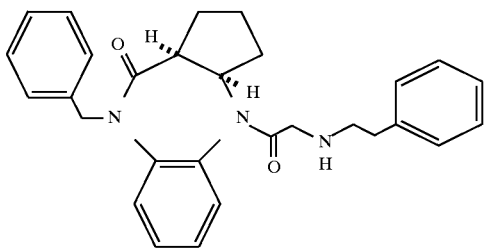
Working Example 198
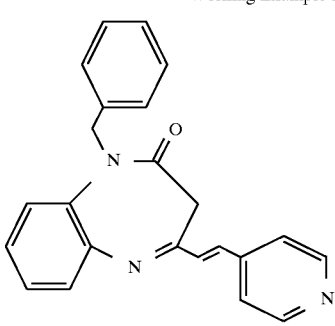
Working Example 199
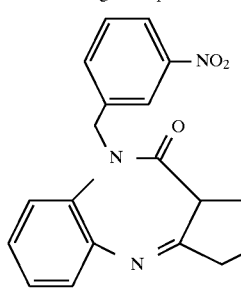
Working Example 200
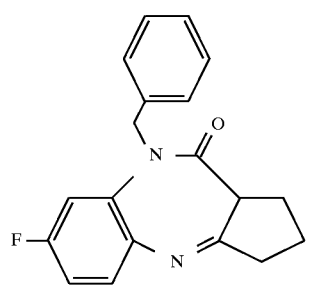
Working Example 201
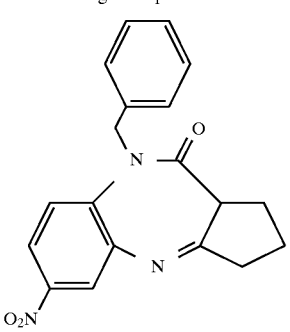
Working Example 202
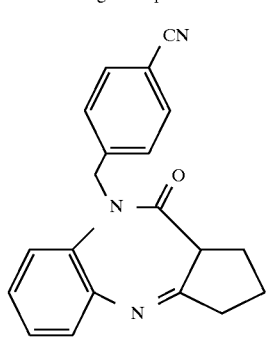
Working Example 203
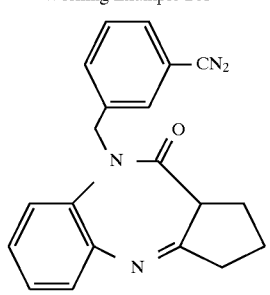

-continued
Working Example 204
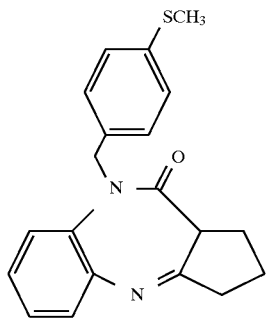
Working Example 205
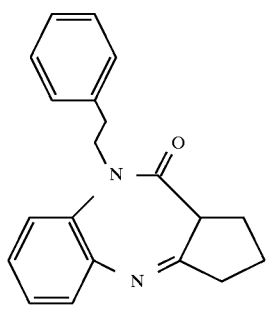
Working Example 206
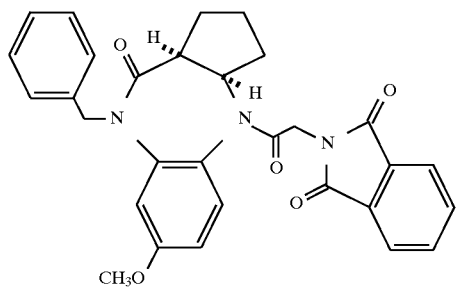
Working Example 207
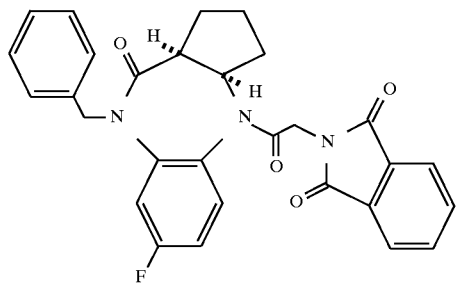
Working Example 208
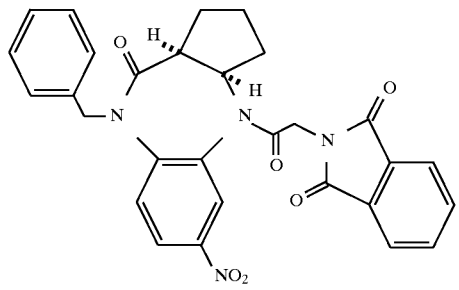
-continued
Working Example 209
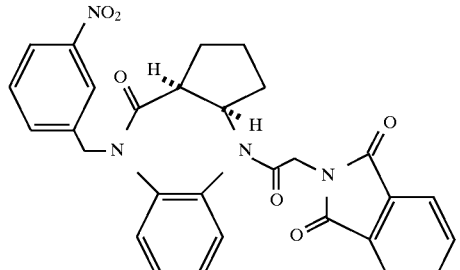
Working Example 210
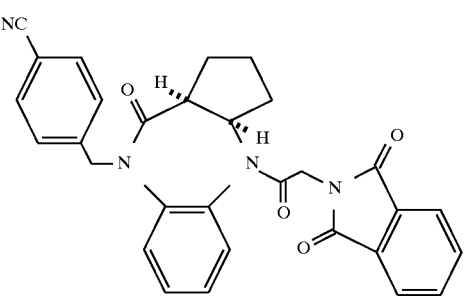
Working Example 211
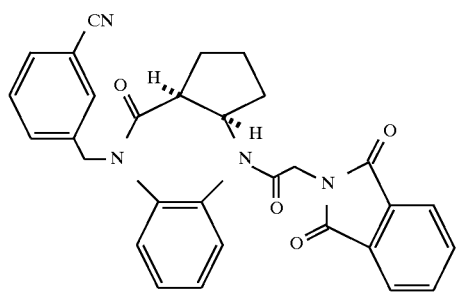
Working Example 212
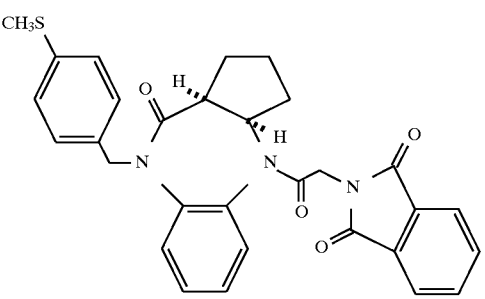
Working Example 213
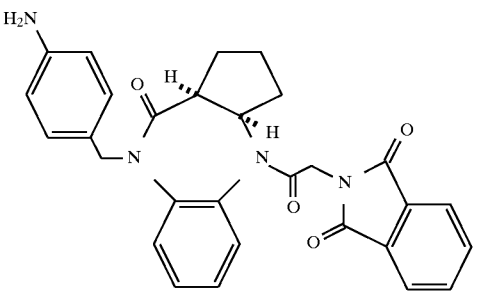

Working Example 214

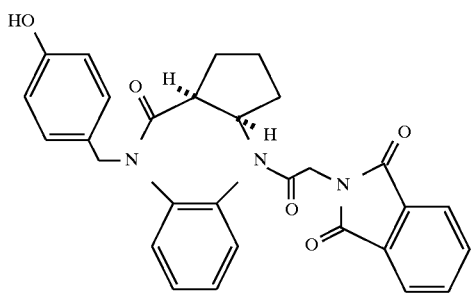

Working Example 215

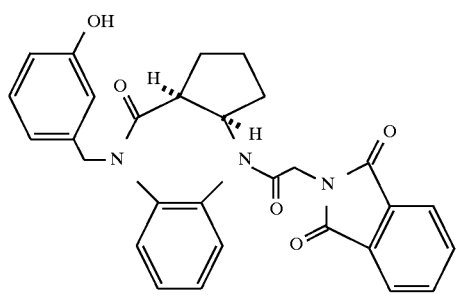

Working Example 216

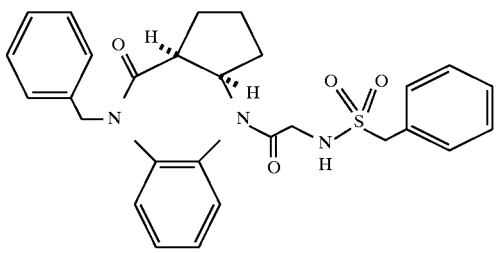

Working Example 217

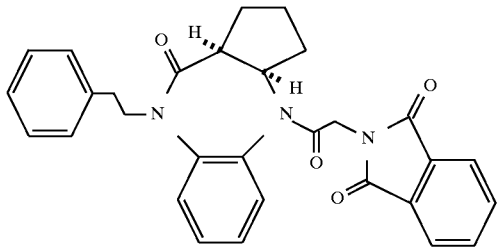

Working Example 218

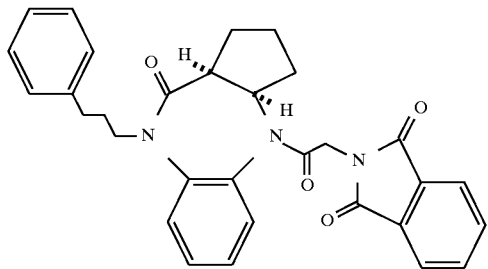

Working Example 219

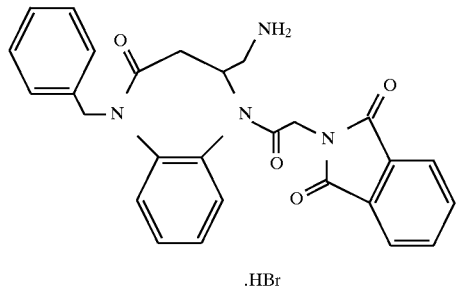

.HBr

Working Example 220

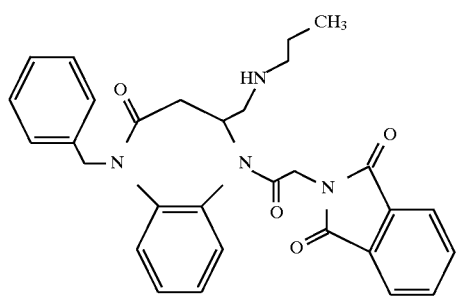

.HCl

Reference Example 1

2,3,3a,4,9,10a-Hexahydrobenzo[b]cyclopenta-[e][1,4]diazepin-10(1H)-one 2,3,9,10a-Tetrahydrobenzo[b]cyclopenta[e][1,4]-diazepin-10(1H)-one (38.3 g, 0.19 mmol) and bromocresol green (30 mg) were suspended in a mixture of methanol (200 mL) and tetrahydrofuran (200 mL), which was cooled to 0° C. To the suspension was added, at the same temperature, sodium cyanoborohydride (13.2 g, 0.21 mmol), to which was then added dropwise gradually a 10% hydrogen chloride-methanol solution until no more color change of the reaction system was observed. To the reaction mixture was added water (500 mL), which was made alkaline with a saturated aqueous solution of sodium hydrogencarbonate, followed by extraction with chloroform three times. Organic layers were combined, washed with water and a saturated aqueous solution of sodium chloride, dried over sodium sulfate and subjected to filtration. The filtrate was concentrated under reduced pressure to give 38.5 g (yield 99%) of the titled compound. The sample for analytical use was prepared by recrystallization from ethanol as a cis-trans mixture (1:1). m.p. 191°–212° C.

$^1$H NMR (CDCl$_3$) δ: 1.5–2.1(4.5H,m), 2.2–2.5(1.5H,m), 2.7–3.0(1H,m), 3.52(0.5H,br s), 3.78(0.5H,m), 4.01(0.5H,m), 4.09(0.5H,br s), 6.6–6.8(1.5H,m), 6.9–7.1(2.5H,m), 7.56(0.5H,br s), 7.60(0.5H,br s)

Reference Example 2

4-(Phthalimidoacetyl)-2,3,3a,4,9,10a-hexahydrobenzo[b]cyclopenta[e][1,4]diazepin-10(1H)-one To a suspension of 2,3,3a,4,9,10a-hexahydrobenzo[b]cyclopenta[e][1,4]diazepin-10(1H)-one (2.02 g, 10 mmol) in 1,2-dichloroethane (15 mL) was added phthalimidoacetyl chloride (2.24 g, 10 mmol),and the mixture was stirred for 15 minutes at room temperature. To the reaction mixture was added a saturated aqueous solution of sodium hydrogencarbonate (10 mL) to give precipitate, which was filtered off. The aqueous layer of the filtrate was seperated. The organic layer was washed with water, dried over magnesium sulfate and subjected to filtration. The filtrate was concentrated under reduced pressure. The concentrate was combined with the precipitate filtered previously, which was washed with methanol, followed by recrystallization from chloroform-methanol to give 2.42 g (yield 62%) of a cis-trans mixture (3:2). m.p. 293°–294° C.

$^1$H NMR (DMSO-d$_6$) δ: 1.0–2.2(6H,m), 2.4–2.7(0.4H, m), 2.8–3.0(0.6H,m), 3.50(0.4H,d,J=16.6 Hz), 3.57(0.6H,d, J=16.6 Hz), 4.21(0.6H,d,J=16.6 Hz), 4.25–4.5(0.4H,m), 4.43(0.4H,d,J=16.6 Hz), 5.55–5.7(0.6H,m), 7.1–7.65(4H, m), 7.87(4H,s), 9.96(0.6H,s), 9.98(0.4H,s).

Reference Example 3

(3aR*,10aS*)-4-(Phthalimidoacetyl)-2,3,3a,4,9,10a-hexahydrobenzo[b]cyclopenta[e][1,4]-diazepin-10 (1H)-one To a solution of (3aR*,10aS*)-9-(4-methoxybenzyl)-4-(phthalimidoacetyl)-2,3,3a,4,9,10a-hexahydrobenzo[b] cyclopenta[e][1,4]diazepin-10(1H)-one (9.89 g, 19 mmol) in chloroform (150 mL) was added a solution of ammonium cerium (IV) nitrate (31.3 g, 57 mmol) and water (5 mL) in acetonitrile (150 mL), and the mixture was stirred for 10 minutes at room temperature. The reaction mixture was poured into water (300 mL), which was subjected to extraction twice with chloroform. Organic layers were combined, washed with water and a saturated aqueous solution of sodium hydrogencarbonate, dried over magnesium sulfate and subjected to filtration. The filtrate was concentrated under reduced pressure. The concentrate was purified by silica-gel column chromatography (chloroform-ethyl acetate 2:1) to a crystalline product, which was washed with chloroform-diisopropyl ether to give 3.7 g (yield 50%) of the titled compound.

$^1$H NMR (DMSO-d$_6$) δ: 1.1–1.5(3H,m), 1.5–1.9(2H,m), 1.9–2.15(1H,m), 2.8–3.0(1H,m), 3.58(1H,d,J=16.8 Hz), 4.21(1H,d,J=16.8 Hz), 5.55–5.7(1H,m), 7.18(1H,dd,J=7.9, 1.3 Hz), 7.23(1H,td,J=7.6,1.4 Hz), 7.4–7.6(2H,m), 7.8–7.95 (3H,m), 9.96(1H,s).

Reference Example 4

Phthalimidoacetyl chloride

A mixture of phthalimidoacetic acid (25.1 g, 0.122 mol) and thionyl chloride (50 mL) was heated for one hour under reflux. The reaction mixture was cooled and, then, concentrated under reduced pressure. The concentrate was recrystallized from dichloromethane-hexane to give 26.4 g (97%) the titled compound, which was used for the subsequent reaction without further purification.

Reference Example 5

(4-Nitrophthalimido)acetic acid

A solution of 4-nitrophthalic anhydride (9.66 g, 50 mmol) and glycine (3.75 g, 50 mmol) in N,N-dimethylformamide was stirred for 30 minutes at 140° C. The reaction mixture was poured into water (150 mL). Resulting precipitate was collected by filtration and washed with water, which was collected by filtration and washed with water, which was recrystallized from ethanol to give 9.69 g (yield 77%) of the titled compound, m.p. 195.5°–196.5° C. (ethanol).

$^1$H NMR (DMSO-d$_6$) δ: 4.39(2H,s), 8.20(1H,d,J=8.2 Hz), 8.57(1H,d,J=1.4 Hz), 8.67(1H,dd,J=8.2,2.0 Hz).

Reference Example 6

4-Phthalimidobutyric acid

A mixture of crushed phthalic anhydride (18.53 g, 0.125 mol) and 4-aminobutyric acid was heated for 30 minutes at 140° C. The reaction mixture was cooled, and resulting precipitate was recrystallized from methanol-water to give 26.26 g (yield 90%) of the titled compound.

$^1$H NMR (CDCl$_3$) δ: 2.02(2H,quintet,J=7.2 Hz), 2.43(2H, t,J=6.8 Hz), 3.77(2H,t,J=6.8 Hz), 7.65–7.9(4H,m).

The proton signal of the carboxylic acid was too broad to determine.

Reference Example 7

2H-1,3-Dioxo-1,3,4,5,6,7-hexahydroisoindole-2-acetic acid

A mixture of 3,4,5,6-tetrahydrophthalic anhydride (7.61 g, 50 mmol) and glycine (3.75 g, 50 mmol) was stirred for one hour at 145° C. The reaction mixture was cooled, which was suspended in ethanol. The suspension was subjected to filtration when hot, and the filtrate was concentrated under reduced pressure. To the concentrate were added dichloromethane and water. The organic layer was separated, and the aqueous layer was subjected to extraction with dichloromethane twice. Organic layers were combined, washed with a saturated aqueous solution of sodium chloride and dried over magnesium sulfate, which was then subjected to filtration. The filtrate was concentrated under reduced pressure. The concentrate was crystallized from ethyl acetate-diisopropylether to give 5.2 g (yield 50%) of the titled compound.

$^1$H NMR (CDCl$_3$) δ: 1.7–1.9(4H,m), 2.2–2.5(4H,m), 4.29 (2H,s), 9.0–9.9(1H,br).

Reference Example 8

Methyl 3-oxo-4-phthalimidobutyrate

To a solution of Meldrum's acid (14.4 g, 0.10 mol) and pyridine (15.8 g, 0.20 mol) in dichloromethane (100 mL) was added dropwise at 0° C., taking 10 minutes, a solution of phthalimidoacetyl chloride (24.6 g,. 0.11 mol) in dichloromethane (50 mL). The mixture was stirred for 30 minutes at the same temperature and for 30 minutes at room temperature. To the reaction mixture was added 1N HCl (200 mL), then insoluble material was filtered off. The aqueous layer was separated, and the organic layer was washed with water, dried over magnesium sulfate and subjected to filtration. The filtrate was concentrated under reduced pressure. The concentrate was suspended in methanol (200 mL), which was refluxed for 1.5 hour. The reaction mixture was left standing for cooling. Crystalline precipitate was collected by filtration and washed with methanol to give the object compound (18.4 g, 70%), m.p.139°–140° C.

$^1$H NMR(CDCl$_3$) δ: 3.61(2H,s), 3.79(3H,s), 4.67(2H,s), 7.7–7.95(4H,m).

Reference Example 9

4-(Phthalimidomethyl)-1,3-dihydro-1,5-benzodiazepin-2(2H)-one

A mixture of methyl 3-oxo-4-phthalimidobutyrate (15.4 g, 59 mmol), o-phenylenediamine (6.37 g, 59 mmol) and xylene (150 mL) was refluxed for 20 minutes using Dean-Stark apparatus. The reaction mixture was cooled, and resulting crystals were collected by filtration and washed with toluene to give the object compound (15.36 g, 81%), m.p.244°–246° C.

$^1$H NMR(DMSO-d$_6$) δ: 3.13(2H,s), 4.65(2H,s), 6.95–7.25 (4H,m), 7.8–8.0(4H,m), 10.43(1H,s).

Reference Example 10

1-Benzyl-4-(phthalimidomethyl)-1,3-dihydro-1,5-benzodiazepin-2(2H)-one

To a suspension of 1-benzyl-4-(phthalimidomethyl)-1,3-dihydro-1,5-benzodiazepin-2(2H)-one (16.7 g,52 mmol) in N,N-dimethylformamide (150 mL) was added at 0° C. sodium hydride (60% liquid paraffin dispersion, 2.3 g, 58 mmol). The mixture was stirred for 5 minutes at the same temperature and, then, for 45 minutes at room temperature. This solution was cooled to 0° C., to which was added dropwise benzyl bromide (7.5 mL, 63 mmol). The mixture was stirred for 5 minutes at 0° C. and, then, for 30 minutes at room temperature. The reaction mixture was poured into a saturated aqueous solution of ammonium chloride (200 mL), which was diluted with water, followed by extraction with ethyl acetate three times. Organic layers were combined and washed with water and a saturated aqueous solution of sodium chloride, which was dried over magnesium sulfate and subjected to filtration. The filtrate was concentrated under reduced pressure. The concentrate was crystallized from ethyl acetate-diethyl ether to give the end product (14.9 g, 70%), m.p.186°–186.5° C.

$^1$H NMR(CDCl$_3$) δ: 2.9–3.2(1H,m), 3.4–3.7(1H,m), 4.7–5.4(4H,m), 7.0–7.35(9H,m), 7.7–8.0(4H,m).

Reference Example 11

9-(4-Benzyloxybenzyl)-2,3,9,10a-tetrahydrobenzo[b]cyclopenta[e][1,4]diazepin-10(1H)-one Employing 4-benzyloxybenzyl bromide, the titled compound was synthesized by substantially the same procedure as in Reference Example 10. Yield 77%.

m.p.124°–126° C. (decomp.)(diethyl ether).

$^1$H NMR(CDCl$_3$) δ: 1.83–2.20(3H,m), 2.62–2.72(2H,m), 2.76–2.90(1H,m), 2.98–3.07(1H,m), 5.00(2H,s), 5.05(2H,s), 6.86(2H,d,J=8.6 Hz), 7.03(2H,d,J=8.6 Hz), 7.10–7.47(9H, m).

Reference Example 12

9-(3-Benzyloxybenzyl)-2,3,9,10a-tetrahydrobenzo[b]cyclopenta[e][1,4]diazepin-10(1H)-one Employing 3-benzyloxybenzyl bromide, the titled compound was synthesized by substantially the same procedure as in reference Example 10. Yield 37%.

m.p.120°–122° C. (diethyl ether).

$^1$H NMR(CDCl$_3$) δ: 1.83–2.18(3H,m), 2.63–2.73(2H,m), 2.76–2.88(1H,m), 2.99–3.07(1H,m), 4.98(1H,d,J=15.6 Hz), 4.99(2H,s), 5.14(1H,d,J=15.6 Hz), 6.67–6.84(3H,m), 7.05–7.47(10H,m).

Reference Example 13

(3aR*,10aS*)-9-(3-phenyl-2-propen-1-yl)-2,3,3a,4,9,10a-hexahydrobenzo[b]cyclopenta[e][1,4]diazepin-10(1H)-one A solution of 2,3,9,10a-tetrahydrobenzo[b]cyclopenta[1,4]diazepin-10(1H)-one (4.0 g, 20 mmol) in N,N-dimethylformamide (20 mL) was cooled at 0° C. To the solution was added sodium hydride (60% liquid paraffin dispersion, 0.84 g, 21 mmol). The mixture was stirred for 5 minutes at the same temperature and, then for 10 minutes at room temperature. The reaction mixture was cooled to 0° C., to which was added dropwise a solution of cinnamyl bromide (4.7 g, 24 mmol) in N,N-dimethylformamide (5 mL). The mixture was stirred for 30 minutes at room temperature. The reaction mixture was poured into a saturated aqueous solution of ammonium chloride (40 mL), which was diluted with water, followed by extraction with ethyl acetate three times. Organic layers were combined, which was washed with water and a saturated aqueous solution of sodium chloride, dried over magnesium sulfate, followed by filtration. The filtrate was concentrated under reduced pressure. The concentrate was subjected to a silica-gel column chromatography (hexane-ethyl acetate 5:1, then 2:1) to give a crude product of 9-(3-phenyl-2-propen-1-yl)-2,3,9,10a-tetrahydrobenzo[b]cyclopenta-[e][1,4]diazepin-10(1H)-one. The crude product was dissolved in methanol (10 mL), to which was added bromocresol green. To the mixture was added at 0° C. sodium cyanoborohydride (1.26 g, 20 mmol), to which was slowly added a 10% HCl-methanol solution until no more change was observed in the color of the solution. To the reaction mixture was added water, which was subjected to extraction with ethylacetate three times. Organic layers were combined, which was washed with water and a saturated aqueous solution of sodium chloride, followed by drying over magnesium sulfate and filtration. The filtrate was concentrated under reduced pressure to give the object compound (6.0 g, 94%) as an oily product.

$^1$H NMR(CDCl$_3$) δ: 1.4–2.2(5H,m), 2.3–2.5(1H,m), 2.8–3.0(1H,m), 3.2–3.7(1H,br), 3.98(1H,ddd,J=10.0,7.8,6.7 Hz), 4.49(1H,ddd,J=15.9,5.8,1.0 Hz), 4.69(1H,ddd,J=15.9, 5.6,1.3 Hz), 6.28(1H,dt,J=15.9,5.7 Hz), 6.59(1H,d,J=15.8 Hz), 6.9–7.4(9H,m).

Reference Example 14

9-(3-Phenylpropyl)-2,3,3a,4,9,10a-hexahydrobenzo[b]cyclopenta[e][1,4]diazepin-10(1H)-one To a solution of 9-(3-phenyl-2-propen-1-yl)-2,3,3a,4,9,10a-hexahydrobenzo[b]cyclopenta[e][1,4]diazepin-10(1H)-one (1.0 g, 3.1 mmol) in methanol (10 mL) was added 10% palladium-carbon (hydrous) (0.1 g). The mixture was stirred for 30 minutes at room temperature under hydrogen atmosphere. The catalyst was filtered off, and the filtrate was concentrated under reduced pressure. To the concentrate were added ethyl acetate and hexane. Insoluble material was filtered off, and the filtrate was concentrated, which was subjected to a silica-gel column chromatography (hexane-ethyl acetate 10:1) to afford the desired product (10.90 g, 90%) as an oily product.

$^1$H NMR(CDCl$_3$) δ: 1.4–2.1(7H,m), 2.3–2.5(1H,m), 2.5–2.75(2H,m). 2.75–2.9(1H,m), 3.3–3.6(1H,br), 3.51(1H, dt,J=13.6,6.8 Hz), 3.93(1H,ddd,J=10.2,7.8,6.6 Hz), 4.27 (1H,dt,J=13.6,7.5 Hz), 6.9–7.3(9H,m).

Reference Example 15

1-Benzyl-4-(phthalimidomethyl)-1,3,4,5-tetrahydro-1,5-benzodiazepin- 2(2H)-one

To a suspension of 1-benzyl-4-(phthalimidomethyl)-1,3-dihydro-1,5-benzodiazepin-1(2H)-one (1.15 g, 2.8 mmol) and bromocresol green in methanol (10 mL) and tetrahydrofuran (5 mL) was added, at 0° C., sodium cyanoborohydride (194 mg, 3.1 mmol). To the mixture was slowly added dropwise a 10% HCl-methanol solution until no more change in the color of the solution was observed. To the reaction mixture was added water. The mixture was subjected to extraction twice with ethylacetate. Organic layers were combined, and washed with water and a saturated aqueous solution of sodium hydrochloride, which was dried over magnesium sulfate and subjected to filtration. The filtrate was concentrated under reduced pressure. The concentrate was purified by silica-gel column chromatography (hexane-ethyl acetate 1:1) to give the desired product (930 mg, 80%). A sample for analytical experiment was prepared by recrystallization from CHCl$^3$-hexane, m.p.127°–130° C.

$^1$H NMR(CDCl$_3$) δ: 2.56(1H,dd,J=12.6,9.6 Hz), 2.65(1H, dd,J=12.6,5.6 Hz), 3.6–3.9(1H,br), 3.73(1H,dd,J=13.8,4.6 Hz), 3.84(1H,dd,J=13.6,6.6 Hz), 4.2–4.4(1H,m), 5.02(1H,d, J=15.8 Hz), 5.12(1H,d,J=15.8 Hz), 6.9–7.3(9H,m), 7.7–7.95 (4H,m).

Reference Example 16

(3aR*,10aS*)-9-(3-nitrobenzyl)2,3,3a,4,9,10a-2,3, 3a,4,9,10a-hexahydrobenzo[b]cyclopenta[e][1,4]-diazepin-10(1H)-one Employing 9-(3-nitrobenzyl)-2,3,3a,4,9,10a-hydrobenzo [b]cyclopenta[e][1,4]diazepin-10(1H)-one, the titled compound was synthesized by substantially the same procedure as in Reference Example 15. Yield 86%.

m.p.169°–171° C. (diethyl ether).

$^1$H NMR(CDCl$_3$) δ: 1.46–2.18(5H,m), 2.32–2.55(1H,m), 2.93–3.05(1H,m), 3.69(1H,br), 3.93–4.12(1H,m), 4.88(1H, d,J=16.2 Hz), 5.49(1H,d,J=16.2 Hz), 6.91–7.47(5H,m), 7.65 (1H,d,J=6.8 Hz), 7.99(1H,d,J=8.0 Hz), 8.34(1H,s).

Reference Example 17

(3aR*,10aS*)-9-Benzyl-7-methoxy-2,3,3a,4,9,10a-hexahydrobenzo[b]cyclopenta[e][1,4]diazepin-10 (1H)-one Employing 9-benzyl-7-methoxy-2,3,9,10a-tetrahydrobenzo[b]cyclopenta[e][1,4]diazepin-10(1H)-one, the titled compound was synthesized by substantially the same procedure as in Reference Example 15. Yield 77%. Oily product.

$^1$H NMR(CDCl$_3$) δ: 1.50–2.11(5H,m), 2.33–2.51(1H,m), 2.87–2.98(1H,m), 2.70–3.30(1H,br), 3.67(3H,s), 3.18(1H, ddd,J=10.2,7.8,7.0 Hz), 5.02(1H,d,J=15.8 Hz), 5.11(1H,d, J=15.8 Hz), 6.58(1H,dd,J=8.4,3.0 Hz), 6.70(1H,d,J=2.4 Hz), 6.84(1H,d,J=8.4 Hz), 7.15–7.38(5H,m).

Reference Example 18

(3aR*,10aS*)-9-Benzyl-7-fluoro-2,3,3a,4,9,10a-hexahydrobenzo[b]cyclopenta[e][1,4]diazepin-10 (1H)-one Employing 9-benzyl-7-fluoro-2,3,9,10a-tetrahydrobenzo [b]cyclopenta[e][1,4]diazepin-10(1H)-one, the titled compound was synthesized by substantially the same procedure as in Reference Example 15. Yield 94%. m.p.124°–126° C. (diethyl ether).

$^1$H NMR(CDCl$_3$) δ: 1.48–2.12(5H,m), 2.36–2.58(1H,m), 2.92(1H,dt,J=7.4,2.2 Hz), 3.00–3.34(1H,br), 3.94(1H,ddd, J=10.0,8.0,6.6 Hz), 5.00(1H,d,J=15.8 Hz), 5.11(1H,d,J=15.8 Hz), 6.66–6.91(3H,m), 7.12–7.31(5H,m).

Reference Example 19

(3aR*,10aS*)-9-Benzyl-6-nitro-2,3,3a,4,9,10a-hexahydrobenzo[b]cyclopenta[e][1,4]diazepin-10 (1H)-one Employing 9-benzyl-6-nitro-2,3,9,10a-tetrahydrobenzo [b]cyclopenta[e][1,4]diazepin-10(1H)-one, the titled compound was synthesized by substantially the same procedure as in Reference Example 15. Yield 89%. m.p.174°–176° C. (diethyl ether).

$^1$H NMR(CDCl$_3$) δ: 1.56–2.18(5H,m), 2.40–2.56(1H,m), 2.83–3.06(1H,m), 3.87(1H,br), 3.95–4.15(1H,m), 5.05(1H, d,J=16.2 Hz), 5.22(1H,d,J=16.2 Hz), 7.10–7.31(6H,m), 7.77–7.86(2H,m).

Reference Example 20

(3aR*,10aS*)-9-(4-cyanobenzyl)-2,3,3a,4,9,10a-hexahydrobenzo[b]cyclopenta[e][1,4]diazepin-10 (1H)-one Employing 9-(4-cyanobenzyl)-2,3,9,10a-tetrahydrobenzo [b]cyclopenta[e][1,4]diazepin-10(1H)-one, the titled compound was synthesized by substantially the same procedure as in Reference Example 15. Yield 65%. m.p.224°–226° C. (decomp.) (diethyl ether).

$^1$H NMR(CDCl$_3$) δ: 1.44–2.13(5H,m), 2.31–2.57(1H,m), 2.90–3.07(1H,m), 3.52(1H,br), 3.90–4.10(1H,m), 4.90(1H, d,J=16.0 Hz), 5.35(1H,d,J=16.0 Hz), 6.89–7.20(4H,m), 7.41–7.54(4H,m).

Reference Example 21

(3aR*,10aS*)-9-(3-cyanobenzyl)-2,3,3a,4,9,10a-hexahydrobenzo[b]cyclopenta[e][1,4]diazepin-10 (1H)-one Employing 9-(3-cyanobenzyl)-2,3,9,10a-tetrahydrobenzo [b][1,4]diazepin-10(1H)-one, the titled compound was synthesized by substantially the same procedure as in Reference Example 15. Yield 57%. Oily product.

$^1$H NMR(CDCl$_3$) δ: 1.47–2.10(5H,m), 2.35–2.51(1H,m), 2.91–3.03(1H,m), 3.50(1H,br), 3.91–4.12(1H,m), 4.85(1H, d,J=16.0 Hz), 5.37(1H,d,J=16.0 Hz), 6.85–7.20(4H,m), 7.28–7.75(4H,m).

Reference Example 22

(3aR*,10aS*)-9-((4-methylthio)-benzyl)-2,3,3a,4,9, 10a-hexahydrobenzo[b]cyclopenta[e][1,4]diazepin-10(1H)-one Employing 9-((4-methylthio)benzyl)-2,3,9,10a-tetrahydrobenzo[b]cyclopenta[e][1,4]diazepin-10(1H)-one, the titled compound was synthesized by substantially the same procedure as in Reference Example 15. Yield 83%. m.p.117°–118° C. (diethyl ether).

$^1$H NMR(CDCl$_3$) δ: 1.43–2.12(5H,m), 2.31–2.57(1H,m), 2.43(3H,s), 2.89–3.00(1H,m), 3.43(1H,br), 3.91–4.05(1H, m), 4.96(1H,d,J=15.8 Hz), 5.10(1H,d,J=15.8 Hz), 6.84–7.28 (8H,m).

Reference Example 23

(3aR*,10aS*)-9-(4-benzyloxybenzyl)-2,3,3a,4,9,10a-hexahydrobenzo[b]cyclopenta[e][1,4]diazepin-10 (1H)-one Employing 9-(4-benzyloxybenzyl)-2,3,9,10a-tetrahydrobenzo[b]cyclopenta[e][1,4]diazepin-10(1H)-one, the titled compound was synthesized by substantially the same procedure as in Reference Example 15. Yield 94%.

m.p.154°–155° C. (diethyl ether).

$^1$H NMR(CDCl$_3$) δ: 1.50–2.11(5H,m), 2.34–2.55(1H,m), 2.88–2.97(1H,m), 3.20–3.52(1H,br), 3.95(1H,ddd,J=10.2, 7.6,6.8 Hz), 4.96(1H,d,J=15.8 Hz), 5.00(2H,s), 5.05(1H,d, J=15.4 Hz), 6.82–7.45(13H,m).

Reference Example 24

(3aR*,10aS*)-9-(3-Benzyloxybenzyl)-2,3,3a,4,9,
10a-hexahydrobenzo[b]cyclopenta[e][1,4]diazepin-
10(1H)-one Employing 9-(3-benzyloxybenzyl)-2,3,9,10a-tetrahydrobenzo[b]cyclopenta[e][1,4]diazepin-10(1H)-one, the titled compound was synthesized by substantially the same procedure as in Reference Example 15. Yield 100%. Oily product.

$^1$H NMR(CDCl$_3$) δ: 1.46–2.14(5H,m), 2.37–2.52(1H,m), 2.84–3.01(1H,m), 3.20–3.52(1H,br), 3.91–4.07(1H,m), 5.01 (1H,d,J=15.8 Hz), 5.01(2H,s), 5.12(1H,d,J=15.4 Hz), 6.65–7.42(13H,m).

Reference Example 25

(3aR*,10aS*)-9-(2-Phenylethyl)-2,3,3a,4,9,10a-
hexahydrobenzo[b]cyclopenta[e][1,4]diazepin-10
(1H)-one Employing 9-(2-phenylethyl)-2,3,9,10a-tetrahydro-benzo[b]cyclopenta[1,4]diazepin-10(1H)-one, the titled compound was synthesized by substantially the same procedure as in Reference Example 15. Yield 100%. Oily product.

$^1$H NMR(CDCl$_3$) δ: 1.4–2.15(5H,m), 2.3–2.55(1H,m), 2.74(1H,ddd,J=13.2,10.5,5.0 Hz), 2.8–2.9(1H,m), 3.00(1H, ddd,J=13.1,10.3,6.2 Hz), 3.78(1H,ddd,J=13.5,10.4,5.1 Hz), 3.93(1H,ddd,J=10.2,7.9,6.6 Hz), 4.26(1H,ddd,J=13.4,10.4, 6.2 Hz), 6.9–7.3(9H,m).

The H signal of NH$_2$ group was too broad to detect.

Reference Example 26

4-(Aminomethyl)-1-benzyl-1,3,4,5-tetrahydro-1,5-
benzodiazepin-2(2H)-one

A suspension of 1-benzyl-4-(phthalimidomethyl)-1,3,4,5-tetrahydro-1,5-benzodiazepin-2(2H)-one (9.82 g, 20 mmol) and hydrazine monohydrate (16 g, 35 mmol) in ethanol (350 ml) was refluxed for 3 hours. The reaction mixture was cooled and subjected to filtration and washed with chloroform. The filtrate was concentrated under reduced pressure. The concentrate was suspended in chloroform, which was again subjected to filtration. The filtrate was concentrated under reduced pressure to afford 8.5 g (yield 86%) of the titled compound as an oily product.

$^1$H NMR(CDCl$_3$) δ: 1.2–1.7(2H,br), 2.39(1H,dd,J=12.6, 8.0 Hz), 2.58(1H,dd,J=12.8,5.4 Hz), 2.67(1H,dd,J=12.6,8.8 Hz), 2.88(1H,dd,J=12.6,4.2 Hz), 3.6–3.9(1H,m), 4.0–4.4 (1H,br), 5.03(1H,d,J=16.0 Hz), 5.12(1H,d,J=16.0 Hz), 6.8–7.3(9H.m).

Reference Example 27

(3aR*,10aS*)-9-(4-Benzyloxybenzyl)-4-
(phthalimidoacetyl)-2,3,3a,4,9,10a-hexahydrobenzo
[b]cyclopenta[e][1,4]diazepin-10(1H)-one To a solution of (3aR*,10aS*)-9-(4-benzyloxybenzyl)-2, 3,3a,4,9,10a-hexahydrobenzo[b ]cyclopenta[e][1,4] diazepin-10(1H)-one (3.1 g, 7.8 mmol) in 1,2-dichloroethane was added phthalimidoacetyl chloride (1.9 g, 8.5 mmol). The mixture was refluxed for 17 hours. To the reaction mixture was added a saturated aqueous solution of sodium hydrogencarbonate. The aqueous layer was separated. The organic layer was washed with a saturated aqueous solution of sodium hydrogencarbonate, dried over magnesium sulfate and subjected to filtration. The filtrate was concentrated under reduced pressure. The concentrate was parified by silica-gel column chromatography (hexane-ethyl acetate 1:3), which was crystallized from diethyl ether to give the desired product (1.9 g, 42%), m.p.179°–181° C.

$^1$H NMR(CDCl$_3$) δ: 1.07–1.48(3H,m), 1.57–1.90(2H,m), 2.02–2.23(1H,m), 3.15(1H,dt,J=11.8,8.8 Hz), 3.31(1H,d,J= 16.4 Hz), 3.98(1H,d,J=16.4 Hz), 4.79(1H,d,J=14.6 Hz), 5.00 (1H,d,J=11.6 Hz), 5.10(1H,d,J=11.6 Hz), 5.47(1H,d,J=14.6 Hz), 5.70–5.83(1H,m), 6.94(2H,d,J=8.8 Hz), 7.16–7.53 (11H,m), 7.64–7.85(4H,m).

Reference Example 28

(3aR*,10aS*)-9-(3-Benzyloxybenzyl)-4-
(phthalimidoacetyl)-2,3,3a,4,9,10a-hexahydrobenzo
[b]cyclopenta[e][1,4]diazepin-10(1H)-one Employing (3aR*,10aS*)-9-(3-benzyloxybenzyl)-2,3,3a, 4,9,10a-hexahydrobenzo[b]cyclopenta[e][1,4]diazepin-10 (1H)-one, the titled compound was synthesized by substantially the same procedure as in Reference Example 27. Yield 36%. m.p.196°–198° C. (diethyl ether).

$^1$H NMR(CDCl$_3$) δ: 1.10–1.43(3H,m), 1.57–1.91(2H,m), 2.0–2.23(1H,m), 3.17(1H,dt,J=11.0,8.8 Hz), 3.17(1H,d,J= 16.4 Hz), 4.03(1H,d,J=16.4 Hz), 5.02(2H,s), 5.09(1H,d,J= 16.0 Hz), 5.19(1H,d,J=16.0 Hz), 5.72–5.83(1H,m), 6.83–6.92(3H,m), 7.20–7.49(10H,m), 7.65–7.90(4H,m).

Reference Example 29

(3aR*,10aS*)-4-(Bromoacetyl)-9-(2-phenylethyl)-2,
3,3a,4,9,10a-hexahydrobenzo[b]cyclopenta-[e][1,4]
diazepin-10(1H)-one Employing (3aR*,10aS*)-9-(2-phenylethyl)-2,3,3a,4,9, 10a-hexahydrobenzo[b]cyclopenta-[e][1,4]diazepin-10(1H) -one and bromoacetyl bromide, the titled compound was synthesized by substantially the same procedure as in Working Example 185. Yield 72%. Oily product.

To a solution of bromoacetyl bromide (0.29 mL, 3.3 mmol) in dichloromethane (5 mL) was added dropwise a solution of (3aR*,10aS*)-9-(2-phenylethyl)-2,3,3a,4,9,10a-hexahydrobenzo [b]cyclopenta[e][1,4]diazepin-10(1H)-one (0.92 g, 3.0 mmol) in dichloromethane (5 mL). The solution was stirred for 3 hours at room temperature. To the reaction mixture was added a saturated aqueous solution of sodium hydrogencarbonate. The aqueous layer was separated, and the organic layer was washed with water and a saturated aqueous solution of sodium chloride, dried over magnesium sulfate and subjected to filtration. The filtrate was concentrated under reduced pressure. The concentrate was purified by silica-gel column chromatography (hexane - ethyl acetate 5:1,then 1:1) to afford the desired product (924 mg, 72%). Oily product.

$^1$H NMR(CDCl$_3$) δ: 0.95–1.5(3H,m), 1.5–1.9(2H,m), 2.15(1H,sext,J=7.2 Hz), 2.8–3.2(3H,m), 3.46(1H,d,J=10.8 Hz), 3.53(1H,d,J=10.8 Hz), 3.9–4.2(2H,m), 5.80(1H,ddd,J= 9.2,8.1,4.1 Hz), 7.05–7.4(8H,m), 7.45(1H,ddd,J=8.1,7.1,1.9 Hz).

Reference Example 30

(3aR*,10aS*)-4-(bromoacetyl)-9-(3-phenylpropyl)-
2,3,3a,4,9,10a-hexahydrobenzo[b]cyclopenta-[e][1,
4]diazepin-10(1H)-one Employing (3aR*,10aS*)-9-(3-phenylpropyl)-2,3,3a,4,9, 10a-hexahydrobenzo[b]cyclopenta[e][1,4]diazepin-10(1H)- one, the titled compound was synthesized by substantially the same procedure as in Reference Example 29. Yield 27%. m.p.130.5°–132.0° C. (diethyl ether).

$^1$H NMR(CDCl$_3$) δ: 0.95–1.2(1H,m), 1.2–1.5(2H,m), 1.55–1.9(2H,m), 1.92(2H,qunit,J=7.8 Hz), 2.14(1H,sext,J=7.2 Hz), 2.64(2H,t,J=7.7 Hz), 3.08(1H,dt,J=11.9,9.1 Hz), 3.53(1H,d,J=11.0 Hz), 3.60(1H,d,J=11.0 Hz), 3.6–3.8(1H,m), 3.95–4.15(1H,m), 5.7–5.9(1H,m), 7.1–7.4(8H,m), 7.46 (1H,td,J=7.4,2.3 Hz).

Reference Example 31

1-Benzyl-4-(benzyloxycarbonylaminomethyl)-5-(phthalimidoacetyl)-1,3,4,5-tetrahydro-1,5-benzodiazepin-2(2H)-one A solution of 4-(aminomethyl)-1-benzyl-1,3,4,5-tetrahydro-1,5-benzodiazepin-2(2H)-one (0.99 g, 3.5 mmol) in 1,2-dichloroethane (15 mL) was cooled to 0° C., to which was added dropwise benzyl chloroformate (0.51 mL, 3.6 mmol). The mixture was stirred for 10 minutes at the same temperature, and for 25 minutes at room temperature. To the reaction mixture was added a saturated aqueous solution of sodium hydrogencarbonate. The aqueous layer was separated, and the organic layer was washed with water and a saturated aqueous solution of sodium chloride, which was dried over magnesium sulfate, followed by filtration. The filtrate was concentrated under reduced pressure to give a crude product of 1-benzyl-4-(benzyloxycarbonyl aminomethyl)-1,3,4,5-tetrahydro-1,5-benzodiazepin-2(2H)-one. This crude product was dissolved in 1,2-dichloroethane (10 mL), to which was added phthalimidoacetyl chloride (0.79 g, 3.5 mmol). The mixture was stirred for 20 minutes at room temperature. To this solution was added 4-dimethylaminopyridine (DMAP) (43 mg, 0.35 mmol). The mixture was stirred for 25 minutes at room temperature, to which was further added DMAP (0.17 g, 1.4 mmol), and the mixture was stirred for 14 hours. To the reaction mixture was added water. The aqueous layer was separated. The organic layer was washed with a saturated aqueous solution of sodium hydrogencarbonate and a saturated aqueous solution of sodium chloride, which was dried over magnesium sulfate and subjected to filtration. The filtrate was concentrated under reduced pressure. The concentrate was recrystallized from chloroform-petroleum ether to afford the end product (1.42 g, 67%). m.p.219°–221° C.

$^1$H NMR(CDCl$_3$) δ: 2.41(1H,t,J=13.0 Hz), 2.63(1H,dd, J=12.9,5.1 Hz), 3.05–3.4(2H,m), 3.18(1H,d,J=16.4 Hz), 3.87(1H,d,J=16.4 Hz), 4.83(1H,d,J=15.0 Hz), 5.10(2H,s), 5.2–5.4(2H,m), 5.41(1H,d,J=15.0 Hz), 7.2–7.9(18H,m).

Formulation Example 1

| (1) Compound of Working Example 36 | 10.0 g |
| (2) Lactose | 60.0 g |
| (3) Corn starch | 35.0 g |
| (4) Gelatin | 3.0 g |
| (5) Magnesium stearate | 2.0 g |

Using 30 ml of a 10 weight % aqueous solution of gelatin (3.0 g in terms of gelatin), a mixture of 10.0 g of the compound produced in Working Example 36, 60.0 g of lactose and 35.0 g of corn starch was granulated through a sieve of 1 mm mesh. The granular product was dried at 40° C., which was sieved again. The granules thus obtained were blended with 2.0 g of magnesium sterate, and the mixture was subjected to compression. The core tablet thus obtained was sugar-coated with an aqueous suspension containing sucrose, titanium dioxide, talc and gum arabic. The coated tablets were polished with bee-wax to prepare 1000 tablets.

Formulation Example 2

| (1) Compound of Working Example 36 | 10.0 g |
| (2) Lactose | 70.0 g |
| (3) Corn starch | 50.0 g |
| (4) Soluble starch | 7.0 g |
| (5) Magnesium stearate | 3.0 g |

With 70ml of an aqueous solution of soluble starch (7.0 g in terms of soluble starch), 10.0 g of the compound produced in Working Example 36 and 3.0 g of magnesium stearate were granulated and dried, followed by blending with 70.0 g of lactose and 50.0 g of corn starch. The mixture was subjected to compression to prepare 1000 tablets.

Experimental Example (A) Preparation of $^{125}$I-leuprorelin

Ten μl of a 3×10$^{-4}$M aqueous solution of leuprorelin and 10μl of 0.01 mg/ml lactoperoxidase in 0.1M Hepes buffer (pH7.4) were put in a tube, to which was added 10 μl of an Na$^{125}$I solution (37 MBq). The mixture was stirred, to which was added 10 μl of 0.001% H$_2$O$_2$, followed by allowing the reaction to proceed for 20 minutes at room temperature. To the reaction mixture was added 700 μl of a 0.05% TFA solution to stop the reaction. The product of was purified by means of a reverse-phase HPLC. Conditions of HPLC were as follows:

$^{125}$I-leuprorelin was eluted with a retention time of 26–27 minutes.

Column: TSK gel ODS-80™CTR (4.6 mm×10 cm)
Eluent: Solvent A (0.05% TFA)
Solvent B (40% CH$_3$CN-0.05% TFA)
0 minute (100% Solvent A)-3 minutes (100% Solvent A)-7 minutes (50% Solvent A+50% Solvent B)-40 minutes (100% Solvent B)
Elution temperature: room temperature
Elution rate: 1 ml/min.

(B) Preparation of membrane fraction of rat pituitary anterior lobes containing GnRH receptors Forty Wister rats (8-week old, male) were killed and the pituitary anterior lobes were collected and washed with an ice-cooled homogenate buffer (25 mM Tris (tris (hydroxylmethyl)aminomethane)-HCl buffer containing 0.3M saccharose, 1 mM EGTA (glycolether diamine tetraacetate), 0.25 mM PMSF (phenylmethylsulfonyl fluoride), 10 U/ml aprotinin, 1 μg/ml pepstatin, 20 μg/ml leupeptin, 100 μg/ml phosphoramidone, 0.03% sodium azide, pH 7.5). In 2 ml of the homogenate buffer, the pituitary gland was suspended, which was homogenated by using a Polytron homogenizer. The homogenate was subjected to centrifuge for 15 minutes with 700×g. The supernatant was put in an ultracentrifugal tube, which was subjected to centrifuge for one hour at 100,000×g to give membrane fraction as precipitate. This precipitate was suspended in 2 ml of an assay buffer (25 mM Tris-HCl containing 1 mM EDTA (ethylenediamine tetraacetate), 0.1% BSA (bovine serum albumin), 0.25 mM PMSF, 1 μg/ml pepstalin, 20 μg/ml leupeptin, 100 μg/ml of phosphoramidon and 0.03% sodium azide, pH 7.5), which was subjected to centrifugal separation for one hour at 100,000× g. The membrane fraction recovered as precipitate was again suspended in 10 ml of the assay buffer, which was distributed into vials and stored at −80° C. until used.

(C) Preparation of membrane fraction of bovine pituitary anterior lobes containing GnRH receptors By substantially the same procedure as in (B) membrane fraction of bovine pituitary anterior lobes containing bovine GnRH receptor was prepared, provided that the supernatant obtained by 10,000×g centrifugation was subjected to centrifugal separation at 100,000×g for one hour to obtain the membrane fraction as precipitate.

(D) Preparation of membrane fraction of CHO (Chinese Hamster Ovary) cells containing human GnRH receptors CHO cells ($10^9$) expressing human GnRH receptors were suspended in a phosphate-buffered saline supplemented with 5 mM EDTA. The suspension was subjected to centrifugal separation for 5 minutes at 100×g. To the pellet of cells was added 10 ml of a homogenate buffer for cells (10 mM $NaHCO_3$, 5 mM EDTA, pH 7.5), which was homogenated by using a Polytron homogenizer. Centrifugal separation was conducted for 15 minutes at 400×g. The supernatant was taken into an ultracentrifugal tube, which was subjected to centrifuge for one hour at 100,000×g to give precipitate of the membrane fraction. The precipitate was suspended in 2 ml of the assay buffer, which was centrifuged for one hour at 100,000×g. The membrane fraction recovered as precipitate was again suspended in 20 ml of the assay buffer, which was distributed to vials and stored at −80° C. until used.

(E) Determination of inhibitory rate of $^{125}$I-leuprorelin binding

In the cases of using rat and human pituitary membrane fractions prepared in (B) and (D), they were respectively diluted with the assay buffer to 200 μg/ml and 188 μl each was distributed to tubes. In the case of using bovine pituitary membrane fraction prepared in (C), it was diluted with the assay buffer to 750 μg/ml and 188 μl each was distributed into tubes. In the case where the membrane fraction of anterior lobes of rat pituitary gland was used, 2 μl of a 0.1 mM compound dissolved in 60% DMSO (dimethylsulfoxide) and 10 μl of 38 nM $^{125}$I-leuprorelin were added thereto simultaneously. In the case where the membrane fraction of anterior lobes of bovine pituitary gland and the membrane fraction derived from the CHO cells expressing human GnRH receptors were used, 2 μl of a 2 mM compound dissolved in 60% DMSO and 10 μl of 38 nM $^{125}$I-leuproprelin were added simultaneously. For determining the maximum binding amount, a solution for reaction supplemented with 2 μl of 60% DMSO and 10 μl of 38 nM $^{125}$I-leuprorelin was prepared. And, for determining the amount of non-specific binding, a solution for reaction supplemented with 2 μl of 100 μM leuprorelin dissolved in 60% DMSO and 10 μl of 38 nM $^{125}$I-leuprorelin were also prepared simultaneously.

In the cases where membrane fractions of anterior lobes of rat and bovine pituitary were used, reaction was allowed to proceed at 4° C. for 90 minutes, while in the case where the membrane fraction derived from the CHO cells expressing human GnRH receptor was used, reaction was allowed to proceed at 25° C. for 60 minutes. The reaction mixtures were respectively subjected to filtration under sucking with Whatman glass filter (GF-F) processed with polyethyleneimine. After completing the filtration, radioactivity of the $^{125}$I-leuprorelin remaining on the filter paper was measured with a γ-counter.

By calculation of (TB-SB)/(TB-NSB)×100 (SB: radioactivity obtained when a compound was added, TB: radioactivity for the maximum binding, NSB: radioactivity for the non-specific binding), the binding inhibitory rate of each test compound was determined. Besides, the inhibitory rates were determined by changing the concentrations of test compounds, and the concentration of a test compound inhibiting the specific binding by 50% ($IC_{50}$ value) was calculated by way of Hill plot. The results are shown in Table 1.

TABLE 1

Test for inhibition of $^{125}$I-leuprorelin binding to human GnRH receptor

| Compound of Working Example | Binding Inhibitory Activity ($IC_{50}$, μM) for human GnRH receptor |
|---|---|
| 36 | 2 |
| 49 | 2 |
| 50 | 24 |
| 51 | 12 |
| 65 | 14 |
| 66 | 8 |
| 69 | 2 |
| 70 | 2 |
| 71 | 9 |
| 72 | 6 |
| 73 | 9 |
| 75 | 3 |
| 76 | 1 |
| 77 | 5 |
| 78 | 5 |
| 80 | 9 |
| 87 | 16 |
| 106 | 5 |
| 108 | 8 |
| 109 | 6 |
| 111 | 4 |
| 112 | 2 |
| 113 | 1 |
| 114 | 0.6 |
| 118 | 2 |
| 119 | 10 |
| 120 | 4 |
| 121 | 11 |
| 128 | 15 |
| 136 | 15 |
| 138 | 14 |
| 139 | 11 |
| 141 | 14 |
| 168 | 3 |
| 169 | 2 |
| 170 | 0.6 |
| 171 | 0.3 |
| 173 | 7 |
| 174 | 5 |
| 175 | 1 |
| 176 | 2 |
| 182 | 2 |
| 184 | 0.8 |
| 191 | 2 |
| 194 | 3 |
| 195 | 0.5 |
| 209 | 2 |
| 210 | 0.4 |
| 212 | 1 |
| 214 | 1 |
| 215 | 2 |
| 217 | 0.7 |

From Table 1, the compound (I) of this invention or salts thereof are shown to have an excellent inhibitory activity for the binding of $^{131}$I-leuprorelin to GnRH receptors.

(F) Effects on ethanol-induced sleep in mice

ICR male mice of 4–5 week old were orally administered with test compounds suspended in a physiological saline solution or 5% gum arabic solution at a dosage of 30 mg/kg (8 animals in each group). Thirty minutes later, test animals were intrapritoneally injected with 25% ethanol (0.2 mL/10 g). The duration of sleep was measured as the time from the onset of righting reflex until the righting reflex was regained. There results were shown in Table 2.

TABLE 2

| Compound (Working Example No.) | Percentage (%) of sleeping time relative to control Numerals with parenthesis ( ) show the amount of compounds administered orally (mg/kg) |
|---|---|
| 17 | 33 (30) |
| 29 | 50 (30) |
| 37 | 145 (30) |
| 63 | 37 (30) |
| 64 | 41 (30) |

(G) Effect on pentobarbital-induced sleep in mice

ICR male mice of 5–6 week old were orally administered with test samples dissolved or suspended in a physiological saline solution or 5% gum solution dosage of 100 mg/kg (2–3 animals in each group), and behavioral observation was conducted at 15, 30, 60 and 120 minutes after the administration. On the compounds by which any specific action was observed, the dosage was gradually reduced, i.e. 50, 20 and 10 mg/kg, and the dosage, by which the action was no longer observed, was determined.

As the next stage, ICR male mice of 4–5 week old were orally administered with test samples dissolved or suspended in a physiological saline solution or 5% gum arabic solution at a dosage which was one rank lower than the dosage determined as above (8 animals in each group). Thirty minutes after the administration, test animals were administered intraperitoneally with sodium pentobarbital at a dosage of 55 mg/kg. The duration of sleep was measured as the time from the onset of righting reflex until the righting reflex was regained. The results were shown in Table 3.

TABLE 3

| Compound (Working Example No.) | Percentage (%) of sleeping time relative to control Numerals with parenthesis ( ) show the amount of compounds administered orally (mg/kg) |
|---|---|
| 5 | 140 (20) |
| 9 | 176 (10) |
| 4 | 140 (50) |
| 37 | 128 (50) |
| 45 | 124 (20) |

From the results shown in Table 2 and Table 3, the compound (I) or salts thereof of this invention are revealed to have excellent action improving sleep disturbances.

The compound (I) or salts thereof of this invention have an excellent GnRH receptor antagonistic action and/or an action of improving sleep disturbances, which are useful as prophylactic and therapeutic agents of especially various diseases in human (for example, prostatic hypertrophy, endometriosis, insomnia, etc.).

We claim:

1. A compound represented by the formula:

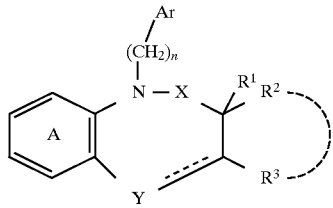

wherein ring A is a benzene ring which may be substituted by 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a formyl, acetyl or propionyl group, a mercapto group and a $C_{1-6}$ alkylmercapto group;

Ar is a $C_{6-14}$ aryl, 2- or 3-thienyl, 2- or 3-furyl, 2- or 3-pyrrolyl, 2-, 4- or 5-imidazolyl, 4- or 5-pyrazolyl, 3-, 4- or 5-isothiazolyl, 3-, 4- or 5-isoxazolyl, 2-, 3- or 4-pyridyl, 2-, 4- or 5-pyrimidinyl, 3- or 4-pyridazinyl, pyrazinyl, benzofuryl, benzothiazolyl, benzoxazolyl, benzoimidazolyl, 1-indolyl, 2- or 3-quinolyl or 1- or 3-isoquinolyl group, which may be substituted by 1 to 5 substituents selected from the group consisting of an amino group, mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a formyl, acetyl or propionyl group, a mercapto group, a $C_{1-6}$ alkylmercapto group, a phenyl group and an oxo group;

$R^1$ is (1) a hydrogen atom, (2) a $C_{1-6}$ alkyl-carbonyl, $C_{6-14}$ aryl-carbonyl, $C_{7-16}$ aralkyl-carbonyl, $C_{1-3}$ alkylsulfonyl or $C_{6-14}$ arylsulfonyl group, which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a formyl, acetyl, or propionyl group, (n) a mercapto group and (o) a $C_{1-6}$ alkylmercapto group, (3) a $C_{1-6}$ alkyl, $C_{2-6}$ alkenyl, $C_{2-6}$ alkynyl, $C_{3-8}$ cycloalkyl, $C_{6-14}$ aryl or $C_{7-16}$ aralkyl group, which may be substituted by 1 to 5 substituents selected from the group consisting of (a) an amino group, (b) a mono-$C_{1-8}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a formyl, acetyl, or propionyl group, (n) a mercapto group, (o) a $C_{1-6}$ alkylmercapto group, (p) a $C_{6-14}$ aryl group, (q) a 2- or 3-thienyl, 2- or 3- furyl, 2- or 3-pyrrolyl, 2-, 4- or 5-imidazolyl, 4- or 5- pyrazolyl, 3-, 4- or 5-isothiazolyl, 3-, 4- or 5-isoxazolyl, 2-, 3- or 4-pyridyl, 2-, 4- or 5-pyrimidinyl, 3- or 4- pyridazinyl, pyrazinyl, benzofuryl, benzothiazolyl, benzoxazolyl, benzoimidazolyl, 1-indolyl, 2- or 3-quinolyl or 1- or 3-isoquinolyl group and (r) a formyloxy, acetoxy or propionyloxy group; (4) a 2- or 3-thienyl, 2- or 3-furyl, 2- or 3-pyrrolyl, 2-, 4- or 5-imidazolyl, 4- or 5-pyrazolyl, 3-, 4- or 5-isothiazolyl, 3-, 4- or 5-isoxazolyl, 2-, 3- or 4-pyridyl, 2-, 4- or 5 pyrimidinyl, 3- or 4-pyridazinyl, pyrazinyl, benzofuryl, benzothiazolyl, benzoxazolyl, benzoimidazolyl, 1-indolyl, 2- or 3-quinolyl, 1- or 3-isoquinolyl, 2-pyrrolidinyl, pyrrolinyl, 2-imidazolidinyl, 2-pyrazolidinyl or 1-piperazinyl group, which may be substituted by 1 to 5 substituents selected from the group consisting of (a) an amino group, (b) a mono-$C_{1-6}$ alkylamino group, (c) a di-$C_{1-6}$ alkylamino group, (d) a halogen atom, (e) a nitro group, (f) a sulfo group, (g) a cyano group, (h) a hydroxyl group, (i) a $C_{1-6}$ alkyl group, (j) a $C_{1-6}$ alkoxy group, (k) a carboxyl group, (l) a $C_{1-6}$ alkoxy-carbonyl group, (m) a formyl, acetyl or propionyl group, (n) a mercapto group and (o) a $C_{1-6}$ alkylmercapto group;

$R^2$ and $R^3$, taken together with the carbons to which they are attached, form a $C_{5-8}$ cycloalkane;

X is a methylene group or a carbonyl group;

n is an integer of 0 to 3; and

----- is a single bond or a double bond; with the proviso that when ----- is a double bond, Y is a nitrogen atom, when ----- is a single bond, Y is —NR$^4$— where R$^4$ is (1) a C$_{1-6}$ alkyl-carbonyl, C$_{6-14}$ aryl-carbonyl, C$_{7-16}$ aralkyl-carbonyl, C$_{1-3}$ alkylsulfonyl or C$_{6-14}$ arylsulfonyl group, (2) —Z—(CH$_2$)$_m$—W in which Z is a methylene group or a carbonyl group, m is an integer of 0 to 5, and W is (i)

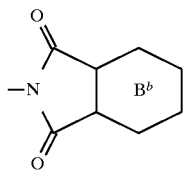

wherein ring B$^b$ a 6-membered saturated or unsaturated cyclic hydrocarbon which may be substituted by 1 to 3 substituents selected from the group consisting of an amino group, a mono-C$_{1-6}$ alkylamino group, a di-C$_{1-6}$ alkylamino group, a halogen atom, a nitro group, a sulfo group, a cyano group, a hydroxyl group, a C$_{1-6}$ alkyl group, a C$_{1-6}$ alkoxy group, a carboxyl group, a C$_{1-6}$ alkoxy-carbonyl group, a formyl, acetyl or propionyl group, a mercapto group and a C$_{1-6}$ alkylmercapto group, or (ii) —NH—CH$_2$—R, —NH—CO—R,

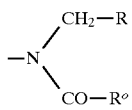

or

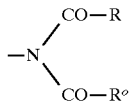

wherein R and R$^0$ are independently (a) a hydrogen atom or (b) a C$_{1-6}$ alkyl, phenyl, 2- or 3-thienyl, 2- or 3-furyl, 2- or 3-pyrrolyl, 2-, 4- or 5-imidazolyl, 4- or 5-pyrazolyl, 3-, 4- or 5-isothiazolyl, 3-, 4- or 5-isoxazolyl, 2-, 3- or 4-pyridyl, 2-, 4- or 5-pyrimidinyl, 3- or 4-pyridazinyl or pyrazinyl group, which may be substituted by 1 to 5 substituents selected from the group consisting of an amino group, a mono-C$_{1-6}$ alkylamino group, a di-C$_{1-6}$ alkylamino group, a halogen atom, a nitro group, a sulfo group, a cyano group, a hydroxyl group, a C$_{1-6}$ alkyl group, a C$_{1-6}$ alkoxy group, a carboxyl group, a C$_{1-6}$ alkoxy-carbonyl group, a formyl, acetyl or propionyl group, a mercapto group, a C$_{1-6}$ alkylmercapto group and a formyloxy, acetoxy or propionyloxy group, or (3) a 2- or 3-thienyl, 2- or 3-furyl, 2- or 3-pyrrolyl, 2-, 4- or 5-imidazolyl, 4- or 5-pyrazolyl, 3-, 4- or 5-isothiazolyl, 3-, 4- or 5-isoxazolyl, 2-, 3- or 4-pyridyl, 2-, 4- or 5-pyrimidinyl, 3- or 4-pyridazinyl, pyrazinyl, benzofuryl, benzothiazolyl, benzoxazolyl, benzoimidazolyl, 1-indolyl, 2- or 3-quinolyl, 1- or 3-isoquinolyl, 2-pyrrolidinyl, pyrrolinyl, 2-imidazolidinyl, 2-pyrazolidinyl or 1-piperazinyl group, which may be substituted by 1 to 5 substituents selected from the group consisting of (a) an amino group, (b) a mono-C$_{1-6}$ alkylamino group, (c) a di-C$_{1-6}$ alkylamino group, (d) a halogen atom, (e) a nitro group, (f) a sulfo group, (g) a cyano group, (h) a hydroxyl group, (i) a C$_{1-6}$ alkyl group, (j) a C$_{1-6}$ alkoxy group, (k) a carboxyl group, (1) a C$_{1-6}$ alkoxy-carbonyl group, (m) a formyl, acetyl or propionyl group, (n) a mercapto group and (o) a C$_{1-6}$ alkymercapto group; or a salt thereof.

2. A compound as claimed in claim 1, wherein ring A is an unsubstituted benzene ring.

3. A compound as claimed in claim 1, wherein Ar is a C$_{6-14}$ aryl group which may be substituted by 1 to 5 substituents selected from the group consisting of an amino group, a mono-C$_{1-6}$ alkylamino group, a di-C$_{1-6}$ alkylamino group, a halogen atom, a nitro group, a sulfo group, a cyano group, a hydroxyl group, a C$_{1-6}$ alkyl group, a C$_{1-6}$ alkoxy group, a carboxyl group, a C$_{1-6}$ alkoxy-carbonyl group, a formyl, acetyl or propionyl group, a mercapto group, a C$_{1-6}$ alkylmercapto group, a phenyl group and an oxo group, and n is 1.

4. A compound as claimed in claim 1, wherein R$^1$ is (i) a hydrogen atoms or (ii) a C$_{7-16}$ aralkyl group which may be substituted by 1 to 5 substituents selected from the group consisting of an amino group, a mono-C$_{1-6}$ alkylamino group, a di-C$_{1-6}$ alkylamino group, a halogen atom, a nitro group, a sulfo group, a cyano group, a hydroxyl group, a C$_{1-6}$ alkyl group, a C$_{1-6}$ alkoxy group, a carboxyl group, a C$_{1-6}$ alkoxy-carbonyl group, a formyl, acetyl or propionyl group, a mercapto group and a C$_{1-6}$ alkylmercapto group.

5. A compound as claimed in claim 1, wherein R$^1$ is a hydrogen atom.

6. A compound as claimed in claim 1 represented by the formula:

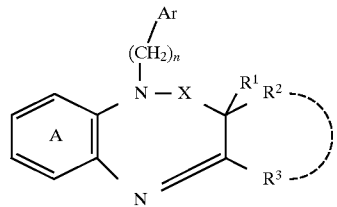

or a salt thereof.

7. A compound as claimed in claim 6, wherein Ar is a 2- or 3-thienyl, 2- or 3-furyl, 2- or 3-pyrrolyl, 2-, 4- or 5-imidazolyl, 4- or 5-pyrazolyl, 3-, 4- or 5-isothiazolyl, 3-, 4- or 5-isoxazolyl, 2-, 3- or 4-pyridyl, 2-, 4- or 5-pyrimidinyl, 3- or 4-pyridazinyl or pyrazinyl group, which may be substituted by 1 to 4 substituents selected from the group consisting of an amino group, a mono-C$_{1-6}$ alkylamino group, a di-C$_{1-6}$ alkylamino group, a halogen atom, a nitro group, a sulfo group, a cyano group, a hydroxyl group, a C$_{1-6}$ alkyl group, a C$_{1-6}$ alkoxy group, a carboxyl group, a C$_{1-6}$ alkoxy-carbonyl group, a formyl, acetyl or propionyl group, a mercapto group, a C$_{1-6}$ alkylmercapto group and a phenyl group.

8. A compound as claimed in claim 1, represented by the formula:

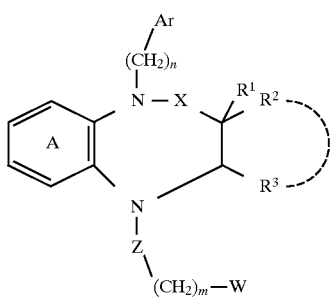

or a salt thereof.

9. A compound as claimed in claim 8, wherein the ring A is a benzene ring which may be substituted by 1 to 3 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a formyl, acetyl or a propionyl group, a mercapto group and a $C_{1-6}$ alkylmercapto group.

10. A compound as claimed in claim 8, wherein the ring A is an unsubstituted benzene ring.

11. A compound as claimed in claim 8, wherein Ar is a $C_{6-14}$ aryl, 2- or 3-thienyl, 2- or 3-furyl, 2- or 3-pyrrolyl, 2-, 4- or 5-imidazolyl, 4- or 5-pyrazolyl, 3-, 4- or 5-isothiazolyl, 3-, 4- or 5-isoxazolyl, 2-, 3- or 4-pyridyl, 2-, 4- or 5-pyrimidinyl, 3- or 4-pyridazinyl or pyrazinyl group, which may be substituted by 1 to 5 substituents selected from the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a formyl, acetyl or propionyl group, a mercapto group, a $C_{1-6}$ alkylmercapto group, a phenyl group and an oxo group.

12. A compound as claimed in claim 8, wherein $R^1$ is (i) a hydrogen atom or (ii) a $C_{7-16}$ aralkyl group which may be substituted by 1 to 5 substituents selected form the group consisting of an amino group, a mono-$C_{1-6}$ alkylamino group, a di-$C_{1-6}$ alkylamino group, a halogen atom, a nitro group, a sulfo group, a cyano group, a hydroxyl group, a $C_{1-6}$ alkyl group, a $C_{1-6}$ alkoxy group, a carboxyl group, a $C_{1-6}$ alkoxy-carbonyl group, a formyl, acetyl or propionyl group, a mercapto group and a $C_{1-6}$ alkylmercapto group.

13. A compound as claimed in claim 8, wherein $R^1$ is a hydrogen atom.

14. A compound as claimed in claim 13, wherein X is a carbonyl group.

15. A compound as claimed in claim 13, wherein Z is a carbonyl group.

16. A compound as claimed in claim 13, wherein n is 1.

17. A compound as claimed in claim 8, wherein $R^1$ is a hydrogen atom, and $R^2$ and $R^3$, taken together, form a cyclopentane.

18. A compound as claimed in claim 8, wherein W is

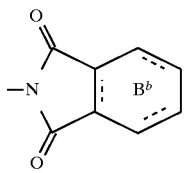

19. A compound as claimed in claim 18, wherein ring $B^b$ is a benzene ring.

20. A compound as claimed in claim 18, wherein W is

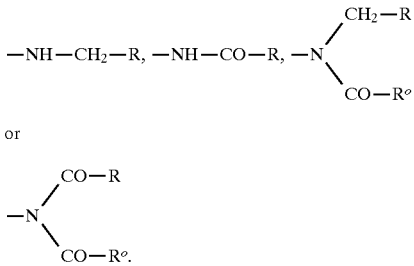

21. A process for producing a compound as claimed in claim 1, which comprises reacting a compound represented by the formula:

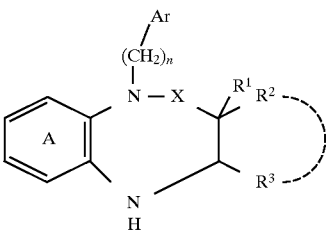

or a salt thereof with a compound represented by the formula: Hal-$R^4$, wherein Hal is a halogen atom.

22. A process for producing a compound represented by the formula as claimed in claim 1:

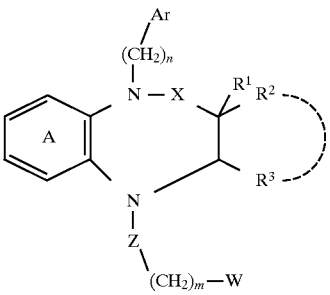

or a salt thereof, which comprises reacting a compound represented by the formula:

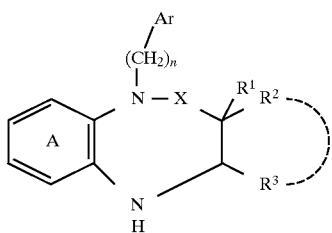

or a salt thereof, with a compound represented by the formula:

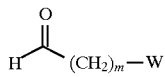

or a salt thereof.

23. A process for producing a compound claimed in claim 1, which comprises reacting a compound represented by the formula:

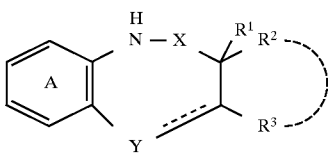

or a salt thereof, with a compound represented by the formula: Ar—$(CH_2)_n$—Hal, wherein Hal is a halogen atom, or a salt thereof.

24. A pharmaceutical composition which comprises a compound as claimed in claim 1 and a pharmaceutically acceptable carrier.

25. A method of controlling fertility comprising administering a pharmaceutical composition as claimed in claim 24 to a patient in need thereof.

26. A method of controlling menstrual cycle comprising administering a pharmaceutical composition as claimed in claim 24 to a patient in need thereof.

* * * * *

UNITED STATES PATENT AND TRADEMARK OFFICE
CERTIFICATE OF CORRECTION

PATENT NO. : 5,834,463
DATED : November 10, 1998
INVENTOR(S) : Shigenori Ohkawa et al.

It is certified that error appears in the above-identified patent and that said Letters Patent is hereby corrected as shown below:

Title page,
Item [56], References Cited,
OTHER PUBLICATIONS, "799 (1985." should read -- 799 (1985). --.

Item [75], Inventors, "Masaomi Miyamoto, Takarazuka," should be deleted.

Column 1,
Line 24, "pipuitary" should read -- pituitary --; and
Line 44, "peptide" should read -- peptides --.

Column 2,
Line 10, "Further more," should read -- Furthermore, --.

Column 3,
Lines 1-9, should read

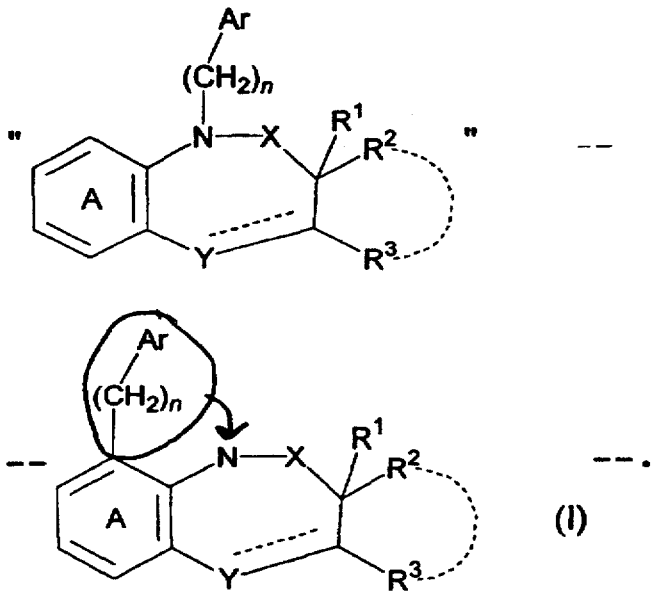

UNITED STATES PATENT AND TRADEMARK OFFICE
CERTIFICATE OF CORRECTION

PATENT NO. : 5,834,463
DATED : November 10, 1998
INVENTOR(S) : Shigenori Ohkawa et al.

It is certified that error appears in the above-identified patent and that said Letters Patent is hereby corrected as shown below:

Column 5,
Lines 6-10, should read

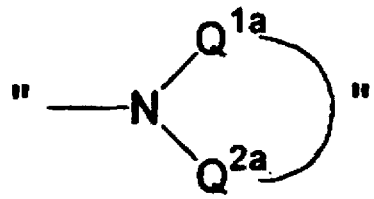

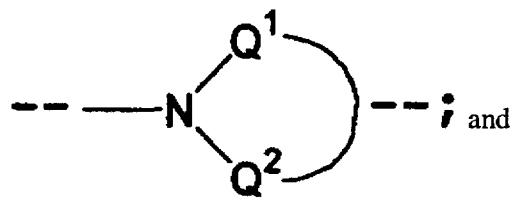 and

Line 49, "a alkylamino" should read -- alkylamino --.

Column 6,
Line 41, "sulfon" should read -- sulfo --.

Column 7,
Lines 5-12, should read

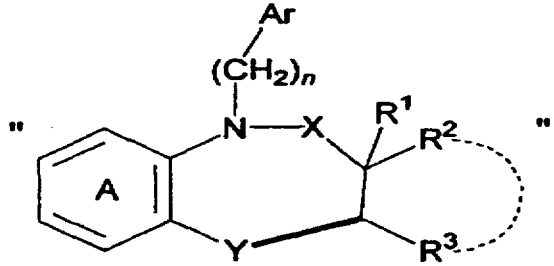

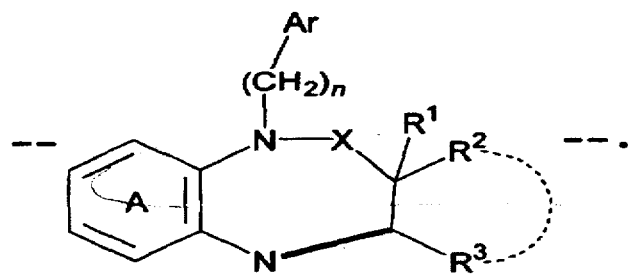.

UNITED STATES PATENT AND TRADEMARK OFFICE
CERTIFICATE OF CORRECTION

PATENT NO. : 5,834,463
DATED : November 10, 1998
INVENTOR(S) : Shigenori Ohkawa et al.

It is certified that error appears in the above-identified patent and that said Letters Patent is hereby corrected as shown below:

Column 12,
Line 43, "have" should read -- has --.

Column 13,
Line 34, "include," should read -- includes, --.

Column 15,
Line 44, "group." should read -- group). --.

Column 16,
Line 46, "Preferable" should read -- Preferably, --.

Column 20,
Lines 23-32,  "  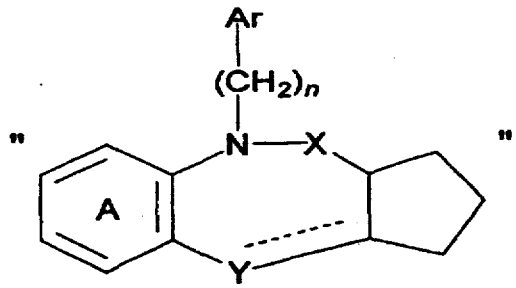  "  should read

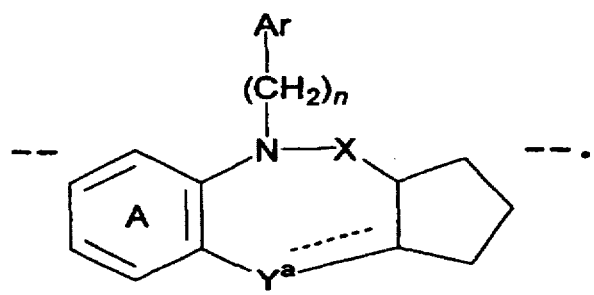

Column 21,
Line 30, "follow." should read -- following. --; and
Line 46, "include" should read -- includes --.

Column 24,
Line 18, "tionae" should read -- tional --.

UNITED STATES PATENT AND TRADEMARK OFFICE
CERTIFICATE OF CORRECTION

PATENT NO. : 5,834,463
DATED : November 10, 1998
INVENTOR(S) : Shigenori Ohkawa et al.

It is certified that error appears in the above-identified patent and that said Letters Patent is hereby corrected as shown below:

Column 31,
Line 33, "organic" should read -- Organic --.

Column 32,
Line 42, "And," should read -- And in order to effect --;
Line 43, "form" should read -- from --; and
Line 61, "solvent." should read -- solvents. --; and
Line 63, "form" should read -- from --.

Column 34,
Line 29, "of, for" should read -- of, for --;
Line 35, "form" should read -- from --; and
Line 57, "may" should read -- may be --.

Column 35,
Line 13, "Examples" should read -- Examples of --;
Line 19, "may" should read -- may be --;
Line 59, "andorogen." should read -- androgen. --; and
Line 63, "sarcadian" should read -- circadian --.

Column 36,
Line 1, "safly used for agents of" should read -- be safely used as an agent to treat --.

Column 37,
Line 2, "the" should read -- from the --.

Column 39,
Line 20, "H" should read -- 'H --.

Column 40,
Line 13, "(diethylether)" should read -- (diethylether) ¶ $^1$H NMR (CDC1$_3$) δ: 2.41 (3H, s), 3.01 (1H,d,J= 11.0Hz), --;
Line 52, "broading" should read -- broadening --.

Column 43,
Line 3, "filtratin," should read -- filtration, --;
Line 28, delete ". To the"; and
Line 29, delete "mixture was added".

Column 44,
Line 58, "5.1691H,d,J= " should read -- 5.16 (1H,d,J= --.

UNITED STATES PATENT AND TRADEMARK OFFICE
CERTIFICATE OF CORRECTION

PATENT NO.     : 5,834,463
DATED          : November 10, 1998
INVENTOR(S)    : Shigenori Ohkawa et al.

It is certified that error appears in the above-identified patent and that said Letters Patent is hereby corrected as shown below:

Column 49,
Line 37, "them" should read -- then --.

Column 52,
Line 53, "the" should read -- of the --.

Column 53,
Line 7, "subjected" should read -- subjected to --.

Column 63,
Line 18, "6.5 . 6.7 (1H,m)," should read -- 6.5-6.7 (1H,m), --.

Column 64,
Line 7, close up right margin.

Column 65,
Lne 46, "25°5-262°C" should read -- 255-262°C --.

Column 66,
Line 34, "the" should read -- of the --.

Column 67,
Line 8, close up left margin.

Column 74,
Line 1, "paraffim" should read -- paraffin --;
Line 33, "H" should read -- ¶ $^1$H --; and
Line 35, "*4.81 (1H,d,J=15.0 Hz)," should read -- 4.81 (1H,d,J=15.0 Hz), --.

Column 75,
Line 38, "subjected" should read -- subjected to --.

Column 78,
Line 60, "(1H-one" should read -- (1H)-one --.

Column 84,
Line 24, "viborourly" should read -- vigorously --.

Column 86,
Line 37, "5.59(2H,d,J=" should read -- 5.59(2H,d,J= --.

UNITED STATES PATENT AND TRADEMARK OFFICE
CERTIFICATE OF CORRECTION

PATENT NO. : 5,834,463
DATED : November 10, 1998
INVENTOR(S) : Shigenori Ohkawa et al.

It is certified that error appears in the above-identified patent and that said Letters Patent is hereby corrected as shown below:

Column 91,
Line 2, "10" shoud be deleted; and
Line 65, "and most portion" should read -- most of which --.

Column 92,
Line 19, "15" should be deleted.

Column 140,

Ex. 203, " 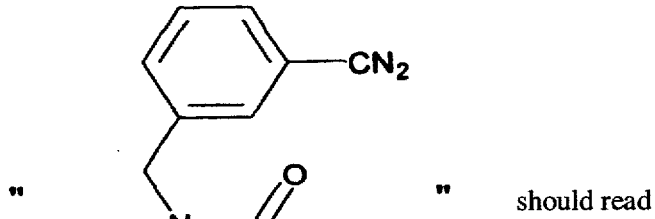 " should read

-- 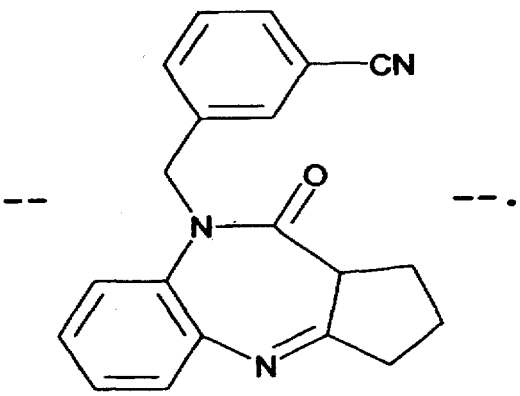 --.

Column 145,
Line 5, "Seperated" should read -- separated --; and
Line 55, "(97%)" should read -- (97%) of --.

UNITED STATES PATENT AND TRADEMARK OFFICE
CERTIFICATE OF CORRECTION

PATENT NO.   : 5,834,463
DATED        : November 10, 1998
INVENTOR(S)  : Shigenori Ohkawa et al.

It is certified that error appears in the above-identified patent and that said Letters Patent is hereby corrected as shown below:

Column 149,
Line 12, "CHCl$^3$-hexane," should read -- CHCl$_3$-hexane, --.

Column 151,
Line 51, "6.8-7.3 (9H.m)." should read -- 6.8-7.3 (9H,m). --.

Column 153,
Line 66, "sterate," should read -- stearate --.

Column 156,
Line 64, "intrapritoneally" should read -- intraperitoneally --.

Column 157,
Line 44, "action" should read -- action in --

Column 159,
Line 21, "B$^b$" should read -- B$^b$ is --.

Column 160,
Line 25, "atoms" should read -- atom --.

Signed and Sealed this

Fifth Day of February, 2002

*Attest:*

JAMES E. ROGAN
*Attesting Officer*   *Director of the United States Patent and Trademark Office*